(12) United States Patent
Kincaid

(10) Patent No.: US 11,603,377 B2
(45) Date of Patent: Mar. 14, 2023

(54) MTORC1 MODULATORS AND USES THEREOF

(71) Applicant: Aeovian Pharmaceuticals, Inc., Walnut Creek, CA (US)

(72) Inventor: John Kincaid, Pleasanton, CA (US)

(73) Assignee: Aeovian Pharmaceuticals, Inc., Berkeley, CA (US)

( * ) Notice: Subject to any disclaimer, the term of this patent is extended or adjusted under 35 U.S.C. 154(b) by 0 days.

(21) Appl. No.: 17/832,240

(22) Filed: Jun. 3, 2022

(65) Prior Publication Data
US 2022/0332727 A1 Oct. 20, 2022

Related U.S. Application Data

(63) Continuation of application No. 17/683,549, filed on Mar. 1, 2022, which is a continuation of application No. PCT/US2021/024536, filed on Mar. 26, 2021.

(60) Provisional application No. 63/054,762, filed on Jul. 21, 2020, provisional application No. 63/054,763, filed on Jul. 21, 2020, provisional application No. 63/054,768, filed on Jul. 21, 2020, provisional application No. 63/019,176, filed on May 1, 2020, provisional application No. 63/001,144, filed on Mar. 27, 2020, provisional application No. 63/001,187, filed on Mar. 27, 2020, provisional application No. 63/001,177, filed on Mar. 27, 2020.

(51) Int. Cl.
*C07D 498/18* (2006.01)

(52) U.S. Cl.
CPC .................. *C07D 498/18* (2013.01)

(58) Field of Classification Search
CPC ........................ C07D 498/18; A61K 31/436
USPC .......................................... 540/456; 514/291
See application file for complete search history.

(56) References Cited

U.S. PATENT DOCUMENTS

| | | | |
|---|---|---|---|
| 10,683,308 B2 | 6/2020 | Saiah et al. | |
| 11,021,492 B2 | 6/2021 | Tzannis et al. | |
| 11,230,557 B2 | 1/2022 | Tzannis et al. | |
| 2016/0138027 A1 | 5/2016 | Gan et al. | |
| 2017/0246305 A1 | 8/2017 | Shokat et al. | |
| 2018/0338918 A1 | 11/2018 | Wang et al. | |
| 2019/0388401 A1 | 12/2019 | Saiah et al. | |
| 2021/0186935 A1 | 6/2021 | O'Neill et al. | |

FOREIGN PATENT DOCUMENTS

| | | |
|---|---|---|
| EP | 3345601 A1 | 7/2018 |
| EP | 3119425 B1 | 9/2020 |
| WO | WO-9402136 A1 | 2/1994 |
| WO | WO-9516691 A1 | 6/1995 |
| WO | WO-0114387 A1 | 3/2001 |
| WO | WO-2006136175 A2 | 12/2006 |
| WO | WO-2007085400 A1 | 8/2007 |
| WO | WO-2009131631 A1 | 10/2009 |
| WO | WO-2017044720 A1 | 3/2017 |
| WO | WO-2019064182 A1 | 4/2019 |
| WO | WO-2019241789 A1 | 12/2019 |
| WO | WO-2020076738 A2 | 4/2020 |
| WO | WO-2020128861 A1 | 6/2020 |
| WO | WO-2020154447 A1 | 7/2020 |
| WO | WO-2021113665 A1 | 6/2021 |
| WO | WO-2021195599 A1 | 9/2021 |
| WO | WO-2022020522 A2 | 1/2022 |
| WO | WO-2022159976 A1 | 7/2022 |

OTHER PUBLICATIONS

Abdel-Magid, Ahmed F. et al. Rapalogs Potential as Practical Alternatives to Rapamycin. ACS medicinal chemistry letters vol. 10,6 (2019): 843-845.

Bermejo, et al. PAMPA—a drug absorption in vitro model: 7. Comparing rat in situ, Caco-2, and PAMPA permeability of fluoroquinolones. European Journal of Pharmaceutical Sciences 21.4 (2004): 429-441.

(Continued)

*Primary Examiner* — Jeffrey H Murray

(74) *Attorney, Agent, or Firm* — Wilson Sonsini Goodrich & Rosati

(57) ABSTRACT

The disclosure provides compounds and salts that show high selectivity and inhibitory activity for mTORC1 and uses thereof for the treatment of disease, such as Formula X:

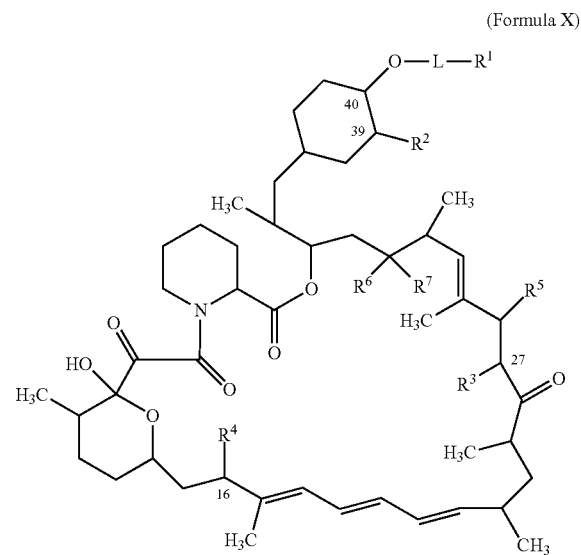

(Formula X)

or a pharmaceutically acceptable salt thereof.

29 Claims, No Drawings

(56) References Cited

OTHER PUBLICATIONS

Butler, Mark S. et al. Natural product and natural product derived drugs in clinical trials. Natural product reports vol. 31,11 (2014): 1612-61.
Co-pending U.S. Appl. No. 17/553,409, inventors Tzannis; Stelios T. et al., filed Dec. 16, 2021.
Co-pending U.S. Appl. No. 17/326,633, inventors Tzannis; Stelios T. et al., filed May 21, 2021.
Co-pending U.S. Appl. No. 17/683,549, inventor Kincaid; John, filed Mar. 1, 2022.
Grinfeld et al. Acid Catalyzed Functionalization of Rapamycin. Tetrahedron Letters, Sep. 12, 1994, 35(37):6835-6838.
National Center for Biotechnology Information. PubChem Compound Summary for CID 124148479. Created Date: Feb. 18, 2017. Available at https://pubchem.ncbi.nlm.nih.gov/compound/124148479. Accessed Nov. 13, 2020.
National Center for Biotechnology Information. PubChem Compound Summary for CID 59032415. Created Date: Aug. 19, 2012. Available at https://pubchem.ncbi.nlm.nih.gov/compound/59032415. Accessed Nov. 13, 2020.
PCT/US2020/014671 International Search Report and Written Opinion dated May 19, 2020.
PCT/US2021/042644 International Search Report and Written Opinion dated Jan. 19, 2022.
PCT/US2021/024536 International Search Report and Written Opinion dated Jun. 9, 2021.
U.S. Appl. No. 17/024,470 Notice of Allowance dated Feb. 18, 2021.
U.S. Appl. No. 17/024,470 Notice of Allowance dated Jan. 27, 2021.
U.S. Appl. No. 17/024,470 Office Action dated Nov. 4, 2020.
U.S. Appl. No. 17/024,486 Final Office Action dated Mar. 4, 2021.
U.S. Appl. No. 17/024,486 Notice of Allowance dated Sep. 15, 2021.
U.S. Appl. No. 17/024,486 Office Action dated Jan. 13, 2021.
Wong, et al. Antifungal activities of rapamycin and its derivatives, prolylrapamycin, 32-desmethylrapamycin, and 32-desmethoxyrapamycin. The Journal of antibiotics 51.5 (1998): 487-491.
EP20745587 Extended European Search Report dated Jul. 22, 2022.
U.S. Appl. No. 17/326,633 Office Action dated Sep. 29, 2022.

MTORC1 MODULATORS AND USES THEREOF

CROSS-REFERENCE

This application is a continuation of U.S. application Ser. No. 17/683,549, filed on Mar. 1, 2022, which is a continuation of International Patent Application No. PCT/US2021/024536 filed Mar. 26, 2021, which claims the benefit of U.S. Provisional Patent Applications Nos. 63/001,187 filed on Mar. 27, 2020; 63/001,144 filed on Mar. 27, 2020; 63/001,177 filed on Mar. 27, 2020; 63/019,176 filed on May 1, 2020; 63/054,763 filed on Jul. 21, 2020; 63/054,762 filed on Jul. 21, 2020; and 63/054,768 filed Jul. 21, 2020; each of which is incorporated herein by reference in its entirety.

BACKGROUND OF THE INVENTION

The therapeutic potential of rapamycin has been established in many chronic diseases, from Alzheimer's and Parkinson's disease to diabetes and cardiovascular disease. However, the prohibitive safety profile of rapamycin for chronic treatment has limited its use for the treatment of various diseases. Rapamycin, an FDA approved compound, inhibits mTOR signaling, leading to extension of lifespan in a number of species, yet it can induce adverse effects, such as peripheral edema, hypercholesterolemia, mucosal ulcerations, abdominal pain, headache, nausea, diarrhea, pain, constipation, hypertriglyceridemia, hypertension, increased creatinine, fever, urinary tract infection, anemia, arthralgia, and thrombocytopenia. Given the complications associated with rapamycin, new agents are needed.

SUMMARY OF THE INVENTION

In a first aspect, the present disclosure provides a compound represented by the structure of Formula I:

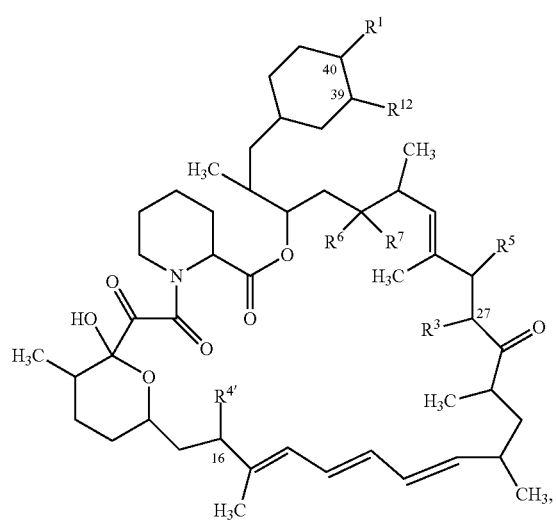

(I)

or a pharmaceutically acceptable salt thereof, wherein:
$R^1$ is selected from —OH, 3- to 10-membered heterocycle, and $C_{3-10}$ carbocycle, wherein the 3- to 10-membered heterocycle and $C_{3-10}$ carbocycle are each optionally substituted with one or more substituents independently selected from: hydroxy, halogen, —CN, —NO$_2$, =O, $C_1$-$C_6$ alkyl, $C_1$-$C_6$ haloalkyl, $C_1$-$C_6$ hydroxyalkyl, $C_1$-$C_6$ alkoxy, $C_1$-$C_6$ alkoxy, 3- to 10-membered heterocycle, and $C_{3-10}$ carbocycle, wherein the 3- to 10-membered heterocycle and $C_{3-10}$ carbocycle are each optionally substituted with one or more substituents independently selected from hydroxy, halogen, —CN, —NO$_2$, $C_1$-$C_6$ alkyl, $C_1$-$C_6$ haloalkyl, $C_1$-$C_6$ hydroxyalkyl, and $C_1$-$C_6$ alkoxy;

$R^2$ is selected from hydrogen and an optionally substituted $C_1$-$C_6$ alkoxy, wherein substituents are independently selected at each occurrence from hydroxy, halogen, —CN, —NO$_2$, $C_1$-$C_6$ alkoxy, 3- to 10-membered heterocycle, and $C_{3-10}$ carbocycle, wherein the 3- to 10-membered heterocycle and $C_{3-10}$ carbocycle are each optionally substituted with one or more substituents independently selected from hydroxy, halogen, —CN, —NO$_2$, $C_1$-$C_6$ alkyl, $C_1$-$C_6$ haloalkyl, $C_1$-$C_6$ hydroxyalkyl, and $C_1$-$C_6$ alkoxy;

$R^3$ is selected from hydrogen and an optionally substituted $C_1$-$C_6$ alkoxy, wherein the substituents are independently selected at each occurrence from hydroxy, halogen, —CN, —NO$_2$, $C_1$-$C_6$ alkoxy, 3- to 10-membered heterocycle, and $C_{3-10}$ carbocycle, wherein the 3- to 10-membered heterocycle and $C_{3-10}$ carbocycle, are each optionally substituted with one or more substituents independently selected from hydroxy, halogen, —CN, —NO$_2$, $C_1$-$C_6$ alkyl, $C_1$-$C_6$ haloalkyl, $C_1$-$C_6$ hydroxyalkyl, and $C_1$-$C_6$ alkoxy; and $R^{4'}$ is selected from, $R^5$ is selected from hydrogen, hydroxy, and an optionally substituted $C_1$-$C_6$ alkoxy, wherein substituents are independently selected at each occurrence from hydroxy, halogen, —CN, —NO$_2$, $C_1$-$C_6$ alkoxy, 3- to 10-membered heterocycle, and $C_{3-10}$ carbocycle, wherein the 3- to 10-membered heterocycle, and $C_{3-10}$ carbocycle are each optionally substituted with one or more substituents independently selected from hydroxy, halogen, —CN, —NO$_2$, $C_1$-$C_6$ alkyl, $C_1$-$C_6$ haloalkyl, $C_1$-$C_6$ hydroxyalkyl, and $C_1$-$C_6$ alkoxy;

$R^6$ and $R^7$ are each independently selected from hydrogen, hydroxy, and $C_1$-$C_6$ alkoxy; or $R^6$ and $R^7$ come together to form $R^{20}$ is selected from hydrogen and optionally substituted $C_1$-$C_6$ alkyl;

$R^{21}$ is selected from optionally substituted $C_1$-$C_6$ alkyl, optionally substituted 3- to 10-membered heterocycle, and optionally substituted $C_{3-10}$ carbocycle;

$R^{22}$ is selected from optionally substituted $C_1$-$C_6$ alkyl, optionally substituted 3- to 10-membered heterocycle, and optionally substituted $C_{3-10}$ carbocycle, and —P(=O)($R^{24}$)$_2$;

$R^{23}$ is selected from optionally substituted $C_1$-$C_6$ alkyl, optionally substituted 3- to 10-membered heterocycle, and optionally substituted $C_{3-10}$ carbocycle;

$R^{24}$ is optionally substituted $C_1$-$C_6$ alkyl;

$R^{100}$ is selected from:
hydrogen and —(CH$_2$—CH$_2$-G)$_y$-V; and
$C_{1-10}$ alkyl, $C_{2-10}$ alkenyl, $C_{2-10}$ alkynyl, wherein each of which is optionally substituted with one or more substituents independently selected from halogen, —OR$^{31}$, —SR$^{31}$, —N(R$^{31}$)$_2$, —C(O)R$^{31}$, —C(O)N(R$^{31}$)$_2$, —N(R$^{31}$)C(O)R$^{31}$, —C(O)OR$^{31}$, —OC(O)R$^{31}$, —S(O)R$^{31}$, —S(O)$_2$R$^{31}$, —P(O)(OR$^{31}$)$_2$, —OP(O)(OR$^{31}$)$_2$, —NO$_2$, —CN, $C_{3-20}$ carbocycle and 3- to 20-membered heterocycle; and
$C_{3-20}$ carbocycle and 3- to 20-membered heterocycle each of which is optionally substituted with one or more substituents independently selected from halogen, —OR$^{31}$, —SR$^{31}$, —N(R$^{31}$)$_2$, —C(O)R$^{31}$, —C(O)N(R$^{31}$)$_2$, —N(R$^{31}$)C(O)R$^{31}$, —C(O)OR$^{31}$, —OC(O)R$^{31}$, —S(O)R$^{31}$, —S(O)$_2$R$^{31}$, —P(O)(OR$^{31}$)$_2$, —OP(O)(OR$^{31}$)$_2$, —NO$_2$, =O, =S, =N(R$^{31}$), —CN, $C_{1-6}$ alkyl, $C_{1-6}$ alkyl-R$^{31}$, $C_{2-6}$ alkenyl, and $C_{2-6}$ alkynyl;

$R^{110'}$ is selected from:
hydrogen, —(CH$_2$—CH$_2$-G)$_y$-V, —S(O)R$^{51'}$, —S(O)$_2$R$^{51'}$, —C(O)R$^{51'}$, —C(O)N(R$^{51'}$)$_2$, and —C(O)OR$^{51'}$; and
$C_{1-10}$ alkyl, $C_{2-10}$ alkenyl, $C_{2-10}$ alkynyl, wherein each of which is optionally substituted with one or more substituents independently selected from halogen, —OR$^{31}$, —SR$^{31}$, —N(R$^{31}$)$_2$, —C(O)R$^{31}$, —C(O)N(R$^{31}$)$_2$, —N(R$^{31}$)C(O)R$^{31}$, —C(O)OR$^{31}$, —OC(O)R$^{31}$, —S(O)R$^{31}$, —S(O)$_2$R$^{31}$, —P(O)(OR$^{31}$)$_2$, —OP(O)(OR$^{31}$)$_2$, —NO$_2$, —CN, $C_{3-20}$ carbocycle and 3- to 20-membered heterocycle; and
$C_{3-20}$ carbocycle and 3- to 20-membered heterocycle each of which is optionally substituted with one or more substituents independently selected from halogen, —OR$^{31}$, —SR$^{31}$, —N(R$^{31}$)$_2$, —C(O)R$^{31}$, —C(O)N(R$^{31}$)$_2$, —N(R$^{31}$)C(O)R$^{31}$, —C(O)OR$^{31}$, —OC(O)R$^{31}$, —S(O)R$^{31}$, —S(O)$_2$R$^{31}$, —P(O)(OR$^{31}$)$_2$, —OP(O)(OR$^{31}$)$_2$, —NO$_2$, =O, =S, =N(R$^{31}$), —CN, $C_{1-6}$ alkyl, $C_{1-6}$ alkyl-R$^{31}$, $C_{2-6}$ alkenyl, and $C_{2-6}$ alkynyl; or $R^{100}$ and $R^{110'}$ together with the nitrogen to which they are bound form a 3-10-membered heterocycle optionally substituted with one or more substituents independently selected from: hydroxy, halogen, —CN, —NO$_2$, $C_1$-$C_6$ alkyl, $C_1$-$C_6$ haloalkyl, $C_1$-$C_6$ hydroxyalkyl, and $C_1$-$C_6$ alkoxy, wherein when R$^1$ is hydroxy, the ring formed by $R^{100}$ and $R^{110}$ is not unsubstituted morpholine, and wherein when one of R$^6$ and R$^7$ are selected from hydroxy and $C_1$-$C_6$ alkoxy or when R$^6$ and R$^7$ come together to form

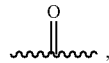, the 3-10-membered heterocycle formed by $R^{100}$ and $R^{110}$ is further optionally substituted with one or more =O;

$R^{120}$ is selected from:
hydrogen, —(CH$_2$—CH$_2$-G)$_y$-V; and
$C_{3-10}$ alkyl, $C_{2-10}$ alkenyl, $C_{2-10}$ alkynyl, each of which is optionally substituted with one or more substituents independently selected from halogen, —OR$^{31}$, —SR$^{31}$, —N(R$^{31}$)$_2$, —C(O)R$^{31}$, —C(O)N(R$^{31}$)$_2$, —N(R$^{31}$)C(O)R$^{31}$, —C(O)OR$^{31}$, —OC(O)R$^{31}$, —S(O)R$^{31}$, —S(O)$_2$R$^{31}$, —P(O)(OR$^{31}$)$_2$, —OP(O)(OR$^{31}$)$_2$, —NO$_2$, —CN, $C_{3-20}$ carbocycle, and 3- to 20-membered heterocycle;
$C_{3-20}$ saturated carbocycle and 3- to 20-membered heterocycle each of which is optionally substituted with one or more substituents independently selected from halogen, —OR$^{31}$, —SR$^{31}$, —N(R$^{31}$)$_2$, —C(O)R$^{31}$, —C(O)N(R$^{31}$)$_2$, —N(R$^{31}$)C(O)R$^{31}$, —C(O)OR$^{31}$, —OC(O)R$^{31}$, —S(O)R$^{31}$, —S(O)$_2$R$^{31}$, —P(O)(OR$^{31}$)$_2$, —OP(O)(OR$^{31}$)$_2$, —NO$_2$, =O, =S, =N(R$^{31}$), —CN, $C_{1-6}$ alkyl, $C_{1-6}$ alkyl-R$^{31}$, $C_{2-6}$ alkenyl, and $C_{2-6}$ alkynyl; or
$C_{1-2}$ alkyl substituted with one or more substituents independently selected from halogen, —OR$^{31}$, —N(R$^{31}$)$_2$, —C(O)R$^{31}$, —C(O)N(R$^{31}$)$_2$, —N(R$^{31}$)C(O)R$^{31}$, —C(O)OR$^{31}$, —OC(O)R$^{31}$, —S(O)R$^{31}$, —S(O)$_2$R$^{31}$, —P(O)(OR$^{31}$)$_2$, —OP(O)(OR$^{31}$)$_2$, —NO$_2$, —CN, $C_{3-20}$ carbocycle and 3- to 20-membered heterocycle;

each G is independently selected from —O—, —NR$^{32}$—, —S—, or —SO$_2$—;
each D is independently selected from —O—, —NR$^{32}$—, —S—, or —SO$_2$—;
each y is selected from 3-20;
each z is selected from 1-20;
each V is selected from hydrogen and optionally substituted —$C_1$-$C_6$ alkyl;
each T is selected from hydrogen and optionally substituted —$C_1$-$C_6$ alkyl;
each $R^{31}$ is independently selected from hydrogen, and $C_{1-10}$ alkyl, $C_{2-10}$ alkenyl, $C_{2-10}$ alkynyl, $C_{3-10}$ carbocycle, and 3- to 10-membered heterocycle, each of which is optionally substituted with one or more substituents independently selected from halogen, —OH, —CN, —NO$_2$, —NH$_2$, =O, =S, $C_{1-10}$ alkyl, —$C_{1-10}$ haloalkyl, —O—$C_{1-10}$ alkyl, $C_{2-10}$ alkenyl, $C_{2-10}$ alkynyl, $C_{3-10}$ carbocycle, and 3- to 10-membered heterocycle; and
$R^{32}$ is independently selected at each occurrence from:
hydrogen; and $C_{1-10}$ alkyl, $C_{2-10}$ alkenyl, $C_{2-10}$ alkynyl, $C_{3-10}$ carbocycle, and 3- to 10-membered heterocycle, each of which is optionally substituted with one or more substituents independently selected from halogen, —OH, —CN, —NO$_2$, —NH$_2$, =O, =S, $C_{1-10}$ alkyl, —$C_{1-10}$ haloalkyl, —O—$C_{1-10}$ alkyl, $C_{2-10}$ alkenyl, $C_{2-10}$ alkynyl, $C_{3-10}$ carbocycle, and 3- to 10-membered heterocycle;
wherein the optional substituents on $R^{20}$, $R^{21}$, $R^{22}$, $R^{23}$, $R^{24}$, $R^{51'}$, V, and T are independently selected at each occurrence from:
halogen, —OR$^{30}$, —N(R$^{30}$)$_2$, —(O—CH$_2$—(CH$_2$)$_p$)$_n$—W, —SR$^{30}$, —C(O)R$^{30}$, —C(O)N(R$^{30}$)$_2$, —N(R$^{30}$)C(O)R$^{30}$, —C(O)OR$^{30}$, —OC(O)R$^{30}$, —S(O)R$^{30}$, —S(O)$_2$R$^{30}$, —P(O)(OR$^{30}$)$_2$, —OP(O)(OR$^{30}$)$_2$, —NO$_2$, =O, =S, =N(R$^{30}$), and —CN;
$C_{1-10}$ alkyl, $C_{2-10}$ alkenyl, $C_{2-10}$ alkynyl, each of which is optionally substituted with one or more substituents independently selected from halogen, —OR$^{30}$, —SR$^{30}$, —N(R$^{30}$)$_2$, —C(O)R$^{30}$, —C(O)N(R$^{30}$)$_2$, —N(R$^{30}$)C(O)R$^{30}$, —C(O)OR$^{30}$, —OC(O)R$^{30}$, —S(O)R$^{30}$, —S(O)$_2$R$^{30}$, —P(O)(OR$^{30}$)$_2$, —OP(O)(OR$^{30}$)$_2$, —NO$_2$, =O, =S, =N(R$^{30}$), —CN, C$_{3-10}$ carbocycle and 3- to 10-membered heterocycle; and C$_{3-10}$ carbocycle and 3- to 10-membered heterocycle each of which is optionally substituted with one or more substituents independently selected from halogen, —OR$^{30}$, —SR$^{30}$, —N(R$^{30}$)$_2$, —C(O)R$^{30}$, —C(O)N(R$^{30}$)$_2$, —N(R$^{30}$)C(O)R$^{30}$, —C(O)OR$^{30}$, —OC(O)R$^{30}$, —S(O)R$^{30}$, —S(O)$_2$R$^{30}$, —P(O)(OR$^{30}$)$_2$, —OP(O)(OR$^{30}$)$_2$, —NO$_2$, =O, =S, =N(R$^{30}$), —CN, C$_{1-6}$ alkyl, C$_{1-6}$ alkyl-R$^{30}$, C$_{2-6}$ alkenyl, and C$_{2-6}$ alkynyl;

R$^{30}$ is independently selected at each occurrence from hydrogen; C$_{1-10}$ alkyl, C$_{2-10}$ alkenyl, C$_{2-10}$ alkynyl, C$_{3-10}$ carbocycle, and 3- to 10-membered heterocycle, each of which is optionally substituted with one or more substituents independently selected from halogen, —OH, —CN, —NO$_2$, —NH$_2$, =O, =S, C$_{1-10}$ alkyl, —C$_{1-10}$ haloalkyl, —O—C$_{1-10}$ alkyl, C$_{2-10}$ alkenyl, C$_{2-10}$ alkynyl, C$_{3-10}$ carbocycle, and 3- to 10-membered heterocycle;

R$^{51'}$ is independently selected at each occurrence from substituted C$_{1-4}$ alkyl, optionally substituted C$_{3-8}$ carbocycle, optionally substituted 3-10 membered heterocycle, —((CH$_2$)$_q$—CH$_2$-D)$_z$-T and optionally substituted C$_{5-30}$ alkyl;

q is selected from 1 to 6;

each p is selected from 1 or 2;

each n is selected from 3-7; and each W is selected from hydrogen, —OH, —C$_1$-C$_4$ alkyl and —O(C$_1$-C$_4$ alkyl).

In certain embodiments, the disclosure provides a method of treating disease comprising chronically administering a compound or salt of Formula (I), (IA), (IB), (IC), (ID), (IE), (IF), or (IG), to a subject in need thereof.

In certain embodiments, the disclosure provides a method of treating disease, wherein the disease is selected from a chronic disease. The chronic disease may be selected from a disease wherein mTORC1 is hyperactivated. The chronic disease may be selected from a disease wherein the the chronic disease would benefit from mTORC1 inhibition. In certain embodiments, the chronic disease may be selected from neurodegenerative disease, a neurocutaneous disease, a neurodevelopmental disorder, mTORopathies, tauopathies, cognitive disorders, epilepsies, autism spectrum disorders, autoimmune diseases, metabolic diseases, cancer, diseases of impaired autophagy, infectious diseases, cardiovascular diseases, muscular atrophy, inflammatory diseases, kidney diseases, pulmonary diseases, eye disorders or diseases of aging that result in hyperactivation of mTORC1 including reduced immune activity in the elderly. The chronic disease may be an mTORopathy, e.g., Tuberous Sclerosis.

In certain embodiments, the disclosure provides a method of treating a disease, wherein the compound may be a compound or salt of Formula (I), (IA), (IB), (IC), (ID), (IE), (IF), or (IG).

In a second aspect, the present disclosure provides a compound represented by the structure of Formula (X):

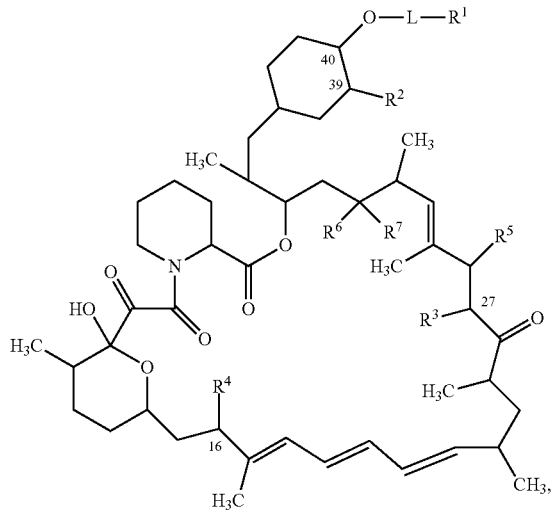

(X)

or a pharmaceutically acceptable salt thereof, wherein:

L is selected from optionally substituted C$_{1-8}$ alkylene;

R$^1$ is a carboxylic acid or a carboxylic acid isostere;

R$^2$ is selected from hydrogen and an optionally substituted C$_1$-C$_6$ alkoxy group, wherein substituents are independently selected at each occurrence from hydroxy, halogen, —CN, —NO$_2$, C$_1$-C$_6$ alkoxy, 3- to 10-membered heterocycle, and C$_{3-10}$ carbocycle, wherein the 3- to 10-membered heterocycle and C$_{3-10}$ carbocycle are each optionally substituted with one or more substituents independently selected from hydroxy, halogen, —CN, —NO$_2$, C$_1$-C$_6$ alkyl, C$_1$-C$_6$ haloalkyl, C$_1$-C$_6$ hydroxyalkyl, C$_1$-C$_6$ alkoxy, and C$_1$-C$_6$ alkoxy C$_1$-C$_6$ alkyl;

R$^3$ is selected from hydrogen and an optionally substituted C$_1$-C$_6$ alkoxy group, wherein the substituents are independently selected at each occurrence from hydroxy, halogen, —CN, —NO$_2$, C$_1$-C$_6$ alkoxy group, 3- to 10-membered heterocycle, and C$_{3-10}$ carbocycle, wherein the 3- to 10-membered heterocycle and C$_{3-10}$ carbocycle, are each optionally substituted with one or more substituents independently selected from hydroxy, halogen, —CN, —NO$_2$, C$_1$-C$_6$ alkyl, C$_1$-C$_6$ haloalkyl, C$_1$-C$_6$ hydroxyalkyl, C$_1$-C$_6$ alkoxy, and C$_1$-C$_6$ alkoxy C$_1$-C$_6$ alkyl; and R$^4$ is selected from

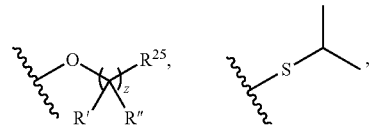

and optionally substituted 3- to 10-membered heterocycle, and when L is optionally substituted C$_{3-8}$ alkylene R$^4$ is further selected from methoxy; and when -L-R$^1$ is ethyl acetate, tert-butyl acetate, benzyl acetate, or methyl 2-phenylacetate, R$^4$ is not methoxy;

wherein the optionally substituted heterocycle of R$^4$ may be substituted with one or more substituents selected from: hydroxy, halogen, —CN, —NO$_2$, C$_1$-C$_6$ alkyl, C$_1$-C$_6$ haloalkyl, =O, C$_1$-C$_6$ hydroxyalkyl, C$_1$-C$_6$ alkoxy, and C$_1$-C$_6$ alkoxy C$_1$-C$_6$ alkyl;

z is 0, 1, 2, 3, 4 or 5;

$R^5$ is selected from hydrogen, hydroxy, and an optionally substituted $C_1$-$C_6$ alkoxy group, wherein substituents are independently selected at each occurrence from hydroxy, halogen, —CN, —NO$_2$, $C_1$-$C_6$ alkoxy group, 3- to 10-membered heterocycle, and $C_{3-10}$ carbocycle, wherein the 3- to 10-membered heterocycle, and $C_{3-10}$ carbocycle are each optionally substituted with one or more substituents independently selected from hydroxy, halogen, —CN, —NO$_2$, $C_1$-$C_6$ alkyl, $C_1$-$C_6$ haloalkyl, $C_1$-$C_6$ hydroxyalkyl, $C_1$-$C_6$ alkoxy, and $C_1$-$C_6$ alkoxy $C_1$-$C_6$ alkyl;

$R^6$ and $R^7$ are each independently selected from hydrogen, hydroxy, and $C_1$-$C_6$ alkoxy; or $R^6$ and $R^7$ come together to form

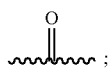;

$R^{25}$ is independently selected at each occurrence from hydrogen, optionally substituted $C_1$-$C_6$ alkyl, -D-(CH$_2$—CH$_2$-G)$_y$-V, optionally substituted $C_{3-20}$ carbocycle, and optionally substituted 3- to 20-membered heterocycle;

wherein when $R^{25}$ is optionally substituted $C_1$-$C_6$ alkyl, the substituents on $C_1$-$C_6$ alkyl are independently selected at each occurrence from halogen, —OH, —CN, —NO$_2$, —NH$_2$, =O, =S, —C(O)N(R$^{31}$)$_2$, —OC(O)N(R$^{31}$)$_2$, —C(O)OR$^{31}$, —P(O)(R$^{31}$)$_2$, —$C_{1-10}$ haloalkyl, —O—$C_{1-10}$ alkyl, —O—$C_{1-10}$ alkyl-CN, —O—$C_{1-10}$ alkyl-C(O)OR$^{31}$, $C_{2-10}$ alkenyl, $C_{2-10}$ alkynyl, $C_{3-20}$ carbocycle, and 3- to 20-membered heterocycle;

wherein when $R^{25}$ is optionally substituted $C_{3-20}$ carbocycle or optionally substituted 3- to 20-membered heterocycle, the substituents on $C_{3-20}$ carbocycle and 3- to 20-membered heterocycle are independently selected at each occurrence from halogen, —OR$^{31}$, —SR$^{31}$, —N(R$^{31}$)$_2$, —C(O)R$^{31}$, —C(O)N(R$^{31}$)$_2$, —N(R$^{31}$)C(O)R$^{31}$, —C(O)OR$^{31}$, —OC(O)R$^{31}$, —S(O)R$^{31}$, —S(O)$_2$R$^{31}$, —P(O)(OR$^{31}$)$_2$, —OP(O)(OR$^{31}$)$_2$, —NO$_2$, =O, =S, =N(R$^{31}$), —CN, $C_{1-6}$ alkyl, $C_{1-6}$ haloalkyl, $C_{2-6}$ alkenyl, and $C_{2-6}$ alkynyl;

wherein D is selected from a bond or —O—;

each G is independently selected from —O—, —NR$^{32}$—, —S—, or —SO$_2$—;

each y is selected from 1-20;

each V is selected from hydrogen and optionally substituted —$C_1$-$C_6$ alkyl;

$R^{30}$ is independently selected at each occurrence from hydrogen; $C_{1-10}$ alkyl, $C_{2-10}$ alkenyl, $C_{2-10}$ alkynyl, $C_{3-10}$ carbocycle, and 3- to 10-membered heterocycle, each of which is optionally substituted with one or more substituents independently selected from halogen, —OH, —OSi($C_1$-$C_6$ alkyl)$_3$, —CN, —NO$_2$, —NH$_2$, =O, =S, $C_{1-10}$ alkyl, —$C_{1-10}$ haloalkyl, —O—$C_{1-10}$ alkyl, $C_{2-10}$ alkenyl, $C_{2-10}$ alkynyl, $C_{3-10}$ carbocycle, and 3- to 10-membered heterocycle;

R' and R" are independently selected at each occurrence from hydrogen, halogen, —OR$^{31}$, and $C_{1-8}$ alkyl optionally substituted with one or more substituents independently selected from halogen and —OR$^{31}$; and $R^{31}$ is independently selected at each occurrence from hydrogen; and $C_{1-10}$ alkyl, $C_{2-10}$ alkenyl, $C_{2-10}$ alkynyl, $C_{3-12}$ carbocycle, and 3- to 12-membered heterocycle, each of which is optionally substituted with one or more substituents independently selected from halogen, —OH, —OSi($C_1$-$C_6$ alkyl)$_3$, —CN, —NO$_2$, —NH$_2$, =O, =S, $C_{1-10}$ alkyl, —$C_{1-10}$ haloalkyl, —O—$C_{1-10}$ alkyl, —O—$C_{1-10}$ alkyl-OH, $C_{2-10}$ alkenyl, $C_{2-10}$ alkynyl, $C_{3-12}$ carbocycle, and 3- to 12-membered heterocycle.

$R^{32}$ is independently selected at each occurrence from: hydrogen; and $C_{1-10}$ alkyl, $C_{2-10}$ alkenyl, $C_{2-10}$ alkynyl, $C_{3-10}$ carbocycle, and 3- to 10-membered heterocycle, each of which is optionally substituted with one or more substituents independently selected from halogen, —OH, —CN, —NO$_2$, —NH$_2$, =O, =S, $C_{1-10}$ alkyl, —$C_{1-10}$ haloalkyl, —O—$C_{1-10}$ alkyl, $C_{2-10}$ alkenyl, $C_{2-10}$ alkynyl, $C_{3-10}$ carbocycle, and 3- to 10-membered heterocycle; and wherein the substituents on V and L are independently selected at each occurrence from:

halogen, —OR$^{30}$, —N(R$^{30}$)$_2$, —SR$^{30}$, —C(O)R$^{30}$, —C(O)N(R$^{30}$)$_2$, —N(R$^{30}$)C(O)R$^{30}$, —C(O)OR$^{30}$, —OC(O)R$^{30}$, —S(O)R$^{30}$, —S(O)$_2$R$^{30}$, —P(O)(OR$^{30}$)$_2$, —OP(O)(OR$^{30}$)$_2$, —NO$_2$, =O, =S, =N(R$^{30}$), and —CN;

$C_{1-10}$ alkyl, $C_{2-10}$ alkenyl, $C_{2-10}$ alkynyl, each of which is optionally substituted with one or more substituents independently selected from halogen, —OR$^{30}$, —SR$^{30}$, —N(R$^{30}$)$_2$, —C(O)R$^{30}$, —C(O)N(R$^{30}$)$_2$, —N(R$^{30}$)C(O)R$^{30}$, —C(O)OR$^{30}$, —OC(O)R$^{30}$, —S(O)R$^{30}$, —S(O)$_2$R$^{30}$, —P(O)(OR$^{30}$)$_2$, —OP(O)(OR$^{30}$)$_2$, —NO$_2$, =O, =S, =N(R$^{30}$), —CN, $C_{3-10}$ carbocycle and 3- to 10-membered heterocycle; and $C_{3-10}$ carbocycle and 3- to 10-membered heterocycle each of which is optionally substituted with one or more substituents independently selected from halogen, —OR$^{30}$, —SR$^{30}$, —N(R$^{30}$)$_2$, —C(O)R$^{30}$, —C(O)N(R$^{30}$)$_2$, —N(R$^{30}$)C(O)R$^{30}$, —C(O)OR$^{30}$, —OC(O)R$^{30}$, —S(O)R$^{30}$, —S(O)$_2$R$^{30}$, —P(O)(OR$^{30}$)$_2$, —OP(O)(OR$^{30}$)$_2$, —NO$_2$, =O, =S, =N(R$^{30}$), —CN, $C_{1-6}$ alkyl, $C_{1-6}$ alkyl-R$^{30}$, $C_{2-6}$ alkenyl, and $C_{2-6}$ alkynyl;

In certain embodiments, the disclosure provides a method of treating disease comprising administering, e.g., chronically administering, a compound or salt of Formula (X), (XA), (XB), (XC), (XD), (XE), (XF), or (XG), to a subject in need thereof.

In certain embodiments, the disclosure provides a method of treating disease, wherein the disease is selected from a chronic disease. The chronic disease may be selected from a disease wherein mTORC1 is hyperactivated. The chronic disease may be selected from a disease wherein the the chronic disease would benefit from mTORC1 inhibition. In certain embodiments, the chronic disease may be selected from neurodegenerative disease, a neurocutaneous disease, a neurodevelopmental disorder, mTORopathies, tauopathies, cognitive disorders, epilepsies, autism spectrum disorders, autoimmune diseases, metabolic diseases, cancer, diseases of impaired autophagy, infectious diseases, cardiovascular diseases, muscular atrophy, inflammatory diseases, kidney diseases, pulmonary diseases, eye disorders or diseases of aging that result in hyperactivation of mTORC1 including reduced immune activity in the elderly. The chronic disease may be an mTORopathy, e.g., Tuberous Sclerosis.

In certain embodiments, the disclosure provides a method of treating a disease, wherein the compound may be a compound or salt of Formula (X), (XA), (XB), (XC), (XD), (XE), (XF), or (XG).

In a third aspect, the present disclosure provides a compound represented by the structure of Formula L:

(L)

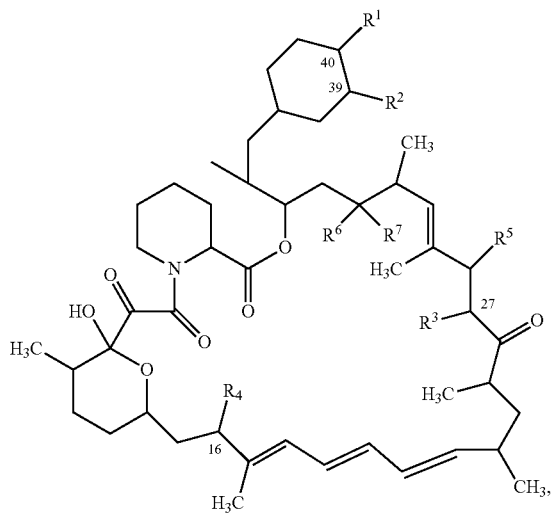

or a pharmaceutically acceptable salt thereof, wherein:

R¹ is selected from

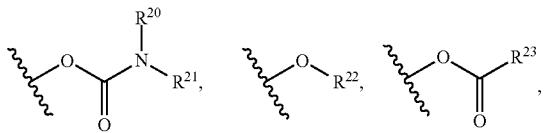

3- to 10-membered heterocycle, and $C_{3-10}$ carbocycle, wherein the 3- to 10-membered heterocycle and $C_{3-10}$ carbocycle are each optionally substituted with one or more substituents independently selected from $R^{33}$;

R² is selected from hydrogen and an optionally substituted $C_1$-$C_6$ alkoxy group, wherein substituents are independently selected at each occurrence from hydroxy, halogen, —CN, —NO$_2$, $C_1$-$C_6$ alkoxy, 3- to 10-membered heterocycle, and $C_{3-10}$ carbocycle, wherein the 3- to 10-membered heterocycle and $C_{3-10}$ carbocycle are each optionally substituted with one or more substituents independently selected from hydroxy, halogen, —CN, —NO$_2$, $C_1$-$C_6$ alkyl, $C_1$-$C_6$ haloalkyl, $C_1$-$C_6$ hydroxyalkyl, $C_1$-$C_6$ alkoxy, and $C_1$-$C_6$ alkoxy $C_1$-$C_6$ alkyl;

R³ is selected from hydrogen and an optionally substituted $C_1$-$C_6$ alkoxy group, wherein the substituents are independently selected at each occurrence from hydroxy, halogen, —CN, —NO$_2$, $C_1$-$C_6$ alkoxy group, 3- to 10-membered heterocycle, and $C_{3-10}$ carbocycle, wherein the 3- to 10-membered heterocycle and $C_{3-10}$ carbocycle, are each optionally substituted with one or more substituents independently selected from hydroxy, halogen, —CN, —NO$_2$, $C_1$-$C_6$ alkyl, $C_1$-$C_6$ haloalkyl, $C_1$-$C_6$ hydroxyalkyl, $C_1$-$C_6$ alkoxy, and $C_1$-$C_6$ alkoxy $C_1$-$C_6$ alkyl; and R⁴ is

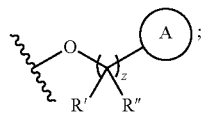

R⁵ is selected from hydrogen, hydroxy, and an optionally substituted $C_1$-$C_6$ alkoxy group, wherein substituents are independently selected at each occurrence from hydroxy, halogen, —CN, —NO$_2$, $C_1$-$C_6$ alkoxy group, 3- to 10-membered heterocycle, and $C_{3-10}$ carbocycle, wherein the 3- to 10-membered heterocycle, and $C_{3-10}$ carbocycle are each optionally substituted with one or more substituents independently selected from hydroxy, halogen, —CN, —NO$_2$, $C_1$-$C_6$ alkyl, $C_1$-$C_6$ haloalkyl, $C_1$-$C_6$ hydroxyalkyl, $C_1$-$C_6$ alkoxy, and $C_1$-$C_6$ alkoxy $C_1$-$C_6$ alkyl;

R⁶ and R⁷ are each independently selected from hydrogen, hydroxy, and $C_{1-6}$ alkoxy; or R⁶ and R⁷ come together to form

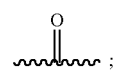

R²⁰ is selected from hydrogen and optionally substituted $C_1$-$C_6$ alkyl;

R²¹ is selected from optionally substituted $C_1$-$C_6$ alkyl, and optionally substituted 3 to 7-membered heterocycle;

R²² is selected from hydrogen, optionally substituted $C_1$-$C_6$ alkyl, —Si(R²⁴)$_3$, and —P(=O)(R²⁴)$_2$;

R²³ is selected from optionally substituted $C_1$-$C_6$ alkyl and optionally substituted 3 to 7-membered heterocycle;

R²⁴ is optionally substituted $C_1$-$C_6$ alkyl;

wherein the substituents on R²⁰, R²¹, R²², R²³, and R²⁴ are independently selected at each occurrence from:
halogen, —OR³⁰, —N(R³⁰)$_2$, —(O—CH$_2$—(CH$_2$)$_p$)$_n$—W, —SR³⁰, —N(R³⁰)$_2$, —C(O)R³⁰, —C(O)N(R³⁰)$_2$, —N(R³⁰)C(O)R³⁰, —C(O)OR³⁰, —OC(O)R³⁰, —S(O)R³⁰, —S(O)$_2$R³⁰, —P(O)(OR³⁰)$_2$, —OP(O)(OR³⁰)$_2$, —NO$_2$, =O, =S, =N(R³⁰), and —CN;

$C_{1-10}$ alkyl, $C_{2-10}$ alkenyl, $C_{2-10}$ alkynyl, each of which is optionally substituted with one or more substituents independently selected from halogen, —OR³⁰, —SR³⁰, —N(R³⁰)$_2$, —C(O)R³⁰, —C(O)N(R³⁰)$_2$, —N(R³⁰)C(O)R³⁰, —C(O)OR³⁰, —OC(O)R³⁰, —S(O)R³⁰, —S(O)$_2$R³⁰, —P(O)(OR³⁰)$_2$, —OP(O)(OR³⁰)$_2$, —NO$_2$, =O, =S, =N(R³⁰), —CN, $C_{3-10}$ carbocycle and 3- to 10-membered heterocycle; and $C_{3-10}$ carbocycle and 3- to 10-membered heterocycle each of which is optionally substituted with one or more substituents independently selected from halogen, —OR³⁰, —SR³⁰, —N(R³⁰)$_2$, —C(O)R³⁰, —C(O)N(R³⁰)$_2$, —N(R³⁰)C(O)R³⁰, —C(O)OR³⁰, —OC(O)R³⁰, —S(O)R³⁰, —S(O)$_2$R³⁰, —P(O)(OR³⁰)$_2$, —OP(O)(OR³⁰)$_2$, —NO$_2$, =O, =S, =N(R³⁰), —CN, $C_{1-6}$ alkyl, $C_{1-6}$ alkyl-R³⁰, $C_{2-6}$ alkenyl, and $C_{2-6}$ alkynyl;

each p is selected from 1 or 2;
each n is selected from 3 to 7;
each W is selected from hydrogen, —OH, —$C_1$-$C_4$ alkyl, and —O($C_1$-$C_4$ alkyl);

$R^{30}$ is independently selected at each occurrence from:
hydrogen; and
$C_{1-10}$ alkyl, $C_{2-10}$ alkenyl, $C_{2-10}$ alkynyl, $C_{3-12}$ carbocycle, and 3- to 12-membered heterocycle, each of which is optionally substituted with one or more substituents independently selected from halogen, —OH, —OSi$(C_1$-$C_6$ alkyl$)_3$, —CN, —NO$_2$, —NH$_2$, =O, =S, $C_{1-10}$ alkyl, —$C_{1-10}$ haloalkyl, —O—$C_{1-10}$ alkyl, $C_{2-10}$ alkenyl, $C_{2-10}$ alkynyl, $C_{3-12}$ carbocycle, 3- to 12-membered heterocycle, and haloalkyl;

z is selected from 0-2;

R' and R" are independently selected from hydrogen, halogen, —OR$^{31}$, and $C_{1-3}$ alkyl optionally substituted with one or more substituents independently selected from halogen and —OR$^{31}$;

Ring A is selected from an optionally substituted $C_3$-$C_5$ carbocycle and optionally substituted 3- to 5-membered heterocycle, wherein substituents on Ring A are independently selected at each occurrence from:

halogen, —OR$^{31}$, —SR$^{31}$, —N(R$^{31}$)$_2$, —C(O)R$^{31}$, —C(O)N(R$^{31}$)$_2$, N(R$^{31}$)C(O)R$^{31}$, —C(O)OR$^{31}$, —OC(O)R$^{31}$, —S(O)R$^{31}$, —S(O)$_2$R$^{31}$, —P(O)(OR$^{31}$)$_2$, —OP(O)(OR$^{31}$)$_2$, —NO$_2$, =O, =S, =N(R$^{31}$), and —CN;

$C_{1-10}$ alkyl, $C_{2-10}$ alkenyl, $C_{2-10}$ alkynyl, each of which is optionally substituted with one or more substituents independently selected from halogen, —OR$^{31}$, —SR$^{31}$, —N(R$^{31}$)$_2$, —C(O)R$^{31}$, —C(O)N(R$^{31}$)$_2$, —N(R$^{31}$)C(O)R$^{31}$, —C(O)OR$^{31}$, —OC(O)R$^{31}$, —S(O)R$^{31}$, —S(O)$_2$R$^{31}$, —P(O)(OR$^{31}$)$_2$, —OP(O)(OR$^{31}$)$_2$, —NO$_2$, =O, =S, =N(R$^{31}$), —CN, $C_{3-10}$ carbocycle and 3- to 10-membered heterocycle; and $C_{3-10}$ carbocycle and 3- to 10-membered heterocycle each of which is optionally substituted with one or more substituents independently selected from halogen, —OR$^{31}$, —SR$^{31}$, —N(R$^{31}$)$_2$, —C(O)R$^{31}$, —C(O)N(R$^{31}$)$_2$, —N(R$^{31}$)C(O)R$^{31}$, —C(O)OR$^{31}$, —OC(O)R$^{31}$, —S(O)R$^{31}$, —S(O)$_2$R$^{31}$, —P(O)(OR$^{31}$)$_2$, —OP(O)(OR$^{31}$)$_2$, —NO$_2$, =O, =S, =N(R$^{31}$), —CN, $C_{1-6}$ alkyl, $C_{2-6}$ alkenyl, $C_{2-6}$ alkynyl;

$R^{31}$ is independently selected at each occurrence from hydrogen; and $C_{1-10}$ alkyl, $C_{2-10}$ alkenyl, $C_{2-10}$ alkynyl, $C_{3-12}$ carbocycle, and 3- to 12-membered heterocycle, each of which is optionally substituted with one or more substituents independently selected from halogen, —OH, —CN, —NO$_2$, —NH$_2$, =O, =S, $C_{1-10}$ alkyl, —$C_{1-10}$ haloalkyl, —O—$C_{1-10}$ alkyl, $C_{2-10}$ alkenyl, $C_{2-10}$ alkynyl, $C_{3-12}$ carbocycle, and 3- to 12-membered heterocycle; and $R^{33}$ is independently selected at each occurrence from hydroxy, halogen, —CN, —NO$_2$, =O, $C_1$-$C_6$ alkyl, $C_1$-$C_6$ haloalkyl, $C_1$-$C_6$ hydroxyalkyl, $C_1$-$C_6$ alkoxy, $C_1$-$C_6$ alkoxy $C_1$-$C_6$ alkyl, 3- to 10-membered heterocycle, and $C_{3-10}$ carbocycle, wherein the 3- to 10-membered heterocycle and $C_{3-10}$ carbocycle are each optionally substituted with one or more substituents independently selected from hydroxy, halogen, —CN, —NO$_2$, $C_1$-$C_6$ alkyl, $C_1$-$C_6$ haloalkyl, $C_1$-$C_6$ hydroxyalkyl, $C_1$-$C_6$ alkoxy, and $C_1$-$C_6$ alkoxy $C_1$-$C_6$ alkyl.

In certain embodiments, the disclosure provides a method of treating disease comprising chronically administering a compound or salt of Formula (L), (LA), (LB), (LC), (LD), (LE), (LF), or (LG) to a subject in need thereof.

In certain embodiments, the disclosure provides a method of treating disease, wherein the disease is selected from a chronic disease. The chronic disease may be selected from a disease wherein mTORC1 is hyperactivated. The chronic disease may be selected from a disease wherein the the chronic disease would benefit from mTORC1 inhibition. In certain embodiments, the chronic disease may be selected from neurodegenerative disease, a neurocutaneous disease, a neurodevelopmental disorder, mTORopathies, tauopathies, cognitive disorders, epilepsies, autism spectrum disorders, autoimmune diseases, metabolic diseases, cancer, diseases of impaired autophagy, infectious diseases, cardiovascular diseases, muscular atrophy, inflammatory diseases, kidney diseases, pulmonary diseases, eye disorders or diseases of aging that result in hyperactivation of mTORC1 including reduced immune activity in the elderly. The chronic disease may be an mTORopathy, e.g., Tuberous Sclerosis.

In certain embodiments, the disclosure provides a method of treating a disease, wherein the compound may be a compound or salt of Formula (L), (LA), (LB), (LC), (LD), (LE), (LF), or (LG).

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

DETAILED DESCRIPTION OF THE INVENTION

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Definitions

Unless defined otherwise, all technical and scientific terms used herein have the same meaning as is commonly understood by one of skill in the art to which this invention belongs. All patents and publications referred to herein are incorporated by reference.

As used in the specification and claims, the singular form "a", "an" and "the" includes plural references unless the context clearly dictates otherwise.

The term "$C_{x-y}$" when used in conjunction with a chemical moiety, such as alkyl, alkenyl, or alkynyl is meant to include groups that contain from x to y carbons in the chain. For example, the term "$C_{1-6}$alkyl" refers to saturated hydrocarbon groups, including straight-chain alkyl and branched-chain alkyl groups that contain from 1 to 6 carbons. The term —$C_{x-y}$alkylene-refers to a substituted or unsubstituted alkylene chain with from x to y carbons in the alkylene chain. For example —$C_{1-6}$alkylene- may be selected from methylene, ethylene, propylene, butylene, pentylene, and hexylene, any one of which is optionally substituted.

The terms "$C_{x-y}$alkenyl" and "$C_{x-y}$alkynyl" refer to unsaturated aliphatic groups analogous in length and possible substitution to the alkyls described above, but that contain at least one double or triple bond, respectively. The term —$C_{x-y}$alkenylene- refers to a substituted or unsubstituted alkenylene chain with from x to y carbons in the alkenylene chain. For example, —$C_{2-6}$alkenylene- may be selected from ethenylene, propenylene, butenylene, pentenylene, and hexenylene, any one of which is optionally substituted. An alkenylene chain may have one double bond or more than one double bond in the alkenylene chain. The term —$C_{x-y}$alkynylene- refers to a substituted or unsubstituted alkynylene chain with from x to y carbons in the alkynylene chain. For example, —$C_{2-6}$alkynylene- may be selected from ethynylene, propynylene, butynylene, pentynylene, and hexynylene, any one of which is optionally substituted. An alkynylene chain may have one triple bond or more than one triple bond in the alkynylene chain.

"Alkylene" refers to a straight divalent hydrocarbon chain linking the rest of the molecule to a radical group, consisting solely of carbon and hydrogen, containing no unsaturation, and preferably having from one to twelve carbon atoms, for example, methylene, ethylene, propylene, butylene, and the like. The alkylene chain is attached to the rest of the molecule through a single bond and to the radical group through a single bond. The points of attachment of the alkylene chain to the rest of the molecule and to the radical group are through the terminal carbons respectively. An alkylene chain may be optionally substituted by one or more substituents such as those substituents described herein.

"Alkenylene" refers to a straight divalent hydrocarbon chain linking the rest of the molecule to a radical group, consisting solely of carbon and hydrogen, containing at least one carbon-carbon double bond, and preferably having from two to twelve carbon atoms. The alkenylene chain is attached to the rest of the molecule through a single bond and to the radical group through a single bond. The points of attachment of the alkenylene chain to the rest of the molecule and to the radical group are through the terminal carbons respectively. An alkenylene chain may be optionally substituted by one or more substituents such as those substituents described herein.

"Alkynylene" refers to a straight divalent hydrocarbon chain linking the rest of the molecule to a radical group, consisting solely of carbon and hydrogen, containing at least one carbon-carbon triple bond, and preferably having from two to twelve carbon atoms. The alkynylene chain is attached to the rest of the molecule through a single bond and to the radical group through a single bond. The points of attachment of the alkynylene chain to the rest of the molecule and to the radical group are through the terminal carbons respectively. An alkynylene chain may be optionally substituted by one or more substituents such as those substituents described herein.

The term "carbocycle" as used herein refers to a saturated, unsaturated or aromatic ring in which each atom of the ring is carbon. Carbocycle may include 3- to 10-membered monocyclic rings, 6- to 12-membered bicyclic rings, and 6- to 12-membered bridged rings. Each ring of a bicyclic carbocycle may be selected from saturated, unsaturated, and aromatic rings. In some embodiments, the carbocycle is an aryl. In some embodiments, the carbocycle is a cycloalkyl. In some embodiments, the carbocycle is a cycloalkenyl. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, are included in the definition of carbocyclic. Exemplary carbocycles include cyclopentyl, cyclohexyl, cyclohexenyl, adamantyl, phenyl, indanyl, and naphthyl. Bicyclic carbocycles may be fused, bridged or spiro-ring systems. A carbocycle may be optionally substituted by one or more substituents such as those substituents described herein. The term "heterocycle" as used herein refers to a saturated, unsaturated or aromatic ring comprising one or more heteroatoms. Exemplary heteroatoms include N, O, Si, P, B, and S atoms. Heterocycles include 3- to 10-membered monocyclic rings, 6- to 12-membered bicyclic rings, and 6- to 12-membered bridged rings. Each ring of a bicyclic heterocycle may be selected from saturated, unsaturated, and aromatic rings. The heterocycle may be attached to the rest of the molecule through any atom of the heterocycle, valence permitting, such as a carbon or nitrogen atom of the heterocycle. In some embodiments, the heterocycle is a heteroaryl. In some embodiments, the heterocycle is a heterocycloalkyl. In an exemplary embodiment, a heterocycle, e.g., pyridyl, may be fused to a saturated or unsaturated ring, e.g., cyclohexane, cyclopentane, or cyclohexene. Exemplary heterocycles include pyrrolidinyl, pyrrolyl, imidazolyl, pyrazolyl, triazolyl, piperidinyl, pyridinyl, pyrimidinyl, pyridazinyl, pyrazinyl, thiophenyl, oxazolyl, thiazolyl, morpholinyl, indazolyl, indolyl, and quinolinyl. Bicyclic heterocycles may be fused, bridged or spiro-ring systems. A heterocycle may be optionally substituted by one or more substituents such as those substituents described herein.

The term "heteroaryl" includes aromatic single ring structures, preferably 5- to 7-membered rings, more preferably 5- to 6-membered rings, whose ring structures include at least one heteroatom, preferably one to four heteroatoms, more preferably one or two heteroatoms. The term "heteroaryl" also includes polycyclic ring systems having two or more rings in which two or more atoms are common to two adjoining rings wherein at least one of the rings is heteroaromatic, e.g., the other rings can be aromatic or non-aromatic carbocyclic, or heterocyclic. Heteroaryl groups include, for example, pyrrole, furan, thiophene, imidazole, oxazole, thiazole, pyrazole, pyridine, pyrazine, pyridazine, and pyrimidine, and the like.

The term "substituted" refers to moieties having substituents replacing a hydrogen on one or more carbons or substitutable heteroatoms, e.g., an NH or $NH_2$ of a compound. It will be understood that "substitution" or "substituted with" includes the implicit proviso that such substitution is in accordance with permitted valence of the substituted atom and the substituent, and that the substitution results in a stable compound, i.e., a compound which does not spontaneously undergo transformation such as by rearrangement, cyclization, elimination, etc. In certain embodiments, substituted refers to moieties having substituents replacing two hydrogen atoms on the same carbon atom, such as substituting the two hydrogen atoms on a single carbon with an oxo, imino or thioxo group. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds.

In some embodiments, substituents may include any substituents described herein, for example: halogen, hydroxy, oxo (=O), thioxo (=S), cyano (—CN), nitro (—NO$_2$), imino (=N—H), oximo (=N—OH), hydrazino (=N—NH$_2$), —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$R$^a$ (where t is 1 or 2), —R$^b$—S(O)$_t$R$^a$ (where t is 1 or 2), and —R$^b$—S(O)$_t$N(R$^a$)$_2$ (where t is 1 or 2); and alkyl, alkenyl, alkynyl, aryl, aralkyl, aralkenyl, aralkynyl, cycloalkyl, cycloalkylalkyl, heterocycloalkyl, heterocycloalkylalkyl, heteroaryl, and heteroarylalkyl any of which may be optionally substituted by alkyl, alkenyl, alkynyl, halogen, haloalkyl, haloalkenyl, haloalkynyl, oxo (=O), thioxo (=S), cyano (—CN), nitro (—NO$_2$), imino (=N—H), oximo (=N—OH), hydrazine (=N—NH$_2$), —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$R$^a$ (where t is 1 or 2), —R$^b$—S(O)$_t$OR$^a$ (where t is 1 or 2) and —R$^b$—S(O)$_t$N(R$^a$)$_2$ (where t is 1 or 2); wherein each R$^a$ is independently selected from hydrogen, alkyl, cycloalkyl, cycloalkylalkyl, aryl, aralkyl, heterocycloalkyl, heterocycloalkylalkyl, heteroaryl, or heteroarylalkyl, wherein each R$^a$, valence permitting, may be optionally substituted with alkyl, alkenyl, alkynyl, halogen, haloalkyl, haloalkenyl, haloalkynyl, oxo (=O), thioxo (=S), cyano (—CN), nitro (—NO$_2$), imino (=N—H), oximo (=N—OH), hydrazine (=N—NH$_2$), —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$R$^a$ (where t is 1 or 2), —R$^b$—S(O)$_t$OR$^a$ (where t is 1 or 2) and —R$^b$—S(O)$_t$N(R$^a$)$_2$ (where t is 1 or 2); and wherein each R$^b$ is independently selected from a direct bond or a straight or branched alkylene, alkenylene, or alkynylene chain, and each R$^c$ is a straight or branched alkylene, alkenylene or alkynylene chain. It will be understood by those skilled in the art that substituents can themselves be substituted, if appropriate.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable excipient" or "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The terms "subject," "individual," and "patient" may be used interchangeably and refer to humans, the as well as non-human mammals (e.g., non-human primates, canines, equines, felines, porcines, bovines, ungulates, lagomorphs, and the like). In various embodiments, the subject can be a human (e.g., adult male, adult female, adolescent male, adolescent female, male child, female child) under the care of a physician or other health worker in a hospital, as an outpatient, or other clinical context. In certain embodiments, the subject may not be under the care or prescription of a physician or other health worker.

As used herein, the phrase "a subject in need thereof" refers to a subject, as described infra, that suffers from, or is at risk for, a pathology to be prophylactically or therapeutically treated with a compound or salt described herein.

The terms "administer", "administered", "administers" and "administering" are defined as providing a composition to a subject via a route known in the art, including but not limited to intravenous, intraarterial, oral, parenteral, buccal, topical, transdermal, rectal, intramuscular, subcutaneous, intraosseous, transmucosal, or intraperitoneal routes of administration. In certain embodiments, oral routes of administering a composition can be used. The terms ""administer", "administered", "administers" and "administering" a compound should be understood to mean providing a compound of the invention or a prodrug of a compound of the invention to the individual in need.

The term "effective amount" or "therapeutically effective amount" refers to that amount of a compound or salt described herein that is sufficient to effect the intended application including but not limited to disease treatment, as defined below. The therapeutically effective amount may vary depending upon the intended application (in vitro or in vivo), or the subject and disease condition being treated, e.g., the weight and age of the subject, the severity of the disease condition, the manner of administration and the like, which can readily be determined by one of ordinary skill in the art. The term can also apply to a dose that can induce a particular response in target cells, e.g., reduction of proliferation or down regulation of activity of a target protein. The specific dose can vary depending on the particular compounds chosen, the dosing regimen to be followed, whether it is administered in combination with other compounds, timing of administration, the tissue to which it is administered, and the physical delivery system in which it is carried.

As used herein, "treatment" or "treating" refers to an approach for obtaining beneficial or desired results with respect to a disease, disorder, or medical condition including, but not limited to, a therapeutic benefit and/or a prophylactic benefit. In certain embodiments, treatment or treating involves administering a compound or composition disclosed herein to a subject. A therapeutic benefit may include the eradication or amelioration of the underlying disorder being treated. Also, a therapeutic benefit may be achieved with the eradication or amelioration of one or more of the physiological symptoms associated with the underlying disorder, such as observing an improvement in the subject, notwithstanding that the subject may still be afflicted with the underlying disorder. In certain embodiments, for prophylactic benefit, the compositions are administered to a subject at risk of developing a particular disease, or to a subject reporting one or more of the physiological symptoms of a disease, even though a diagnosis of this disease may not have been made. Treating can include, for example, reducing, delaying or alleviating the severity of one or more symptoms of the disease or condition, or it can include reducing the frequency with which symptoms of a disease, defect, disorder, or adverse condition, and the like, are experienced by a patient. Treating can be used herein to refer to a method that results in some level of treatment or amelioration of the disease or condition, and can contemplate a range of results directed to that end, including but not restricted to prevention of the condition entirely.

In certain embodiments, the term "prevent" or "preventing" as related to a disease or disorder may refer to a compound that, in a statistical sample, reduces the occurrence of the disorder or condition in the treated sample relative to an untreated control sample, or delays the onset or reduces the severity of one or more symptoms of the disorder or condition relative to the untreated control sample.

A "therapeutic effect," as that term is used herein, encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

The term "selective inhibition" or "selectively inhibit" as referred to a biologically active agent refers to the agent's ability to preferentially reduce the target signaling activity as compared to off-target signaling activity, via direct or interact interaction with the target.

Introduction

The mechanistic target of rapamycin (mTOR) signaling pathway integrates both intracellular and extracellular signals and serves as a central regulator of cell metabolism, growth, proliferation and survival. In particular, mTOR complex 1 (mTORC1) positively regulates cell growth and proliferation by promoting many anabolic processes, including biosynthesis of proteins, lipids and organelles, and by limiting catabolic processes such as autophagy. Much of the knowledge about mTORC1 function comes from the use of the bacterial macrolide rapamycin.

Rapamycin is believed to inhibit mTORC1 directly and mTORC2 indirectly upon chronic treatment. Recent evidence has revealed that inhibition of mTORC1 is responsible for effects related to lifespan extension, while inhibition of mTORC2 is uncoupled from longevity and is responsible for several of the adverse effects of rapamycin, such as impaired insulin sensitivity, glucose homeostasis, and lipid dysregulation.

Studies of rapamycin and related rapalogs reveal that these compounds form binary complexes with FKB binding proteins such as FKBP12 and FKBP51. This binary complex can allosterically inhibit the functionality of mTORC1 by binding to the FRB domain of mTOR. FKBP12 and FKBP51 direct binding assays provide a method to assess the relative binding affinity of rapalogs to the specified FKBP. While not wishing to be bound by any particular mechanistic theory, it may be preferred that binding of a rapalog to an FKB protein, e.g., FKBP12 or FKBP51, is similar, equivalent or stronger relative to rapamycin binding to said FKB protein.

The ternary complex formation assay provides a method to assess the relative binding affinity of the rapalog/FKB binary complex to the FRB domain of mTOR. Different binding affinities for mTOR exhibited by rapalog/FKB complexes may result in different pharmacology and safety profiles relative to the known rapalogs, rapamycin and everolimus.

In certain aspects, the disclosure provides compounds and salts thereof, and methods of use for the treatment of diseases. In certain embodiments, compounds described herein are referred to as rapalogs which refers to the shared core structure of the compounds described herein relative to rapamycin. In certain aspects, the compounds described herein display similar direct binding properties, e.g., similar or improved FKB binding, relative to known compounds, such as rapamycin and everolimus. In certain aspects, the compounds described herein display altered ternary binding affinity, e.g. diminished binding affinity to the FRB domain of mTOR, relative to known compounds, such as rapamycin or everolimus.

In certain embodiments, compounds or salts of the disclosure are evaluated for direct binding to FKBP12 and/or FKBP51. In certain embodiments, compounds or salts of the disclosure are evaluated for ternary complex formation with MTORC1 and FKBP12. In certain embodiments, a compound or salt thereof has potent binding to FKBP12 and/or FKBP51.

In certain aspects, compounds of the disclosure are grouped in Compound Groups 1, 2, and 3. Each of these compound groups describes distinct chemical structure groupings. Any duplication of variables in one group relative to another group is not intended to imply interchangeability for that variable with a variable of one of the other groups. For example, the description of $R^1$ in compounds of Group 1 applies only to compounds of Group 1 and not to Group 2 or Group 3.

Compound Group 1

In a first aspect, the present disclosure provides a compound represented by the structure of Formula I:

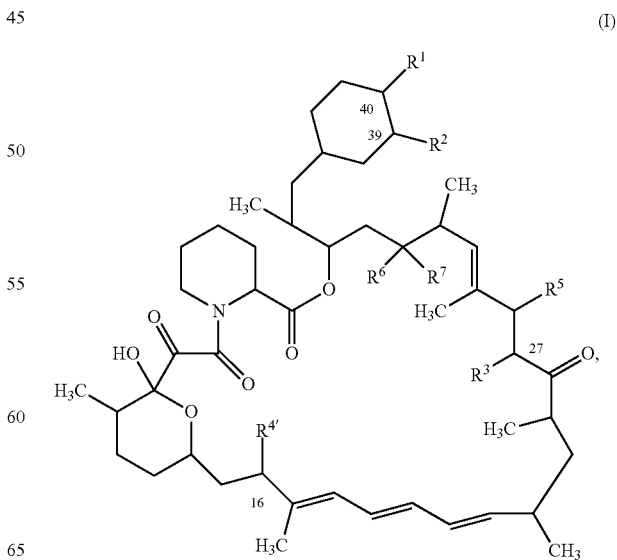

(I)

or a pharmaceutically acceptable salt thereof, wherein:
$R^1$ is selected from —OH,

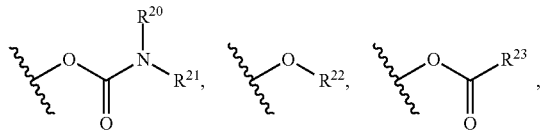

3- to 10-membered heterocycle, and $C_{3-10}$ carbocycle, wherein the 3- to 10-membered heterocycle and $C_{3-10}$ carbocycle are each optionally substituted with one or more substituents independently selected from: hydroxy, halogen, —CN, —NO$_2$, =O, $C_1$-$C_6$ alkyl, $C_1$-$C_6$ haloalkyl, $C_1$-$C_6$ hydroxyalkyl, $C_1$-$C_6$ alkoxy, $C_1$-$C_6$ alkoxy, 3- to 10-membered heterocycle, and $C_{3-10}$ carbocycle, wherein the 3- to 10-membered heterocycle and $C_{3-10}$ carbocycle are each optionally substituted with one or more substituents independently selected from hydroxy, halogen, —CN, —NO$_2$, $C_1$-$C_6$ alkyl, $C_1$-$C_6$ haloalkyl, $C_1$-$C_6$ hydroxyalkyl, and $C_1$-$C_6$ alkoxy;

$R^2$ is selected from hydrogen and an optionally substituted $C_1$-$C_6$ alkoxy, wherein substituents are independently selected at each occurrence from hydroxy, halogen, —CN, —NO$_2$, $C_1$-$C_6$ alkoxy, 3- to 10-membered heterocycle, and $C_{3-10}$ carbocycle, wherein the 3- to 10-membered heterocycle and $C_{3-10}$ carbocycle are each optionally substituted with one or more substituents independently selected from hydroxy, halogen, —CN, —NO$_2$, $C_1$-$C_6$ alkyl, $C_1$-$C_6$ haloalkyl, $C_1$-$C_6$ hydroxyalkyl, and $C_1$-$C_6$ alkoxy;

$R^3$ is selected from hydrogen and an optionally substituted $C_1$-$C_6$ alkoxy, wherein the substituents are independently selected at each occurrence from hydroxy, halogen, —CN, —NO$_2$, $C_1$-$C_6$ alkoxy, 3- to 10-membered heterocycle, and $C_{3-10}$ carbocycle, wherein the 3- to 10-membered heterocycle and $C_{3-10}$ carbocycle, are each optionally substituted with one or more substituents independently selected from hydroxy, halogen, —CN, —NO$_2$, $C_1$-$C_6$ alkyl, $C_1$-$C_6$ haloalkyl, $C_1$-$C_6$ hydroxyalkyl, and $C_1$-$C_6$ alkoxy; and $R^{4'}$ is selected from,

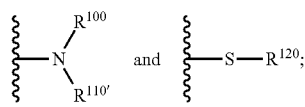

$R^5$ is selected from hydrogen, hydroxy, and an optionally substituted $C_1$-$C_6$ alkoxy, wherein substituents are independently selected at each occurrence from hydroxy, halogen, —CN, —NO$_2$, $C_1$-$C_6$ alkoxy, 3- to 10-membered heterocycle, and $C_{3-10}$ carbocycle, wherein the 3- to 10-membered heterocycle, and $C_{3-10}$ carbocycle are each optionally substituted with one or more substituents independently selected from hydroxy, halogen, —CN, —NO$_2$, $C_1$-$C_6$ alkyl, $C_1$-$C_6$ haloalkyl, $C_1$-$C_6$ hydroxyalkyl, and $C_1$-$C_6$ alkoxy;

$R^6$ and $R^7$ are each independently selected from hydrogen, hydroxy, and $C_1$-$C_6$ alkoxy; or $R^6$ and $R^7$ come together to form

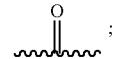

$R^{20}$ is selected from hydrogen and optionally substituted $C_1$-$C_6$ alkyl;
$R^{21}$ is selected from optionally substituted $C_1$-$C_6$ alkyl, optionally substituted 3- to 10-membered heterocycle, and optionally substituted $C_{3-10}$ carbocycle;
$R^{22}$ is selected from optionally substituted $C_1$-$C_6$ alkyl, optionally substituted 3- to 10-membered heterocycle, and optionally substituted $C_{3-10}$ carbocycle, and —P(=O)(R$^{24}$)$_2$;
$R^{23}$ is selected from optionally substituted $C_1$-$C_6$ alkyl, optionally substituted 3- to 10-membered heterocycle, and optionally substituted $C_{3-10}$ carbocycle;
$R^{24}$ is optionally substituted $C_1$-$C_6$ alkyl;
$R^{100}$ is selected from:
  hydrogen and —(CH$_2$—CH$_2$-G)$_y$-V; and
  $C_{1-10}$ alkyl, $C_{2-10}$ alkenyl, $C_{2-10}$ alkynyl, wherein each of which is optionally substituted with one or more substituents independently selected from halogen, —OR$^{31}$, —SR$^{31}$, —N(R$^{31}$)$_2$, —C(O)R$^{31}$, —C(O)N(R$^{31}$)$_2$, —N(R$^{31}$)C(O)R$^{31}$, —C(O)OR$^{31}$, —OC(O)R$^{31}$, —S(O)R$^{31}$, —S(O)$_2$R$^{31}$, —P(O)(OR$^{31}$)$_2$, —OP(O)(OR$^{31}$)$_2$, —NO$_2$, —CN, $C_{3-20}$ carbocycle and 3- to 20-membered heterocycle; and
  $C_{3-20}$ carbocycle and 3- to 20-membered heterocycle each of which is optionally substituted with one or more substituents independently selected from halogen, —OR$^{31}$, —SR$^{31}$, —N(R$^{31}$)$_2$, —C(O)R$^{31}$, —C(O)N(R$^{31}$)$_2$, —N(R$^{31}$)C(O)R$^{31}$, —C(O)OR$^{31}$, —OC(O)R$^{31}$, —S(O)R$^{31}$, —S(O)$_2$R$^{31}$, —P(O)(OR$^{31}$)$_2$, —OP(O)(OR$^{31}$)$_2$, —NO$_2$, =O, =S, =N(R$^{31}$), —CN, $C_{1-6}$ alkyl, $C_{1-6}$ alkyl-R$^{31}$, $C_{2-6}$ alkenyl, and $C_{2-6}$ alkynyl;
$R^{110'}$ is selected from:
  hydrogen, —(CH$_2$—CH$_2$-G)$_y$-V, —S(O)R$^{51'}$, —S(O)$_2$R$^{51'}$, —C(O)R$^{51'}$, —C(O)N(R')$_2$, and —C(O)OR$^{51'}$; and
  $C_{1-10}$ alkyl, $C_{2-10}$ alkenyl, $C_{2-10}$ alkynyl, wherein each of which is optionally substituted with one or more substituents independently selected from halogen, —OR$^{31}$, —SR$^{31}$, —N(R$^{31}$)$_2$, —C(O)R$^{31}$, —C(O)N(R$^{31}$)$_2$, —N(R$^{31}$)C(O)R$^{31}$, —C(O)OR$^{31}$, —OC(O)R$^{31}$, —S(O)R$^{31}$, —S(O)$_2$R$^{31}$, —P(O)(OR$^{31}$)$_2$, —OP(O)(OR$^{31}$)$_2$, —NO$_2$, —CN, $C_{3-20}$ carbocycle and 3- to 20-membered heterocycle; and
  $C_{3-20}$ carbocycle and 3- to 20-membered heterocycle each of which is optionally substituted with one or more substituents independently selected from halogen, —OR$^{31}$, —SR$^{31}$, —N(R$^{31}$)$_2$, —C(O)R$^{31}$, —C(O)N(R$^{31}$)$_2$, —N(R$^{31}$)C(O)R$^{31}$, —C(O)OR$^{31}$, —OC(O)R$^{31}$, —S(O)R$^{31}$, —S(O)$_2$R$^{31}$, —P(O)(OR$^{31}$)$_2$, —OP(O)(OR$^{31}$)$_2$, —NO$_2$, =O, =S, =N(R$^{31}$), —CN, $C_{1-6}$ alkyl, $C_{1-6}$ alkyl-R$^{31}$, $C_{2-6}$ alkenyl, and $C_{2-6}$ alkynyl; or
$R^{100}$ and $R^{110'}$ together with the nitrogen to which they are bound form a 3-10-membered heterocycle optionally substituted with one or more substituents independently selected from: hydroxy, halogen, —CN, —NO$_2$, $C_1$-$C_6$ alkyl, $C_1$-$C_6$ haloalkyl, $C_1$-$C_6$ hydroxyalkyl, and $C_1$-$C_6$ alkoxy, wherein when $R^1$ is hydroxy, the ring formed by $R^{100}$ and $R^{110}$ is not unsubstituted morpholine, and wherein when one of $R^6$ and $R^7$ are selected from hydroxy and $C_1$-$C_6$ alkoxy or when $R^6$ and $R^7$ come together to form

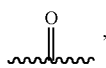

the 3-10-membered heterocycle formed by $R^{100}$ and $R^{110}$ is further optionally substituted with one or more =O;

$R^{120}$ is selected from:
hydrogen, —(CH$_2$—CH$_2$-G)$_y$-V; and $C_{3-10}$ alkyl, $C_{2-10}$ alkenyl, $C_{2-10}$ alkynyl, each of which is optionally substituted with one or more substituents independently selected from halogen, —OR$^{31}$, —SR$^{31}$, —N(R$^{31}$)$_2$, —C(O)R$^{31}$, —C(O)N(R$^{31}$)$_2$, —N(R$^{31}$)C(O)R$^{31}$, —C(O)OR$^{31}$, —OC(O)R$^{31}$, —S(O)R$^{31}$, —S(O)$_2$R$^{31}$, —P(O)(OR$^{31}$)$_2$, —OP(O)(OR$^{31}$)$_2$, —NO$_2$, —CN, $C_{3-20}$ carbocycle, and 3- to 20-membered heterocycle; and $C_{3-20}$ saturated carbocycle and 3- to 20-membered heterocycle each of which is optionally substituted with one or more substituents independently selected from halogen, —OR$^{31}$, —SR$^{31}$, —N(R$^{31}$)$_2$, —C(O)R$^{31}$, —C(O)N(R$^{31}$)$_2$, —N(R$^{31}$)C(O)R$^{31}$, —C(O)OR$^{31}$, —OC(O)R$^{31}$, —S(O)R$^{31}$, —S(O)$_2$R$^{31}$, —P(O)(OR$^{31}$)$_2$, —OP(O)(OR$^{31}$)$_2$, —NO$_2$, =O, =S, =N(R$^{31}$), —CN, $C_{1-6}$ alkyl, $C_{1-6}$ alkyl-R$^{31}$, $C_{2-6}$ alkenyl, and $C_{2-6}$ alkynyl; or $C_{1-2}$ alkyl substituted with one or more substituents independently selected from halogen, —OR$^{31}$, —N(R$^{31}$)$_2$, —C(O)R$^{31}$, —C(O)N(R$^{31}$)$_2$, —N(R$^{31}$)C(O)R$^{31}$, —C(O)OR$^{31}$, —OC(O)R$^{31}$, —S(O)R$^{31}$, —S(O)$_2$R$^{31}$, —P(O)(OR$^{31}$)$_2$, —OP(O)(OR$^{31}$)$_2$, —NO$_2$, —CN, $C_{3-20}$ carbocycle and 3- to 20-membered heterocycle;

each G is independently selected from —O—, —NR$^{32}$—, —S—, or —SO$_2$—;

each D is independently selected from —O—, —NR$^{32}$—, —S—, or —SO$_2$—;

each y is selected from 3-20;
each z is selected from 1-20;
each V is selected from hydrogen and optionally substituted —C$_1$-C$_6$ alkyl;
each T is selected from hydrogen and optionally substituted —C$_1$-C$_6$ alkyl;
each R$^{31}$ is selected from hydrogen, and $C_{1-10}$ alkyl, $C_{2-10}$ alkenyl, $C_{2-10}$ alkynyl, $C_{3-10}$ carbocycle, and 3- to 10-membered heterocycle, each of which is optionally substituted with one or more substituents independently selected from halogen, —OH, —CN, —NO$_2$, —NH$_2$, =O, =S, $C_{1-10}$ alkyl, —C$_{1-10}$ haloalkyl, —O—C$_{1-10}$ alkyl, $C_{2-10}$ alkenyl, $C_{2-10}$ alkynyl, $C_{3-10}$ carbocycle, and 3- to 10-membered heterocycle; and $R^{32}$ is independently selected at each occurrence from:
hydrogen; and $C_{1-10}$ alkyl, $C_{2-10}$ alkenyl, $C_{2-10}$ alkynyl, $C_{3-10}$ carbocycle, and 3- to 10-membered heterocycle, each of which is optionally substituted with one or more substituents independently selected from halogen, —OH, —CN, —NO$_2$, —NH$_2$, =O, =S, $C_{1-10}$ alkyl, —C$_{1-10}$ haloalkyl, —O—C$_{1-10}$ alkyl, $C_{2-10}$ alkenyl, $C_{2-10}$ alkynyl, $C_{3-10}$ carbocycle, and 3- to 10-membered heterocycle;

wherein the optional substituents on R$^{20}$, R$^{21}$, R$^{22}$, R$^{23}$, R$^{24}$, R$^{51'}$, V, and T are independently selected at each occurrence from:
halogen, —OR$^{30}$, —N(R$^{30}$)$_2$, —(O—CH$_2$—(CH$_2$)$_p$)$_n$—W, —SR$^{30}$, —C(O)R$^{30}$, —C(O)N(R$^{30}$)$_2$, —N(R$^{30}$)C(O)R$^{30}$, —C(O)OR$^{30}$, —OC(O)R$^{30}$, —S(O)R$^{30}$, —S(O)$_2$R$^{30}$, —P(O)(OR$^{30}$)$_2$, —OP(O)(OR$^{30}$)$_2$, —NO$_2$, =O, =S, =N(R$^{30}$), and —CN;

$C_{1-10}$ alkyl, $C_{2-10}$ alkenyl, $C_{2-10}$ alkynyl, each of which is optionally substituted with one or more substituents independently selected from halogen, —OR$^{30}$, —SR$^{30}$, —N(R$^{30}$)$_2$, —C(O)R$^{30}$, —C(O)N(R$^{30}$)$_2$, —N(R$^{30}$)C(O)R$^{30}$, —C(O)OR$^{30}$, —OC(O)R$^{30}$, —S(O)R$^{30}$, —S(O)$_2$R$^{30}$, —P(O)(OR$^{30}$)$_2$, —OP(O)(OR$^{30}$)$_2$, —NO$_2$, =O, =S, =N(R$^{30}$), —CN, $C_{3-10}$ carbocycle and 3- to 10-membered heterocycle; and $C_{3-10}$ carbocycle and 3- to 10-membered heterocycle each of which is optionally substituted with one or more substituents independently selected from halogen, —OR$^{30}$, —SR$^{30}$, —N(R$^{30}$)$_2$, —C(O)R$^{30}$, —C(O)N(R$^{30}$)$_2$, —N(R$^{30}$)C(O)R$^{30}$, —C(O)OR$^{30}$, —OC(O)R$^{30}$, —S(O)R$^{30}$, —S(O)$_2$R$^{30}$, —P(O)(OR$^{30}$)$_2$, —OP(O)(OR$^{30}$)$_2$, —NO$_2$, =O, =S, =N(R$^{30}$), —CN, $C_{1-6}$ alkyl, $C_{1-6}$ alkyl-R$^{30}$, $C_{2-6}$ alkenyl, and $C_{2-6}$ alkynyl;

$R^{30}$ is independently selected at each occurrence from hydrogen; $C_{1-10}$ alkyl, $C_{2-10}$ alkenyl, $C_{2-10}$ alkynyl, $C_{3-10}$ carbocycle, and 3- to 10-membered heterocycle, each of which is optionally substituted with one or more substituents independently selected from halogen, —OH, —CN, —NO$_2$, —NH$_2$, =O, =S, $C_{1-10}$ alkyl, —C$_{1-10}$ haloalkyl, —O—C$_{1-10}$ alkyl, $C_{2-10}$ alkenyl, $C_{2-10}$ alkynyl, $C_{3-10}$ carbocycle, and 3- to 10-membered heterocycle;

$R^{51'}$ is independently selected at each occurrence from substituted $C_{1-4}$ alkyl, optionally substituted $C_{3-8}$ carbocycle, optionally substituted 3-10 membered heterocycle, —((CH$_2$)$_q$—CH$_2$-D)$_z$-T and optionally substituted $C_{5-30}$ alkyl;

q is selected from 1 to 6;
each p is selected from 1 or 2;
each n is selected from 3-7; and
each W is selected from hydrogen, —OH, —C$_1$-C$_4$ alkyl and —O(C$_1$-C$_4$ alkyl).

In some embodiments, the compound of Formula (I) is represented by Formula (IZ):

(IZ)

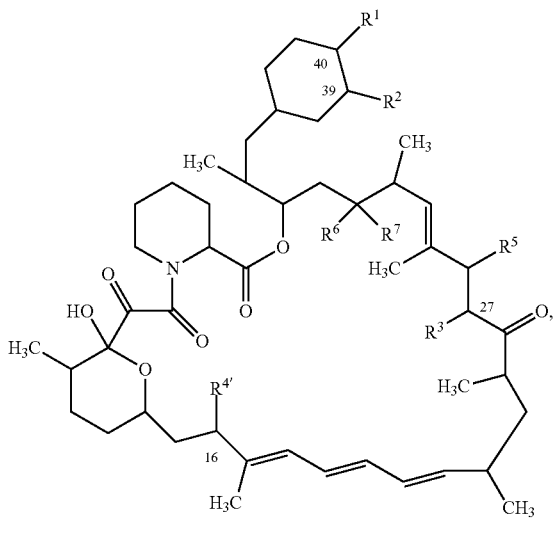

or a pharmaceutically acceptable salt thereof, wherein:

$R^1$ is selected from —OH,

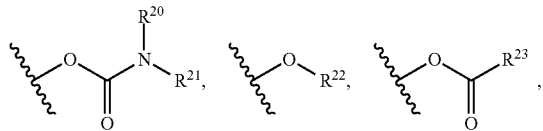

3- to 10-membered heterocycle, and $C_{3-10}$ carbocycle, wherein the 3- to 10-membered heterocycle and $C_{3-10}$ carbocycle are each optionally substituted with one or more substituents independently selected from: hydroxy, halogen, —CN, —NO$_2$, =O, $C_1$-$C_6$ alkyl, $C_1$-$C_6$ haloalkyl, $C_1$-$C_6$ hydroxyalkyl, $C_1$-$C_6$ alkoxy, $C_1$-$C_6$ alkoxy, 3- to 10-membered heterocycle, and $C_{3-10}$ carbocycle, wherein the 3- to 10-membered heterocycle and $C_{3-10}$ carbocycle are each optionally substituted with one or more substituents independently selected from hydroxy, halogen, —CN, —NO$_2$, $C_1$-$C_6$ alkyl, $C_1$-$C_6$ haloalkyl, $C_1$-$C_6$ hydroxyalkyl, and $C_1$-$C_6$ alkoxy;

$R^2$ is selected from hydrogen and an optionally substituted $C_1$-$C_6$ alkoxy, wherein substituents are independently selected at each occurrence from hydroxy, halogen, —CN, —NO$_2$, $C_1$-$C_6$ alkoxy, 3- to 10-membered heterocycle, and $C_{3-10}$ carbocycle, wherein the 3- to 10-membered heterocycle and $C_{3-10}$ carbocycle are each optionally substituted with one or more substituents independently selected from hydroxy, halogen, —CN, —NO$_2$, $C_1$-$C_6$ alkyl, $C_1$-$C_6$ haloalkyl, $C_1$-$C_6$ hydroxyalkyl, and $C_1$-$C_6$ alkoxy;

$R^3$ is selected from hydrogen and an optionally substituted $C_1$-$C_6$ alkoxy, wherein the substituents are independently selected at each occurrence from hydroxy, halogen, —CN, —NO$_2$, $C_1$-$C_6$ alkoxy, 3- to 10-membered heterocycle, and $C_{3-10}$ carbocycle, wherein the 3- to 10-membered heterocycle and $C_{3-10}$ carbocycle, are each optionally substituted with one or more substituents independently selected from hydroxy, halogen, —CN, —NO$_2$, $C_1$-$C_6$ alkyl, $C_1$-$C_6$ haloalkyl, $C_1$-$C_6$ hydroxyalkyl, and $C_1$-$C_6$ alkoxy; and $R^4$ is selected from

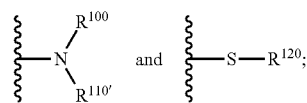

$R^5$ is selected from hydrogen, hydroxy, and an optionally substituted $C_1$-$C_6$ alkoxy, wherein substituents are independently selected at each occurrence from hydroxy, halogen, —CN, —NO$_2$, $C_1$-$C_6$ alkoxy, 3- to 10-membered heterocycle, and $C_{3-10}$ carbocycle, wherein the 3- to 10-membered heterocycle, and $C_{3-10}$ carbocycle are each optionally substituted with one or more substituents independently selected from hydroxy, halogen, —CN, —NO$_2$, $C_1$-$C_6$ alkyl, $C_1$-$C_6$ haloalkyl, $C_1$-$C_6$ hydroxyalkyl, and $C_1$-$C_6$ alkoxy;

$R^6$ and $R^7$ are each independently selected from hydrogen, hydroxy, and $C_1$-$C_6$ alkoxy; or $R^6$ and $R^7$ come together to form

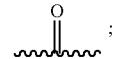

$R^{20}$ is selected from hydrogen and optionally substituted $C_1$-$C_6$ alkyl;

$R^{21}$ is selected from optionally substituted $C_1$-$C_6$ alkyl, optionally substituted 3- to 10-membered heterocycle, and optionally substituted $C_{3-10}$ carbocycle;

$R^{22}$ is selected from optionally substituted $C_1$-$C_6$ alkyl, optionally substituted 3- to 10-membered heterocycle, and optionally substituted $C_{3-10}$ carbocycle, and —P(=O)(R$^{24}$)$_2$;

$R^{23}$ is selected from optionally substituted $C_1$-$C_6$ alkyl, optionally substituted 3- to 10-membered heterocycle, and optionally substituted $C_{3-10}$ carbocycle;

$R^{24}$ is optionally substituted $C_1$-$C_6$ alkyl;

$R^{100}$ is selected from:
  hydrogen and —(CH$_2$—CH$_2$-G)$_y$-V; and
  $C_{1-10}$ alkyl, $C_{2-10}$ alkenyl, $C_{2-10}$ alkynyl, wherein each of which is optionally substituted with one or more substituents independently selected from halogen, —OR$^{31}$, —SR$^{31}$, —N(R$^{31}$)$_2$, —C(O)R$^{31}$, —C(O)N(R$^{31}$)$_2$, —N(R$^{31}$)C(O)R$^{31}$, —C(O)OR$^{31}$, —OC(O)R$^{31}$, —S(O)R$^{31}$, —S(O)$_2$R$^{31}$, —P(O)(OR$^{31}$)$_2$, —OP(O)(OR$^{31}$)$_2$, —NO$_2$, —CN, $C_{3-20}$ carbocycle and 3- to 20-membered heterocycle; and
  $C_{3-20}$ carbocycle and 3- to 20-membered heterocycle each of which is optionally substituted with one or more substituents independently selected from halogen, —OR$^{31}$, —SR$^{31}$, —N(R$^{31}$)$_2$, —C(O)R$^{31}$, —C(O)N(R$^{31}$)$_2$, —N(R$^{31}$)C(O)R$^{31}$, —C(O)OR$^{31}$, —OC(O)R$^{31}$, —S(O)R$^{31}$, —S(O)$_2$R$^{31}$, —P(O)(OR$^{31}$)$_2$, —OP(O)(OR$^{31}$)$_2$, —NO$_2$, =O, =S, =N(R$^{31}$), —CN, $C_{1-6}$ alkyl, $C_{1-6}$ alkyl-R$^{31}$, $C_{2-6}$ alkenyl, and $C_{2-6}$ alkynyl;

$R^{110}$ is selected from:
  hydrogen, —(CH$_2$—CH$_2$-G)$_y$-V, —S(O)R$^1$, —S(O)$_2$R$^{51}$, —C(O)R$^{51}$, —C(O)N(R$^{51}$)$_2$, and —C(O)OR$^{51}$; and
  $C_{1-10}$ alkyl, $C_{2-10}$ alkenyl, $C_{2-10}$ alkynyl, wherein each of which is optionally substituted with one or more substituents independently selected from halogen, —OR$^{31}$, —SR$^{31}$, —N(R$^{31}$)$_2$, —C(O)R$^{31}$, —C(O)N(R$^{31}$)$_2$, —N(R$^{31}$)C(O)R$^{31}$, —C(O)OR$^{31}$, —OC(O)R$^{31}$, —S(O)R$^{31}$, —S(O)$_2$R$^{31}$, —P(O)(OR$^{31}$)$_2$, —OP(O)(OR$^{31}$)$_2$, —NO$_2$, —CN, $C_{3-20}$ carbocycle and 3- to 20-membered heterocycle; and
  $C_{3-20}$ carbocycle and 3- to 20-membered heterocycle each of which is optionally substituted with one or more substituents independently selected from halogen, —OR$^{31}$, —SR$^{31}$, —N(R$^{31}$)$_2$, —C(O)R$^{31}$, —C(O)N(R$^{31}$)$_2$, —N(R$^{31}$)C(O)R$^{31}$, —C(O)OR$^{31}$, —OC(O)R$^{31}$, —S(O)R$^{31}$, —S(O)$_2$R$^{31}$, —P(O)(OR$^{31}$)$_2$, —OP(O)(OR$^{31}$)$_2$, —NO$_2$, =O, =S, =N(R$^{31}$), —CN, $C_{1-6}$ alkyl, $C_{1-6}$ alkyl-R$^{31}$, $C_{2-6}$ alkenyl, and $C_{2-6}$ alkynyl; or $R^{100}$ and $R^{110}$ together with the nitrogen to which they are bound form a 3-10-membered heterocycle optionally substituted with one or more substituents independently selected from: hydroxy, halogen, —CN, —NO$_2$, $C_1$-$C_6$ alkyl, $C_1$-$C_6$ haloalkyl, $C_1$-$C_6$ hydroxyalkyl, and $C_1$-$C_6$ alkoxy, wherein when $R^1$ is hydroxy, the ring formed by $R^{100}$ and $R^{110}$ is not unsubstituted morpholine, and wherein when one of $R^6$ and $R^7$ are selected from hydroxy and $C_1$-$C_6$ alkoxy or when $R^6$ and $R^7$ come together to form

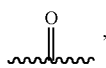

the 3-10-membered heterocycle formed by $R^{100}$ and $R^{110}$ is further optionally substituted with one or more =O;

$R^{120}$ is selected from:
- hydrogen, —$(CH_2—CH_2-G)_y$-V; and
- $C_{3-10}$ alkyl, $C_{2-10}$ alkenyl, $C_{2-10}$ alkynyl, each of which is optionally substituted with one or more substituents independently selected from halogen, —$OR^{31}$, —$SR^{31}$, —$N(R^{31})_2$, —$C(O)R^{31}$, —$C(O)N(R^{31})_2$, —$N(R^{31})C(O)R^{31}$, —$C(O)OR^{31}$, —$OC(O)R^{31}$, —$S(O)R^{31}$, —$S(O)_2R^{31}$, —$P(O)(OR^{31})_2$, —$OP(O)(OR^{31})_2$, —$NO_2$, —CN, $C_{3-20}$ carbocycle, and 3- to 20-membered heterocycle; and
- $C_{3-20}$ saturated carbocycle and 3- to 20-membered heterocycle each of which is optionally substituted with one or more substituents independently selected from halogen, —$OR^{31}$, —$SR^{31}$, —$N(R^{31})_2$, —$C(O)R^{31}$, —$C(O)N(R^{31})_2$, —$N(R^{31})C(O)R^{31}$, —$C(O)OR^{31}$, —$OC(O)R^{31}$, —$S(O)R^{31}$, —$S(O)_2R^{31}$, —$P(O)(OR^{31})_2$, —$OP(O)(OR^{31})_2$, —$NO_2$, =O, =S, =$N(R^{31})$, —CN, $C_{1-6}$ alkyl, $C_{1-6}$ alkyl-$R^{31}$, $C_{2-6}$ alkenyl, and $C_{2-6}$ alkynyl; or
- $C_{1-2}$ alkyl substituted with one or more substituents independently selected from halogen, —$OR^{31}$, —$N(R^{31})_2$, —$C(O)R^{31}$, —$C(O)N(R^{31})_2$, —$N(R^{31})C(O)R^{31}$, —$C(O)OR^{31}$, —$OC(O)R^{31}$, —$S(O)R^{31}$, —$S(O)_2R^{31}$, —$P(O)(OR^{31})_2$, —$OP(O)(OR^{31})_2$, —$NO_2$, —CN, $C_{3-20}$ carbocycle and 3- to 20-membered heterocycle;

each G is independently selected from —O—, —$NR^{32}$—, —S—, or —$SO_2$—;

each D is independently selected from —O—, —$NR^{32}$—, —S—, or —$SO_2$—;

each y is selected from 3-20;

each z is selected from 1-20;

each V is selected from hydrogen and optionally substituted —$C_1$-$C_6$ alkyl;

each T is selected from hydrogen and optionally substituted —$C_1$-$C_6$ alkyl;

each $R^{31}$ is independently selected from hydrogen, and $C_{1-10}$ alkyl, $C_{2-10}$ alkenyl, $C_{2-10}$ alkynyl, $C_{3-10}$ carbocycle, and 3- to 10-membered heterocycle, each of which is optionally substituted with one or more substituents independently selected from halogen, —OH, —CN, —$NO_2$, —$NH_2$, =O, =S, $C_{1-10}$ alkyl, —$C_{1-10}$ haloalkyl, —O—$C_{1-10}$ alkyl, $C_{2-10}$ alkenyl, $C_{2-10}$ alkynyl, $C_{3-10}$ carbocycle, and 3- to 10-membered heterocycle; and $R^{32}$ is independently selected at each occurrence from: hydrogen; and $C_{1-10}$ alkyl, $C_{2-10}$ alkenyl, $C_{2-10}$ alkynyl, $C_{3-10}$ carbocycle, and 3- to 10-membered heterocycle, each of which is optionally substituted with one or more substituents independently selected from halogen, —OH, —CN, —$NO_2$, —$NH_2$, =O, =S, $C_{1-10}$ alkyl, —$C_{1-10}$ haloalkyl, —O—$C_{1-10}$ alkyl, $C_{2-10}$ alkenyl, $C_{2-10}$ alkynyl, $C_{3-10}$ carbocycle, and 3- to 10-membered heterocycle;

wherein the optional substituents on $R^{20}$, $R^{21}$, $R^{22}$, $R^{23}$, $R^{24}$, $R^{51}$, V, and T are independently selected at each occurrence from:
- halogen, —$OR^{30}$, —$N(R^{30})_2$, —(O—$CH_2$—$(CH_2)_p)_n$—W, —$SR^{30}$, —$C(O)R^{30}$, —$C(O)N(R^{30})_2$, —$N(R^{30})C(O)R^{30}$, —$C(O)OR^{30}$, —$OC(O)R^{30}$, —$S(O)R^{30}$, —$S(O)_2R^{30}$, —$P(O)(OR^{30})_2$, —$OP(O)(OR^{30})_2$, —$NO_2$, =O, =S, =$N(R^{30})$, and —CN;
- $C_{1-10}$ alkyl, $C_{2-10}$ alkenyl, $C_{2-10}$ alkynyl, each of which is optionally substituted with one or more substituents independently selected from halogen, —$OR^{30}$, —$SR^{30}$, —$N(R^{30})_2$, —$C(O)R^{30}$, —$C(O)N(R^{30})_2$, —$N(R^{30})C(O)R^{30}$, —$C(O)OR^{30}$, —$OC(O)R^{30}$, —$S(O)R^{30}$, —$S(O)_2R^{30}$, —$P(O)(OR^{30})_2$, —$OP(O)(OR^{30})_2$, —$NO_2$, =O, =S, =$N(R^{30})$, —CN, $C_{3-10}$ carbocycle and 3- to 10-membered heterocycle; and
- $C_{3-10}$ carbocycle and 3- to 10-membered heterocycle each of which is optionally substituted with one or more substituents independently selected from halogen, —$OR^{30}$, —$SR^{30}$, —$N(R^{30})_2$, —$C(O)R^{30}$, —$C(O)N(R^{30})_2$, —$N(R^{30})C(O)R^{30}$, —$C(O)OR^{30}$, —$OC(O)R^{30}$, —$S(O)R^{30}$, —$S(O)_2R^{30}$, —$P(O)(OR^{30})_2$, —$OP(O)(OR^{30})_2$, —$NO_2$, =O, =S, =$N(R^{30})$, —CN, $C_{1-6}$ alkyl, $C_{1-6}$ alkyl-$R^{30}$, $C_{2-6}$ alkenyl, and $C_{2-6}$ alkynyl;

$R^{30}$ is independently selected at each occurrence from hydrogen; $C_{1-10}$ alkyl, $C_{2-10}$ alkenyl, $C_{2-10}$ alkynyl, $C_{3-10}$ carbocycle, and 3- to 10-membered heterocycle, each of which is optionally substituted with one or more substituents independently selected from halogen, —OH, —CN, —$NO_2$, —$NH_2$, =O, =S, $C_{1-10}$ alkyl, —$C_{1-10}$ haloalkyl, —O—$C_{1-10}$ alkyl, $C_{2-10}$ alkenyl, $C_{2-10}$ alkynyl, $C_{3-10}$ carbocycle, and 3- to 10-membered heterocycle;

$R^{51}$ is independently selected at each occurrence from —$((CH_2)_q$—$CH_2$-D$)_z$-T and optionally substituted $C_{5-30}$ alkyl;

q is selected from 1 to 6;

each p is selected from 1 or 2;

each n is selected from 3-7; and each W is selected from hydrogen, —OH, —$C_1$-$C_4$ alkyl and —$O(C_1$-$C_4$ alkyl).

In certain embodiments, the compound of Formula (I) is represented by Formula (IA):

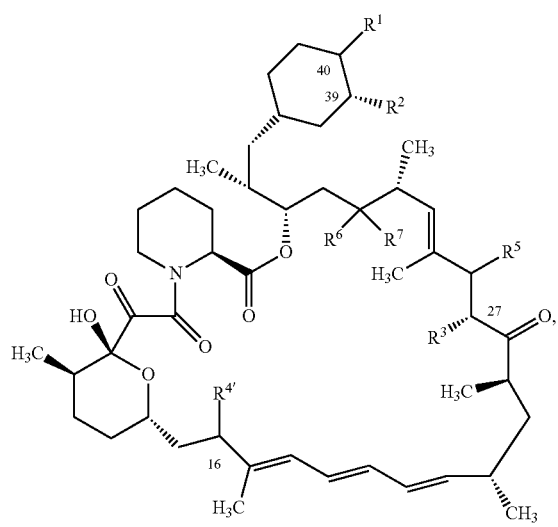

(IA)

or a salt thereof.

In certain embodiments, the compound of Formula (I) is represented by Formula (IB):

(IB)

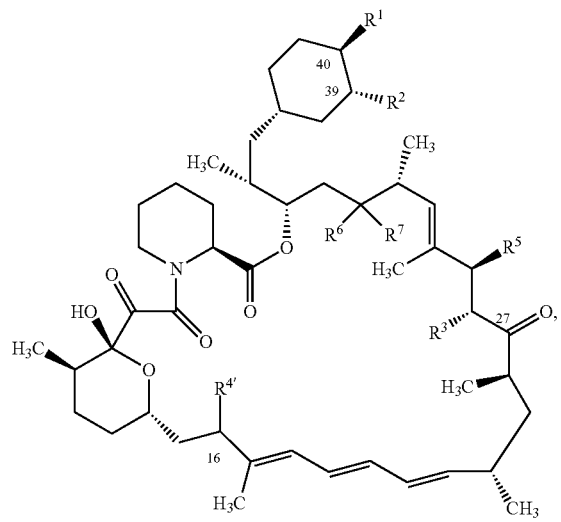

or a salt thereof.

In certain embodiments, the compound of Formula (I) is represented by Formula (IC):

(IC)

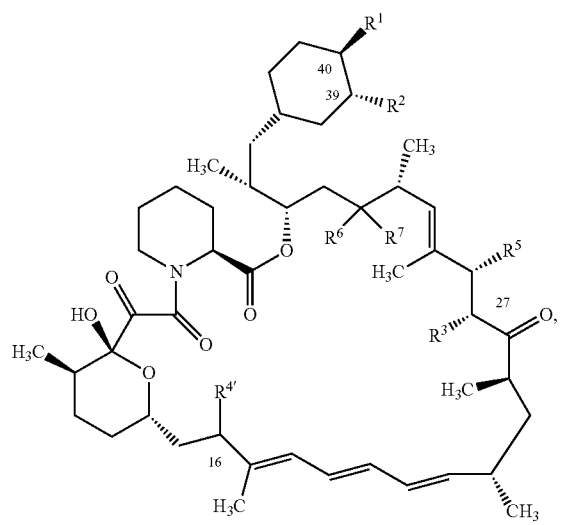

or a salt thereof.

In certain embodiments, the compound of Formula (I) is represented by Formula (ID):

(ID)

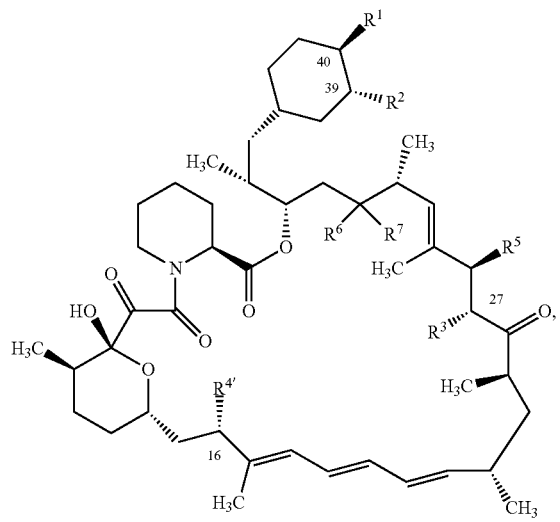

or a salt thereof.

In certain embodiments, the compound of Formula (I) is represented by Formula (IE):

(IE)

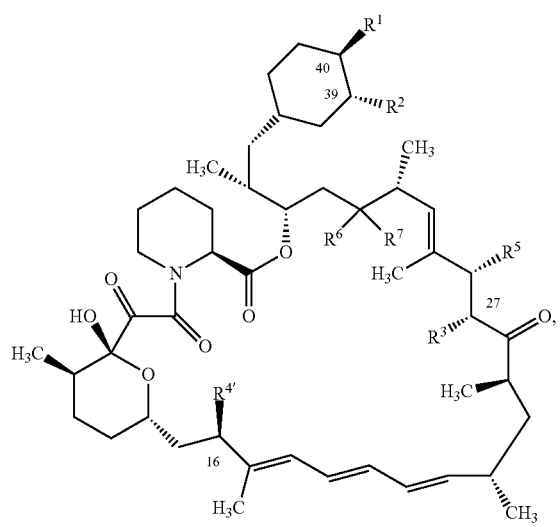

or a salt thereof.

In certain embodiments, the compound of Formula (I) is represented by Formula (IF):

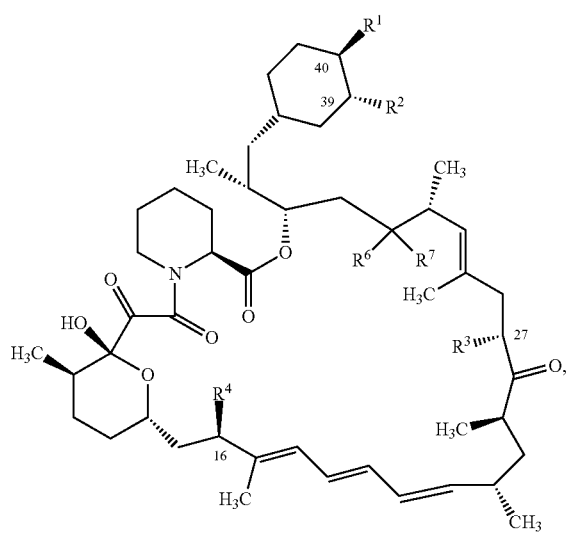

or a salt thereof.

In certain embodiments, the compound of Formula (I) is represented by Formula (IG):

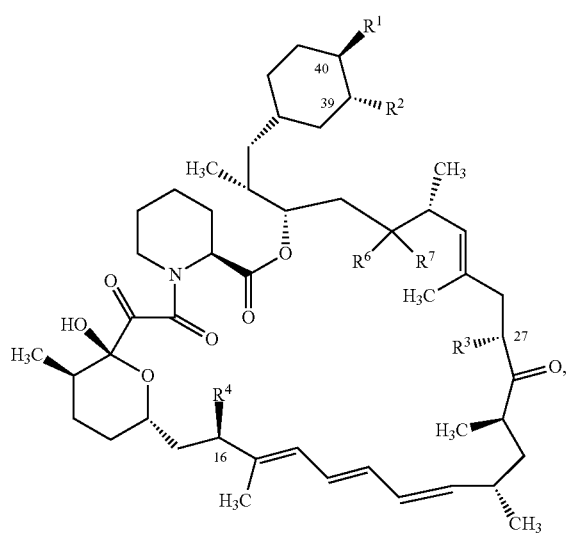

or a salt thereof.

In some embodiments, for the compound or salt of Formula (I), (IA), (IB), (IC), (ID), (IE), (IF), or (IG), $R^{51'}$ is represented by $R^{51}$.

In some embodiments, for the compound or salt of Formula (I), (IA), (IB), (IC), (ID), (IE), (IF), or (IG), $R^{100'}$ is represented by $R^{100}$.

In some embodiments, for the compound or salt of Formula (I), (IA), (IB), (IC), (ID), (IE), (IF), or (IG), $R^{4'}$ is $R^4$.

In some embodiments, for the compound or salt of Formula (I), (IA), (IB), (IC), (ID), (IE), (IF), or (IG),

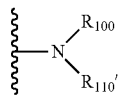

is represented by

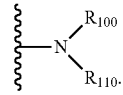

In some embodiments, for the compound or salt of Formula (I), (IA), (IB), (IC), (ID), (IE), (IF), or (IG), $R^{100}$ and $R^{110'}$ come together with the nitrogen to which they are bound form a 3-10-membered heteroaryl optionally substituted with one or more substituents independently selected from: hydroxy, halogen, —CN, —NO$_2$, C$_1$-C$_6$ alkyl, C$_1$-C$_6$ haloalkyl, C$_1$-C$_6$ hydroxyalkyl, and C$_1$-C$_6$ alkoxy.

In some embodiments, for the compound or salt of Formula (I), (IA), (IB), (IC), (ID), (IE), (IF), or (IG), $R^{100}$ and $R^{110'}$ together with the nitrogen to which they are bound form a 3-10-membered heterocycle optionally substituted with one or more substituents independently selected from: hydroxy, halogen, —CN, —NO$_2$, C$_1$-C$_6$ alkyl, C$_1$-C$_6$ haloalkyl, C$_1$-C$_6$ hydroxyalkyl, and C$_1$-C$_6$ alkoxy, wherein when $R^1$ is hydroxy, the ring formed by $R^{100}$ and $R^{110}$ is not unsubstituted morpholine.

In some embodiments, for the compound or salt of Formula (I), (IA), (IB), (IC), (ID), (IE), (IF), or (IG), $R^{100}$ and $R^{110'}$ come together with the nitrogen to which they are bound form a 3-5 membered saturated heterocycle optionally substituted with one or more substituents independently selected from: hydroxy, halogen, —CN, —NO$_2$, C$_1$-C$_6$ alkyl, C$_1$-C$_6$ haloalkyl, C$_1$-C$_6$ hydroxyalkyl, and C$_1$-C$_6$ alkoxy.

In some embodiments, for the compound or salt of Formula (I), (IZ), (IA), (IB), (IC), (ID), (IE), (IF), or (IG), when $R^6$ and $R^7$ come together to form

and $R^1$ is hydroxy, $R^4$ is not

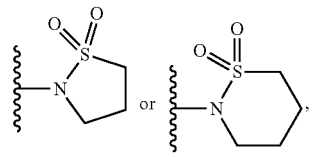

and when $R^6$ and $R^7$ come together to form

and $R^1$ is

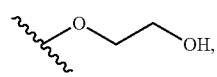 [SMILES: *OCCO]

$R^4$ is not

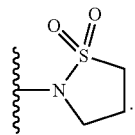

In some cases, $R^4$ is not

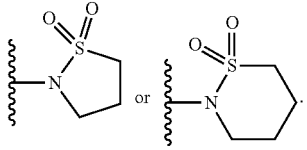

In some cases, $R^4$ is not

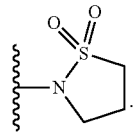

In some cases, $R^4$ is not

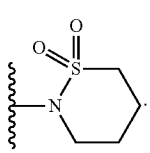

In some cases, $R^4$ may not be

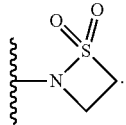

In some embodiments, for the compound or salt of Formula (I), (IA), (IB), (IC), (ID), (IE), (IF), or (IG), $R^{100}$ and $R^{110'}$ do not come together with the nitrogen to which they are bound to form a 3-10-membered ring.

In some embodiments, for the compound or salt of Formula (I), (IZ), (IA), (IB), (IC), (ID), (IE), (IF), or (IG), $R^4$ is

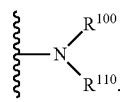

In some embodiments, $R^{100}$ is selected from the same moiety as $R^{110}$, for example, $R^{100}$ is ethyl and $R^{110}$ is ethyl. In some embodiments, $R^{100}$ is different than $R^{110}$. In some embodiments, $R^{100}$ is H. In some embodiments, $R^{110}$ is selected from: —(CH$_2$—CH$_2$-G)$_y$-V; and C$_{1-10}$ alkyl optionally substituted with one or more substituents independently selected from halogen, —OR$^{31}$, —SR$^{31}$, —N(R$^{31}$)$_2$, —C(O)R$^{31}$, —C(O)N(R$^{31}$)$_2$, —N(R$^{31}$)C(O)R$^{31}$, —C(O)OR$^{31}$, —OC(O)R$^{31}$, —S(O)R$^{31}$, —S(O)$_2$R$^{31}$, —P(O)(OR$^{31}$)$_2$, —OP(O)(OR$^{31}$)$_2$, —NO$_2$, —CN, C$_{3-20}$ carbocycle and 3- to 20-membered heterocycle.

In some embodiments, for the compound or salt of Formula (I), (IZ), (IA), (IB), (IC), (ID), (IE), (IF), or (IG), $R^4$ is

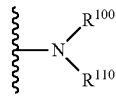

and $R^{110}$ is selected from —(CH$_2$—CH$_2$-G)$_y$-V. In some embodiments, y of —(CH$_2$—CH$_2$-G)$_y$-V is 1 to 1000. In some embodiments, y is 1 to 800. In some embodiments, y is 1 to 500. In some embodiments, y is 1 to 300. In some embodiments, y is 1 to 100. In some embodiments, y is 1 to 50. In some embodiments, y is 1 to 25. In some embodiments, y is 3 to 1000. In some embodiments, y is 10 to 1000. In some embodiments, y is 50 to 1000. In some embodiments, y is 100 to 1000. In some embodiments, y is 200 to 1000. In some embodiments, y is 500 to 1000. In some embodiments, y of —(CH$_2$—CH$_2$-G)$_y$-V for $R^{110}$ is 3 to 10. In some embodiments, y of —(CH$_2$—CH$_2$-G)$_y$-V for $R^{110}$ is 5 to 10. In some embodiments, y is 1, 2, 3, 4, 5, 6, 7, 8, 9, 10, 11, 12, 13, 14, 15, 16, 17, 18, 19, 20, 25, or 100.

In some embodiments, for the compound or salt of Formula (I), (IZ), (IA), (IB), (IC), (ID), (IE), (IF), or (IG), $R^4$ is

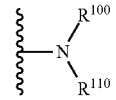

and $R^{110}$ is selected from —(CH$_2$—CH$_2$-G)$_y$-V, wherein G of —(CH$_2$—CH$_2$-G)$_y$-V is —O—. In some embodiments, each G of —(CH$_2$—CH$_2$-G)$_y$-V for $R^{110}$ is —NR$^{32}$—. In some embodiments, each $R^{32}$ of —NR$^{32}$— is independently selected from hydrogen; and C$_{1-10}$ alkyl, each of which is optionally substituted with one or more substituents independently selected from halogen, —OH, C$_{1-10}$ alkyl, —C$_{1-10}$ haloalkyl, and —O—C$_{1-10}$ alkyl.

In some embodiments, for the compound or salt of Formula (I), (IZ), (IA), (IB), (IC), (ID), (IE), (IF), or (IG), $R^4$ is

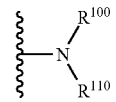

and $R^{110}$ is selected from —(CH$_2$—CH$_2$-G)$_y$-V, wherein each V of $R^{110}$ is optionally substituted —C$_1$-C$_{10}$ alkyl. In some embodiments, each V of $R^{110}$ is optionally substituted —C$_1$-C$_6$ alkyl. In some embodiments, the —C$_1$-C$_6$ alkyl on V of $R^{110}$ is optionally substituted with one or more substituents independently selected from halogen, —OR$^{30}$, —N(R$^{30}$)$_2$, —(O—CH$_2$—(CH$_2$)$_p$)$_n$—W, —SR$^{30}$, —C(O)R$^{30}$, —C(O)N(R$^{30}$)$_2$, —N(R$^{30}$)C(O)R$^{30}$, —C(O)OR$^{30}$, —OC(O)R$^{30}$, —S(O)R$^{30}$, —S(O)$_2$R$^{30}$, —P(O)(OR$^{30}$)$_2$, —OP(O)(OR$^{30}$)$_2$, —NO$_2$, =O, =S, =N(R$^{30}$), and —CN.

In some embodiments, for the compound or salt of Formula (I), (IA), (IB), (IC), (ID), (IE), (IF), or (IG), —$C_1$-$C_6$ alkyl on V of $R^{110}$ is substituted with one or more substituents independently selected from —$OR^{30}$ and —$N(R^{30})_2$. In some embodiments, the —$C_1$-$C_6$ alkyl on V of $R^{110}$ is substituted with one or more —$N(R^{30})_2$. In some embodiments, the —$C_1$-$C_6$ alkyl on V of $R^{110}$ is substituted with one or more —$OR^{30}$. In some embodiments, each $R^{30}$ is selected from hydrogen; and $C_{1-5}$ alkyl, $C_{3-6}$ carbocycle, and 3- to 6-membered heterocycle, each of which is optionally substituted with one or more substituents independently selected from halogen, —OH, —CN, —$NO_2$, —$NH_2$, =O, =S, $C_{1-10}$ alkyl, —$C_{1-10}$ haloalkyl, and —O—$C_{1-10}$ alkyl.

In some embodiments, for the compound or salt of Formula (I), (IA), (IB), (IC), (ID), (IE), (IF), or (IG), $R^4$ is

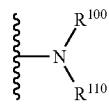

and $R^{100}$ and $R^{110}$ of

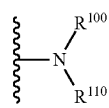

come together with the nitrogen to which they are bound form a 3-, 4-, 5-, 7-, or 8-membered heterocycle optionally substituted with one or more substituents independently selected from: hydroxy, halogen, —CN, —$NO_2$, $C_1$-$C_6$ alkyl, $C_1$-$C_6$ haloalkyl, $C_1$-$C_6$ hydroxyalkyl, and $C_1$-$C_6$ alkoxy. In some embodiments, the 3- to 8-heterocycle is unsaturated. In some embodiments, the 3- to 8-heterocycle is saturated.

In some embodiments, for the compound or salt of Formula (I), (IZ), (IA), (IB), (IC), (ID), (IE), (IF), or (IG), $R^4$ is

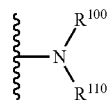

wherein $R^{100}$ and $R^{110}$ together with the nitrogen to which they are bound form a 3-10-membered heterocycle optionally substituted with one or more substituents independently selected from: hydroxy, halogen, —CN, —$NO_2$, $C_1$-$C_6$ alkyl, $C_1$-$C_6$ haloalkyl, $C_1$-$C_6$ hydroxyalkyl, and $C_1$-$C_6$ alkoxy, wherein when $R^1$ is hydroxy, the ring formed by $R^{100}$ and $R^{110}$ is not unsubstituted morpholine, and wherein when one of $R^6$ and $R^7$ are selected from hydroxy and $C_1$-$C_6$ alkoxy or when $R^6$ and $R^7$ come together to form

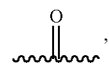

the 3-10-membered heterocycle formed by $R^{100}$ and $R^{110}$ is further optionally substituted with one or more =O.

In some embodiments, for the compound or salt of Formula (I), (IZ), (IA), (IB), (IC), (ID), (IE), (IF), or (IG), $R^4$ is

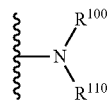

wherein $R^{100}$ and $R^{110}$ together with the nitrogen to which they are bound form a 3-10-membered heterocycle optionally substituted with one or more substituents independently selected from: hydroxy, halogen, —CN, —$NO_2$, $C_1$-$C_6$ alkyl, $C_1$-$C_6$ haloalkyl, $C_1$-$C_6$ hydroxyalkyl, and $C_1$-$C_6$ alkoxy, wherein when $R^1$ is hydroxy, the ring formed by $R^{100}$ and $R^{110}$ is substituted morpholine, and wherein when one of $R^6$ and $R^7$ are selected from hydroxy and $C_1$-$C_6$ alkoxy or when $R^6$ and $R^7$ come together to form

the 3-10-membered heterocycle formed by $R^{100}$ and $R^{110}$ is further optionally substituted with one or more =O.

In some embodiments, for the compound or salt of Formula (I), (IZ), (IA), (IB), (IC), (ID), (IE), (IF), or (IG), $R^4$ is

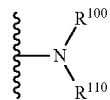

wherein $R^{100}$ and $R^{110}$ together with the nitrogen to which they are bound form a heterocycle. The heterocycle may be selected from a 3-10-membered heterocycle, 3-8-membered heterocycle, 3-6-membered heterocycle, 3-5-membered heterocycle, 4-10-membered heterocycle, 4-8-membered heterocycle, 4-6-membered heterocycle, and 4-5-membered heterocycle, any of which is optionally substituted with one or more substituents independently selected from: hydroxy, halogen, —CN, —$NO_2$, $C_1$-$C_6$ alkyl, $C_1$-$C_6$ haloalkyl, $C_1$-$C_6$ hydroxyalkyl, =O, and $C_1$-$C_6$ alkoxy. In some embodiments, the heterocycle is optionally substituted with one or more substituents selected from hydroxy, halogen, —CN, —$NO_2$, $C_1$-$C_6$ alkyl, $C_1$-$C_6$ haloalkyl, $C_1$-$C_6$ hydroxyalkyl, and $C_1$-$C_6$ alkoxy. In some embodiments, the heterocycle is optionally substituted with one or more substituents selected from hydroxy, $C_1$-$C_6$ alkyl, $C_1$-$C_6$ haloalkyl, $C_1$-$C_6$ hydroxyalkyl, =O, and $C_1$-$C_6$ alkoxy. In some embodiments, the heterocycle is unsaturated. In some embodiments, the heterocycle is saturated. In some embodiments, the heterocycle is aromatic. In some embodiments, the heterocycle further comprises at least a second heteroatom. In some embodiments, the second heteroatom is selected from nitrogen, oxygen, and sulfur. In some embodiments, the second heteroatom is selected from nitrogen and sulfur. In some embodiments, the second heteroatom is selected from oxygen and sulfur. In some embodiments, the second heteroatom is selected from nitrogen and oxygen. In some embodiments, the second hetereoatom is sulfur. In some embodiments, the second heteroatom is nitrogen. In some embodiments, the second heteroatom is oxygen.

In some embodiments, for the compound or salt of Formula (I), (IZ), (IA), (IB), (IC), (ID), (IE), (IF), or (IG), $R^4$ is

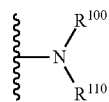

wherein $R^{100}$ and $R^{110}$ together with the nitrogen to which they are bound form a 3-10-membered heterocycle optionally substituted with one or more substituents independently selected from: hydroxy, halogen, —CN, —NO$_2$, C$_1$-C$_6$ alkyl, C$_1$-C$_6$ haloalkyl, C$_1$-C$_6$ hydroxyalkyl, and C$_1$-C$_6$ alkoxy, wherein when $R^1$ is hydroxy, the ring formed by $R^{100}$ and $R^{110}$ is not

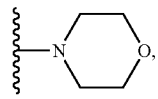

and wherein when one of $R^6$ and $R^7$ are selected from hydroxy and C$_1$-C$_6$ alkoxy or when $R^6$ and $R^7$ come together to form

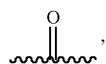

the 3-10-membered heterocycle formed by $R^{100}$ and $R^{110}$ is further optionally substituted with one or more =O.

In some embodiments, for the compound or salt of Formula (I), (IZ), (IA), (IB), (IC), (ID), (IE), (IF), or (IG), $R^4$ is

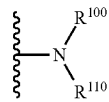

and, $R^{100}$ and $R^{110}$ of

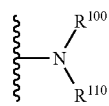

come together with the nitrogen to which they are bound form an aziridine, 2H-azirine, azetidine, 2,3-dihydroazete, 1,3-diazetidine, pyrrolidine, 2-pyrroline, 2H-pyrrole, 1H-pyrrole, pyrazolidine, imidazolidine, 2-pyrazoline, 2-imidazoline, pyrazole, imidazole, 1,2,4-triazole, 1,2,3-triazole, tetrazole, oxazole, isoxazole, isothiazole, thiazole, 1,2,5-oxadiazole, 1,2,3-oxadiazole, 1,3,4-thiadiazole, 1,2,5-thiadiazole, 2,4-thiazolidinedione, succinimide, oxazine, thiomorpholine, thiazine, 2-oxazolidone, hydantoin, cytosine, thymine, uracil, thiomorpholine dioxide, piperidine, pyridine, piperazine, pyridazine, pyrimidine, pyrazine, triazine, 2,3-dihydroazepine, 2,5-dihydroazepine, 4,5-dihydroazepine, azepine, 2H-azepine, 3H-azepine, 4H-azepine, 1,2-diazepine, 1,3-diazepine, 1,4-diazepine, 1,4-thiazepine, azocane, and azocine, each of which is optionally substituted with one or more substituents independently selected from: hydroxy, halogen, —CN, —NO$_2$, C$_1$-C$_6$ alkyl, C$_1$-C$_6$ haloalkyl, C$_1$-C$_6$ hydroxyalkyl, and C$_1$-C$_6$ alkoxy.

In some embodiments, for the compound or salt of Formula (I), (IZ), (IA), (IB), (IC), (ID), (IE), (IF), or (IG), $R^4$ is

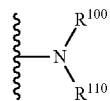

and, $R^{100}$ and $R^{110}$ of

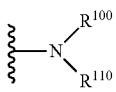

come together with the nitrogen to which they are bound to form an aziridine, 2H-azirine, azetidine, 2,3-dihydroazete, 1,3-diazetidine, pyrrolidine, 2-pyrroline, 2H-pyrrole, 1H-pyrrole, pyrazolidine, imidazolidine, 2-pyrazoline, 2-imidazoline, pyrazole, imidazole, 1,2,4-triazole, 1,2,3-triazole, tetrazole, oxazole, isoxazole, isothiazole, thiazole, 1,2,5-oxadiazole, 1,2,3-oxadiazole, 1,3,4-thiadiazole, 1,2,5-thiadiazole, 2,4-thiazolidinedione, succinimide, oxazine, thiomorpholine, thiazine, 2-oxazolidone, hydantoin, cytosine, thymine, uracil, thiomorpholine dioxide, piperidine, pyridine, piperazine, pyridazine, pyrimidine, pyrazine, triazine, 2,3-dihydroazepine, 2,5-dihydroazepine, 4,5-dihydroazepine, azepine, 2H-azepine, 3H-azepine, 4H-azepine, 1,2-diazepine, 1,3-diazepine, 1,4-diazepine, 1,4-thiazepine, azocane, azocine, 1,2-thiazetidine, isothiazolidine, and imidazolidine, each of which is optionally substituted with one or more substituents independently selected from: hydroxy, halogen, —CN, —NO$_2$, C$_1$-C$_6$ alkyl, C$_1$-C$_6$ haloalkyl, C$_1$-C$_6$ hydroxyalkyl, and C$_1$-C$_6$ alkoxy.

In some embodiments, for the compound or salt of Formula (I), (IZ), (IA), (IB), (IC), (ID), (IE), (IF), or (IG), $R^4$ is

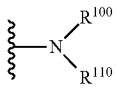

and, $R^{100}$ and $R^{110}$ of

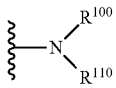

come together with the nitrogen to which they are bound to form an aziridine, 2H-azirine, azetidine, 2,3-dihydroazete, 1,3-diazetidine, pyrrolidine, 2-pyrroline, 2H-pyrrole, 1H-pyrrole, pyrazolidine, imidazolidine, 2-pyrazoline, 2-imidazoline, pyrazole, imidazole, 1,2,4-triazole, 1,2,3-triazole, tetrazole, oxazole, isoxazole, isothiazole, thiazole, 1,2,5-oxadiazole, 1,2,3-oxadiazole, 1,3,4-thiadiazole, 1,2,5-thiadiazole, 2,4-thiazolidinedione, succinimide, oxazine, thiomorpholine, thiazine, 2-oxazolidone, hydantoin, cytosine, thymine, uracil, thiomorpholine dioxide, piperidine, pyridine, piperazine, pyridazine, pyrimidine, pyrazine, triazine, 2,3-dihydroazepine, 2,5-dihydroazepine, 4,5-dihydroazepine, azepine, 2H-azepine, 3H-azepine, 4H-azepine, 1,2-diazepine, 1,3-diazepine, 1,4-diazepine, 1,4-thiazepine, azocane, azocine, 1,2-thiazetidine, isothiazolidine, and imidazolidine, each of which is optionally substituted with one or more substituents independently selected from: hydroxy, halogen, —CN, —NO$_2$, C$_1$-C$_6$ alkyl, C$_1$-C$_6$ haloalkyl, C$_1$-C$_6$ hydroxyalkyl, =O, and C$_1$-C$_6$ alkoxy.

In some embodiments, for the compound or salt of Formula (I), (IZ), (IA), (IB), (IC), (ID), (IE), (IF), or (IG), R$^4$ is

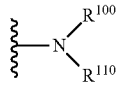

and, R$^{100}$ and R$^{110}$ of

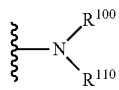

come together with the nitrogen to which they are bound to form azetidine, 1,2-thiazetidine, isothiazolidine, and imidazolidine, each of which is optionally substituted with one or more substituents independently selected from: hydroxy, halogen, —CN, —NO$_2$, C$_1$-C$_6$ alkyl, C$_1$-C$_6$ haloalkyl, C$_1$-C$_6$ hydroxyalkyl, C$_1$-C$_6$ alkoxy, =O, when one of R$^6$ and R$^7$ are selected from hydroxy and C$_1$-C$_6$ alkoxy or when R$^6$ and R$^7$ come together to form

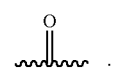

In some embodiments, for the compound or salt of Formula (I), (IZ), (IA), (IB), (IC), (ID), (IE), (IF), or (IG), R$^4$ is

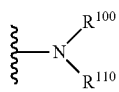

and, R$^{100}$ and R$^{110}$ of

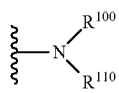

come together with the nitrogen to which they are bound to form

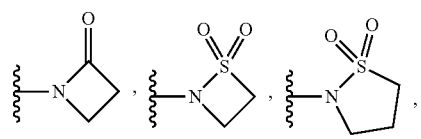

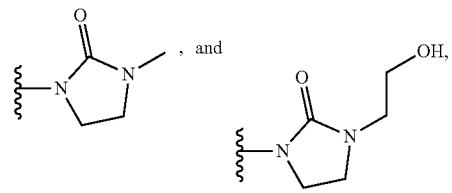

and one of R$^6$ and R$^7$ are selected from hydroxy and C$_1$-C$_6$ alkoxy or R$^6$ and R$^7$ come together to form

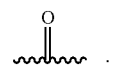

In some embodiments, for the compound or salt of Formula (I), (IZ), (IA), (IB), (IC), (ID), (IE), (IF), or (IG), R$^4$ is

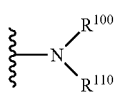

and, R$^{100}$ and R$^{110}$ of

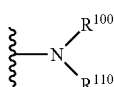

come together with the nitrogen to which they are bound to form

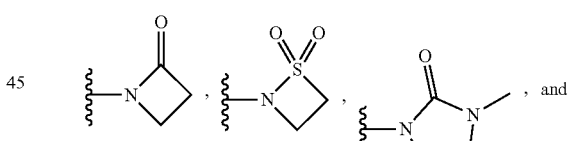

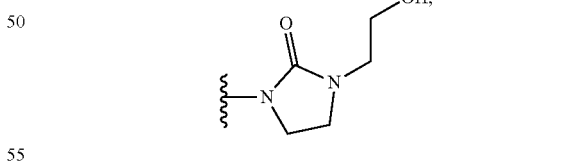

when one of R$^6$ and R$^7$ are selected from hydroxy and C$_1$-C$_6$ alkoxy or when R$^6$ and R$^7$ come together to form

In some embodiments, for the compound or salt of Formula (I), (IZ), (IA), (IB), (IC), (ID), (IE), (IF), or (IG), R$^4$ is

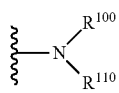

and, $R^{100}$ and $R^{110}$ of

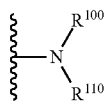

come together with the nitrogen to which they are bound to form

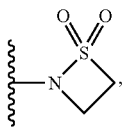

and $R^1$ is not selected from

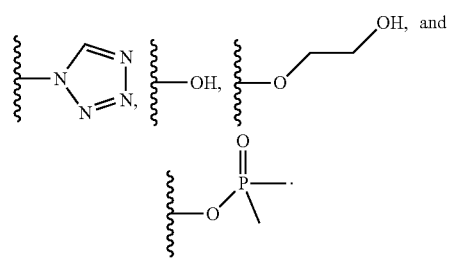

In some embodiments, for the compound or salt of Formula (I), (IA), (IB), (IC), (ID), (IE), (IF), or (IG), $R^4$ is

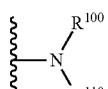

and, $R^{100}$ and $R^{110}$ of

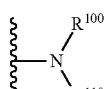

come together with the nitrogen to which they are bound to form

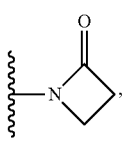

when $R^1$ is not selected from

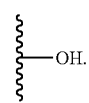

In some embodiments, for the compound or salt of Formula (I), (IZ), (IA), (IB), (IC), (ID), (IE), (IF), or (IG), $R^4$ is

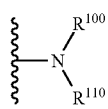

and, $R^{100}$ and $R^{110}$ of

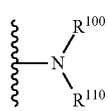

come together with the nitrogen to which they are bound to form

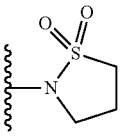

when $R^1$ is not selected from

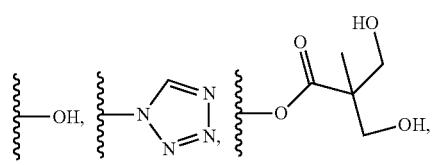

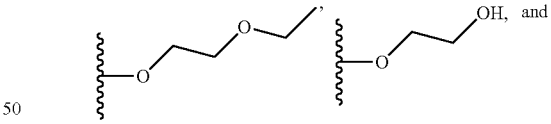

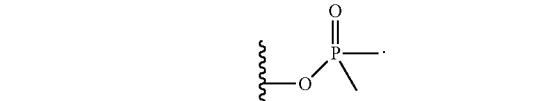

In some embodiments, for the compound or salt of Formula (I), (IZ), (IA), (IB), (IC), (ID), (IE), (IF), or (IG), $R^4$ is

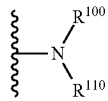

and, $R^{100}$ and $R^{110}$ of

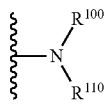

come together with the nitrogen to which they are bound to form

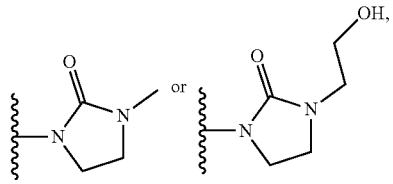

when $R^1$ is not selected from

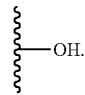

In some embodiments, for the compound or salt of Formula (I), (IZ), (IA), (IB), (IC), (ID), (IE), (IF), or (IG), $R^4$ is

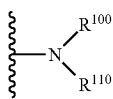

and, $R^{100}$ and $R^{110}$ of

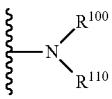

come together with the nitrogen to which they are bound form an azetidine-2-one, thiazetidine 1,1-dioxide, or isothiazolidine 1,1-dioxide, any of which is substituted with one or more substituents independently selected from: hydroxy, halogen, —CN, —NO$_2$, $C_1$-$C_6$ alkyl, $C_1$-$C_6$ haloalkyl, $C_1$-$C_6$ hydroxyalkyl, and $C_1$-$C_6$ alkoxy.

In some embodiments, for the compound or salt of Formula (I), (IZ), (IA), (IB), (IC), (ID), (IE), (IF), or (IG), $R^4$ is

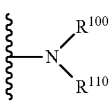

wherein $R^{100}$ is hydrogen or $C_{1-10}$ alkyl; and $R^{110}$ is selected from —(CH$_2$—CH$_2$-G)$_y$-V, —S(O)R$^{51}$, —S(O)$_2$R$^{51}$, —C(O)R$^{51}$, —C(O)N(R$^{51}$)$_2$, and —C(O)OR$^{51}$; or $R^{100}$ and $R^{110}$ together with the nitrogen to which they are bound form a 3-10-membered heterocycle optionally substituted with one or more substituents selected from: hydroxy, halogen, —CN, —NO$_2$, $C_1$-$C_6$ alkyl, $C_1$-$C_6$ haloalkyl, $C_1$-$C_6$ hydroxyalkyl, and $C_1$-$C_6$ alkoxy, and =O.

In some embodiments, for the compound or salt of Formula (I), (IZ), (IA), (IB), (IC), (ID), (IE), (IF), or (IG), $R^4$ is

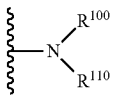

wherein $R^{100}$ is hydrogen or $C_{1-10}$ alkyl; and $R^{110}$ is selected from —(CH$_2$—CH$_2$-G)$_y$-V, —S(O)R$^{51}$, and —S(O)$_2$R$^{51}$; or $R^{100}$ and $R^{110}$ together with the nitrogen to which they are bound form a 3-10-membered heterocycle optionally substituted with one or more substituents selected from: hydroxy, halogen, —CN, —NO$_2$, $C_1$-$C_6$ alkyl, $C_1$-$C_6$ haloalkyl, $C_1$-$C_6$ hydroxyalkyl, and $C_1$-$C_6$ alkoxy, and =O.

In some embodiments, for the compound or salt of Formula (I), (IZ), (IA), (IB), (IC), (ID), (IE), (IF), or (IG), $R^4$ is

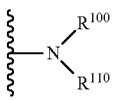

wherein $R^{100}$ is hydrogen or $C_{1-10}$ alkyl; and $R^{110}$ is selected from —S(O)R$^{51}$, and —S(O)$_2$R$^{51}$; or $R^{100}$ and $R^{110}$ together with the nitrogen to which they are bound form a 3-10-membered heterocycle optionally substituted with one or more substituents selected from: hydroxy, halogen, —CN, —NO$_2$, $C_1$-$C_6$ alkyl, $C_1$-$C_6$ haloalkyl, $C_1$-$C_6$ hydroxyalkyl, and $C_1$-$C_6$ alkoxy, and =O.

In some embodiments, for the compound or salt of Formula (I), (IZ), (IA), (IB), (IC), (ID), (IE), (IF), or (IG), $R^4$ is

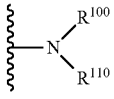

wherein $R^{100}$ is hydrogen or $C_{1-10}$ alkyl; and $R^{110}$ is selected from —S(O)R$^{51}$, and —S(O)$_2$R$^{51}$; or $R^{100}$ and $R^{110}$ together with the nitrogen to which they are bound form a 3-10-membered heterocycle optionally substituted with one or more substituents selected from: hydroxy, halogen, —CN, —NO$_2$, $C_1$-$C_6$ alkyl, $C_1$-$C_6$ haloalkyl, $C_1$-$C_6$ hydroxyalkyl, and $C_1$-$C_6$ alkoxy, and =O.

In some embodiments, for the compound or salt of Formula (I), (IZ), (IA), (IB), (IC), (ID), (IE), (IF), or (IG), $R^{51}$ is independently selected at each occurrence from —((CH$_2$)$_q$—CH$_2$-D)$_z$-T and optionally substituted $C_{5-30}$ alkyl; wherein q is independently selected at at each occurrence from 1 to 6, each D is independently selected from —O—, —NR$^{32}$—, —S—, or —SO$_2$—; each z is selected from 1-20; and each T is selected from hydrogen and optionally substituted —$C_1$-$C_6$ alkyl. In some embodiments, $R^{51}$, is independently selected at each occurrence from —((CH$_2$)$_q$—CH$_2$-D)$_z$-T. In some embodiments, $R^{51}$, is optionally substituted $C_{5-30}$ alkyl. In some embodiments, q is independently selected at at each occurrence from 1 to 6, 1 to 5, 1 to 4, 1 to 3, or 1 to 2. In some embodiments, q is 1 to 5. In some embodiments, q is 1 to 4. In some embodiments, q is 1 to 3. In some embodiments, q is 1 to 2. In some embodiments, q is 6. In some embodiments, q is 5. In some embodiments, q is 4. In some embodiments, q is 3. In some embodiments, q is 2. In some embodiments, q is 1. In some embodiments, D is independently selected at each occurrence from —O—, —NR$^{32}$—, or —SO$_2$—. In some embodiments, D is independently selected at each occurrence from —O—, —NR$^{32}$—, or —SO$_2$—. In some embodiments, D is independently selected at each occurrence from —O— or —NR$^{32}$. In some embodiments, D is independently selected at each occurrence from —O—. In some embodiments, z is selected from 1 to 500. In some embodiments, z is selected from 1 to 50. In some embodiments, z is selected from 1 to 300. In some embodiments, z is selected from 3 to 500. In some embodiments, z is selected from 3 to 250. In some embodiments, z is selected from 3 to 50. In some embodiments, z is selected from 3 to 25. In some embodiments, z is selected from 3 to 20. In some embodiments, z is selected from 3 to 10. In some embodiments, z is selected from 3. In some embodiments, z is selected from 20. In some embodiments, T is is selected from hydrogen and optionally substituted —C$_1$-C$_6$ alkyl. In some embodiments, T is hydrogen. In some embodiments, T is selected from optionally substituted —C$_1$-C$_6$ alkyl. In some embodiments, T is selected from unsubstituted —C$_1$-C$_6$ alkyl. In some embodiments, R$^{32}$ of —NR$^{32}$— is selected from hydrogen and C$_{1-10}$ alkyl. In some embodiments, R$^4$ is selected from

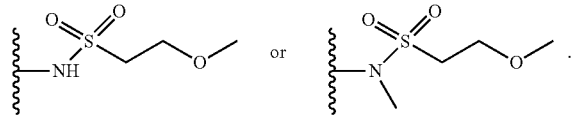

In some embodiments, R$^{32}$ of —NR$^{32}$— is hydrogen. In some embodiments, R$^{32}$ of —NR$^{32}$— is selected from C$_{1-10}$ alkyl.

In some embodiments, for the compound or salt of Formula (I), (IZ), (IA), (IB), (IC), (ID), (IE), (IF), or (IG), R$^{51}$ is independently selected at each occurrence from —((CH$_2$)$_q$—CH$_2$-D)$_z$-T and optionally substituted C$_{5-30}$ alkyl; wherein q is independently selected at at each occurrence from 1 to 6, each D is independently selected from —O—, —NR$^{32}$—, —S—, or —SO$_2$—; each z is selected from 1-20; and each T is selected from hydrogen and optionally substituted —C$_1$-C$_6$ alkyl.

In some embodiments, for the compound or salt of Formula (I), (IZ), (IA), (IB), (IC), (ID), (IE), (IF), or (IG), R$^{51}$ is independently selected at each occurrence from —((CH$_2$)$_q$—CH$_2$-D)$_z$-T and optionally substituted C$_{5-30}$ alkyl; wherein q is independently selected at at each occurrence from 1 to 6, each D is independently selected from —O—, —NR$^{32}$—, —S—, or —SO$_2$—; each z is selected from 3-20; and each T is selected from hydrogen and optionally substituted —C$_1$-C$_6$ alkyl. In some embodiments, R$^{51}$ is optionally substituted C$_{5-30}$ alkyl. In some embodiments, R$^{51}$ is selected C$_{5-30}$ alkyl, is selected from optionally substituted C$_{5-25}$ alkyl, optionally substituted C$_{5-20}$ alkyl, optionally substituted C$_{5-15}$ alkyl, and optionally substituted C$_{5-10}$ alkyl. In some embodiments, R$^{51}$ is optionally substituted C$_{5-10}$ alkyl. In some embodiments, the C$_{5-30}$ alkyl is optionally substituted with one or more substituents selected from halogen, —OR$^{30}$, —N(R$^{30}$)$_2$, —(O—CH$_2$—(CH$_2$)$_p$)$_n$—W, —SR$^{30}$, —C(O)R$^{30}$, —C(O)N(R$^{30}$)$_2$, —N(R$^{30}$)C(O)R$^{30}$, —C(O)OR$^{30}$, —OC(O)R$^{30}$, —S(O)R$^{30}$, —S(O)$_2$R$^{30}$, —P(O)(OR$^{30}$)$_2$, —OP(O)(OR$^{30}$)$_2$, —NO$_2$, =O, =S, =N(R$^{30}$), and —CN. In some embodiments, the C$_{5-30}$ alkyl is optionally substituted with one or more substituents selected from —OR$^{30}$, —N(R$^{30}$)$_2$, —SR$^{30}$, —C(O)R$^{30}$, —C(O)N(R$^{30}$)$_2$, —N(R$^{30}$)C(O)R$^{30}$, —C(O)OR$^{30}$, —OC(O)R$^{30}$, —S(O)R$^{30}$, —S(O)$_2$R$^{30}$, —NO$_2$, and —CN. In some embodiments, the C$_{5-30}$ alkyl is optionally substituted with one or more substituents selected from —OR$^{30}$. In some embodiments, each R$^{30}$ is independently selected at each occurrence from hydrogen and C$_{1-10}$ alkyl. In some embodiments, R$^{30}$ of —OR$^{30}$ is independently selected from hydrogen and C$_{1-10}$ alkyl. In some embodiments, R$^{30}$ of —OR$^{30}$ is independently selected from C$_{1-10}$ alkyl.

In some embodiments, for the compound or salt of Formula (I), (IZ), (IA), (IB), (IC), (ID), (IE), (IF), or (IG), R$^{51}$, is selected from a C$_{3-8}$ carbocycle. In some embodiments, R$^{51}$, is a C$_{3-6}$ carbocycle. In some embodiments, R$^{51}$, is selected from a C$_{3-6}$ cycloalkyl.

In some embodiments, for the compound or salt of Formula (I), (IZ), (IA), (IB), (IC), (ID), (IE), (IF), or (IG), R$^4$ is

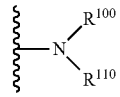

wherein R$^{100}$ is hydrogen or C$_{1-10}$ alkyl; and R$^{110}$ is selected from —S(O)$_2$R$^{51}$; or R$^{100}$ and R$^{110}$ together with the nitrogen to which they are bound form a 3-10-membered heterocycle optionally substituted with one or more substituents selected from: hydroxy, halogen, —CN, —NO$_2$, C$_1$-C$_6$ alkyl, C$_1$-C$_6$ haloalkyl, C$_1$-C$_6$ hydroxyalkyl, and C$_1$-C$_6$ alkoxy, and =O.

In some embodiments, for the compound or salt of Formula (I), (IZ), (IA), (IB), (IC), (ID), (IE), (IF), or (IG), R$^{100}$ and R$^{110}$ are each further independently selected from —SR$^{31}$, —N(R$^{31}$)$_2$, —C(O)R$^{31}$, —C(O)N(R$^{31}$)$_2$, —N(R$^{31}$)C(O)R$^{31}$, —C(O)OR$^{31}$, —OC(O)R$^{31}$, —S(O)R$^{31}$, —S(O)$_2$R$^{31}$, —P(O)(OR$^{31}$)$_2$, —OP(O)(OR$^{31}$)$_2$, —NO$_2$, —CN, optionally substituted C$_{3-20}$ carbocycle and optionally substituted 3- to 20-membered heterocycle, when R$^1$ is not hydroxy. In some embodiments, for the compound or salt of Formula (I), (IA), (IB), (IC), (ID), (IE), (IF), or (IG), R$^{100}$ and R$^{110}$ are each further independently selected from —S(O)R$^{31}$, —S(O)$_2$R$^{31}$, —NO$_2$, —CN, optionally substituted C$_{3-20}$ carbocycle and optionally substituted 3- to 20-membered heterocycle, when R$^1$ is not hydroxy. In some embodiments, R$^{100}$ and R$^{110}$ are each further independently selected from —S(O)R$^{31}$ and —S(O)$_2$R$^{31}$, when R$^1$ is not hydroxy. In some embodiments, each R$^{31}$ is independently selected at each occurrence from hydrogen; and C$_{1-10}$ alkyl, wherein the C$_{1-10}$ alkyl is optionally substituted with one or more substituents independently selected from halogen, —OH, —CN, —NO$_2$, —NH$_2$, =O, =S, C$_{1-10}$ alkyl, —C$_{1-10}$ haloalkyl, and —O—C$_{1-10}$ alkyl. In some embodiments, the C$_{1-10}$ alkyl is optionally substituted with one or more substituents independently selected from —O—C$_{1-10}$ alkyl.

In some embodiments, for the compound or salt of Formula (I), (IZ), (IA), (IB), (IC), (ID), (IE), (IF), or (IG), R$^4$ is

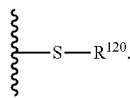

In some embodiments, $R^{120}$ of $R^4$ is selected from: hydrogen, —$(CH_2$—$CH_2$-G$)_y$-V; and $C_{3-10}$ alkyl optionally substituted with one or more substituents independently selected from halogen, —$OR^{31}$, —$SR^{31}$, —$N(R^{31})_2$, —$C(O)R^{31}$, —$C(O)N(R^{31})_2$, —$N(R^{31})C(O)R^{31}$, —$C(O)OR^{31}$, —$OC(O)R^{31}$, —$NO_2$, —$CN$, $C_{3-20}$ carbocycle, and 3- to 20-membered heterocycle; and $C_{3-20}$ saturated carbocycle and 3- to 20-membered heterocycle each of which is optionally substituted with one or more substituents independently selected from halogen, —$OR^{31}$, —$SR^{31}$, —$N(R^{31})_2$, —$C(O)R^{31}$, —$C(O)N(R^{31})_2$, —$N(R^{31})C(O)R^{31}$, —$C(O)OR^{31}$, —$OC(O)R^{31}$, —$NO_2$, =O, =S, =$N(R^{31})$, —$CN$, $C_{1-6}$ alkyl, $C_{1-6}$ alkyl-$R^{31}$, $C_{2-6}$ alkenyl, and $C_{2-6}$ alkynyl.

In some embodiments, for the compound or salt of Formula (I), (IZ), (IA), (IB), (IC), (ID), (IE), (IF), or (IG), $R^4$ is

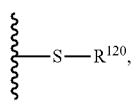

and $R^{120}$ of $R^4$ is hydrogen.

In some embodiments, for the compound or salt of Formula (I), (IZ), (IA), (IB), (IC), (ID), (IE), (IF), or (IG), $R^4$ is

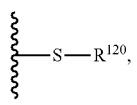

and $R^{120}$ of $R^4$ is —$(CH_2$—$CH_2$-G$)_y$-V.

In some embodiments, for the compound or salt of Formula (I), (IZ), (IA), (IB), (IC), (ID), (IE), (IF), or (IG), $R^4$ is

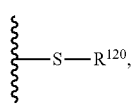

and $R^{120}$ of $R^4$ is $C_{3-10}$ alkyl optionally substituted with one or more substituents independently selected from halogen, —$OR^{31}$, —$SR^{31}$, —$N(R^{31})_2$, —$C(O)R^{31}$, —$C(O)N(R^{31})_2$, —$N(R^{31})C(O)R^{31}$, —$C(O)OR^{31}$, —$OC(O)R^{31}$, —$NO_2$, —$CN$, $C_{3-20}$ carbocycle, and 3- to 20-membered heterocycle. In some embodiments, $R^{120}$ of $R^4$ is $C_{3-10}$ alkyl, optionally substituted with one or more substituents independently selected from —$OR^{31}$, —$SR^{31}$, and —$N(R^{31})_2$, wherein each $R^{31}$ is independently selected from hydrogen, and $C_{1-10}$ alkyl, $C_{2-10}$ alkenyl, $C_{2-10}$ alkynyl, $C_{3-10}$ carbocycle, and 3- to 10-membered heterocycle.

In some embodiments, for the compound or salt of Formula (I), (IZ), (IA), (IB), (IC), (ID), (IE), (IF), or (IG), $R^4$ is

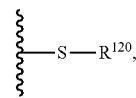

and $R^{120}$ of $R^4$ is $C_{1-2}$ alkyl substituted with one or more substituents independently selected from halogen, —$OR^{31}$, —$N(R^{31})_2$, —$C(O)R^{31}$, —$C(O)N(R^{31})_2$, —$N(R^{31})C(O)R^{31}$, —$C(O)OR^{31}$, —$OC(O)R^{31}$, —$S(O)R^{31}$, —$S(O)_2R^{31}$, —$P(O)(OR^{31})_2$, —$OP(O)(OR^{31})_2$, —$NO_2$, —$CN$, $C_{3-20}$ carbocycle and 3- to 20-membered heterocycle.

In some embodiments, for the compound or salt of Formula (I), (IZ), (IA), (IB), (IC), (ID), (IE), (IF), or (IG), for the compound or salt of Formula (I), (IA), (IB), (IC), (ID), (IE), (IF), or (IG), $R^4$ is

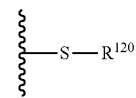

and $R^{120}$ is selected from —$(CH_2$—$CH_2$-G$)_y$-V, wherein y of —$(CH_2$—$CH_2$-G$)_y$-V for $R^{120}$ is 1 to 1000. In some embodiments, y is 1 to 800. In some embodiments, y is 1 to 500. In some embodiments, y is 1 to 300. In some embodiments, y is 1 to 100. In some embodiments, y is 1 to 50. In some embodiments, y is 1 to 25. In some embodiments, y is 3 to 1000. In some embodiments, y is 10 to 1000. In some embodiments, y is 50 to 1000. In some embodiments, y is 100 to 1000. In some embodiments, y is 200 to 1000. In some embodiments, y is 500 to 1000. In some embodiments, y of —$(CH_2$—$CH_2$-G$)_y$-V for $R^{120}$ is 3 to 10. In some embodiments, y of —$(CH_2$—$CH_2$-G$)_y$-V for $R^{120}$ is 5 to 10. In some embodiments, y is 1, 2, 3, 4, 5, 6, 7, 8, 9, 10, 11, 12, 13, 14, 15, 16, 17, 18, 19, 20, 25, or 100.

In some embodiments, for the compound or salt of Formula (I), (IZ), (IA), (IB), (IC), (ID), (IE), (IF), or (IG), $R^2$ is selected from hydrogen and an optionally substituted $C_1$-$C_6$ alkoxy, wherein substituents are independently selected at each occurrence from hydroxy, halogen, —CN, —$NO_2$, and $C_1$-$C_6$ alkoxy. In some embodiments, $R^2$ is selected from hydrogen and an optionally substituted $C_1$-$C_6$ alkoxy, wherein substituents are independently selected at each occurrence from hydroxy, halogen, —$NO_2$, and $C_1$-$C_6$ alkoxy.

In some embodiments, for the compound or salt of Formula (I), (IZ), (IA), (IB), (IC), (ID), (IE), (IF), or (IG), $R^2$ is selected from hydrogen and $C_1$-$C_6$ alkoxy. In some embodiments, $R^2$ is selected from hydrogen and —OMe. In some embodiments, $R^2$ is —OMe.

In some embodiments, for the compound or salt of Formula (I), (IZ), (IA), (IB), (IC), (ID), (IE), (IF), or (IG), $R^3$ is selected from hydrogen and an optionally substituted $C_1$-$C_6$ alkoxy, wherein the substituents are independently selected at each occurrence from hydroxy and $C_1$-$C_6$ alkoxy. In some embodiments, $R^3$ is selected from hydrogen and $C_1$-$C_6$ alkoxy.

In some embodiments, for the compound or salt of Formula (I), (IZ), (IA), (IB), (IC), (ID), (IE), (IF), or (IG), $R^3$ is selected from $C_1$-$C_6$ alkoxy. In some embodiments, $R^3$ is —OMe.

In some embodiments, for the compound or salt of Formula (I), (IZ), (IA), (IB), (IC), (ID), (IE), (IF), or (IG), $R^5$ is selected from hydrogen, hydroxy, and an optionally substituted $C_1$-$C_6$ alkoxy, wherein substituents are independently selected at each occurrence from hydroxy, halogen, —CN, —NO$_2$, and C$_1$-C$_6$ alkoxy.

In some embodiments, for the compound or salt of Formula (I), (IZ), (IA), (IB), (IC), (ID), (IE), (IF), or (IG), R$^5$ is, hydroxy.

In some embodiments, for the compound or salt of Formula (I), (IZ), (IA), (IB), (IC), (ID), (IE), (IF), or (IG), R$^6$ and R$^7$ are each independently selected from hydrogen and hydroxy. In some embodiments, R$^6$ and R$^7$ are each hydrogen. In some embodiments, R$^6$ is hydrogen and R$^7$ hydroxy. In some embodiments, R$^6$ and R$^7$ come together to form

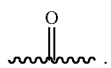.

In some embodiments, for the compound or salt of Formula (I), (IZ), (IA), (IB), (IC), (ID), (IE), (IF), or (IG), R$^1$ is selected from

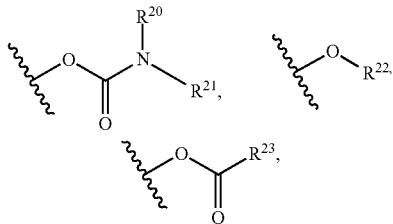

and optionally substituted 3- to 10-membered heterocycle. In some embodiments, for the compound or salt of Formula (I), (IA), (IB), (IC), (ID), (IE), (IF), or (IG), R$^1$ is selected from

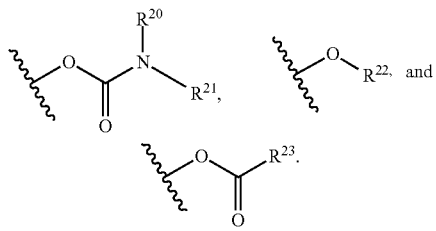

In some embodiments, for the compound or salt of Formula (I), (IA), (IB), (IC), (ID), (IE), (IF), or (IG), R$^1$ is selected from hydroxy.

In some embodiments, for the compound or salt of Formula (I), (IZ), (IA), (IB), (IC), (ID), (IE), (IF), or (IG), R$^1$ is selected from

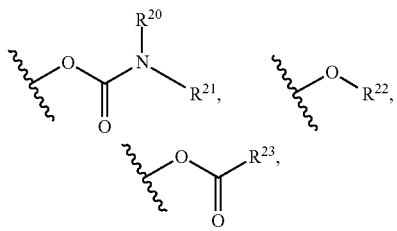

optionally substituted C$_{3\text{-}10}$ carbocycle and optionally substituted 3- to 10-membered heterocycle.

In some embodiments, for the compound or salt of Formula (I), (IZ), (IA), (IB), (IC), (ID), (IE), (IF), or (IG), R$^1$ is selected from

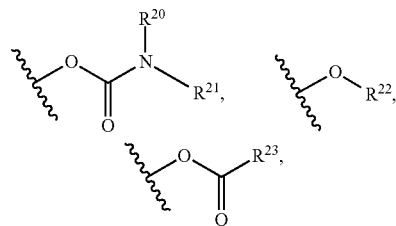

and optionally substituted 3- to 10-membered heterocycle.

In some embodiments, for the compound or salt of Formula (I), (IZ), (IA), (IB), (IC), (ID), (IE), (IF), or (IG), R$^1$ is selected from —OH.

In some embodiments, for the compound or salt of Formula (I), (IZ), (IA), (IB), (IC), (ID), (IE), (IF), or (IG), R$^1$ is selected from: —OH,

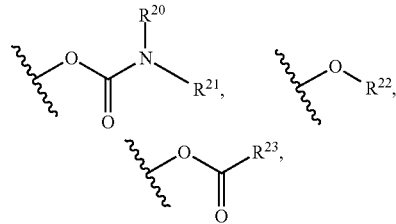

optionally substituted 3- to 10-membered heterocycle, and optionally substituted C$_{3\text{-}10}$ carbocycle.

In some embodiments, for the compound or salt of Formula (I), (IZ), (IA), (IB), (IC), (ID), (IE), (IF), or (IG), R$^1$ is selected from: —OH,

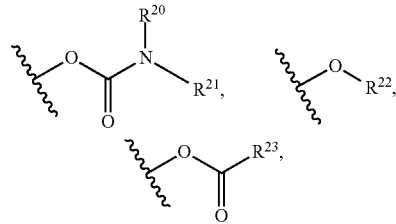

and optionally substituted 3- to 10-membered heterocycle.

In some embodiments, for the compound or salt of Formula (I), (IZ), (IA), (IB), (IC), (ID), (IE), (IF), or (IG), R$^1$ is an optionally substituted 3- to 10-membered heterocycle. In some embodiments, the optionally substituted heterocycle is 3-, 4-, 5-, 6-, 7-, 8-, 9-, or a 10-membered heterocycle. In some embodiments, the optionally substituted 3- to 10-membered heterocycle is a 3- or 4-membered heterocycle, a 5- or 6-membered heterocycle, a 7- or 8-membered heterocycle, or a 9- or 10-membered heterocycle.

In some embodiments, for the compound or salt of Formula (I), (IZ), (IA), (IB), (IC), (ID), (IE), (IF), or (IG), R$^1$ is an optionally substituted 5- to 6-membered heterocycle comprising at least 1 heteroatom that is selected from oxygen, nitrogen, sulfur, boron, phosphorus, silicon, selenium, and any combination thereof. In some embodiments, the optionally substituted 5- to 6-membered heterocycle comprises at least 1 heteroatom that is selected from oxygen, nitrogen, sulfur, and any combination thereof.

In some embodiments, for the compound or salt of Formula (I), (IZ), (IA), (IB), (IC), (ID), (IE), (IF), or (IG), the optionally substituted 5- to 6-membered heterocycle of $R^1$ comprises at least 1 nitrogen. In some embodiments, the optionally substituted 5- to 6-membered heterocycle of $R^1$ is selected from

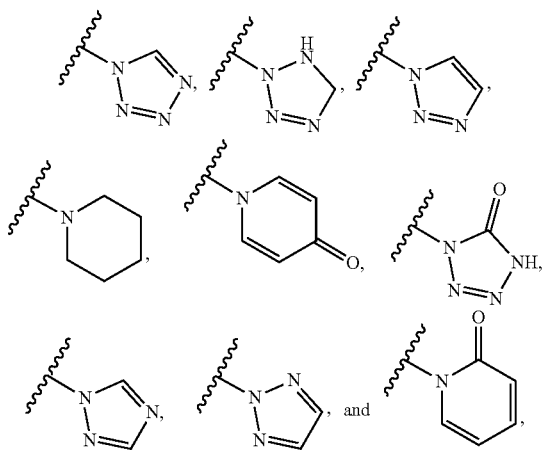

any of which is optionally substituted with one or more substituents independently selected from: hydroxy, halogen, —CN, —NO$_2$, =O, $C_1$-$C_6$ alkyl, $C_1$-$C_6$ haloalkyl, $C_1$-$C_6$ hydroxyalkyl, $C_1$-$C_6$ alkoxy, 3- to 10-membered heterocycle, and $C_{3-10}$ carbocycle, wherein the 3- to 10-membered heterocycle and $C_{3-10}$ carbocycle are each optionally substituted with one or more substituents independently selected from hydroxy, halogen, —CN, —NO$_2$, $C_1$-$C_6$ alkyl, $C_1$-$C_6$ haloalkyl, $C_1$-$C_6$ hydroxyalkyl, and $C_1$-$C_6$ alkoxy. In some embodiments, the one or more substituents are independently selected from hydroxy, =O, $C_1$-$C_6$ alkyl, 3- to 8-membered heterocycle, and $C_{3-8}$ carbocycle, wherein the 3- to 8-membered heterocycle and $C_{3-8}$ carbocycle are each optionally substituted with one or more substituents independently selected from hydroxy, halogen, —CN, —NO$_2$, $C_1$-$C_6$ alkyl, $C_1$-$C_6$ haloalkyl, $C_1$-$C_6$ hydroxyalkyl, and $C_1$-$C_6$ alkoxy.

In some embodiments, for the compound or salt of Formula (I), (IZ), (IA), (IB), (IC), (ID), (IE), (IF), or (IG), $R^1$ is

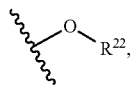

In some embodiments, for the compound or salt of Formula (I), (IA), (IB), (IC), (ID), (IE), (IF), or (IG), $R^{22}$ of $R^1$ is selected from optionally substituted $C_1$-$C_6$ alkyl, and —P(=O)(R$^{24}$)$_2$.

In some embodiments, for the compound or salt of Formula (I), (IZ), (IA), (IB), (IC), (ID), (IE), (IF), or (IG), $R^{22}$ of $R^1$ is hydrogen.

In some embodiments, for the compound or salt of Formula (I), (IZ), (IA), (IB), (IC), (ID), (IE), (IF), or (IG), $R^{22}$ of $R^1$ is —P(=O)(R$^{24}$)$_2$, and $R^{24}$ is selected from optionally substituted $C_{1-10}$ alkyl. In some embodiments, $R^1$ is

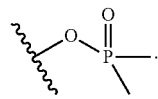

In some embodiments, for the compound or salt of Formula (I), (IZ), (IA), (IB), (IC), (ID), (IE), (IF), or (IG), $R^{22}$ of $R^1$ is $C_1$-$C_6$ alkyl optionally substituted with one or more substituents selected from —N(R$^{30}$)$_2$, —(O—CH$_2$—(CH$_2$)$_p$)$_n$—W, —OR$^{30}$, optionally substituted $C_{3-10}$ carbocycle, and optionally substituted 3- to 10-membered heterocycle, and $R^{30}$ is selected from hydrogen and optionally substituted $C_{1-10}$ alkyl. In some embodiments, $R^{22}$ of $R^1$, is $C_1$-$C_6$ alkyl substituted with one or more substituents selected from —N(R$^{30}$)$_2$, —(O—CH$_2$—(CH$_2$)$_p$)$_n$—W, and —OR$^{30}$.

In some embodiments, for the compound or salt of Formula (I), (IZ), (IA), (IB), (IC), (ID), (IE), (IF), or (IG), $R^{22}$ of $R^1$ is $C_1$-$C_6$ alkyl substituted with one or more substituents selected from —N(R$^{30}$)$_2$. In some embodiments, $R^1$ is

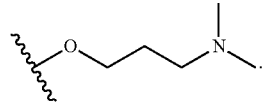

In some embodiments, for the compound or salt of Formula (I), (IZ), (IA), (IB), (IC), (ID), (IE), (IF), or (IG), $R^{22}$ of $R^1$ is $C_1$-$C_6$ alkyl substituted with one or more substituents selected from —(O—CH$_2$—(CH$_2$)$_p$)$_n$—W, wherein n is 1 to 1000. In some embodiments, n is 1 to 800. In some embodiments, n is 1 to 500. In some embodiments, n is 1 to 300. In some embodiments, n is 1 to 100. In some embodiments, n is 1 to 50. In some embodiments, n is 1 to 25. In some embodiments, n is 3 to 1000. In some embodiments, n is 10 to 1000. In some embodiments, n is 50 to 1000. In some embodiments, n is 100 to 1000. In some embodiments, n is 200 to 1000. In some embodiments, n is 500 to 1000. In some embodiments, n is 1, 2, 3, 4, 5, 6, 7, 8, 9, 10, 11, 12, 13, 14, 15, 16, 17, 18, 19, 20, 25, or 100. In some embodiments, p is 1 to 1000. In some embodiments, p is 1 to 800. In some embodiments, p is 1 to 500. In some embodiments, p is 1 to 300. In some embodiments, p is 1 to 100. In some embodiments, p is 1 to 50. In some embodiments, p is 1 to 25. In some embodiments, p is 3 to 1000. In some embodiments, p is 10 to 1000. In some embodiments, p is 50 to 1000. In some embodiments, p is 100 to 1000. In some embodiments, p is 200 to 1000. In some embodiments, p is 500 to 1000. In some embodiments, p is 1, 2, 3, 4, 5, 6, 7, 8, 9, 10, 11, 12, 13, 14, 15, 16, 17, 18, 19, 20, 25, or 100.

In some embodiments, for the compound or salt of Formula (I), (IZ), (IA), (IB), (IC), (ID), (IE), (IF), or (IG), $R^{22}$ of $R^1$ is $C_1$-$C_6$ alkyl substituted with one or more substituents selected from —(O—CH$_2$—(CH$_2$)$_p$)$_n$—W, and —OR$^{30}$. In some embodiments, $R^1$ is selected from:

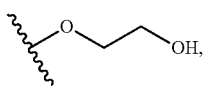

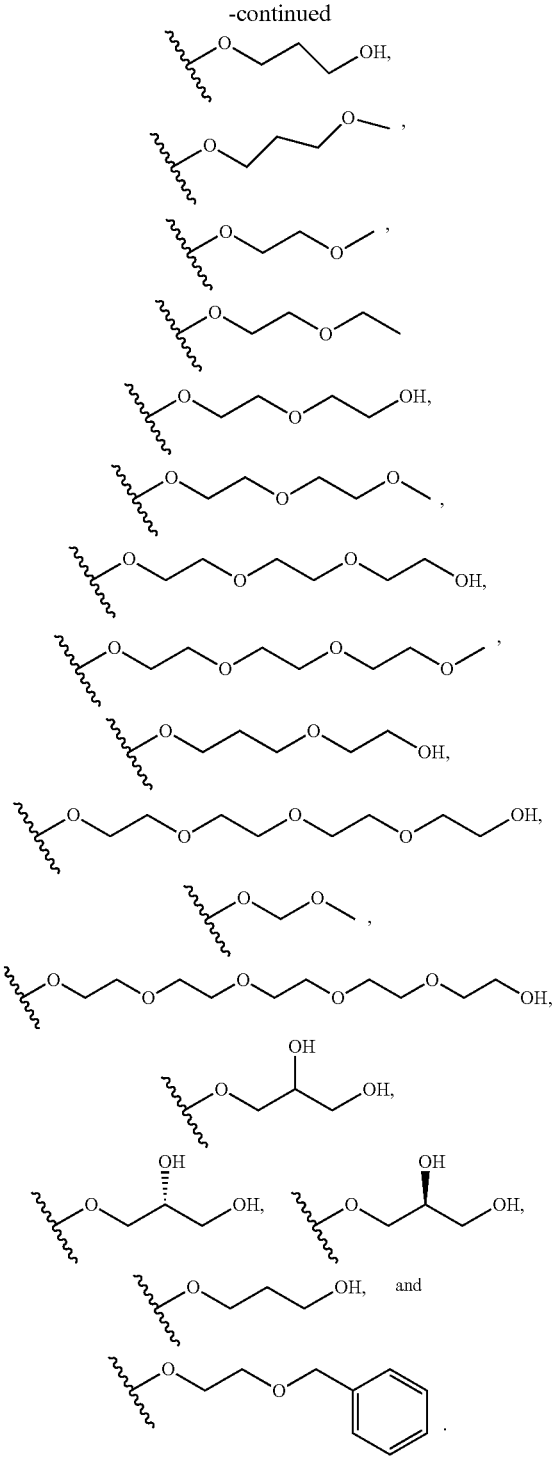

In some embodiments, for the compound or salt of Formula (I), (IZ), (IA), (IB), (IC), (ID), (IE), (IF), or (IG), $R^{22}$ of $R^1$ is $C_1$-$C_6$ alkyl substituted with substituents selected from an optionally substituted $C_{3-10}$ carbocycle. In some embodiments, the optionally substituted $C_{3-10}$ carbocycle is selected from a $C_{3-6}$ carbocycle. In certain embodiments, the $C_{3-6}$ carbocycle is unsaturated. In certain embodiments, the $C_{3-6}$ carbocycle is saturated. In some embodiments, the optionally substituted $C_{3-6}$ carbocycle is selected from

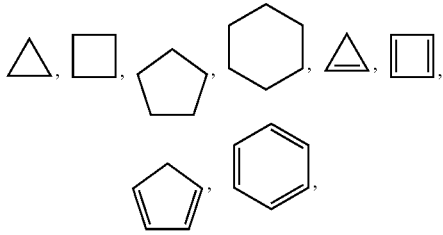

In some embodiments, $R^{22}$ of $R^1$ is $C_1$-$C_6$ alkyl substituted with phenyl. In some embodiments, $R^1$ is selected from:

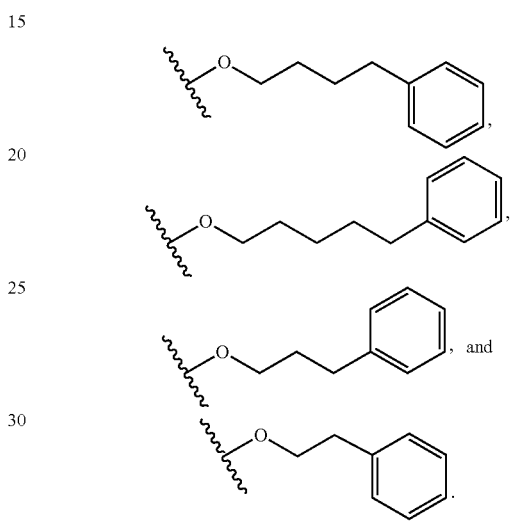

In some embodiments, for the compound or salt of Formula (I), (IZ), (IA), (IB), (IC), (ID), (IE), (IF), or (IG), $R^{22}$ of $R^1$ is $C_1$-$C_6$ alkyl substituted with one or more substituents selected from an optionally substituted 3- to 6-membered heterocycle. In some embodiments, the optionally substituted 3- to 6-membered heterocycle comprises at least one heteroatom selected from N, O, S, and any combination thereof.

In some embodiments, for the compound or salt of Formula (I), (IZ), (IA), (IB), (IC), (ID), (IE), (IF), or (IG), $R^{22}$ is $C_1$-$C_6$ alkyl substituted with one or more substituents selected from optionally substituted 3- to 8-membered heterocycle. In some embodiments, $R^{22}$ is $C_2$-$C_3$ alkyl substituted with one or more substituents selected from optionally substituted 3- to 8-membered heterocycle. In some embodiments, $R^{22}$ of $R^1$ is $C_1$-$C_6$ alkyl substituted with one or more substituents selected from an optionally substituted 3- to 8-membered heterocycle wherein the optionally substituted 3- to 8-membered heterocycle comprises at least one heteroatom selected from N and O. In some embodiments, the 3- to 8-membered heterocycle of $R^{22}$ is saturated. In some embodiments, the 3- to 8-membered heterocycle of $R^{22}$ is substituted with one or more substituents selected from —S(O)$_2$R$^{30}$, $C_{1-6}$ alkyl and —OR$^{30}$. In some embodiments, $R^{30}$ of —S(O)$_2$R$^{30}$ is selected from $C_{1-10}$ alkyl and $R^{30}$ of —OR$^{30}$ is selected from hydrogen and $C_{1-6}$ alkyl. In some embodiments, $R^{22}$ of $R^1$ is $C_1$-$C_6$ alkyl substituted with one or more substituents selected from an optionally substituted 3- to 6-membered heterocycle wherein the optionally substituted 3- to 6-membered heterocycle comprises at least one heteroatom selected from N and O. In some embodiments, the 3- to 6-membered heterocycle is substituted with one or more substituents selected from optionally substituted $C_{1-6}$ alkyl and —$OR^{30}$. In some embodiments, $R^1$ is selected from:
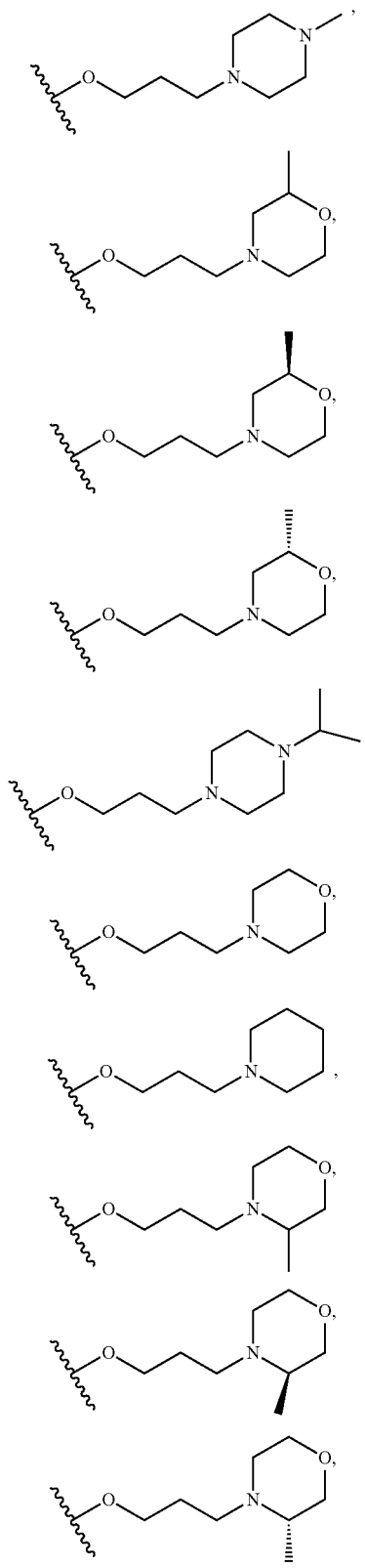
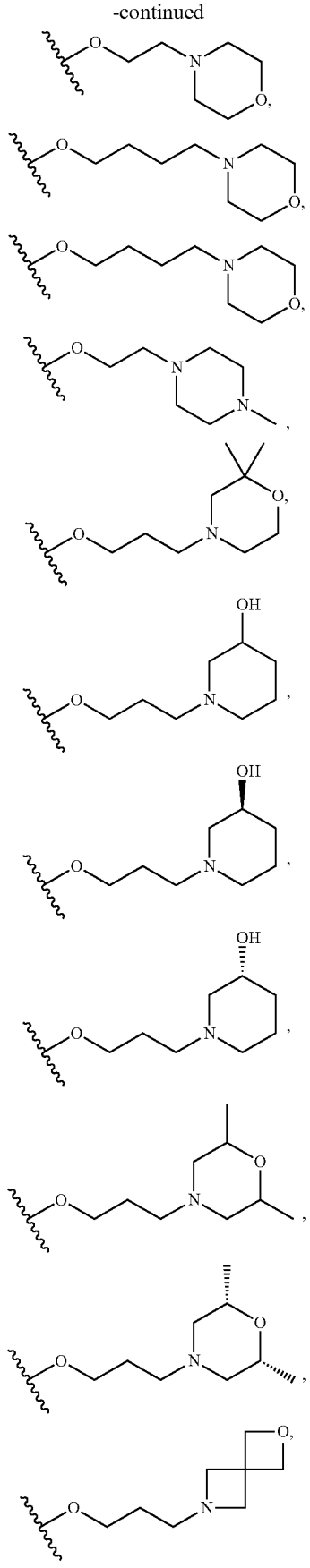

-continued
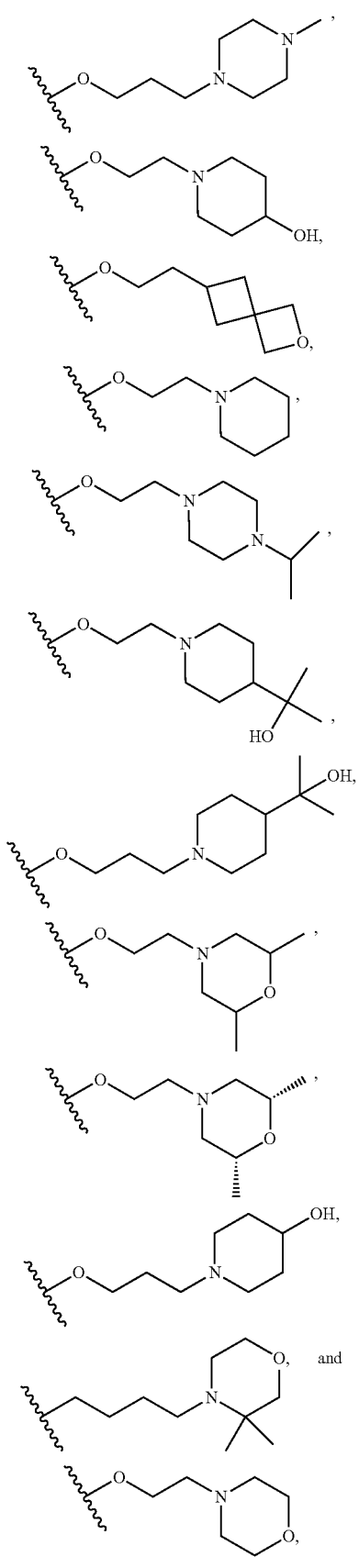
In some embodiments, for the compound or salt of Formula (I), (IZ), (IA), (IB), (IC), (ID), (IE), (IF), or (IG), R¹ is selected from:
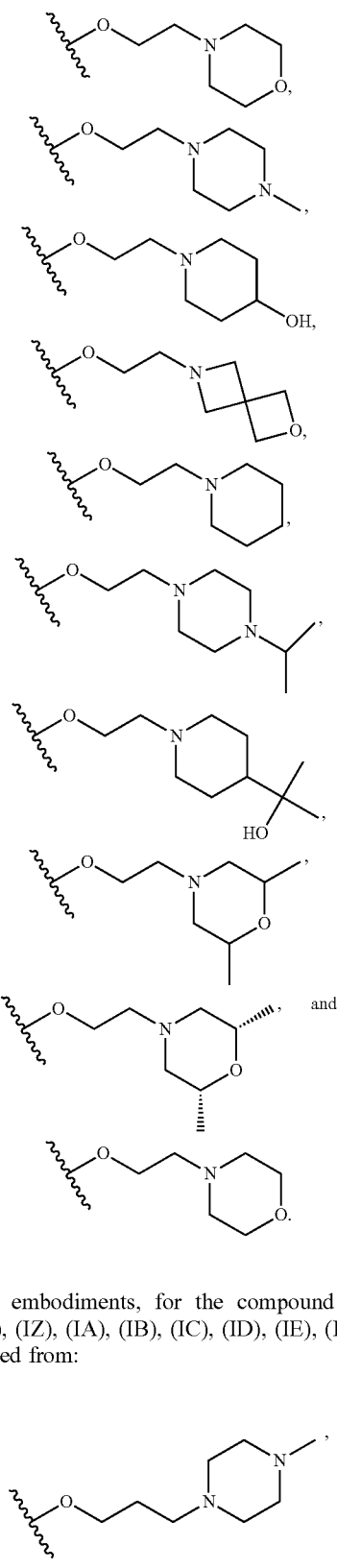
In some embodiments, for the compound or salt of Formula (I), (IZ), (IA), (IB), (IC), (ID), (IE), (IF), or (IG), R¹ is selected from:

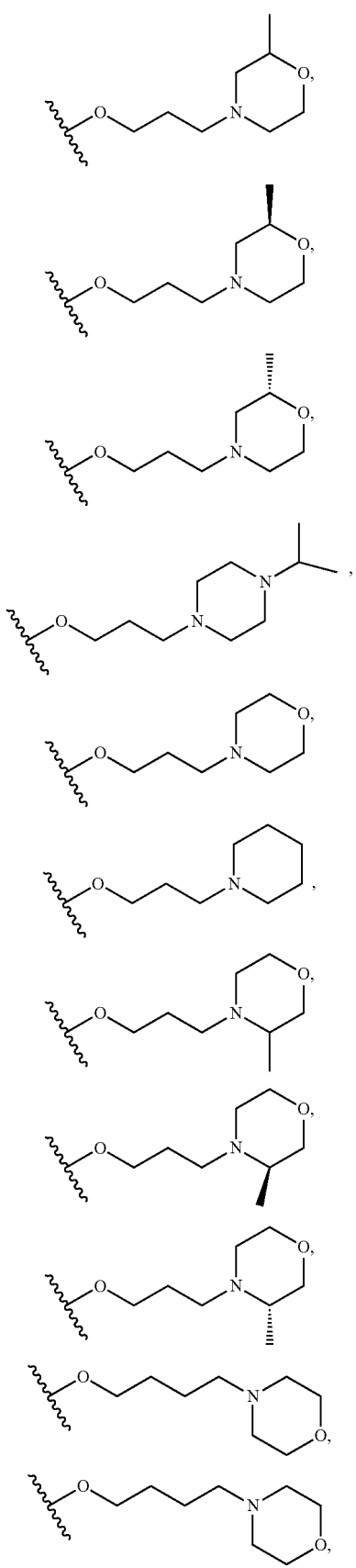
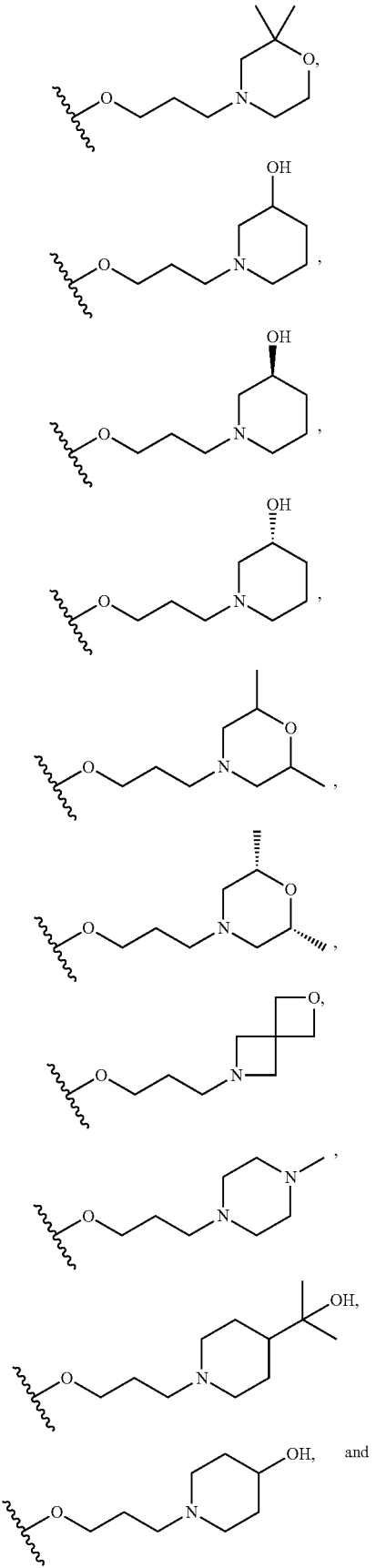

-continued

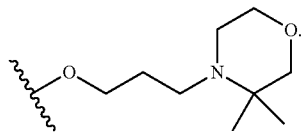

In some embodiments, for the compound or salt of Formula (I), (IZ), (IA), (IB), (IC), (ID), (IE), (IF), or (IG), $R^1$ is

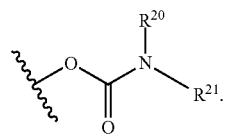

In some embodiments, $R^{20}$ of $R^1$ is selected from hydrogen and optionally substituted $C_1$-$C_3$ alkyl. In some embodiments, $R^{21}$ of $R^1$ is selected from hydrogen and optionally substituted $C_1$-$C_3$ alkyl. In some embodiments, $R^{21}$ of $R^1$ is an optionally substituted $C_{1-10}$ alkyl. In some embodiments, $R^{21}$ of $R^1$ is $C_{1-10}$ alkyl substituted with one or more substituents selected from —$OR^{30}$, —$N(R^{30})_2$, —(O—$CH_2$—$(CH_2)_p)_n$—W, optionally substituted $C_{3-10}$ carbocycle and optionally substituted 3- to 10-membered heterocycle. In some embodiments, $R^1$ is selected from:

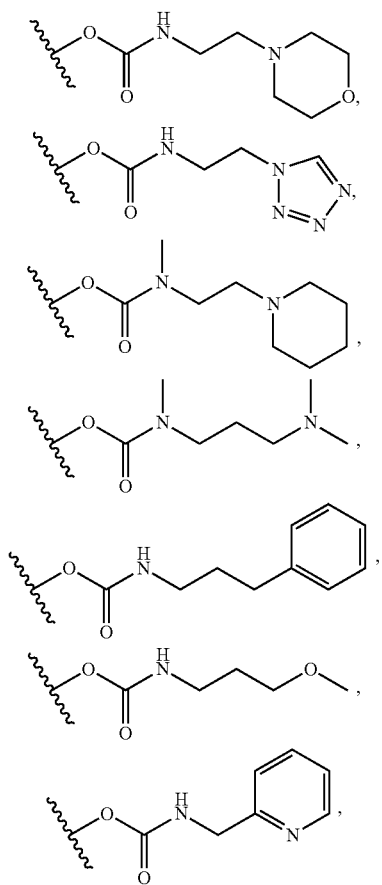

-continued

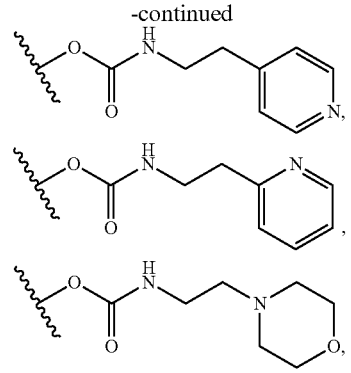

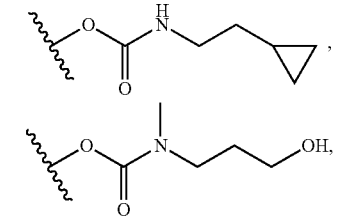

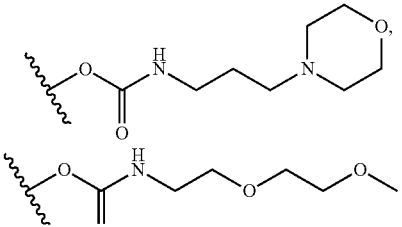

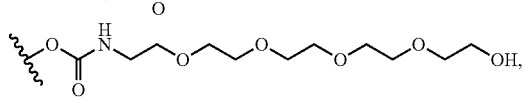

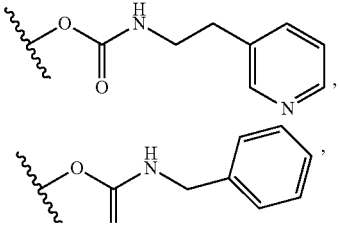

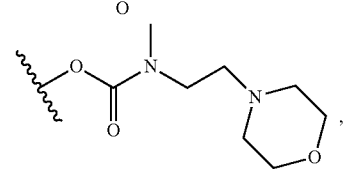

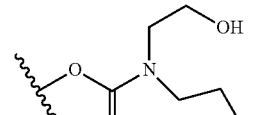

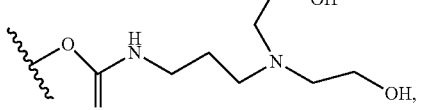

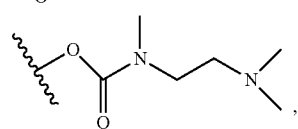

-continued

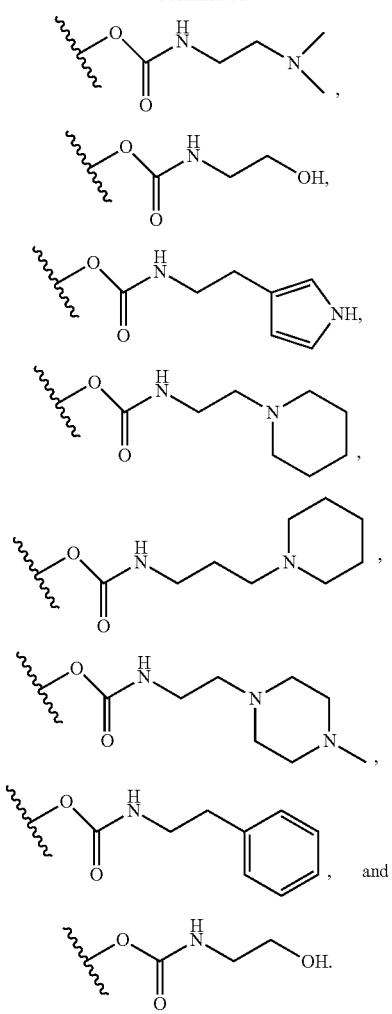

In some embodiments, for the compound or salt of Formula (I), (IZ), (IA), (IB), (IC) (ID), (IE), (IF), or (IG), $R^1$ is

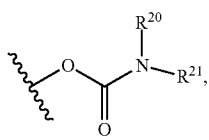

wherein $R^{21}$ of $R^1$ is an optionally substituted 3- to 7-membered heterocycle. In some embodiments, the 3- to 7-membered heterocycle is substituted with one or more substituents selected from —$OR^{30}$ and optionally substituted $C_{1-10}$ alkyl. In some embodiments, $R^1$ is selected from:

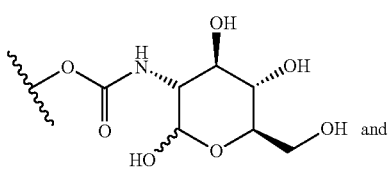

-continued

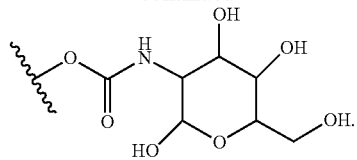

In some embodiments, for the compound or salt of Formula (I), (IZ), (IA), (IB), (IC), (ID), (IE), (IF), or (IG), $R^1$ is

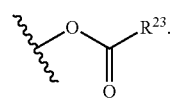

In some embodiments, $R^{23}$ of $R^1$ is an optionally substituted $C_1$-$C_6$ alkyl. In some embodiments, $C_1$-$C_6$ alkyl is substituted with one or more substituents selected from —$OR^{30}$, —$N(R^{30})_2$, optionally substituted $C_{1-10}$ alkyl, optionally substituted $C_{3-10}$ carbocycle and 3- to 10-membered heterocycle. In some embodiments, $R^1$ is selected from:

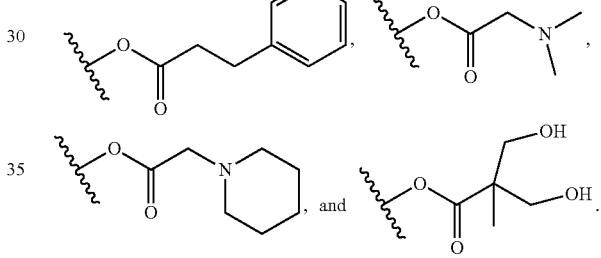

In some embodiments, for the compound or salt of Formula (I), (IZ), (IA), (IB), (IC), (ID), (IE), (IF), or (IG), $R^{23}$ of $R^1$ is an optionally substituted 3- to 7-membered heterocycle. In some embodiments, the 3- to 7-membered heterocycle is substituted with one or more substituents selected from optionally substituted $C_{1-10}$ alkyl. In some embodiments, $R^1$ is selected from:

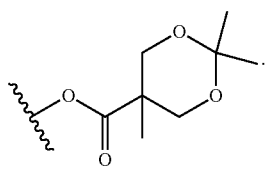 [SMILES: *OC(=O)C1(C)COC(C)(C)OC1]

In some embodiments, for the compound or salt of Formula (I), (IZ), (IA), (IB), (IC), (ID), (IE), (IF), or (IG), $R^1$ is selected from:

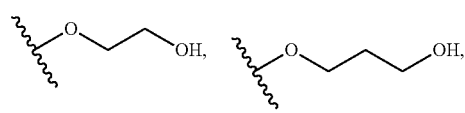

63
-continued
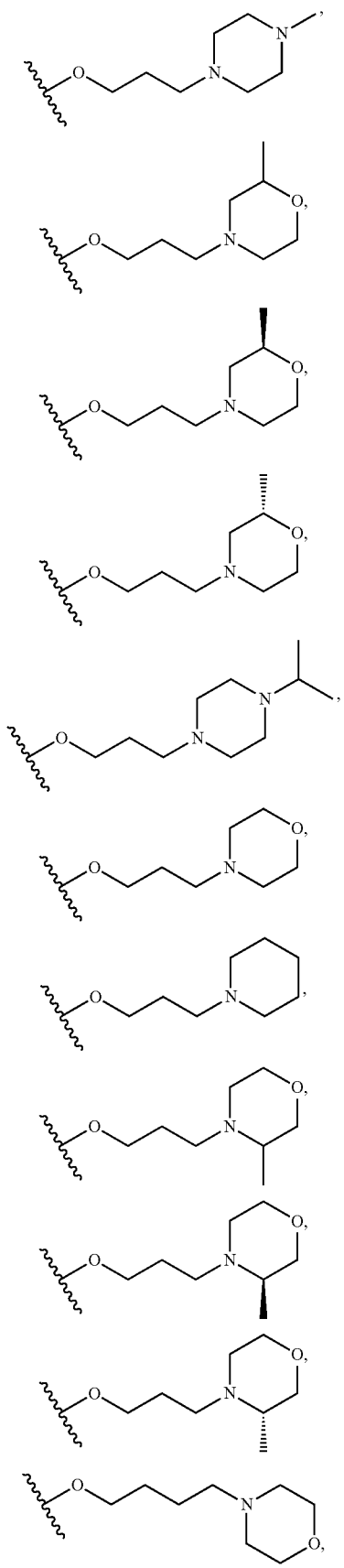
64
-continued
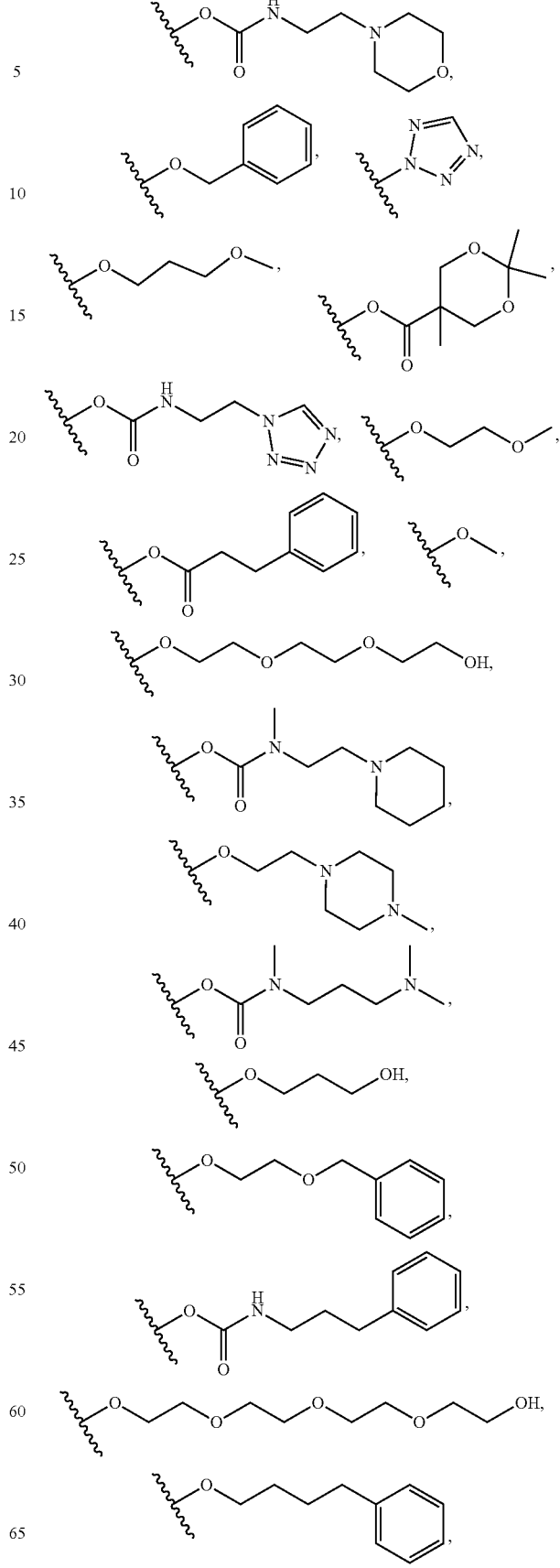

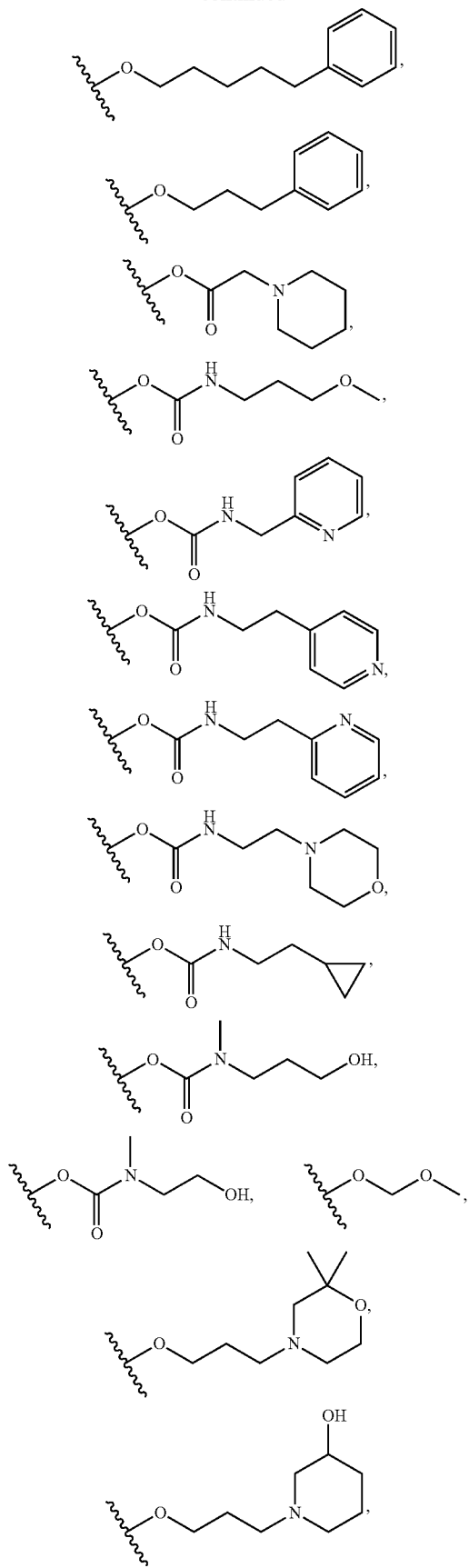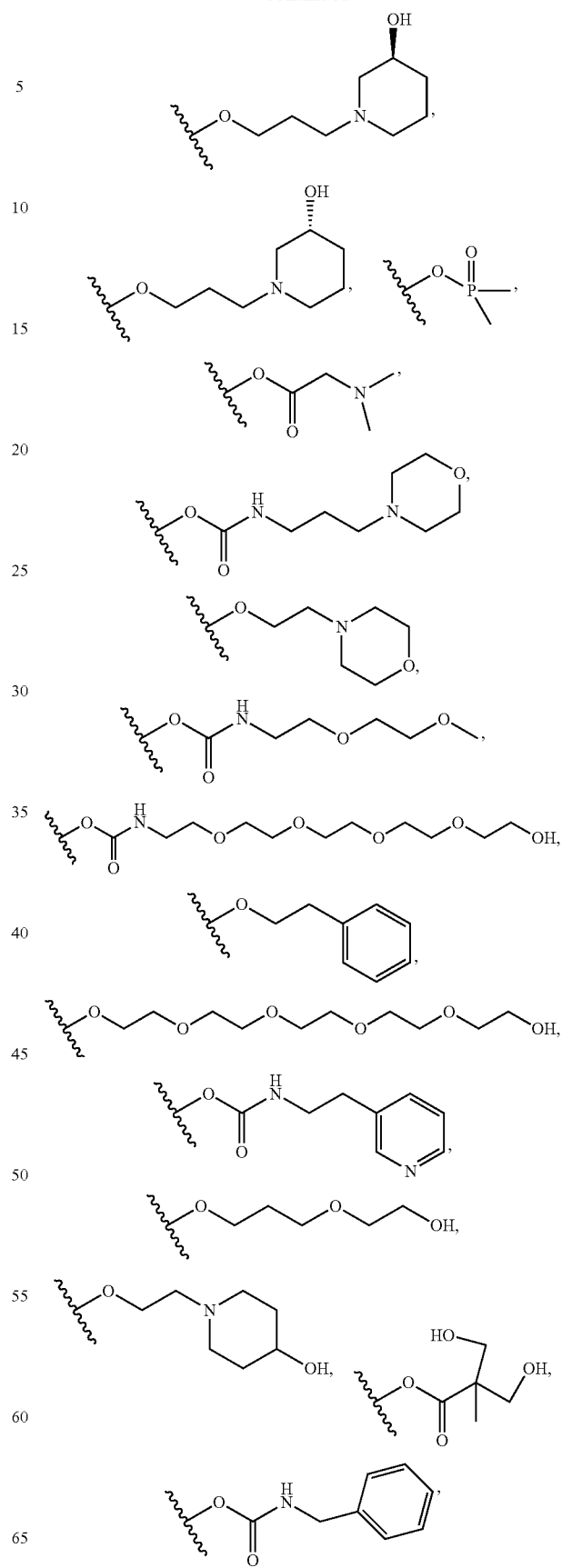

-continued
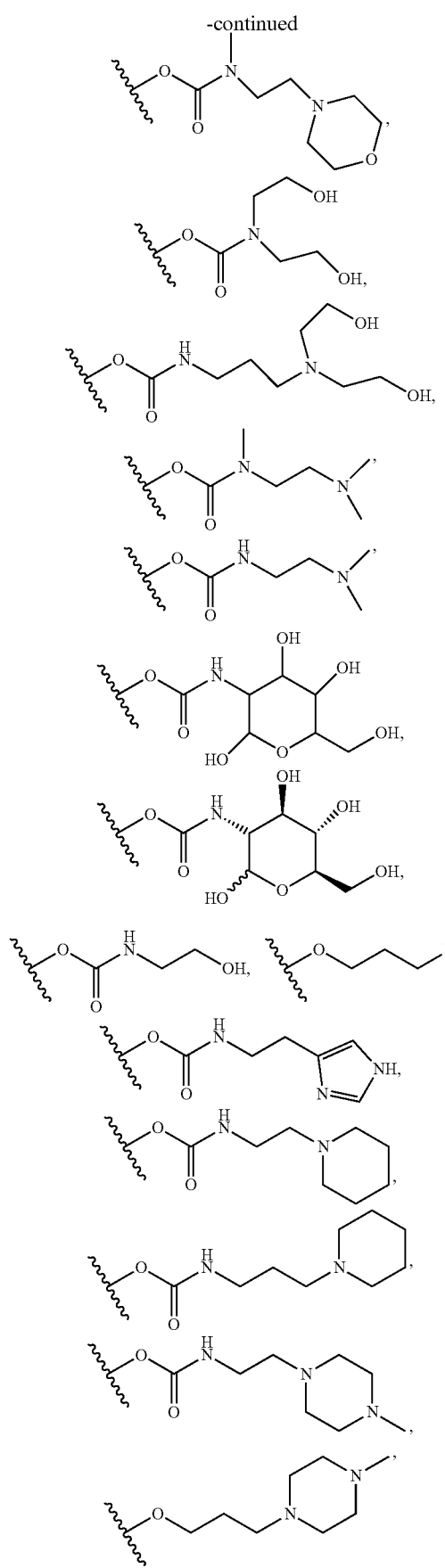
-continued
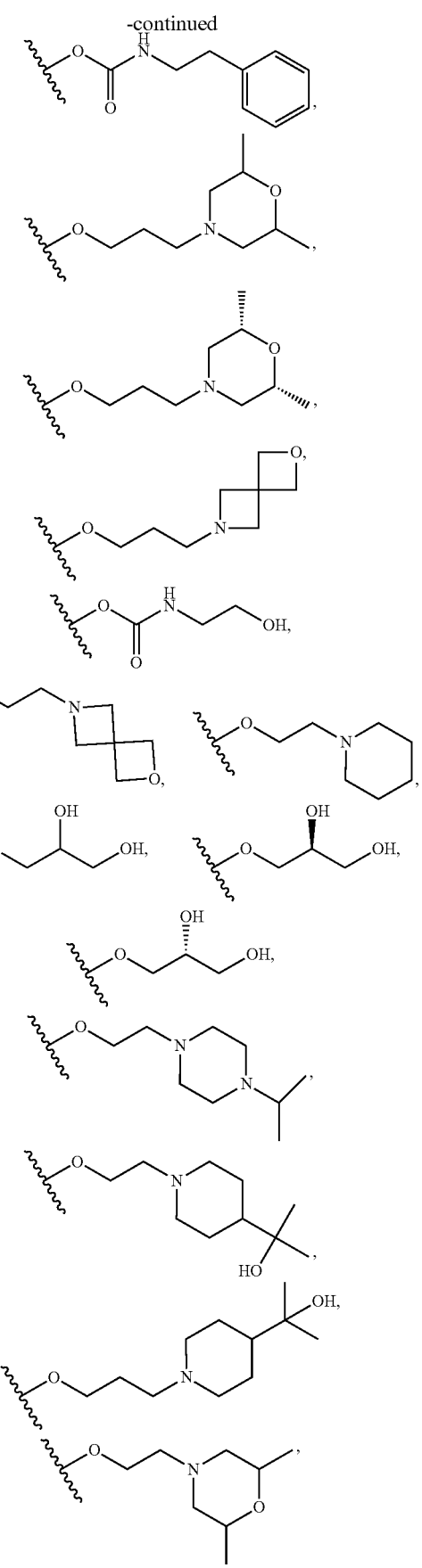

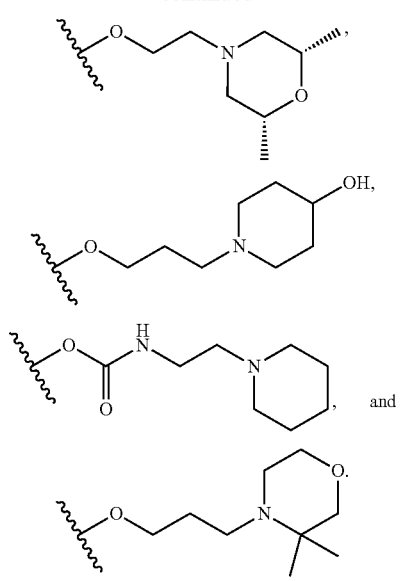
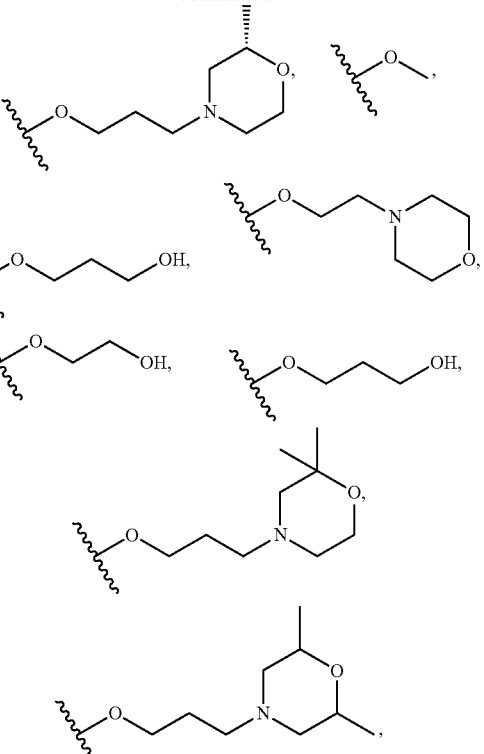
In some embodiments, for the compound or salt of Formula (I), (IZ), (IA), (IB), (IC), (ID) (IE), (IF) or (IG), $R^1$ is selected from:
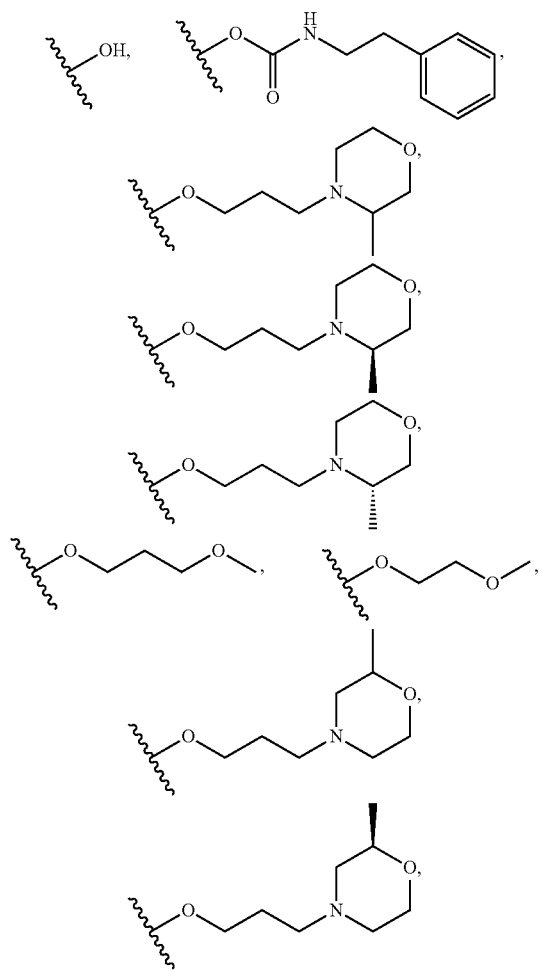
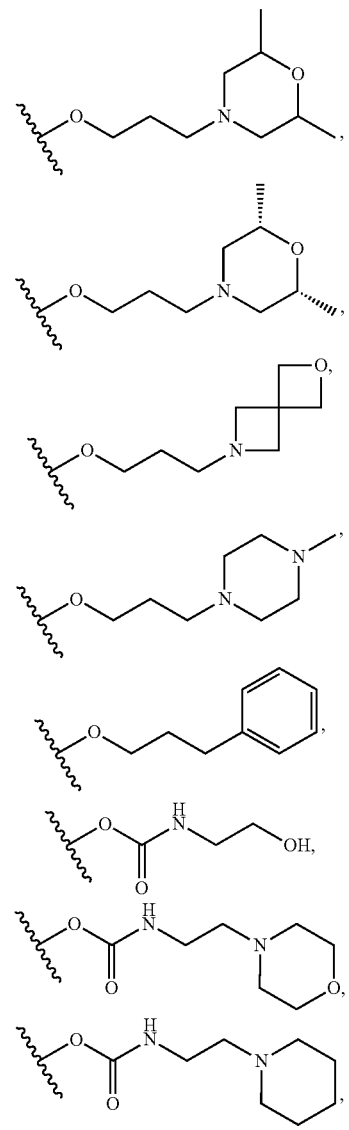

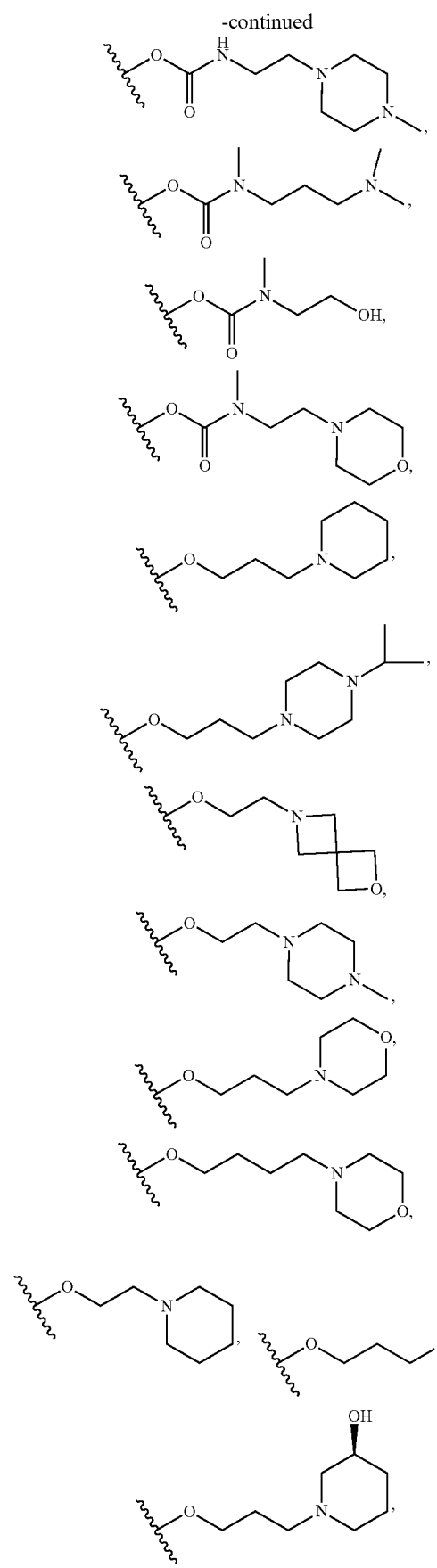
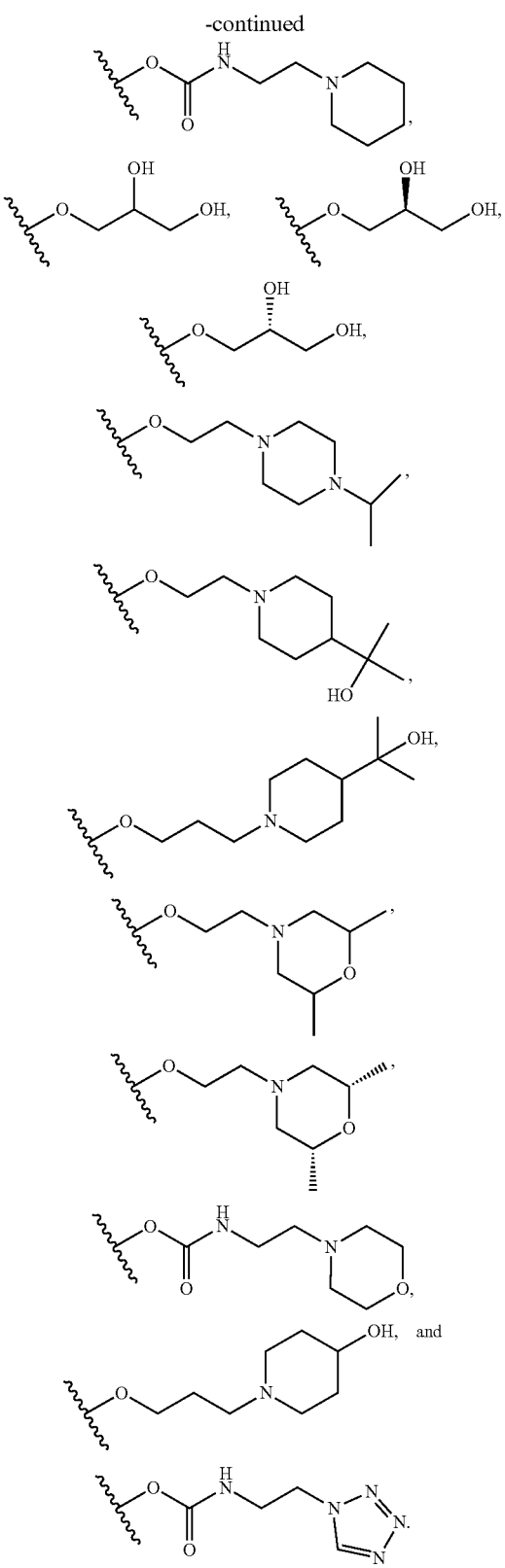
In some embodiments, for the compound or salt of Formula (I), (IZ), (IA), (IB), (IC), (ID), (IE), (IF), or (IG), R[1] is selected from:

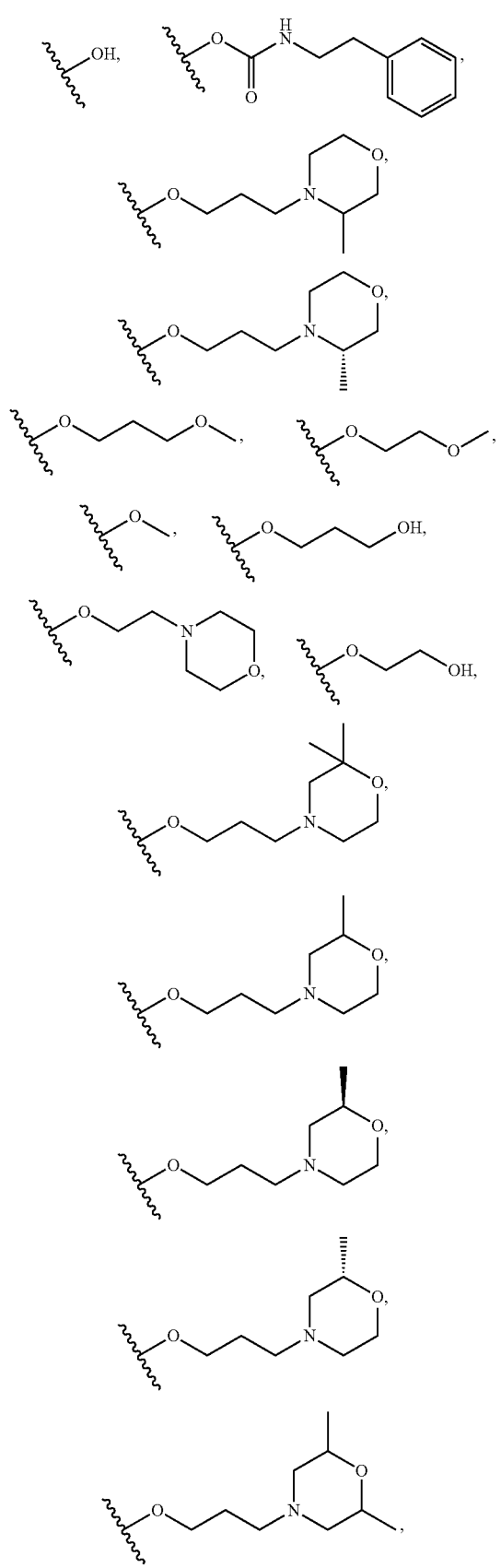
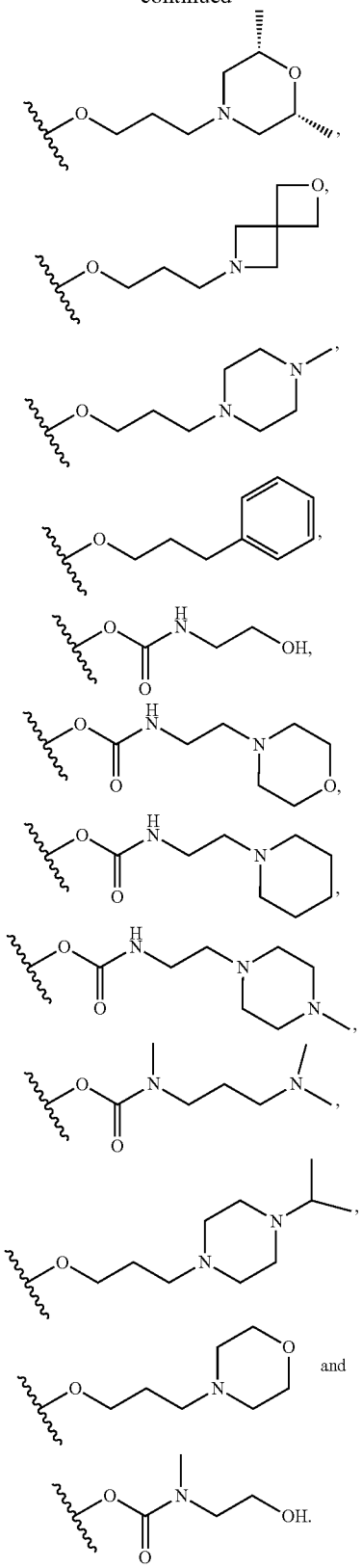
In some embodiments, for the compound or salt of Formula (I), (IZ), (IA), (IB), (IC), (ID), (IE), (IF), or (IG), $R^1$ is selected from:

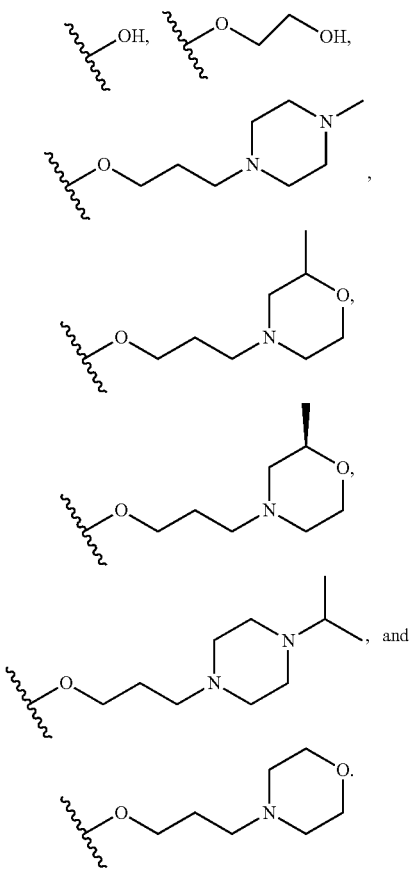

In some embodiments, for the compound or salt of Formula (I), (IA), (IB), (IC), (ID), (IE), (IF), or (IG), $R^1$ is selected from:

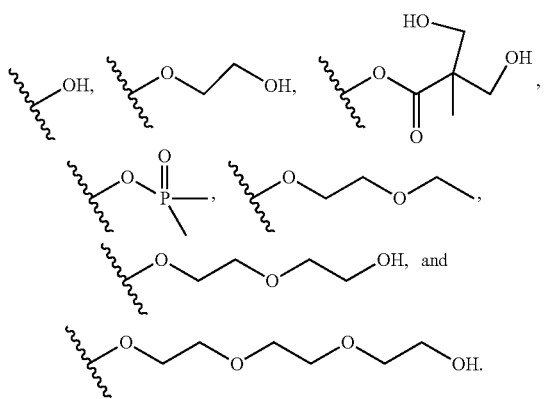

In some embodiments, for the compound or salt of Formula (I), (IA), (IB), (IC), (ID), (IE), (IF), or (IG):

$R^1$ is selected from

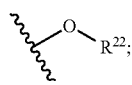

$R^2$ is selected from hydrogen and an optionally substituted $C_1$-$C_6$ alkoxy, such as $R^2$ is a $C_1$-$C_6$ alkoxy group, and preferably $R^2$ is —OCH$_3$;

$R^3$ is selected from an optionally substituted $C_1$-$C_6$ alkoxy group, such as $R^3$ is a $C_1$-$C_6$ alkoxy group, and preferably $R^3$ is —OCH$_3$;

$R^{4'}$ is selected from

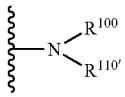

$R^5$ is selected from hydroxy, and an optionally substituted $C_1$-$C_6$ alkoxy, such as $R^5$ is a $C_1$-$C_6$ alkoxy group, and preferably $R^5$ is hydroxy;

$R^6$ and $R^7$ come together to form

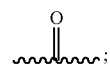

$R^{22}$ is selected from $C_1$-$C_6$ alkyl, such as $R^{22}$ is a $C_2$-$C_4$ alkyl, wherein the $C_1$-$C_6$ alkyl or $C_2$-$C_4$ alkyl is substituted with an optionally substituted saturated 3- to 8-membered heterocycle, oxo, —O—$C_{1-10}$ alkyl, —NR$^{30}$—S(O)$_2$R$^{30}$, —SO$_2$—N(R$^{30}$)$_2$, or —S(O)$_2$R$^{30}$, wherein the substitutents on the 3- to 8-membered saturated heterocycle of $R^{22}$ are independently selected from —NR$^{52}$—SO$_2$—R$^{30}$, —SO$_2$—N(R$^{52}$)$_2$, —S(O)$_2$R$^{30}$, $C_{1-6}$ alkyl, $C_{1-6}$ hydroxyalkyl, and —OR$^{30}$, and wherein R$^{30}$ of —S(O)$_2$R$^{30}$ is selected from $C_{1-10}$ alkyl and R$^{30}$ of —OR$^{30}$ is selected from hydrogen and $C_{1-6}$ alkyl;

$R^{100}$ is selected from hydrogen and $C_{1-10}$ alkyl;

$R^{110'}$ is selected from —S(O)$_2$R$^{51'}$, wherein R$^{51'}$ is selected from substituted $C_{1-4}$ alkyl, —((CH$_2$)$_q$—CH$_2$-D)$_z$-T, optionally substituted $C_{1-30}$ alkyl, optionally substituted $C_{3-8}$ carbocycle, and optionally substituted 3-10 membered heterocycle;

$R^{52}$ is selected from hydrogen and $C_{1-10}$ alkyl;

$R^{30}$ is independently selected at each occurrence from hydrogen; $C_{1-10}$ alkyl, $C_{2-10}$ alkenyl, $C_{2-10}$ alkynyl, $C_{3-10}$ carbocycle, and 3- to 10-membered heterocycle, each of which is optionally substituted with one or more substituents independently selected from halogen, —OH, —CN, —NO$_2$, —NH$_2$, =O, =S, $C_{1-10}$ alkyl, —C$_{1-10}$ haloalkyl, —O—$C_{1-10}$ alkyl, $C_{2-10}$ alkenyl, $C_{2-10}$ alkynyl, $C_{3-10}$ carbocycle, and 3- to 10-membered heterocycle;

q is selected from 1 to 6;

each z is selected from 1-20; and each T is selected from hydrogen and optionally substituted —$C_1$-$C_6$ alkyl.

In some embodiments, for the compound or salt of Formula (I), (IA), (IB), (IC), (ID), (IE), (IF), or (IG): $R^{51'}$ is independently selected at each occurrence from —((CH$_2$)$_q$—CH$_2$-D)$_z$-T, optionally substituted $C_{1-30}$ alkyl, optionally substituted $C_{3-8}$ carbocycle, and optionally substituted 3-10 membered heterocycle. In some embodiments, $R^{51'}$ is independently selected at each occurrence from —((CH$_2$)$_q$—CH$_2$-D)$_z$-T, optionally substituted $C_{3-8}$ carbocycle, and optionally substituted 3-10 membered heterocycle. In some embodiments, $R^{51'}$ is independently selected at each occurrence from —((CH$_2$)$_q$—CH$_2$-D)$_z$-T, $C_{3-8}$ carbocycle, and 3-10 membered heterocycle.

In some embodiments, for the compound or salt of Formula (I), (IA), (IB), (IC), (ID), (IE), (IF), or (IG): $R^{51'}$ is selected from —(($CH_2$)$_q$—$CH_2$-D)$_z$-T. In some embodiments, $R^{51'}$ is selected from $C_{1-30}$ alkyl. In some embodiments, $R^{51'}$ is selected from unsubstituted $C_{1-30}$ alkyl. In some embodiments, $R^{51'}$ is selected from $C_{3-8}$ carbocycle. In some embodiments, $R^{51'}$ is selected from unsubstituted $C_{3-6}$ carbocycle. In some embodiments, $R^{51'}$ is selected from $C_{3-5}$ carbocycle. In some embodiments, $R^{51'}$ is selected from 3-6 membered heterocycle. In some embodiments, $R^{51'}$ is selected from unsubstituted 3-6 membered heterocycle. In some embodiments, q is selected from 1 to 6. In some embodiments, each D is independently selected from —O—. In some embodiments, z is selected from 1-10. In some embodiments, T is selected from hydrogen and $C_1$-$C_6$ alkyl. In some embodiments, the optional substituents of $R^{51'}$ on optionally substituted $C_{1-30}$ alkyl, optionally substituted $C_{3-8}$ carbocycle, and optionally substituted 3-10 membered heterocycle are independently selected at each occurrence from:

halogen, —$OR^{30'}$, —$N(R^{30'})_2$, —(O—$CH_2$—($CH_2$)$_p$)$_n$—W, —$SR^{30'}$, —$C(O)R^{30'}$, —$C(O)N(R^{30'})_2$, —$N(R^{30'})C(O)R^{30'}$, —$C(O)OR^{30'}$, —$OC(O)R^{30'}$, —$S(O)R^{30'}$, —$S(O)_2R^{30'}$, —$P(O)(OR^{30'})_2$, —$OP(O)(OR^{30'})_2$, —$NO_2$, =O, =S, =$N(R^{30'})$, and —CN;

$C_{1-10}$ alkyl, $C_{2-10}$ alkenyl, $C_{2-10}$ alkynyl, each of which is optionally substituted with one or more substituents independently selected from halogen, —$OR^{30'}$, —$SR^{30'}$, —$N(R^{30'})_2$, —$C(O)R^{30'}$, —$C(O)N(R^{30'})_2$, —$N(R^{30'})C(O)R^{30'}$, —$C(O)OR^{30'}$, —$OC(O)R^{30'}$, —$S(O)R^{30'}$, —$S(O)_2R^{30'}$, —$P(O)(OR^{30'})_2$, —$OP(O)(OR^{30'})_2$, —$NO_2$, =O, =S, =$N(R^{30'})$, —CN, $C_{3-10}$ carbocycle and 3- to 10-membered heterocycle; and $C_{3-10}$ carbocycle and 3- to 10-membered heterocycle each of which is optionally substituted with one or more substituents independently selected from halogen, —$OR^{30'}$, —$SR^{30'}$, —$N(R^{30'})_2$, —$C(O)R^{30'}$, —$C(O)N(R^{30'})_2$, —$N(R^{30'})C(O)R^{30'}$, —$C(O)OR^{30'}$, —$OC(O)R^{30'}$, —$S(O)R^{30'}$, —$S(O)_2R^{30'}$, —$P(O)(OR^{30'})_2$, —$OP(O)(OR^{30'})_2$, —$NO_2$, =O, =S, =$N(R^{30'})$, —CN, $C_{1-6}$ alkyl, $C_{1-6}$ alkyl-$R^{30'}$, $C_{2-6}$ alkenyl, and $C_{2-6}$ alkynyl.

In some embodiments, $R^{30'}$ of $R^{51'}$ is independently selected at each occurrence from hydrogen; $C_{1-10}$ alkyl, $C_{2-10}$ alkenyl, $C_{2-10}$ alkynyl, $C_{3-10}$ carbocycle, and 3- to 10-membered heterocycle, each of which is optionally substituted with one or more substituents independently selected from halogen, —OH, —CN, —$NO_2$, —$NH_2$, =O, =S, $C_{1-10}$ alkyl, —$C_{1-10}$ haloalkyl, —O—$C_{1-10}$ alkyl, $C_{2-10}$ alkenyl, $C_{2-10}$ alkynyl, $C_{3-10}$ carbocycle, and 3- to 10-membered heterocycle.

In some embodiments, for the compound or salt of Formula (I), (IA), (IB), (IC), (ID), (IE), (IF), or (IG):
$R^1$ is selected from: —OH, and

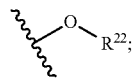

$R^2$ is selected from hydrogen and an optionally substituted $C_1$-$C_6$ alkoxy, wherein substituents are independently selected at each occurrence from hydroxy, halogen, —CN, —$NO_2$, $C_1$-$C_6$ alkoxy, 3- to 10-membered heterocycle, and $C_{3-10}$ carbocycle, wherein the 3- to 10-membered heterocycle and $C_{3-10}$ carbocycle are each optionally substituted with one or more substituents independently selected from hydroxy, halogen, —CN, —$NO_2$, $C_1$-$C_6$ alkyl, $C_1$-$C_6$ haloalkyl, $C_1$-$C_6$ hydroxyalkyl, and $C_1$-$C_6$ alkoxy;

$R^3$ is selected from hydrogen and an optionally substituted $C_1$-$C_6$ alkoxy, wherein the substituents are independently selected at each occurrence from hydroxy, halogen, —CN, —$NO_2$, $C_1$-$C_6$ alkoxy, 3- to 10-membered heterocycle, and $C_{3-10}$ carbocycle, wherein the 3- to 10-membered heterocycle and $C_{3-10}$ carbocycle, are each optionally substituted with one or more substituents independently selected from hydroxy, halogen, —CN, —$NO_2$, $C_1$-$C_6$ alkyl, $C_1$-$C_6$ haloalkyl, $C_1$-$C_6$ hydroxyalkyl, and $C_1$-$C_6$ alkoxy; and $R^{4'}$ is selected from,

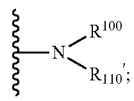

$R^5$ is selected from hydrogen, hydroxy, and an optionally substituted $C_1$-$C_6$ alkoxy, wherein substituents are independently selected at each occurrence from hydroxy, halogen, —CN, —$NO_2$, $C_1$-$C_6$ alkoxy, 3- to 10-membered heterocycle, and $C_{3-10}$ carbocycle, wherein the 3- to 10-membered heterocycle, and $C_{3-10}$ carbocycle are each optionally substituted with one or more substituents independently selected from hydroxy, halogen, —CN, —$NO_2$, $C_1$-$C_6$ alkyl, $C_1$-$C_6$ haloalkyl, $C_1$-$C_6$ hydroxyalkyl, and $C_1$-$C_6$ alkoxy;

$R^6$ and $R^7$ come together to form

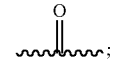

$R^{22}$ is selected from optionally substituted $C_1$-$C_6$ alkyl, optionally substituted 3- to 10-membered heterocycle, and optionally substituted $C_{3-10}$ carbocycle, and —P(=O)($R^{24}$)$_2$;

$R^{100}$ is selected from:
hydrogen and —($CH_2$—$CH_2$-G)$_y$-V; and
$C_{1-10}$ alkyl, $C_{2-10}$ alkenyl, $C_{2-10}$ alkynyl, wherein each of which is optionally substituted with one or more substituents independently selected from halogen, —$OR^{31}$, —$SR^{31}$, —$N(R^{31})_2$, —$C(O)R^{31}$, —$C(O)N(R^{31})_2$, —$N(R^{31})C(O)R^{31}$, —$C(O)OR^{31}$, —$OC(O)R^{31}$, —$S(O)R^{31}$, —$S(O)_2R^{31}$, —$P(O)(OR^{31})_2$, —$OP(O)(OR^{31})_2$, —$NO_2$, —CN, $C_{3-20}$ carbocycle and 3- to 20-membered heterocycle; and $C_{3-20}$ carbocycle and 3- to 20-membered heterocycle each of which is optionally substituted with one or more substituents independently selected from halogen, —$OR^{31}$, —$SR^{31}$, —$N(R^{31})_2$, —$C(O)R^{31}$, —$C(O)N(R^{31})_2$, —$N(R^{31})C(O)R^{31}$, —$C(O)OR^{31}$, —$OC(O)R^{31}$, —$S(O)R^{31}$, —$S(O)_2R^{31}$, —$P(O)(OR^{31})_2$, —$OP(O)(OR^{31})_2$, —$NO_2$, =O, =S, =$N(R^{31})$, —CN, $C_{1-6}$ alkyl, $C_{1-6}$ alkyl-$R^{31}$, $C_{2-6}$ alkenyl, and $C_{2-6}$ alkynyl;

$R^{110'}$ is selected from:
hydrogen, —($CH_2$—$CH_2$-G)$_y$-V, —$S(O)R^{51'}$, —$S(O)_2R^{51'}$, —$C(O)R^{51'}$, —$C(O)N(R^{51'})_2$, and —$C(O)OR^{51'}$; and $C_{1-10}$ alkyl, $C_{2-10}$ alkenyl, $C_{2-10}$ alkynyl, wherein each of which is optionally substituted with one or more substituents independently selected from halogen, —$OR^{31}$, —SR³¹, —N(R³¹)₂, —C(O)R³¹, —C(O)N(R³¹)₂, —N(R³¹)C(O)R³¹, —C(O)OR³¹, —OC(O)R³¹, —S(O)R³¹, —S(O)₂R³¹, —P(O)(OR³¹)₂, —OP(O)(OR³¹)₂, —NO₂, —CN, $C_{3-20}$ carbocycle and 3- to 20-membered heterocycle; and $C_{3-20}$ carbocycle and 3- to 20-membered heterocycle each of which is optionally substituted with one or more substituents independently selected from halogen, —OR³¹, —SR³¹, —N(R³¹)₂, —C(O)R³¹, —C(O)N(R³¹)₂, —N(R³¹)C(O)R³¹, —C(O)OR³¹, —OC(O)R³¹, —S(O)R³¹, —S(O)₂R³¹, —P(O)(OR³¹)₂, —OP(O)(OR³¹)₂, —NO₂, =O, =S, =N(R³¹), —CN, $C_{1-6}$ alkyl, $C_{1-6}$ alkyl-R³¹, $C_{2-6}$ alkenyl, and $C_{2-6}$ alkynyl; or $R^{100}$ and $R^{110'}$ together with the nitrogen to which they are bound form a 3-10-membered heterocycle optionally substituted with one or more substituents independently selected from: hydroxy, halogen, —CN, —NO₂, $C_1$-$C_6$ alkyl, $C_1$-$C_6$ haloalkyl, $C_1$-$C_6$ hydroxyalkyl, and $C_1$-$C_6$ alkoxy, wherein when $R^1$ is hydroxy, the ring formed by $R^{100}$ and $R^{110}$ is not unsubstituted morpholine each G is independently selected from —O—, —NR³²—, —S—, or —SO₂—;

each D is independently selected from —O—, —NR³²—, —S—, or —SO₂—;

each y is selected from 3-20;

each z is selected from 1-20;

each V is selected from hydrogen and optionally substituted —$C_1$-$C_6$ alkyl;

each T is selected from hydrogen and optionally substituted —$C_1$-$C_6$ alkyl;

each $R^{31}$ is independently selected from hydrogen, and $C_{1-10}$ alkyl, $C_{2-10}$ alkenyl, $C_{2-10}$ alkynyl, $C_{3-10}$ carbocycle, and 3- to 10-membered heterocycle, each of which is optionally substituted with one or more substituents independently selected from halogen, —OH, —CN, —NO₂, —NH₂, =O, =S, $C_{1-10}$ alkyl, —$C_{1-10}$ haloalkyl, —O—$C_{1-10}$ alkyl, $C_{2-10}$ alkenyl, $C_{2-10}$ alkynyl, $C_{3-10}$ carbocycle, and 3- to 10-membered heterocycle; and $R^{32}$ is independently selected at each occurrence from: hydrogen; and $C_{1-10}$ alkyl, $C_{2-10}$ alkenyl, $C_{2-10}$ alkynyl, $C_{3-10}$ carbocycle, and 3- to 10-membered heterocycle, each of which is optionally substituted with one or more substituents independently selected from halogen, —OH, —CN, —NO₂, —NH₂, =O, =S, $C_{1-10}$ alkyl, —$C_{1-10}$ haloalkyl, —O—$C_{1-10}$ alkyl, $C_{2-10}$ alkenyl, $C_{2-10}$ alkynyl, $C_{3-10}$ carbocycle, and 3- to 10-membered heterocycle;

wherein the optional substituents on $R^{22}$, $R^{51}$, V, and T are independently selected at each occurrence from:
halogen, —OR³⁰, —N(R³⁰)₂, —(O—CH₂—(CH₂)ₚ)ₙ—W, —SR³⁰, —C(O)R³⁰, —C(O)N(R³⁰)₂, —N(R³⁰)C(O)R³⁰, —C(O)OR³⁰, —OC(O)R³⁰, —S(O)R³⁰, —S(O)₂R³⁰, —P(O)(OR³⁰)₂, —OP(O)(OR³⁰)₂, —NO₂, =O, =S, =N(R³⁰), and —CN;

$C_{1-10}$ alkyl, $C_{2-10}$ alkenyl, $C_{2-10}$ alkynyl, each of which is optionally substituted with one or more substituents independently selected from halogen, —OR³⁰, —SR³⁰, —N(R³⁰)₂, —C(O)R³⁰, —C(O)N(R³⁰)₂, —N(R³⁰)C(O)R³⁰, —C(O)OR³⁰, —OC(O)R³⁰, —S(O)R³⁰, —S(O)₂R³⁰, —P(O)(OR³⁰)₂, —OP(O)(OR³⁰)₂, —NO₂, =O, =S, =N(R³⁰), —CN, $C_{3-10}$ carbocycle and 3- to 10-membered heterocycle; and $C_{3-10}$ carbocycle and 3- to 10-membered heterocycle each of which is optionally substituted with one or more substituents independently selected from halogen, —OR³⁰, —SR³⁰, —N(R³⁰)₂, —C(O)R³⁰, —C(O)N(R³⁰)₂, —N(R³⁰)C(O)R³⁰, —C(O)OR³⁰, —OC(O)R³⁰, —S(O)R³⁰, —S(O)₂R³⁰, —P(O)(OR³⁰)₂, —OP(O)(OR³⁰)₂, —NO₂, =O, =S, =N(R³⁰), —CN, $C_{1-6}$ alkyl, $C_{2-6}$ alkenyl, and $C_{2-6}$ alkynyl;

$R^{30}$ is independently selected at each occurrence from hydrogen; $C_{1-10}$ alkyl, $C_{2-10}$ alkenyl, $C_{2-10}$ alkynyl, $C_{3-10}$ carbocycle, and 3- to 10-membered heterocycle, each of which is optionally substituted with one or more substituents independently selected from halogen, —OH, —CN, —NO₂, —NH₂, =O, =S, $C_{1-10}$ alkyl, —$C_{1-10}$ haloalkyl, —O—$C_{1-10}$ alkyl, $C_{2-10}$ alkenyl, $C_{2-10}$ alkynyl, $C_{3-10}$ carbocycle, and 3- to 10-membered heterocycle;

$R^{51'}$ is independently selected at each occurrence from optionally substituted $C_{3-8}$ carbocycle, optionally substituted 3-10 membered heterocycle, —((CH₂)_q—CH₂-D)_z-T and optionally substituted $C_{5-30}$ alkyl; wherein $C_{3-10}$ carbocycle and 3- to 10-membered heterocycle each of which is optionally substituted with one or more substituents independently selected from halogen, —OR³⁰, —SR³⁰, —N(R³⁰)₂, —C(O)R³⁰, —C(O)N(R³⁰)₂, —N(R³⁰)C(O)R³⁰, —C(O)OR³⁰, —OC(O)R³⁰, —S(O)R³⁰, —S(O)₂R³⁰, —P(O)(OR³⁰)₂, —OP(O)(OR³⁰)₂, —NO₂, =O, =S, =N(R³⁰), —CN, $C_{1-6}$ alkoxy, $C_{1-6}$ alkyl, $C_{2-6}$ alkenyl, and $C_{2-6}$ alkynyl;

q is selected from 1 to 6;
each p is selected from 1 or 2;
each n is selected from 3-7; and
each W is selected from hydrogen, —OH, —$C_1$-$C_4$ alkyl and —O($C_1$-$C_4$ alkyl).

In some embodiments, for the compound or salt of Formula (I), (IA), (IB), (IC), (ID), (IE), (IF), or (IG),
$R^1$ is selected from

$R^{22}$ is selected from optionally substituted $C_1$-$C_6$ alkyl;
wherein the substituents on $R^{22}$, is independently selected at each occurrence from: —S(O)R³⁰, and —S(O)₂R³⁰, preferably —S(O)₂R³⁰;
$R^2$ is selected from hydrogen and an optionally substituted $C_1$-$C_6$ alkoxy;
$R^3$ is selected from hydrogen and an optionally substituted $C_1$-$C_6$ alkoxy;
$R^{4'}$ is selected from

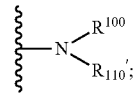

$R^5$ is selected from hydrogen, hydroxy, and an optionally substituted $C_1$-$C_6$ alkoxy;
$R^6$ and $R^7$ are each independently selected from hydrogen, hydroxy, and $C_1$-$C_6$ alkoxy; or $R^6$ and $R^7$ come together to form

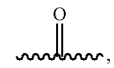

preferably $R^6$ and $R^7$ come together to form

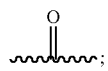

$R^{100}$ is selected from:
hydrogen and
$C_{1-10}$ alkyl;
$R^{110'}$ is selected from:
—S(O)$R^{51'}$ and —S(O)$_2R^{51'}$, preferably S(O)$_2R^{51'}$;
$R^{51'}$ is independently selected at each occurrence from substituted $C_{1-4}$ alkyl, optionally substituted $C_{3-8}$ carbocycle, optionally substituted 3-10 membered heterocycle, —((CH$_2$)$_q$—CH$_2$-D)$_z$-T and optionally substituted $C_{5-30}$ alkyl;
wherein the substituents on $R^{51'}$, and T are independently selected at each occurrence from:
halogen, —OR$^{30}$, —N(R$^{30}$)$_2$, —SR$^{30}$, —C(O)R$^{30}$, —C(O)N(R$^{30}$)$_2$, —N(R$^{30}$)C(O)R$^{30}$, —C(O)OR$^{30}$, —OC(O)R$^{30}$, —S(O)R$^{30}$, —S(O)$_2$R$^{30}$, —P(O)(OR$^{30}$)$_2$, —OP(O)(OR$^{30}$)$_2$, —NO$_2$, =O, =S, =N(R$^{30}$), and —CN;
$R^{30}$ is independently selected at each occurrence from hydrogen; $C_{1-10}$ alkyl, $C_{3-6}$ carbocycle, and 3- to 6-membered heterocycle, each of which is optionally substituted with one or more substituents independently selected from halogen, —OH, —CN, —NO$_2$, —NH$_2$, =O, =S, $C_{1-10}$ alkyl, —$C_{1-10}$ haloalkyl, —O—$C_{1-10}$ alkyl, $C_{3-6}$ carbocycle, and 3- to 6-membered heterocycle;
each D is independently selected from —O—;
q is selected from 1 to 6;
each z is selected from 1-20;
each T is selected from hydrogen and optionally substituted —$C_1$-$C_6$ alkyl;
In some embodiments, for the compound or salt of Formula (I), (IZ), (IA), (IB), (IC), (ID), (IE), (IF), or (IG), —OH and

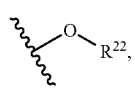

wherein $R^{22}$ is $C_1$-$C_6$ alkyl substituted with one or more substituents selected from —(O—CH$_2$—(CH$_2$)$_p$)$_n$—W and —OR$^{30}$; and $R^{4'}$ is selected from

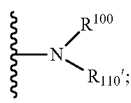

wherein $R^{100}$ is selected from: hydrogen and $C_{1-10}$ alkyl; and $R^{110'}$ is selected from: —S(O)$R^{51'}$ and —S(O)$_2R^{51'}$, preferably S(O)$_2R^{51'}$.

In some embodiments, for the compound or salt of Formula (I), (IZ), (IA), (IB), (IC), (ID), (IE), (IF), or (IG), $R^1$ is selected from: —OH and

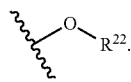

In some embodiments, for the compound or salt of Formula (I), (IZ), (IA), (IB), (IC), (ID), (IE), (IF), or (IG), $R^1$ is

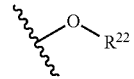

and $R^{22}$ is selected from optionally substituted $C_1$-$C_6$ alkyl, preferably an optionally substituted $C_{2-4}$ alkyl. In some embodiments, $R^{22}$ is an optionally substituted $C_{2-3}$ alkyl.

In some embodiments, for the compound or salt of Formula (I), (IZ), (IA), (IB), (IC), (ID), (IE), (IF), or (IG), $R^1$ is

and $R^{22}$ is selected from substituted $C_1$-$C_6$ alkyl, preferably a substituted $C_{2-4}$ alkyl.

In some embodiments, for the compound or salt of Formula (I), (IZ), (IA), (IB), (IC), (ID), (IE), (IF), or (IG), the substituents on $R^{22}$ are independently selected from —OR$^{30}$, —(O—CH$_2$—(CH$_2$)$_p$)$_n$—W, —S(O)R$^{30}$, —S(O)$_2$R$^{30}$, =O, =S, =N(R$^{30}$), and —CN.

In some embodiments, for the compound or salt of Formula (I), (IZ), (IA), (IB), (IC), (ID), (IE), (IF), or (IG), the optional substituents on $R^{22}$ are independently selected from —OR$^{30}$, —S(O)$_2$R$^{30}$, and =O.

In some embodiments, for the compound or salt of Formula (I), (IZ), (IA), (IB), (IC), (ID), (IE), (IF), or (IG), $R^{30}$ of —OR$^{30}$ and —S(O)$_2$R$^{30}$, are independently selected from hydrogen and $C_{1-10}$ alkyl, wherein the $C_{1-10}$ alkyl is optionally substituted with one or more substituents independently selected from halogen, —OH, —CN, —NO$_2$, —NH$_2$, =O, =S, —$C_{1-10}$ haloalkyl, —O—$C_{1-10}$ alkyl, $C_{2-10}$ alkenyl, $C_{2-10}$ alkynyl, $C_{3-10}$ carbocycle, and 3- to 10-membered heterocycle.

In some embodiments, for the compound or salt of Formula (I), (IA), (IB), (IC), (ID), (IE), (IF), or (IG), $R^{30}$ of —OR$^{30}$ and —S(O)$_2$R$^{30}$ is independently selected at each occurrence from hydrogen and $C_{1-10}$ alkyl.

In some embodiments, for the compound or salt of Formula (I), (IA), (IB), (IC), (ID), (IE), (IF), or (IG), $R^1$ is selected from

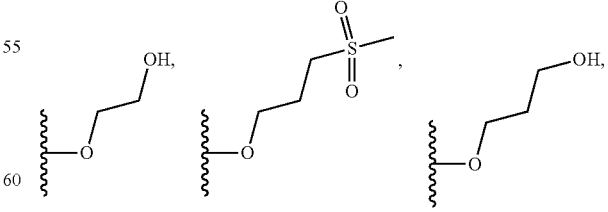

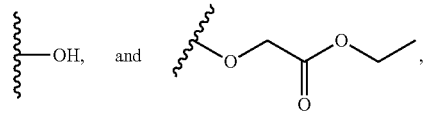

In some embodiments, for the compound or salt of Formula (I), (IA), (IB), (IC), (ID), (IE), (IF), or (IG), $R^1$ is selected from

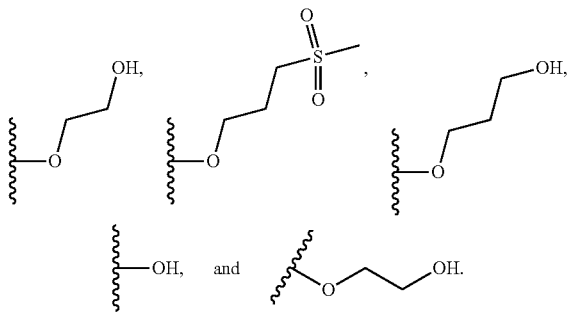

In some embodiments, for the compound or salt of Formula (I), (IA), (IB), (IC), (ID), (IE), (IF), or (IG), $R^{4'}$ is

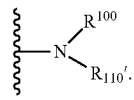

In some cases, $R^{100}$ of

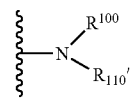

is selected from: hydrogen and $C_{1-10}$ alkyl.

In some embodiments, for the compound or salt of Formula (I), (IA), (IB), (IC), (ID), (IE), (IF), or (IG), $R^{110'}$ of

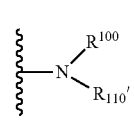

is selected from: hydrogen, $-S(O)R^{51'}$, and $-S(O)_2R^{51'}$. In some cases, $R^{110'}$ of

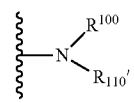

is selected from: $-S(O)_2R^{51'}$.

In some embodiments, for the compound or salt of Formula (I), (IA), (IB), (IC), (ID), (IE), (IF), or (IG), $R^{51'}$ is independently selected at each occurrence from substituted $C_{1-4}$ alkyl, optionally substituted $C_{3-8}$ carbocycle, optionally substituted 3-10 membered heterocycle, $-((CH_2)_q-CH_2-D)_z-T$ and optionally substituted $C_{5-30}$ alkyl.

In some embodiments, for the compound or salt of Formula (I), (IA), (IB), (IC), (ID), (IE), (IF), or (IG), $R^{51'}$ is independently selected at each occurrence from substituted $C_{1-4}$ alkyl, optionally substituted $C_{3-8}$ carbocycle, $-((CH_2)_q-CH_2-D)_z-T$ and optionally substituted $C_{5-30}$ alkyl.

In some embodiments, for the compound or salt of Formula (I), (IA), (IB), (IC), (ID), (IE), (IF), or (IG), $R^{51'}$ is independently selected at each occurrence from substituted $C_{1-4}$ alkyl, optionally substituted $C_{3-8}$ carbocycle, and $-((CH_2)_q-CH_2-D)_z-T$.

In some embodiments, for the compound or salt of Formula (I), (IA), (IB), (IC), (ID), (IE), (IF), or (IG), wherein $R^{51'}$ is independently selected at each occurrence from substituted $C_{1-4}$ alkyl, optionally substituted $C_{3-8}$ carbocycle, optionally substituted 3-10 membered heterocycle, $-((CH_2)_q-CH_2-D)_z-T$ and optionally substituted $C_{5-30}$ alkyl. In some cases z is 3-10. In some cases, z is 3-8. In some cases, z is 4-8. In some cases, z is 5-10.

In some embodiments, for the compound or salt of Formula (I), (IA), (IB), (IC), (ID), (IE), (IF), or (IG), $R^{51'}$ independently selected at each occurrence from substituted $C_{1-4}$ alkyl, optionally substituted $C_{3-6}$ carbocycle and optionally substituted 3- to 6-membered heterocycle. In some cases, $R^{51'}$ independently selected at each occurrence from substituted $C_{1-4}$ alkyl, $C_{3-6}$ carbocycle and 3- to 6-membered heterocycle.

In some embodiments, for the compound or salt of Formula (I), (IA), (IB), (IC), (ID), (IE), (IF), or (IG), $R^{51'}$ is independently selected at each occurrence from substituted $C_{1-4}$ alkyl, saturated $C_{3-6}$ carbocycle and saturated 5 to 6-membered heterocycle.

In some embodiments, for the compound or salt of Formula (I), (IA), (IB), (IC), (ID), (IE), (IF), or (IG), $R^{51'}$ is independently selected at each occurrence from substituted $C_{1-4}$ alkyl and saturated $C_{3-6}$ carbocycle.

In some embodiments, for the compound or salt of Formula (I), (IA), (IB), (IC), (ID), (IE), (IF), or (IG), the $C_{1-4}$ alkyl of $R^{51'}$ is substituted with one or more substituents independently selected from $-OR^{30}$, $C_{3-10}$ carbocycle and 3- to 10-membered heterocycle.

In some embodiments, for the compound or salt of Formula (I), (IA), (IB), (IC), (ID), (IE), (IF), or (IG), $C_{1-4}$ alkyl of $R^{51'}$ is substituted with one or more substituents selected from $-OR^{30}$, and saturated $C_{3-6}$ carbocycle.

In some embodiments, for the compound or salt of Formula (I), (IA), (IB), (IC), (ID), (IE), (IF), or (IG), the $C_{1-4}$ alkyl of $R^{51'}$ is substituted with one or more substituents independently selected from $-OR^{30}$, and $-((CH_2)_q-CH_2-D)_z-T$, wherein z is 3 to 20, D is $-O-$, and T is selected from hydrogen and optionally substituted $-C_1-C_6$ alkyl.

In some embodiments, for the compound or salt of Formula (I), (IA), (IB), (IC), (ID), (IE), (IF), or (IG), the $C_{1-4}$ alkyl of $R^{51'}$ is substituted with one or more substituents independently selected from $-((CH_2)_q-CH_2-D)_z-T$, wherein z is 1 to 20, D is $-O-$, and T is selected from hydrogen and optionally substituted $-C_1-C_6$ alkyl.

In some embodiments, for the compound or salt of Formula (I), (IA), (IB), (IC), (ID), (IE), (IF), or (IG), the z of $-((CH_2)_q-CH_2-D)_z-T$ for $R^{51'}$ is selected from 1 to 10. In some cases, z is selected from 1 to 5. In some cases, z is selected from 3 to 5.

In some embodiments, for the compound or salt of Formula (I), (IA), (IB), (IC), (ID), (IE), (IF), or (IG), $R^{30}$ of $-OR^{30}$ for $R^{51'}$ is selected from hydrogen and $C_{1-10}$ alkyl, wherein the $C_{1-10}$ alkyl is optionally substituted with one or more substituents independently selected from halogen, $-OH$, $-CN$, $-NO_2$, $-NH_2$, $=O$, $=S$, $C_{1-10}$ alkyl, $-C_{1-10}$ haloalkyl, and $-O-C_{1-10}$ alkyl.

In some embodiments, for the compound or salt of Formula (I), (IA), (IB), (IC), (ID), (IE), (IF), or (IG), $R^{30}$ of $-OR^{30}$ for $R^{51'}$ is selected from $C_{1-10}$ alkyl wherein the $C_{1-10}$ alkyl is optionally substituted with one or more substituents independently selected from —O—$C_{1-10}$ alkyl.

In some embodiments, for the compound or salt of Formula (I), (IA), (IB), (IC), (ID), (IE), (IF), or (IG), $R^{30}$ of —$OR^{30}$ for $R^{51'}$ is selected from $C_{1-3}$ alkyl wherein the $C_{1-10}$ alkyl is optionally substituted with one or more substituents independently selected from —O—$C_{1-3}$ alkyl.

In some embodiments, for the compound or salt of Formula (I), (IA), (IB), (IC), (ID), (IE), (IF), or (IG), $R^4$ is selected from

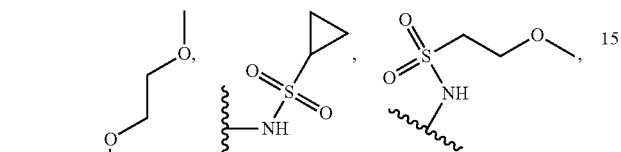

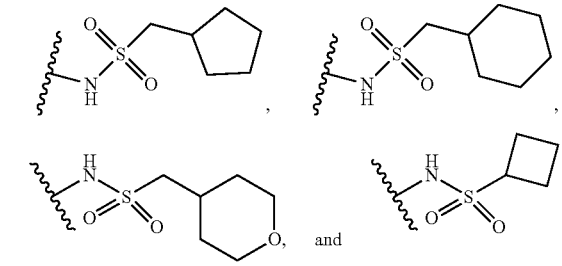

In some embodiments, for the compound or salt of Formula (I), (IA), (IB), (IC), (ID), (IE), (IF), or (IG), $R^4$ is selected from

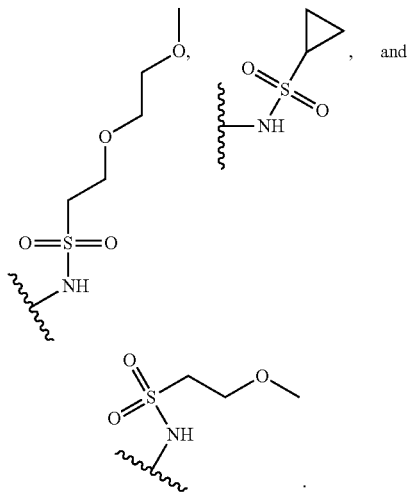

In some embodiments, for the compound or salt of Formula (I), (IA), (IB), (IC), (ID), (IE), (IF), or (IG), $R^4$ is selected from

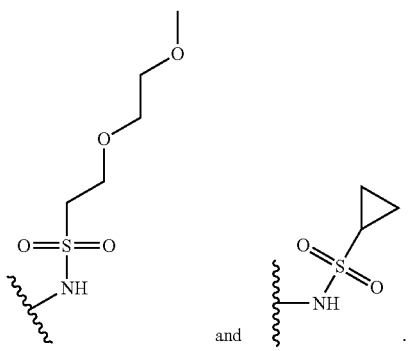 [SMILES: *NS(=O)(=O)CCOCCOC ; *NS(=O)(=O)C1CC1]

In some cases, $R^4$ is selected from

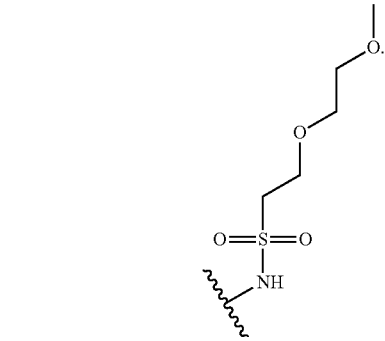

In some embodiments, for the compound or salt of Formula (I), (IA), (IB), (IC), (ID), (IE), (IF), or (IG), $R^4$ is selected from

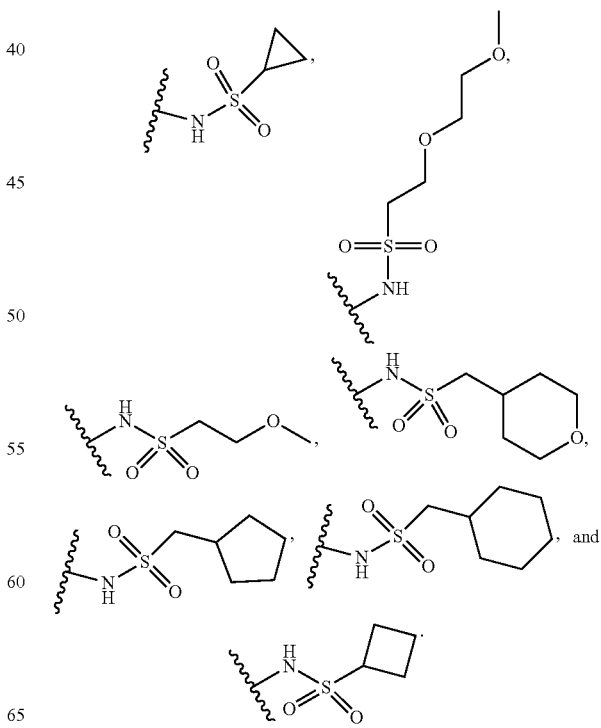

In some embodiments, for the compound or salt of Formula (I), (IA), (IB), (IC), (ID), (IE), (IF), or (IG), $R^4$ is selected from

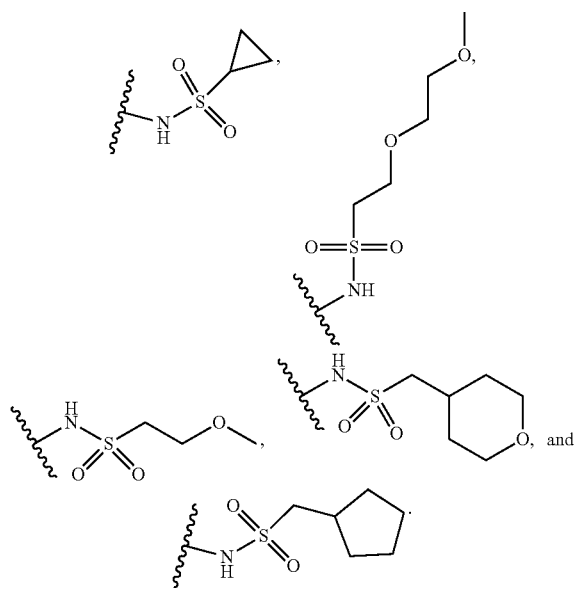

In some embodiments, for the compound or salt of Formula (I), (IA), (IB), (IC), (ID), (IE), (IF), or (IG), $R^4$ is selected from

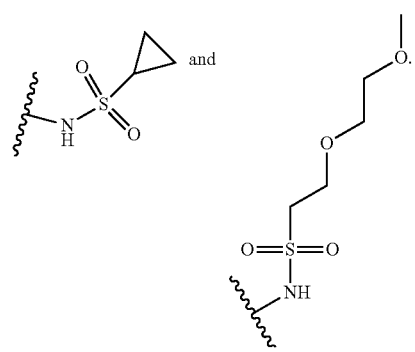 [SMILES: *NS(=O)(=O)C1CC1 ; *NS(=O)(=O)CCOCCOC]

In some embodiments, for the compound or salt of Formula (I), (IA), (IB), (IC), (ID), (IE), (IF), or (IG), $R^1$ is selected from

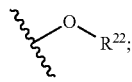

$R^{22}$ is selected from optionally substituted $C_1$-$C_6$ alkyl;
wherein the substituents on $R^{22}$, is independently selected at each occurrence from: —S(O)$R^{30}$, and —S(O)$_2R^{30}$, preferably —S(O)$_2R^{30}$, wherein $R^{30}$ is independently selected at each occurrence from hydrogen and $C_{1-10}$ alkyl, wherein the $C_{1-10}$ alkyl is optionally substituted with one or more substituents independently selected from halogen, —OH, —CN, —NO$_2$, —NH$_2$, =O, =S, —O—$C_{1-10}$ alkyl, $C_{2-10}$ alkenyl, $C_{2-10}$ alkynyl, $C_{3-10}$ carbocycle, and 3- to 10-membered heterocycle.

In some embodiments, for the compound or salt of Formula (I), (IA), (IB), (IC), (ID), (IE), (IF), or (IG), $R^1$ is selected from —OH and

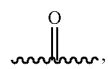

$R^2$ is selected from an optionally substituted $C_1$-$C_6$ alkoxy preferably —OCH$_3$;
$R^3$ is selected from an optionally substituted $C_1$-$C_6$ alkoxy, preferably —OCH$_3$; and
$R^{4'}$ is selected from,

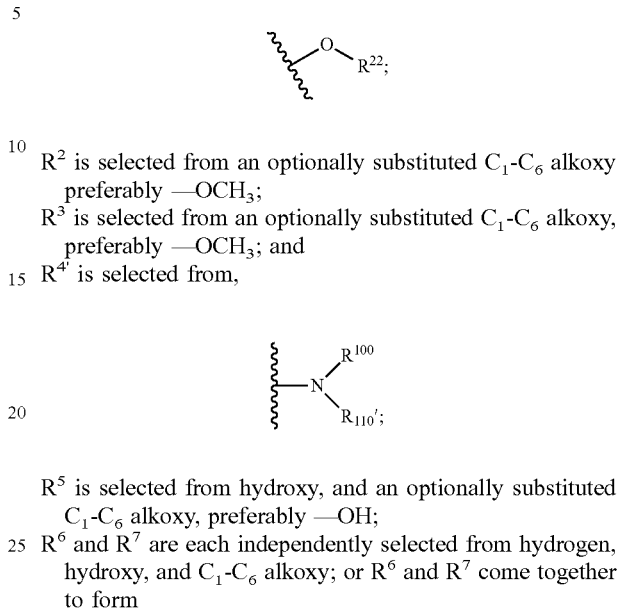

$R^5$ is selected from hydroxy, and an optionally substituted $C_1$-$C_6$ alkoxy, preferably —OH;
$R^6$ and $R^7$ are each independently selected from hydrogen, hydroxy, and $C_1$-$C_6$ alkoxy; or $R^6$ and $R^7$ come together to form preferably $R^{22}$ is selected from optionally substituted $C_1$-$C_6$ alkyl;
$R^{100}$ is selected from:
 hydrogen and
 $C_{1-10}$ alkyl;
$R^{110'}$ is selected from:
 hydrogen and —S(O)$_2R^{51'}$, preferably —S(O)$_2R^{51'}$;
wherein the optional substituents on $R^{22}$, $R^{51'}$, and T are independently selected at each occurrence from:
 halogen, —OR$^{30}$, —N(R$^{30}$)$_2$, —(O—CH$_2$—(CH$_2$)$_p$)$_n$—W, —NO$_2$, =O, =S, —S(O)$_2R^{30}$, and —CN; and
 $C_{3-10}$ carbocycle and 3-6 membered heterocycle, each of which is optionally substituted with one or more substituents independently selected from halogen, —OH, —NO$_2$, =O, =S, —CN, $C_{1-6}$ alkyl, —O—$C_{1-6}$ alkyl;
$R^{30}$ is independently selected at each occurrence from hydrogen; $C_{1-10}$ alkyl, $C_{3-10}$ carbocycle, and 3- to 10-membered heterocycle, each of which is optionally substituted with one or more substituents independently selected from halogen, —OH, —CN, —NO$_2$, —NH$_2$, =O, =S, $C_{1-10}$ alkyl, —$C_{1-10}$ haloalkyl, and —O—$C_{1-10}$ alkyl;
$R^{51'}$ is independently selected at each occurrence from substituted $C_{1-4}$ alkyl, optionally substituted $C_{3-8}$ carbocycle, and —((CH$_2$)$_q$—CH$_2$-D)$_z$-T;
each D is independently selected from —O—;

each T is selected from hydrogen and optionally substituted —$C_1$-$C_6$ alkyl;
z is selected from 1 to 10;
q is selected from 1 to 6;
each p is selected from 1 or 2;
each n is selected from 3-7; and
each W is selected from hydrogen, —OH, —$C_1$-$C_4$ alkyl and —O($C_1$-$C_4$ alkyl).
In some embodiments, the compound or salt of Formula (I), (IA), (IB), (IC), (ID), (IE), (IF), or (IG) is selected from:
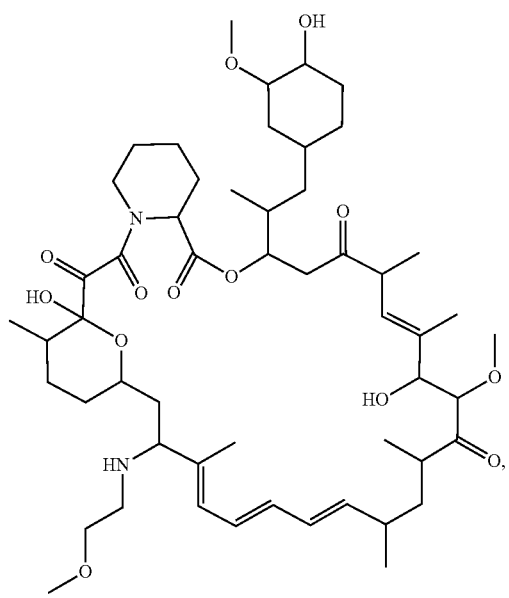
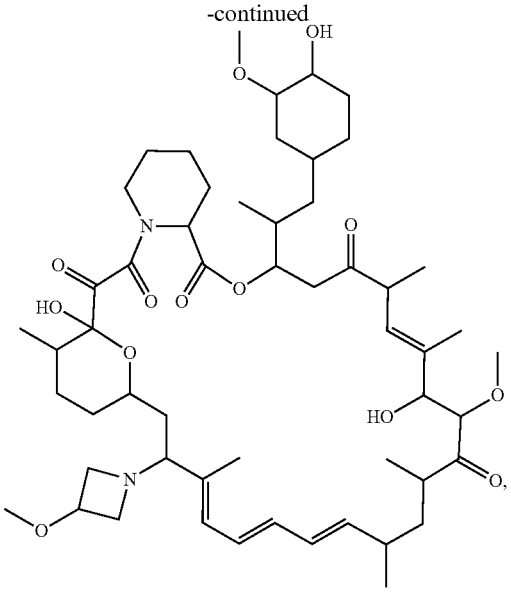
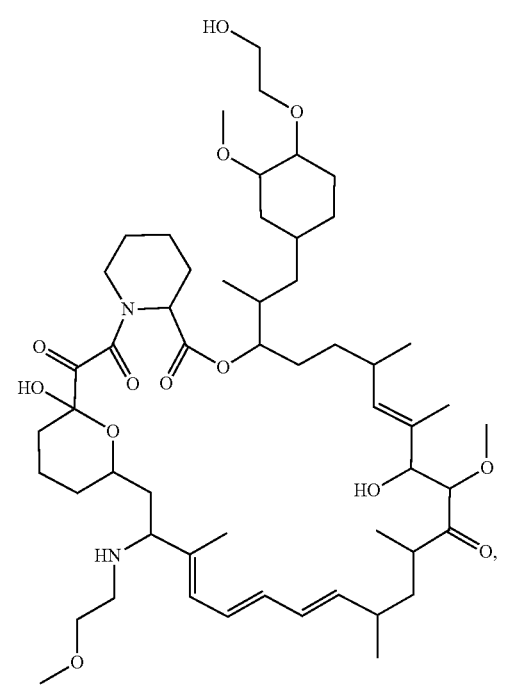
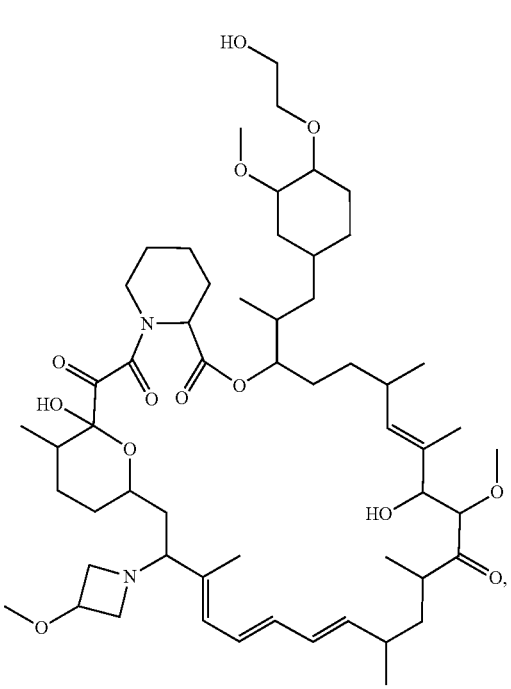

91
-continued
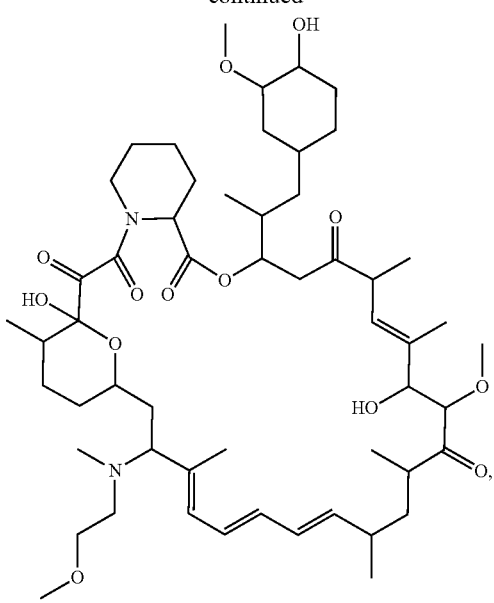
92
-continued
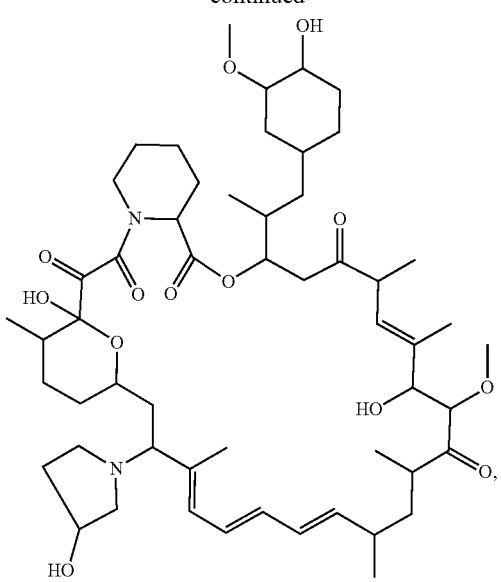
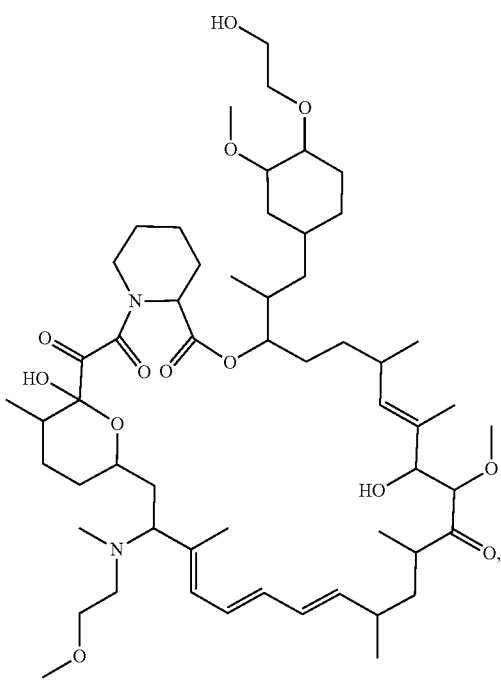
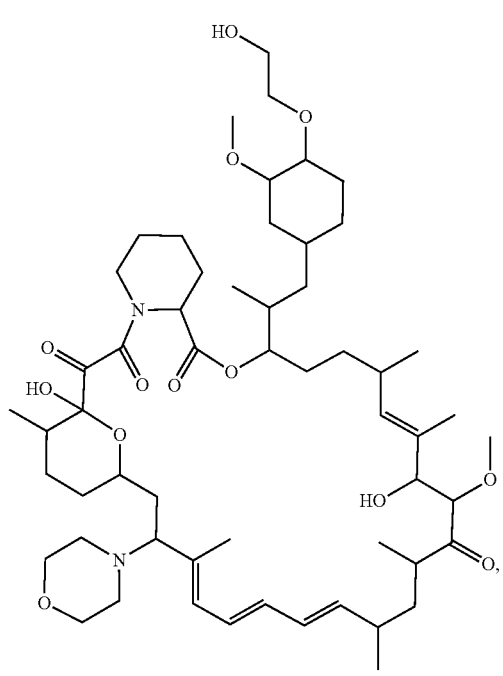

93
-continued
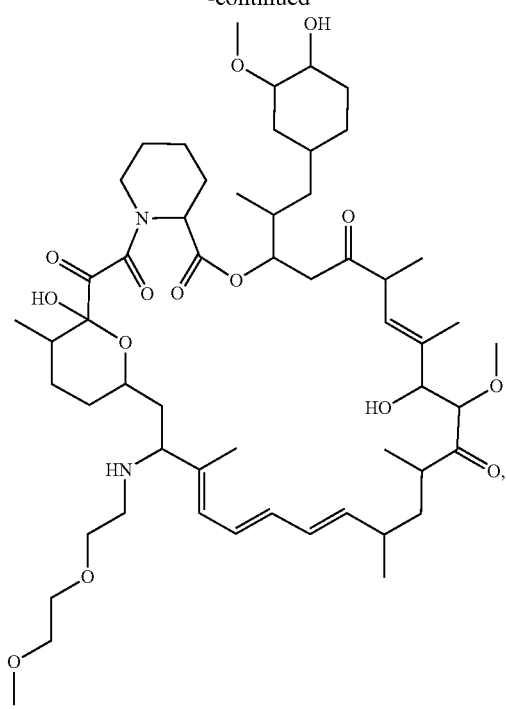
94
-continued
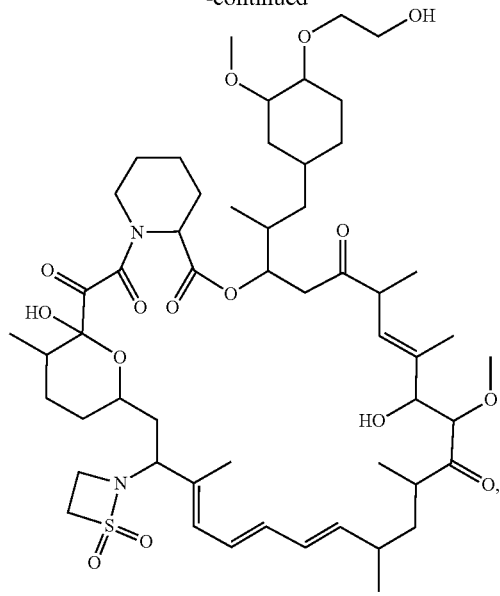
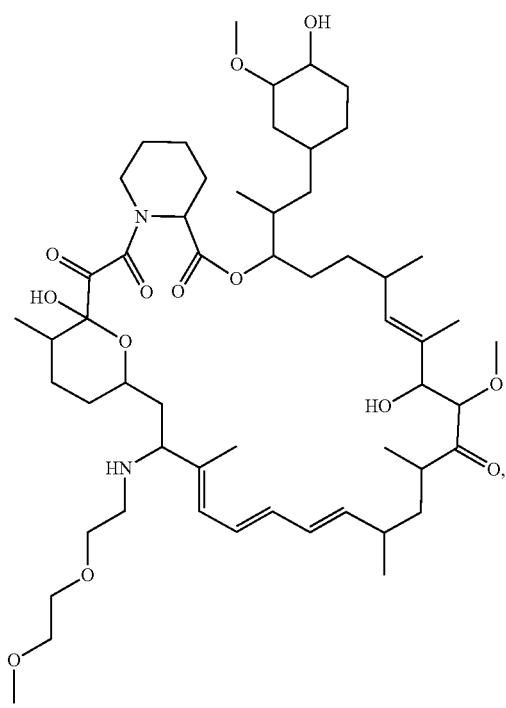
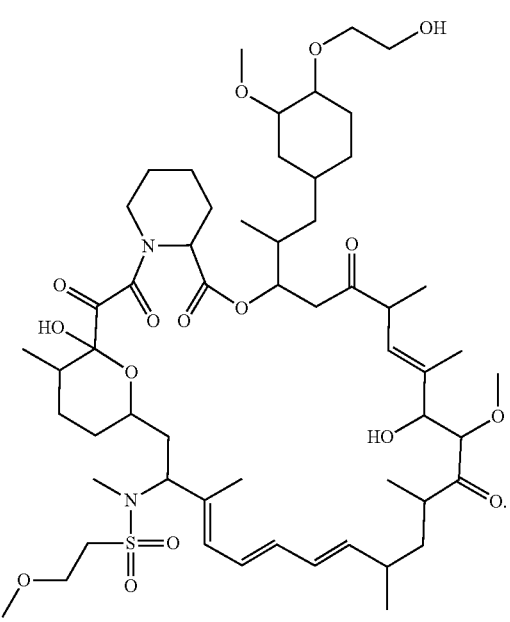
Compound Group 2
In a second aspect, the present disclosure provides a compound represented by the structure of Formula X:

(X)

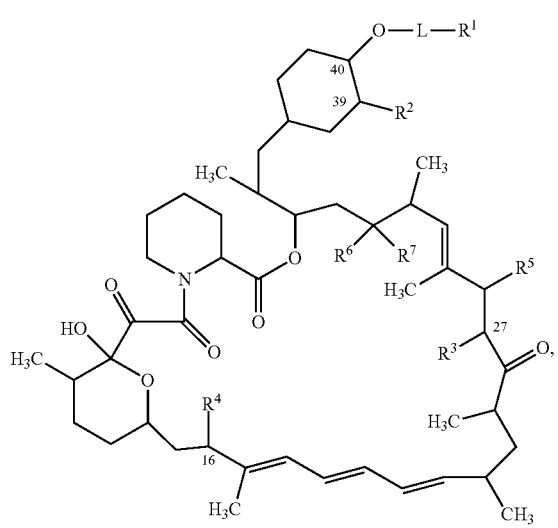

or a pharmaceutically acceptable salt thereof, wherein:

L is selected from optionally substituted $C_{1-8}$ alkylene;

$R^1$ is a carboxylic acid or a carboxylic acid isostere;

$R^2$ is selected from hydrogen and an optionally substituted $C_1$-$C_6$ alkoxy group, wherein substituents are independently selected at each occurrence from hydroxy, halogen, —CN, —NO$_2$, $C_1$-$C_6$ alkoxy, 3- to 10-membered heterocycle, and $C_{3-10}$ carbocycle, wherein the 3- to 10-membered heterocycle and $C_{3-10}$ carbocycle are each optionally substituted with one or more substituents independently selected from hydroxy, halogen, —CN, —NO$_2$, $C_1$-$C_6$ alkyl, $C_1$-$C_6$ haloalkyl, $C_1$-$C_6$ hydroxyalkyl, $C_1$-$C_6$ alkoxy, and $C_1$-$C_6$ alkoxy $C_1$-$C_6$ alkyl;

$R^3$ is selected from hydrogen and an optionally substituted $C_1$-$C_6$ alkoxy group, wherein the substituents are independently selected at each occurrence from hydroxy, halogen, —CN, —NO$_2$, $C_1$-$C_6$ alkoxy group, 3- to 10-membered heterocycle, and $C_{3-10}$ carbocycle, wherein the 3- to 10-membered heterocycle and $C_{3-10}$ carbocycle, are each optionally substituted with one or more substituents independently selected from hydroxy, halogen, —CN, —NO$_2$, $C_1$-$C_6$ alkyl, $C_1$-$C_6$ haloalkyl, $C_1$-$C_6$ hydroxyalkyl, $C_1$-$C_6$ alkoxy, and $C_1$-$C_6$ alkoxy $C_1$-$C_6$ alkyl; and $R^4$ is selected from

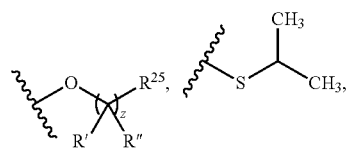

and optionally substituted 3- to 10-membered heterocycle, and when L is optionally substituted $C_{3-8}$ alkylene $R^4$ is further selected from methoxy; and when -L-$R^1$ is ethyl acetate, tert-butyl acetate, benzyl acetate, or methyl 2-phenylacetate, $R^4$ is not methoxy;

wherein the optionally substituted heterocycle of $R^4$ may be substituted with one or more substituents selected from: hydroxy, halogen, —CN, —NO$_2$, $C_1$-$C_6$ alkyl, $C_1$-$C_6$ haloalkyl, =O, $C_1$-$C_6$ hydroxyalkyl, $C_1$-$C_6$ alkoxy, and $C_1$-$C_6$ alkoxy $C_1$-$C_6$ alkyl;

z is 0, 1, 2, 3, 4 or 5;

$R^5$ is selected from hydrogen, hydroxy, and an optionally substituted $C_1$-$C_6$ alkoxy group, wherein substituents are independently selected at each occurrence from hydroxy, halogen, —CN, —NO$_2$, $C_1$-$C_6$ alkoxy group, 3- to 10-membered heterocycle, and $C_{3-10}$ carbocycle, wherein the 3- to 10-membered heterocycle, and $C_{3-10}$ carbocycle are each optionally substituted with one or more substituents independently selected from hydroxy, halogen, —CN, —NO$_2$, $C_1$-$C_6$ alkyl, $C_1$-$C_6$ haloalkyl, $C_1$-$C_6$ hydroxyalkyl, $C_1$-$C_6$ alkoxy, and $C_1$-$C_6$ alkoxy $C_1$-$C_6$ alkyl;

$R^6$ and $R^7$ are each independently selected from hydrogen, hydroxy, and $C_1$-$C_6$ alkoxy; or $R^6$ and $R^7$ come together to form

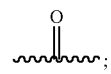

$R^{25}$ is independently selected at each occurrence from hydrogen, optionally substituted $C_1$-$C_6$ alkyl, -D-(CH$_2$—CH$_2$-G)$_y$-V, optionally substituted $C_{3-20}$ carbocycle, and optionally substituted 3- to 20-membered heterocycle, wherein when $R^{25}$ is optionally substituted $C_1$-$C_6$ alkyl, the substituents on $C_1$-$C_6$ alkyl are independently selected at each occurrence from halogen, —OH, —CN, —NO$_2$, —NH$_2$, =O, =S, —C(O)N(R$^{31}$)$_2$, —OC(O)N(R$^{31}$)$_2$, —C(O)OR$^{31}$, —P(O)(R$^{31}$)$_2$, —C$_{1-10}$ haloalkyl, —O—C$_{1-10}$ alkyl, —O—C$_{1-10}$ alkyl-CN, —O—C$_{1-10}$ alkyl-C(O)OR$^{31}$, C$_{2-10}$ alkenyl, C$_{2-10}$ alkynyl, C$_3$-20 carbocycle, and 3- to 20-membered heterocycle;

wherein when $R^{25}$ is optionally substituted $C_{3-20}$ carbocycle or optionally substituted 3- to 20-membered heterocycle, the substituents on $C_{3-20}$ carbocycle and 3- to 20-membered heterocycle are independently selected at each occurrence from halogen, —OR$^{31}$, —SR$^{31}$, —N(R$^{31}$)$_2$, —C(O)R$^{31}$, —C(O)N(R$^{31}$)$_2$, —N(R$^{31}$)C(O)R$^{31}$, —C(O)OR$^{31}$, —OC(O)R$^{31}$, —S(O)R$^{31}$, —S(O)$_2$R$^{31}$, —P(O)(OR$^{31}$)$_2$, —OP(O)(OR$^{31}$)$_2$, —NO$_2$, =O, =S, =N(R$^{31}$), —CN, $C_{1-6}$ alkyl, $C_{1-6}$ haloalkyl, $C_{2-6}$ alkenyl, and $C_{2-6}$ alkynyl;

wherein D is selected from a bond or —O—;

each G is independently selected from —O—, —NR$^{32}$—, —S—, or —SO$_2$—;

each y is selected from 1-20;

each V is selected from hydrogen and optionally substituted —$C_1$-$C_6$ alkyl;

$R^{30}$ is independently selected at each occurrence from hydrogen; $C_{1-10}$ alkyl, $C_{2-10}$ alkenyl, $C_{2-10}$ alkynyl, $C_{3-10}$ carbocycle, and 3- to 10-membered heterocycle, each of which is optionally substituted with one or more substituents independently selected from halogen, —OH, —OSi(C$_1$-$C_6$ alkyl)$_3$, —CN, —NO$_2$, —NH$_2$, =O, =S, $C_{1-10}$ alkyl, —$C_{1-10}$ haloalkyl, —O—$C_{1-10}$ alkyl, $C_{2-10}$ alkenyl, $C_{2-10}$ alkynyl, $C_{3-10}$ carbocycle, and 3- to 10-membered heterocycle;

R' and R" are independently selected at each occurrence from hydrogen, halogen, —OR$^{31}$, and $C_{1-8}$ alkyl optionally substituted with one or more substituents independently selected from halogen and —OR$^{31}$; and $R^{31}$ is independently selected at each occurrence from: hydrogen; and $C_{1-10}$ alkyl, $C_{2-10}$ alkenyl, $C_{2-10}$ alkynyl, $C_{3-12}$ carbocycle, and 3- to 12-membered heterocycle, each of which is optionally substituted with one or more substituents independently selected from halogen, —OH, —OSi(C$_1$-C$_6$ alkyl)$_3$, —CN, —NO$_2$, —NH$_2$, =O, =S, C$_{1-10}$ alkyl, —C$_{1-10}$ haloalkyl, —O—C$_{1-10}$ alkyl, —O—C$_{1-10}$ alkyl-OH, C$_{2-10}$ alkenyl, C$_{2-10}$ alkynyl, C$_{3-12}$ carbocycle, and 3- to 12-membered heterocycle;

R$^{32}$ is independently selected at each occurrence from: hydrogen; and C$_{1-10}$ alkyl, C$_{2-10}$ alkenyl, C$_{2-10}$ alkynyl, C$_{3-10}$ carbocycle, and 3- to 10-membered heterocycle, each of which is optionally substituted with one or more substituents independently selected from halogen, —OH, —CN, —NO$_2$, —NH$_2$, =O, =S, C$_{1-10}$ alkyl, —C$_{1-10}$ haloalkyl, —O—C$_{1-10}$ alkyl, C$_{2-10}$ alkenyl, C$_{2-10}$ alkynyl, C$_{3-10}$ carbocycle, and 3- to 10-membered heterocycle; and wherein the substituents on V and L are independently selected at each occurrence from:

halogen, —OR$^{30}$, —N(R$^{30}$)$_2$, —SR$^{30}$, —C(O)R$^{30}$, —C(O)N(R$^{30}$)$_2$, —N(R$^{30}$)C(O)R$^{30}$, —C(O)OR$^{30}$, —OC(O)R$^{30}$, —S(O)R$^{30}$, —S(O)$_2$R$^{30}$, —P(O)(OR$^{30}$)$_2$, —OP(O)(OR$^{30}$)$_2$, —NO$_2$, =O, =S, =N(R$^{30}$), and —CN;

C$_{1-10}$ alkyl, C$_{2-10}$ alkenyl, C$_{2-10}$ alkynyl, each of which is optionally substituted with one or more substituents independently selected from halogen, —OR$^{30}$, —SR$^{30}$, —N(R$^{30}$)$_2$, —C(O)R$^{30}$, —C(O)N(R$^{30}$)$_2$, —N(R$^{30}$)C(O)R$^{30}$, —C(O)OR$^{30}$, —OC(O)R$^{30}$, —S(O)R$^{30}$, —S(O)$_2$R$^{30}$, —P(O)(OR$^{30}$)$_2$, —OP(O)(OR$^{30}$)$_2$, —NO$_2$, =O, =S, =N(R$^{30}$), —CN, C$_{3-10}$ carbocycle and 3- to 10-membered heterocycle; and C$_{3-10}$ carbocycle and 3- to 10-membered heterocycle each of which is optionally substituted with one or more substituents independently selected from halogen, —OR$^{30}$, —SR$^{30}$, —N(R$^{30}$)$_2$, —C(O)R$^{30}$, —C(O)N(R$^{30}$)$_2$, —N(R$^{30}$)C(O)R$^{30}$, —C(O)OR$^{30}$, —OC(O)R$^{30}$, —S(O)R$^{30}$, —S(O)$_2$R$^{30}$, —P(O)(OR$^{30}$)$_2$, —OP(O)(OR$^{30}$)$_2$, —NO$_2$, =O, =S, =N(R$^{30}$), —CN, C$_{1-6}$ alkyl, C$_{1-6}$ haloalkyl, C$_{2-6}$ alkenyl, and C$_{2-6}$ alkynyl.

In certain embodiments, the compound of Formula (X) is represented by Formula (XA):

(XA)

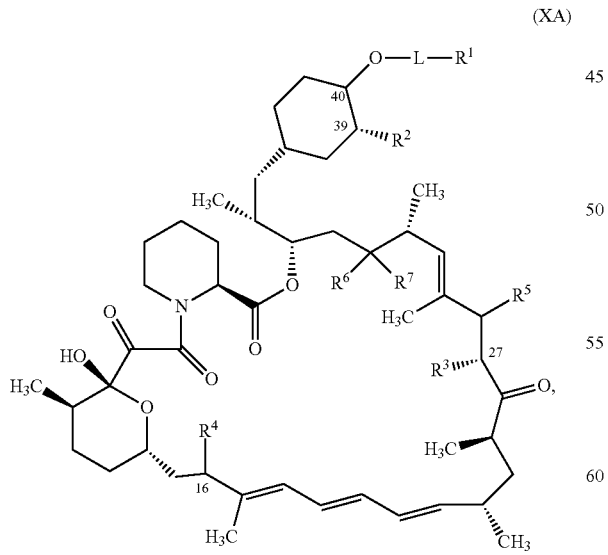

or a salt thereof.

In certain embodiments, the compound of Formula (X) is represented by Formula (XB):

(XB)

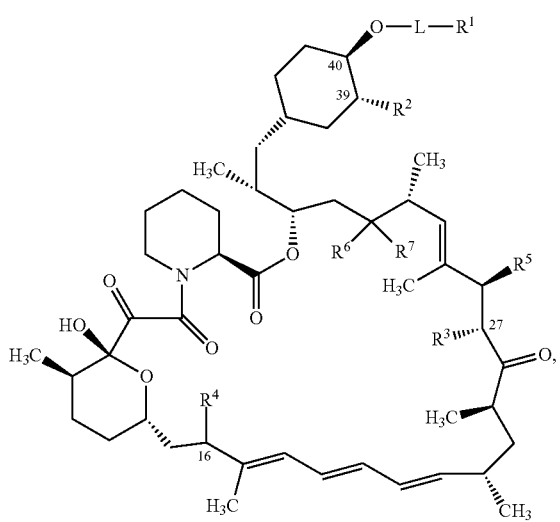

or a salt thereof.

In certain embodiments, the compound of Formula (X) is represented by Formula (XC):

(XC)

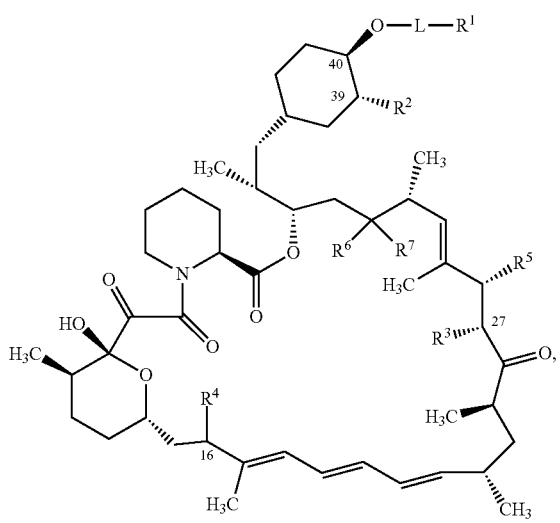

or a salt thereof.

In certain embodiments, the compound of Formula (X) is represented by Formula (XD):

(XD)

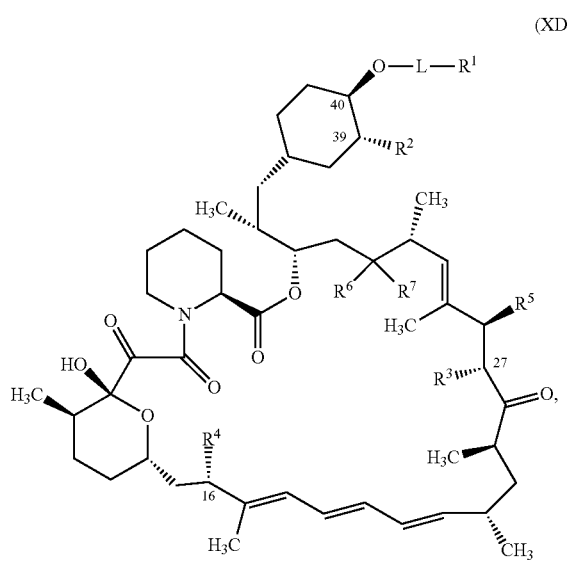

or a salt thereof.

In certain embodiments, the compound of Formula (X) is represented by Formula (XE):

(XE)

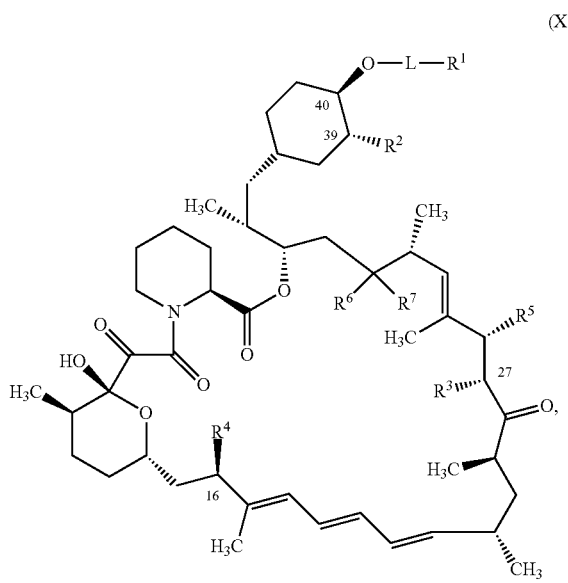

or a salt thereof.

In certain embodiments, the compound of Formula (X) is represented by Formula (XF):

(XF)

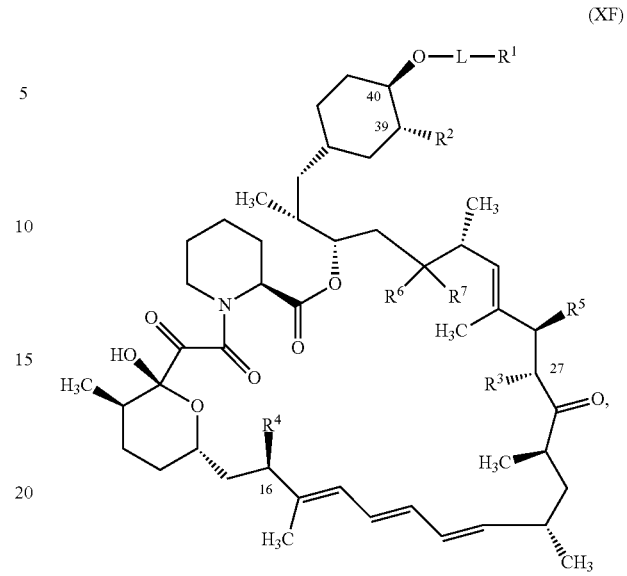

or a salt thereof.

In certain embodiments, the compound of Formula (X) is represented by Formula (XG):

(XG)

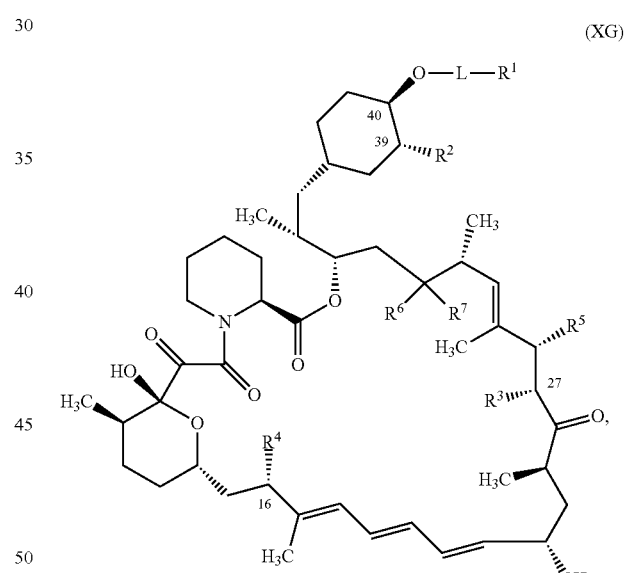

or a salt thereof.

In certain embodiments, for the compound or salt of Formula (X), (XA), (XB), (XC), (XD), (XE), (XF), or (XG), $R^1$ is a carboxylic acid isotere. The carboxylic acid functional group can be an important constituent of a pharmacophore, however, the presence of this moiety can also be responsible for significant drawbacks, including metabolic instability, toxicity, as well as limited passive diffusion across biological membranes. To avoid potential shortcomings while retaining the desired attributes of the carboxylic acid moiety, $R^1$ may be selected from a carboxylic acid isostere. A carboxylic acid isostere is a chemical moiety that demonstrates similar or improved physical properties and biological properties relative to a carboxylic acid group.

In some embodiments, for the compound or salt of Formula (X), (XA), (XB), (XC), (XD), (XE), (XF), or (XG), the carboxylic acid isostere of $R^1$ is selected from: ester, hydroxamic acid, hydroxamic ester, phosphonic acid, phosphinic acid, sulfonic acid, sulfinic acid, sulfone, sulfonamide, acylsulfonamide, sulfonylurea, acylurea, tetrazole, thiazolidinedione, oxazolidinedione, oxadiazol-5(4H)-one, thiadiazol-5(4H)-thione, oxathiadiazole-2-oxide, oxadiazol-5(4H)-thione, isoxazole, tetramic acid, cyclopentane 1,3-dione, cyclopentane 1,2-dione, squaric acid, and substituted phenol.

In some embodiments, for the compound or salt of Formula (X), (XA), (XB), (XC), (XD), (XE), (XF), or (XG), the carboxylic acid isostere of $R^1$ is selected from: hydroxamic acid, hydroxamic ester, phosphonic acid, phosphinic acid, sulfonic acid, sulfinic acid, a sulfone, sulfonamide, acylsulfonamide, sulfonylurea, acylurea, tetrazole, thiazolidinedione, oxazolidinedione, oxadiazol-5(4H)-one, thiadiazol-5(4H)-thione, oxathiadiazole-2-oxide, oxadiazol-5(4H)-thione, isoxazole, tetramic acid, cyclopentane 1,3-dione, cyclopentane 1,2-dione, squaric acid, and substituted phenol.

In some embodiments, for the compound or salt of Formula (X), (XA), (XB), (XC), (XD), (XE), (XF), or (XG), $R^1$ of -L-$R^1$ is selected from: ester, carboxylic acid, hydroxamic acid, hydroxamic ester, phosphonic acid, phosphinic acid, sulfonic acid, sulfinic acid, a sulfone, sulfonamide, acylsulfonamide, sulfonylurea, acylurea, tetrazole, thiazolidinedione, oxazolidinedione, oxadiazol-5(4H)-one, thiadiazol-5(4H)-thione, oxathiadiazole-2-oxide, oxadiazol-5(4H)-thione, isoxazole, tetramic acid, cyclopentane 1,3-dione, cyclopentane 1,2-dione, squaric acid, and substituted phenol.

In some embodiments, for the compound or salt of Formula (X), (XA), (XB), (XC), (XD), (XE), (XF), or (XG), $R^1$ of -L-$R^1$ is selected from: carboxylic acid, hydroxamic acid, hydroxamic ester, phosphonic acid, phosphinic acid, sulfonic acid, sulfinic acid, sulfonamide, a sulfone, acylsulfonamide, sulfonylurea, acylurea, tetrazole, thiazolidinedione, oxazolidinedione, oxadiazol-5(4H)-one, thiadiazol-5(4H)-thione, oxathiadiazole-2-oxide, oxadiazol-5(4H)-thione, isoxazole, tetramic acid, cyclopentane 1,3-dione, cyclopentane 1,2-dione, squaric acid, and substituted phenol.

In some embodiments, for the compound or salt of Formula (X), (XA), (XB), (XC), (XD), (XE), (XF), or (XG), when $R^1$ of -L-$R^1$ is selected from: carboxylic acid, hydroxamic acid, hydroxamic ester, phosphonic acid, phosphinic acid, sulfonic acid, sulfinic acid, sulfonamide, sulfone, acylsulfonamide, sulfonylurea, acylurea, tetrazole, thiazolidinedione, oxazolidinedione, oxadiazol-5(4H)-one, thiadiazol-5(4H)-thione, oxathiadiazole-2-oxide, oxadiazol-5(4H)-thione, isoxazole, tetramic acid, cyclopentane 1,3-dione, cyclopentane 1,2-dione, squaric acid, and substituted phenol, $R^4$ is not methoxy.

In some embodiments, for the compound or salt of Formula (X), (XA), (XB), (XC), (XD), (XE), (XF), or (XG), when $R^1$ of -L-$R^1$ is selected from: ester, carboxylic acid, hydroxamic acid, hydroxamic ester, phosphonic acid, phosphinic acid, sulfonic acid, sulfinic acid, sulfonamide, sulfone, acylsulfonamide, sulfonylurea, acylurea, tetrazole, thiazolidinedione, oxazolidinedione, oxadiazol-5(4H)-one, thiadiazol-5(4H)-thione, oxathiadiazole-2-oxide, oxadiazol-5(4H)-thione, isoxazole, tetramic acid, cyclopentane 1,3-dione, cyclopentane 1,2-dione, squaric acid, and substituted phenol, $R^4$ is not methoxy.

In some embodiments, for the compound or salt of Formula (X), (XA), (XB), (XC), (XD), (XE), (XF), or (XG), $R^1$ of -L-$R^1$ is carboxylic acid. In some embodiments, -L-$R^1$ is represented by

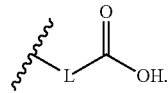

In some embodiments, when -L-$R^1$ is represented by

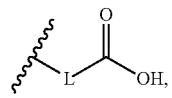

$R^4$ is not methoxy. In some embodiments, when -L-$R^1$ is represented by

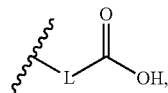

L is unsubstituted. In some embodiments, when -L-$R^1$ is represented by

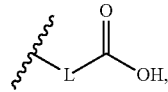

and L is selected from $C_{3-8}$ alkylene, L is unsubstituted. In some embodiments, when -L-$R^1$ is represented by

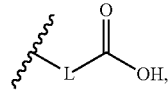

and L is selected from $C_{1-2}$ alkylene, L is substituted.

In some embodiments, for the compound or salt of Formula (X), (XA), (XB), (XC), (XD), (XE), (XF), or (XG), $R^1$ of -L-$R^1$ is an ester. In some embodiments, -L-$R^1$ is represented by

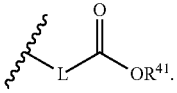

In some embodiments, $R^{41}$ is selected from a $C_{1-6}$ alkyl and benzyl. In some embodiments, $R^{41}$ is a $C_{1-6}$ alkyl. In some embodiments, $R^{41}$ is a $C_{1-4}$ alkyl. In some embodiments, $R^{41}$ is a methyl. In some embodiments, $R^{41}$ is a ethyl. In some embodiments, $R^{41}$ is selected from isopropyl and t-butyl. In some embodiments, $R^{41}$ is isopropyl. In some embodiments, $R^{41}$ is n-propyl. In some embodiments, $R^{41}$ is t-butyl. In some embodiments, $R^{41}$ is n-butyl. In some embodiments, $R^{41}$ is benzyl. In some embodiments, -L-$R^1$ is In some embodiments, -L-R¹ is

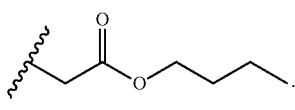 [SMILES: *CC(=O)OCCCC]

In some embodiments, -L-R¹ is

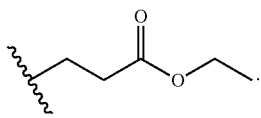 [SMILES: *CCC(=O)OCC]

In some embodiments, when -L-R¹ is represented by

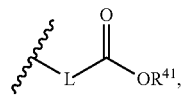

L is selected from C$_{2-8}$ alkylene. In some embodiments, when -L-R¹ is represented by

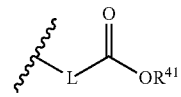

and L is C$_1$ alkylene, R⁴ is not methoxy. In some embodiments, -L-R¹ is represented by

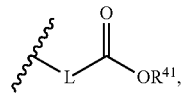

R⁴ is not methoxy. In some embodiments, when -L-R¹ is ethyl acetate, tert-butyl acetate, benzyl acetate or methyl 2-phenylacetate, R⁴ is not methoxy. In some embodiments, when -L-R¹ is selected from

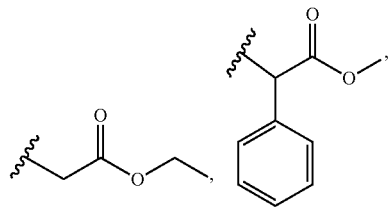

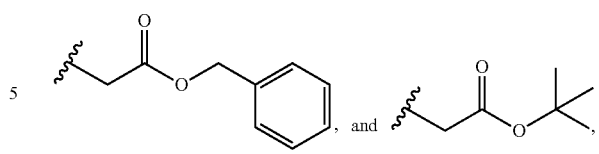

R⁴ is not methoxy. In some embodiments, when -L-R¹ is

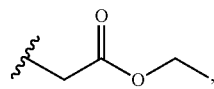

R⁴ is not methoxy. In some embodiments, when -L-R¹ is

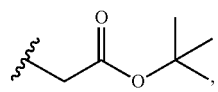

R⁴ is not methoxy.
In some embodiments, when -L-R¹ is

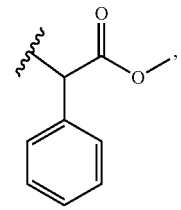

R⁴ is not methoxy. In some embodiments, when -L-R¹ is

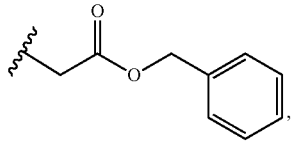 [SMILES: *CC(=O)OCc1ccccc1]

R⁴ is not methoxy.
In some embodiments, for the compound or salt of Formula (X), (XA), (XB), (XC), (XD), (XE), (XF), or (XG), R¹ of -L-R¹ is hydroxamic ester. In some embodiments, -L-R¹ is represented by

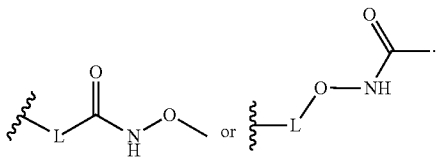

In some embodiments, -L-R¹ is represented by

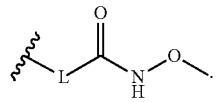

In some embodiments, -L-R¹ is represented

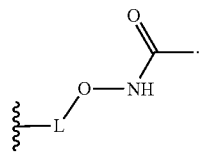

In some embodiments, for the compound or salt of Formula (X), (XA), (XB), (XC), (XD), (XE), (XF), or (XG), R¹ of -L-R¹ is selected from: hydroxamic acid, phosphonic acid, phosphinic acid, sulfonic acid, sulfinic acid, sulfonamide, sulfone, acylsulfonamide, sulfonylurea, acylurea, tetrazole, thiazolidinedione, oxazolidinedione, oxadiazol-5(4H)-one, thiadiazol-5(4H)-thione, oxathiadiazole-2-oxide, oxadiazol-5(4H)-thione, isoxazole, tetramic acid, cyclopentane 1,3-dione, cyclopentane 1,2-dione, squaric acid, and substituted phenol.

In some embodiments, for the compound or salt of Formula (X), (XA), (XB), (XC), (XD), (XE), (XF), or (XG), R¹ of -L-R¹ is hydroxamic acid. In some embodiments, -L-R¹ is represented by

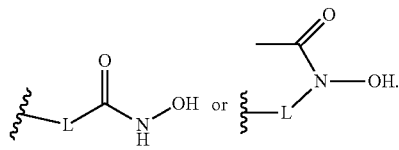

In some embodiments, -L-R¹ is represented by

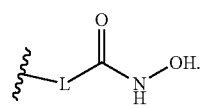

In some embodiments, -L-R¹ is represented by

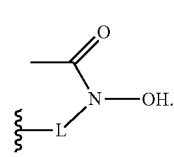

In some embodiments, for the compound or salt of Formula (X), (XA), (XB), (XC), (XD), (XE), (XF), or (XG), R¹ of -L-R¹ is phosphoric acid. In some embodiments, -L-R¹ is represented by

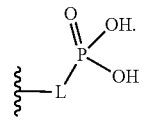

In some embodiments, for the compound or salt of Formula (X), (XA), (XB), (XC), (XD), (XE), (XF), or (XG), R¹ of -L-R¹ is phosphonic acid. In some embodiments, -L-R¹ is represented by

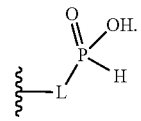

In some embodiments, for the compound or salt of Formula (X), (XA), (XB), (XC), (XD), (XE), (XF), or (XG), R¹ of -L-R¹ is sulfonic acid. In some embodiments, -L-R¹ is represented by

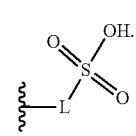

In some embodiments, the carboxylic acid isostere of R¹ may be a salt, for example -L-R¹ is represented by

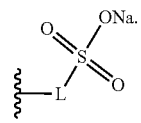

In some embodiments, for the compound or salt of Formula (X), (XA), (XB), (XC), (XD), (XE), (XF), or (XG), R¹ of -L-R¹ is sulfinic acid. In some embodiments, -L-R¹ is represented by

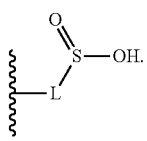

In some embodiments, for the compound or salt of Formula (X), (XA), (XB), (XC), (XD), (XE), (XF), or (XG), R¹ of -L-R¹ is sulfonamide. In some embodiments, -L-R¹ is represented by

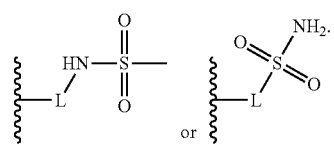

In some embodiments, -L-R¹ is represented by

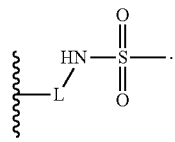

In some embodiments, -L-R¹ is represented by

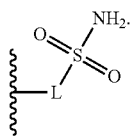

In some embodiments, for the compound or salt of Formula (X), (XA), (XB), (XC), (XD), (XE), (XF), or (XG), R¹ of -L-R¹ is sulfone. In some embodiments, -L-R¹ is represented by

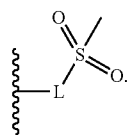

In some embodiments, for the compound or salt of Formula (X), (XA), (XB), (XC), (XD), (XE), (XF), or (XG), R¹ of -L-R¹ is acylsulfonamide. In some embodiments, -L-R¹ is represented by

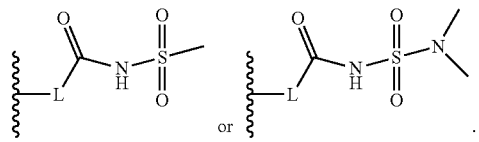

In some embodiments, -L-R¹ is represented by

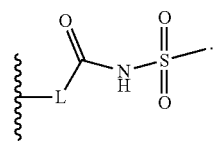

In some embodiments, -L-R¹ is represented by

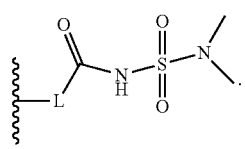

In some embodiments, for the compound or salt of Formula (X), (XA), (XB), (XC), (XD), (XE), (XF), or (XG), R¹ of -L-R¹ is sulfonyl urea. In some embodiments, -L-R¹ is represented by

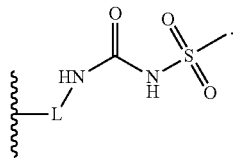

In some embodiments, for the compound or salt of Formula (X), (XA), (XB), (XC), (XD), (XE), (XF), or (XG), R¹ of -L-R¹ is acylurea. In some embodiments, -L-R¹ is represented by

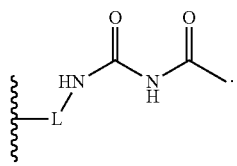

In some embodiments, for the compound or salt of Formula (X), (XA), (XB), (XC), (XD), (XE), (XF), or (XG), R¹ of -L-R¹ is tetrazole. In some embodiments, -L-R¹ is represented by

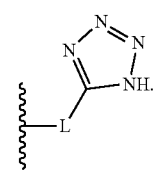

In some embodiments, for the compound or salt of Formula (X), (XA), (XB), (XC), (XD), (XE), (XF), or (XG), R¹ of -L-R¹ is thiazolidinedione. In some embodiments, -L-R¹ is represented by

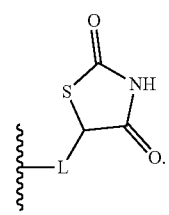

In some embodiments, for the compound or salt of Formula (X), (XA), (XB), (XC), (XD), (XE), (XF), or (XG), R¹ of -L-R¹ is oxazolidinedione. In some embodiments, -L-R¹ is represented by

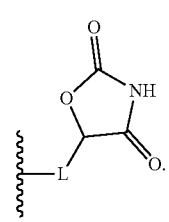

In some embodiments, for the compound or salt of Formula (X), (XA), (XB), (XC), (XD), (XE), (XF), or (XG), $R^1$ of -L-$R^1$ is oxadiazol-5(4H)-one. In some embodiments, -L-$R^1$ is represented by

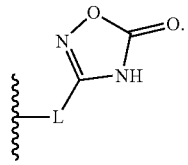

In some embodiments, for the compound or salt of Formula (X), (XA), (XB), (XC), (XD), (XE), (XF), or (XG), $R^1$ of -L-$R^1$ is thiadiazol-5(4H)-thione. In some embodiments, -L-$R^1$ is represented by

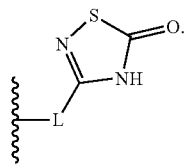

In some embodiments, for the compound or salt of Formula (X), (XA), (XB), (XC), (XD), (XE), (XF), or (XG), $R^1$ of -L-$R^1$ is oxathiadiazole-2-oxide. In some embodiments, -L-$R^1$ is represented by

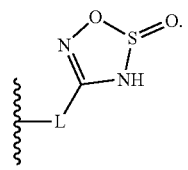

In some embodiments, for the compound or salt of Formula (X), (XA), (XB), (XC), (XD), (XE), (XF), or (XG), $R^1$ of -L-$R^1$ is oxadiazol-5(4H)-thione. In some embodiments, -L-$R^1$ is represented by

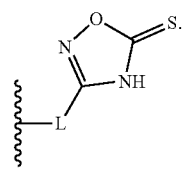

In some embodiments, for the compound or salt of Formula (X), (XA), (XB), (XC), (XD), (XE), (XF), or (XG), $R^1$ of -L-$R^1$ is isoxazole. In some embodiments, -L-$R^1$ is represented by

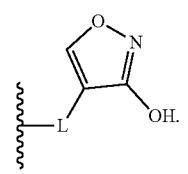

In some embodiments, for the compound or salt of Formula (X), (XA), (XB), (XC), (XD), (XE), (XF), or (XG), $R^1$ of -L-$R^1$ is tetramic acid. In some embodiments, -L-$R^1$ is represented by

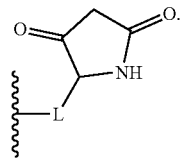

In some embodiments, for the compound or salt of Formula (X), (XA), (XB), (XC), (XD), (XE), (XF), or (XG), $R^1$ of -L-$R^1$ is cyclopentane 1,3-dione. In some embodiments, -L-$R^1$ is represented by

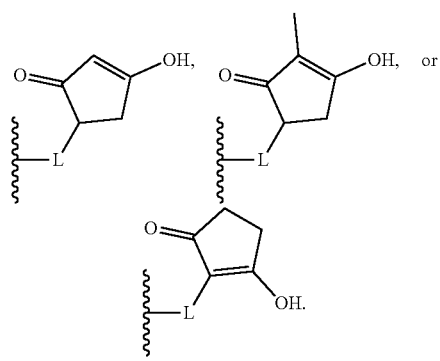

In some embodiments, -L-$R^1$ is represented by

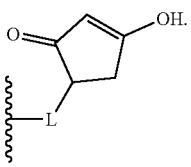

In some embodiments, -L-$R^1$ is represented by

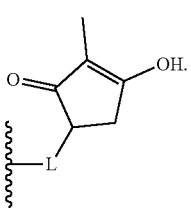

In some embodiments, -L-$R^1$ is represented by

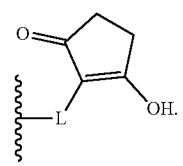

In some embodiments, for the compound or salt of Formula (X), (XA), (XB), (XC), (XD), (XE), (XF), or (XG), $R^1$ of -L-$R^1$ is cyclopentane 1,2-dione. In some embodiments, -L-$R^1$ is represented by

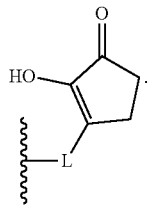

In some embodiments, for the compound or salt of Formula (X), (XA), (XB), (XC), (XD), (XE), (XF), or (XG), $R^1$ of -L-$R^1$ is squaric acid. In some embodiments, -L-$R^1$ is represented by

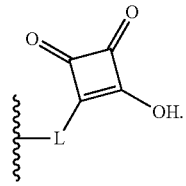

In some embodiments, -L-$R^1$ is represented by

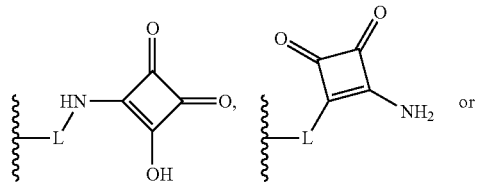

In some embodiments, -L-$R^1$ is represented by

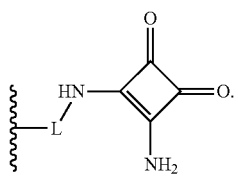

In some embodiments, -L-$R^1$ is represented by

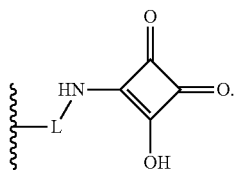

In some embodiments, -L-$R^1$ is represented by

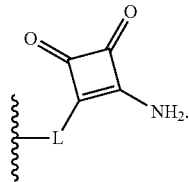

In some embodiments, -L-$R^1$ is represented by

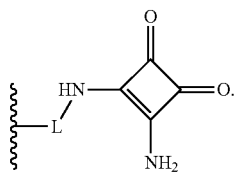

In some embodiments, for the compound or salt of Formula (X), (XA), (XB), (XC), (XD), (XE), (XF), or (XG), $R^1$ of -L-$R^1$ is substituted phenol. In some embodiments, the substituted phenol of -L-$R^1$ is optionally substituted with one or more substituents independently selected from: halogen, —S—, —S(O)—, and —S(O)$_2$—. In some embodiments, -L-$R^1$ is represented by

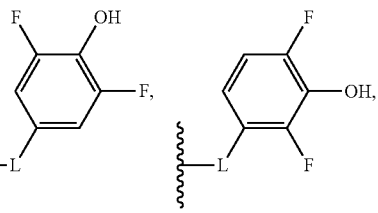

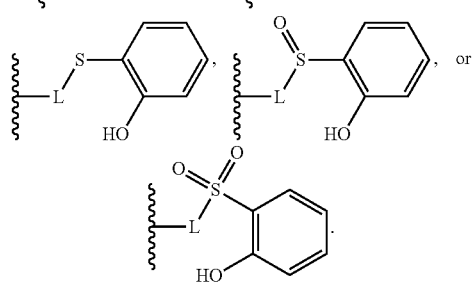

In some embodiments, for the compound or salt of Formula (X), (XA), (XB), (XC), (XD), (XE), (XF), or (XG), the substituted phenol of -L-$R^1$ is substituted with one or more substituents selected from halogen. In some embodiments, -L-$R^1$ is represented by

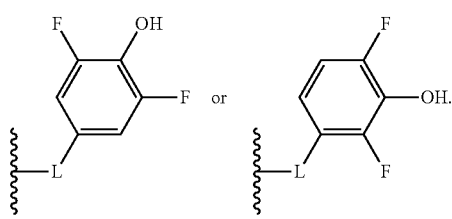

In some embodiments, -L-R¹ is represented by

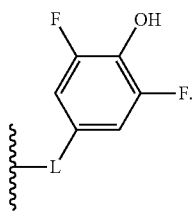

In some embodiments, -L-R¹ is represented by

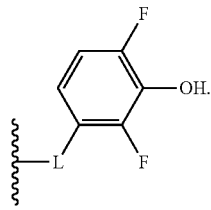

In some embodiments, for the compound or salt of Formula (X), (XA), (XB), (XC), (XD), (XE), (XF), or (XG), -L-R¹ is represented by

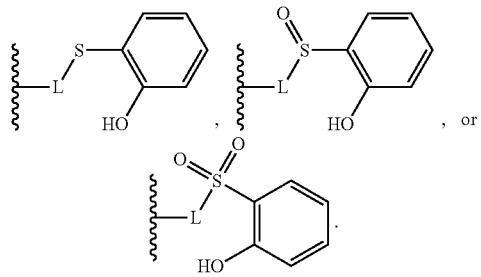

In some embodiments, -L-R¹ is represented by

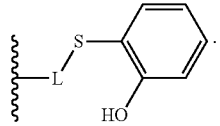

In some embodiments, -L-R¹ is represented by

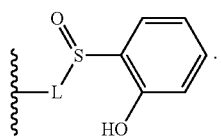

In some embodiments, -L-R¹ is represented by

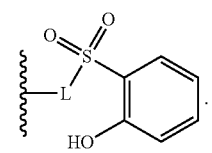

In some embodiments, for the compound or salt of Formula (X), (XA), (XB), (XC), (XD), (XE), (XF), or (XG), -L-R¹ is represented by

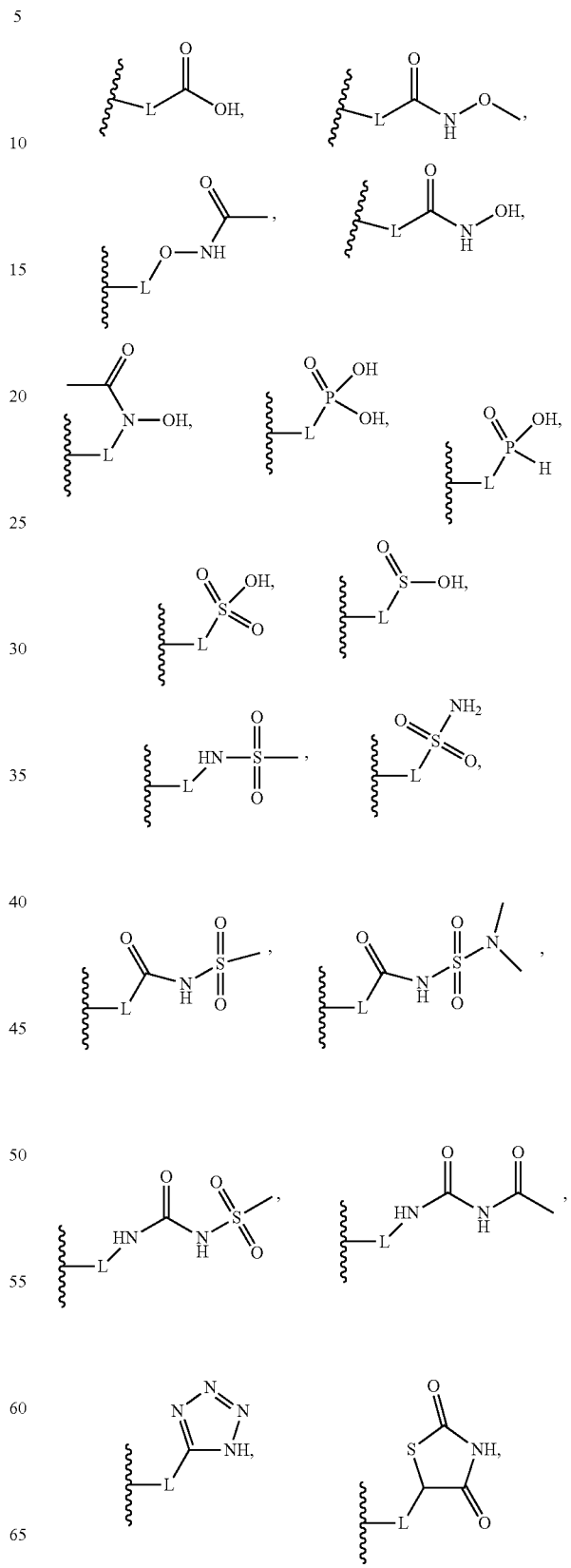

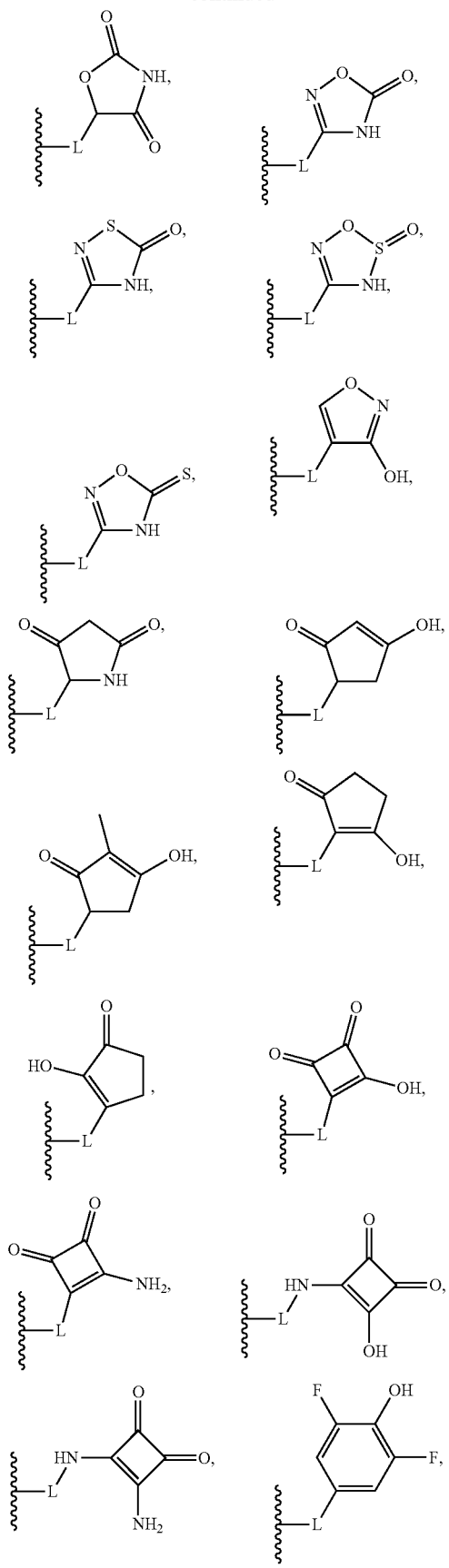
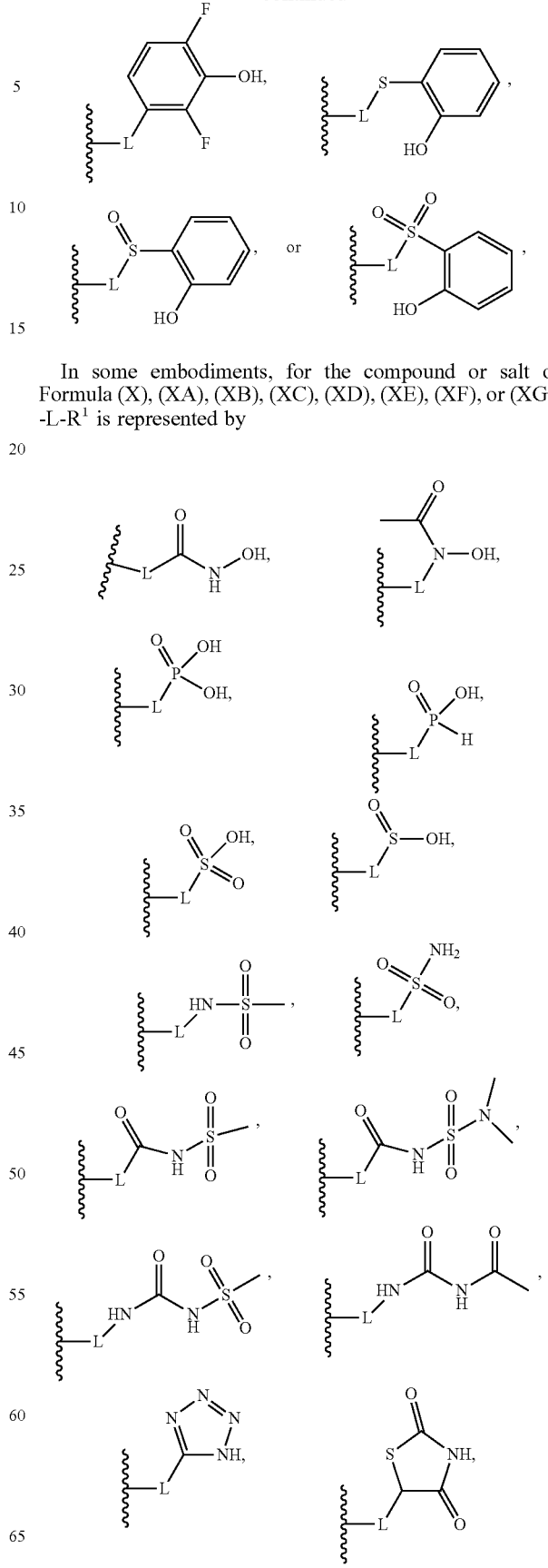
In some embodiments, for the compound or salt of Formula (X), (XA), (XB), (XC), (XD), (XE), (XF), or (XG), -L-R[1] is represented by

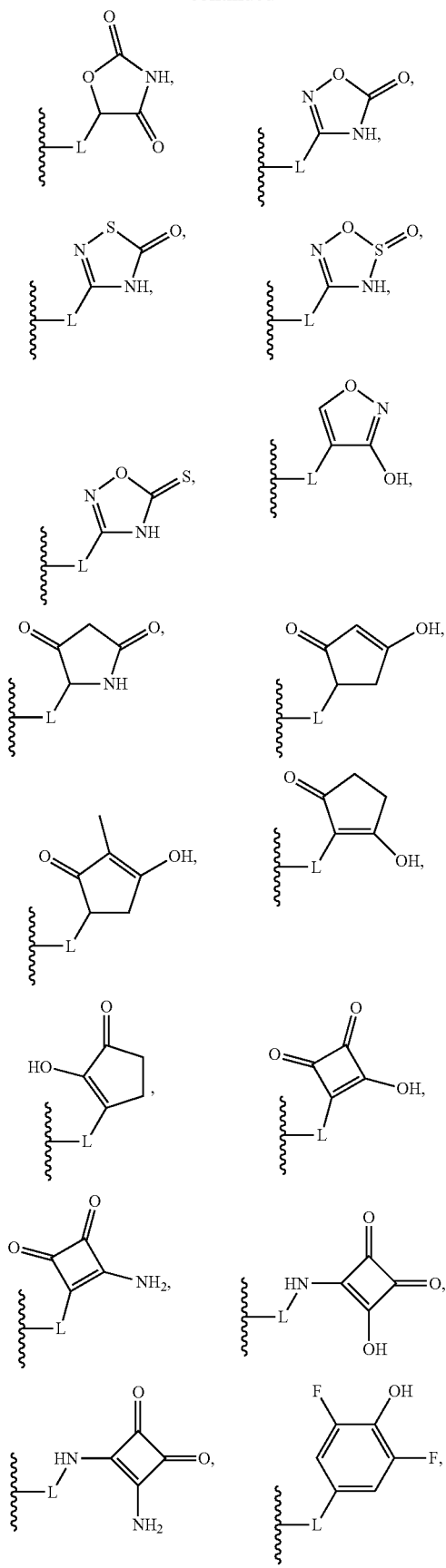

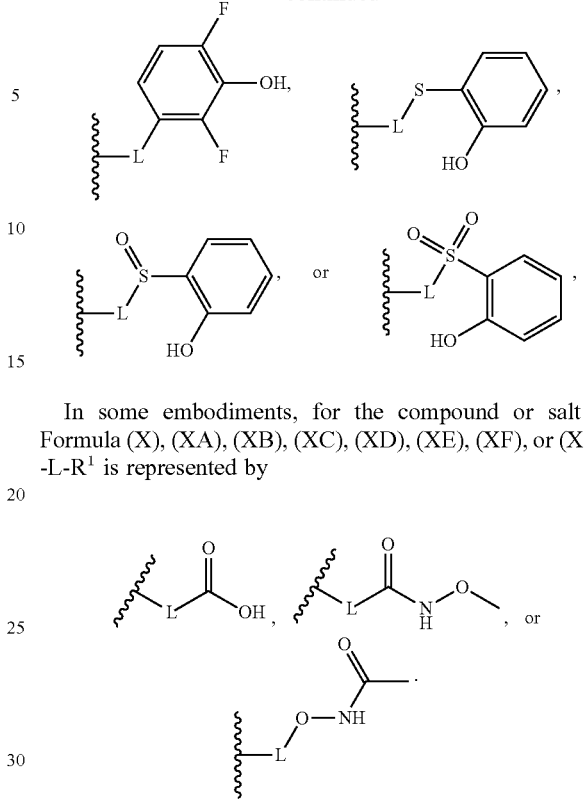

In some embodiments, for the compound or salt of Formula (X), (XA), (XB), (XC), (XD), (XE), (XF), or (XG), -L-R$^1$ is represented by

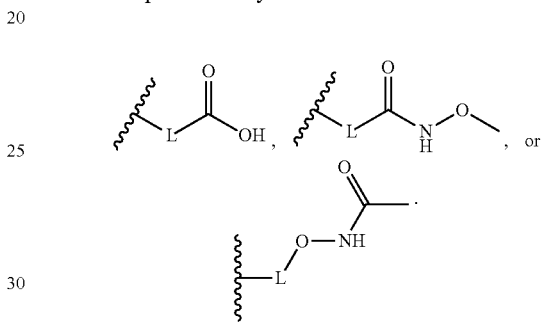

In some embodiments, for the compound or salt of Formula (X), (XA), (XB), (XC), (XD), (XE), (XF), or (XG), L is an optionally substituted Cis alkylene. In some embodiments, the optionally substituted $C_{1-8}$ alkylene is selected from methylene, ethylene, propylene, butylene, pentylene, hexylene, heptylene, and octylene. In some embodiments, for the compound or salt of Formula (X), (XA), (XB), (XC), (XD), (XE), (XF), or (XG), when L is an optionally substituted $C_{1-2}$ alkylene, R$^4$ is not methoxy. In some embodiments, for the compound or salt of Formula (X), (XA), (XB), (XC), (XD), (XE), (XF), or (XG), L is optionally substituted by one or more substituents independently selected from halogen, —OR$^{30}$, —N(R$^{30}$)$_2$, —SR$^{30}$, —C(O)R$^{30}$, —C(O)N(R$^{30}$)$_2$, —N(R$^{30}$)C(O)R$^{30}$, —C(O)OR$^{30}$, —OC(O)R$^{30}$, —S(O)R$^{30}$, —S(O)$_2$R$^{30}$, —NO$_2$, =O, $C_{1-10}$ alkyl, $C_{1-10}$ haloalkyl, and —CN. In some embodiments, for the compound or salt of Formula (X), (XA), (XB), (XC), (XD), (XE), (XF), or (XG), L is optionally substituted by one or more substituents independently selected from halogen, —OR$^{30}$, —N(R$^{30}$)$_2$, —SR$^{30}$, —C(O)R$^{30}$, —C(O)N(R$^{30}$)$_2$, —(O—CH$_2$—(CH$_2$)$_p$)$_n$—W, —N(R$^{30}$)C(O)R$^{30}$, —C(O)OR$^{30}$, —OC(O)R$^{30}$, —S(O)R$^{30}$, —S(O)$_2$R$^{30}$, —NO$_2$, $C_{1-10}$ alkyl, $C_{1-10}$ haloalkyl, and —CN. In some embodiments, for the compound or salt of Formula (X), (XA), (XB), (XC), (XD), (XE), (XF), or (XG), L is optionally substituted by one or more substituents independently selected from halogen, —OR$^{30}$, —N(R$^{30}$)$_2$, —SR$^{30}$, —C(O)R$^{30}$, —C(O)N(R$^{30}$)$_2$, —N(R$^{30}$)C(O)R$^{30}$, —C(O)OR$^{30}$, —OC(O)R$^{30}$, —S(O)R$^{30}$, —S(O)$_2$R$^{30}$, —NO$_2$, $C_{1-10}$ alkyl, $C_{1-10}$ haloalkyl, and —CN. In some embodiments, for the compound or salt of Formula (X), (XA), (XB), (XC), (XD), (XE), (XF), or (XG), L is unsubstituted, e.g., L is methylene, ethylene or propylene.

In some embodiments, for the compound or salt of Formula (X), (XA), (XB), (XC), (XD), (XE), (XF), or (XG), L is an optionally substituted $C_{1-8}$ alkylene wherein L is optionally substituted by one or more substituents independently selected from —(O—CH$_2$—(CH$_2$)$_p$)$_n$—W, wherein each p is selected from 1 or 2; each n is selected from 3-7; and each W is selected from hydrogen, —OH, —C$_1$-C$_4$ alkyl and —O(C$_1$-C$_4$ alkyl).

In some embodiments, for the compound or salt of Formula (X), (XA), (XB), (XC), (XD), (XE), (XF), or (XG), when L is an optionally substituted $C_{3-8}$ alkylene, $R^4$ is further selected from methoxy.

In some embodiments, for the compound or salt of Formula (X), (XA), (XB), (XC), (XD), (XE), (XF), or (XG), L is an optionally substituted $C_{3-8}$ alkylene selected from propylene, butylene, pentylene, hexylene, heptylene, and octylene any one of which is optionally substituted by one or more substituents independently selected from halogen, —OR$^{30}$, —N(R$^{30}$)$_2$, —SR$^{30}$, —C(O)R$^{30}$, —C(O)N(R$^{30}$)$_2$, —N(R$^{30}$)C(O)R$^{30}$, —C(O)OR$^{30}$, —OC(O)R$^{30}$, —S(O)R$^{30}$, —S(O)$_2$R$^{30}$, —NO$_2$, =O, $C_{1-10}$ alkyl, $C_{1-10}$ haloalkyl, and —CN. In some embodiments, for the compound or salt of Formula (X), (XA), (XB), (XC), (XD), (XE), (XF), or (XG), L is optionally substituted by one or more substituents independently selected from halogen, —OR$^{30}$, —N(R$^{30}$)$_2$, —SR$^{30}$, —C(O)R$^{30}$, —C(O)N(R$^{30}$)$_2$, —N(R$^{30}$)C(O)R$^{30}$, —C(O)OR$^{30}$, —OC(O)R$^{30}$, —S(O)R$^{30}$, —S(O)$_2$R$^{30}$, —NO$_2$, $C_{1-10}$ alkyl, $C_{1-10}$ haloalkyl, and —CN.

In some embodiments, for the compound or salt of Formula (X), (XA), (XB), (XC), (XD), (XE), (XF), or (XG), L is a substituted $C_{1-8}$ alkylene. In some embodiments, the substituted $C_{1-8}$ alkylene is selected from methylene, ethylene, propylene, butylene, pentylene, hexylene, heptylene, and octylene.

In some embodiments, for the compound or salt of Formula (X), (XA), (XB), (XC), (XD), (XE), (XF), or (XG), when L is a substituted $C_{3-8}$ alkylene, $R^4$ is further selected from methoxy.

In some embodiments, for the compound or salt of Formula (X), (XA), (XB), (XC), (XD), (XE), (XF), or (XG), L is a $C_{3-8}$ alkylene substituted with one or more substituents independently selected from halogen, —OR$^{30}$, —N(R$^{30}$)$_2$, —SR$^{30}$, —C(O)R$^{30}$, —C(O)N(R$^{30}$)$_2$, —N(R$^{30}$)C(O)R$^{30}$, —C(O)OR$^{30}$, —OC(O)R$^{30}$, —S(O)R$^{30}$, —S(O)$_2$R$^{30}$, —NO$_2$, $C_{1-10}$ alkyl, $C_{1-10}$ haloalkyl, and —CN.

In some embodiments, for the compound or salt of Formula (X), (XA), (XB), (XC), (XD), (XE), (XF), or (XG), L is a $C_{3-8}$ alkylene substituted with one or more substituents independently selected from halogen, —OR$^{30}$, —N(R$^{30}$)$_2$, —SR$^{30}$, —C(O)R$^{30}$, —C(O)N(R$^{30}$)$_2$, —N(R$^{30}$)C(O)R$^{30}$, —C(O)OR$^{30}$, —OC(O)R$^{30}$, —S(O)R$^{30}$, —S(O)$_2$R$^{30}$, —NO$_2$, =O, $C_{1-10}$ alkyl, $C_{1-10}$ haloalkyl, and —CN.

In some embodiments, for the compound or salt of Formula (X), (XA), (XB), (XC), (XD), (XE), (XF), or (XG), $R^2$ is selected from hydrogen and an optionally substituted $C_1$-$C_6$ alkoxy group, wherein substituents are independently selected at each occurrence from hydroxy, halogen, —CN, —NO$_2$, and $C_1$-$C_6$ alkoxy. In some embodiments, $R^2$ is selected from hydrogen and an optionally substituted $C_1$-$C_6$ alkoxy, wherein substituents are independently selected at each occurrence from hydroxy, halogen, —NO$_2$, and $C_1$-$C_6$ alkoxy.

In some embodiments, for the compound or salt of Formula (X), (XA), (XB), (XC), (XD), (XE), (XF), or (XG), $R^2$ is selected from hydrogen and $C_1$-$C_6$ alkoxy. In some embodiments, $R^2$ is selected from hydrogen and —OMe. In some embodiments, $R^2$ is —OMe.

In some embodiments, for the compound or salt of Formula (X), (XA), (XB), (XC), (XD), (XE), (XF), or (XG), $R^3$ is selected from hydrogen and an optionally substituted $C_1$-$C_6$ alkoxy, wherein the substituents are independently selected at each occurrence from hydroxy and $C_1$-$C_6$ alkoxy. In some embodiments, $R^3$ is selected from hydrogen and $C_1$-$C_6$ alkoxy.

In some embodiments, for the compound or salt of Formula (X), (XA), (XB), (XC), (XD), (XE), (XF), or (XG), $R^3$ is selected from $C_1$-$C_6$ alkoxy. In some embodiments, $R^3$ is —OMe.

In some embodiments, for the compound or salt of Formula (X), (XA), (XB), (XC), (XD), (XE), (XF), or (XG), $R^5$ is selected from hydrogen, hydroxy, and an optionally substituted $C_1$-$C_6$ alkoxy group, wherein substituents are independently selected at each occurrence from hydroxy, halogen, —CN, —NO$_2$, and $C_1$-$C_6$ alkoxy.

In some embodiments, for the compound or salt of Formula (X), (XA), (XB), (XC), (XD), (XE), (XF), or (XG), $R^5$ is hydroxy.

In some embodiments, for the compound or salt of Formula (X), (XA), (XB), (XC), (XD), (XE), (XF), or (XG), $R^6$ and $R^7$ are each independently selected from hydrogen, hydroxy, and $C_1$-$C_6$ alkoxy. In some cases, $R^6$ and $R^7$ are each independently selected from hydrogen and hydroxy. In some embodiments, $R^6$ and $R^7$ are each hydrogen. In some embodiments, $R^6$ is hydrogen and $R^7$ is $C_1$-$C_6$ alkoxy. In some embodiments, $R^6$ is hydrogen and $R^7$ is. In some embodiments, $R^6$ and $R^7$ come together to form

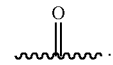

In some embodiments, for the compound or salt of Formula (X), (XA), (XB), (XC), (XD), (XE), (XF), or (XG), $R^4$ is selected from

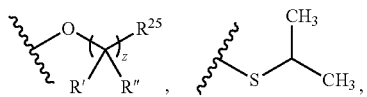

and optionally substituted 3- to 10-membered heterocycle.

In some embodiments, for the compound or salt of Formula (X), (XA), (XB), (XC), (XD), (XE), (XF), or (XG), $R^4$ is

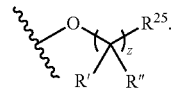

In some embodiments, z is 0, 1, 2, 3, 4 or 5. In some embodiments, z is 1, 2, 3, 4 or 5. In some embodiments, z is 1, 2 or 3. In some embodiments, z is 2, 3 or 4. In some embodiments, when z is 0, $R^{25}$ is selected from: optionally substituted $C_1$-$C_6$ alkyl, optionally substituted 3- to 10-membered heterocycle, and optionally substituted $C_{3-10}$ carbocycle. In some embodiments, when z is 1, $R^{25}$ is selected from: optionally substituted $C_1$-$C_6$ alkyl, optionally substituted 3- to 10-membered heterocycle, and optionally substituted $C_{3-10}$ carbocycle.

In some embodiments, for the compound or salt of Formula (X), (XA), (XB), (XC), (XD), (XE), (XF), or (XG), each R' and R" of

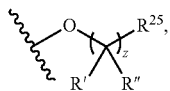

is independently selected from hydrogen, —OR$^{31}$, and C$_{1-3}$ alkyl optionally substituted with one or more —OR$^{31}$. In some embodiments, R' and R" are the same substitutent, for example R' is methyl and R" is methyl or R' is hydrogen and R" is hydrogen. In some embodiments, each R' and R" are independently selected from a different substituent, for example R' is methyl and R" is ethyl. In some embodiments, each R' and R" are independently selected from hydrogen and C$_{1-3}$ alkyl optionally substituted with one or more —OR$^{31}$. In some embodiments, R' and R" are each C$_{1-3}$ alkyl optionally substituted with one or more —OR$^{31}$. In some embodiments, R' and R" are each hydrogen.

In some embodiments, for the compound or salt of Formula (X), (XA), (XB), (XC), (XD), (XE), (XF), or (XG), R$^{25}$ of

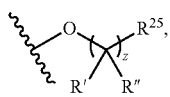

is selected from hydrogen, optionally substituted C$_1$-C$_6$ alkyl, -D-(CH$_2$—CH$_2$-G)$_y$-V, optionally substituted 3- to 10-membered heterocycle, and optionally substituted C$_{3-10}$ carbocycle.

In some embodiments, for the compound or salt of Formula (X), (XA), (XB), (XC), (XD), (XE), (XF), or (XG), R$^{25}$ of

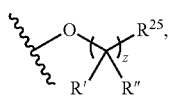

is hydrogen. In some embodiments, R$^4$ is

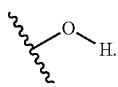

In some embodiments, for the compound or salt of Formula (X), (XA), (XB), (XC), (XD), (XE), (XF), or (XG), R$^{25}$ of

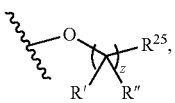

is an optionally substituted C$_1$-C$_6$ alkyl. In some embodiments, the optionally substituted C$_1$-C$_6$ alkyl of R$^{25}$ is substituted with one or more selected from —OH and —O—C$_{1-6}$ alkyl. In some embodiments R$^4$ is selected from:

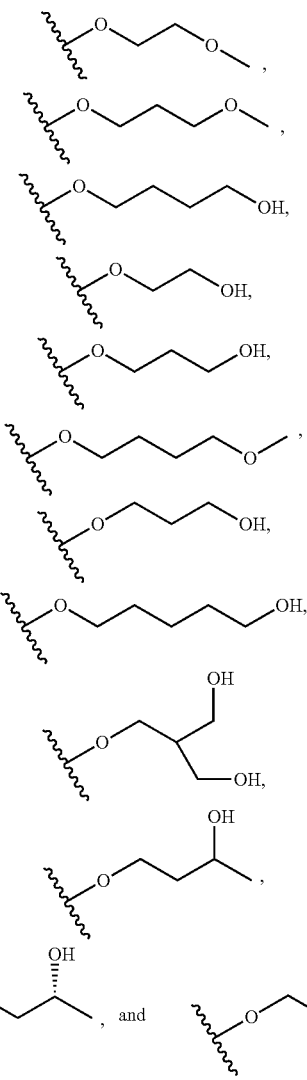

In some embodiments, R$^4$ is

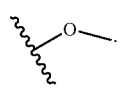

In some embodiments, for the compound or salt of Formula (X), (XA), (XB), (XC), (XD), (XE), (XF), or (XG), R$^{25}$ of

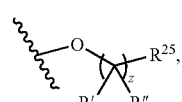

is a substituted C$_1$-C$_6$ alkyl with substituents selected from —P(O)(R$^{31}$)$_2$. In some embodiments, R$^{31}$ of —P(O)(R$^{31}$)$_2$ is a C$_{1-6}$ alkyl substituted with one or more substituents selected —OH and —O—C$_{1-6}$ alkyl. In some embodiments, R$^4$ is represented by

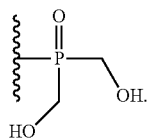

In some embodiments, for the compound or salt of Formula (X), (XA), (XB), (XC), (XD), (XE), (XF), or (XG), $R^{25}$ of

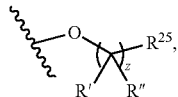

is -D-(CH$_2$—CH$_2$-G)$_y$-V. In some embodiments, D is a bond. In some embodiments, D is —O—. In some embodiments, y of -D-(CH$_2$—CH$_2$-G)$_y$-V is 1 to 1000. In some embodiments, y is 1 to 800. In some embodiments, y is 1 to 500. In some embodiments, y is 1 to 300. In some embodiments, y is 1 to 100. In some embodiments, y is 1 to 50. In some embodiments, y is 1 to 25, such as 1 to 10 or 1 to 8. In some embodiments, y is 3 to 1000. In some embodiments, y is 10 to 1000. In some embodiments, y is 50 to 1000. In some embodiments, y is 100 to 1000. In some embodiments, y is 200 to 1000. In some embodiments, y is 500 to 1000. In some embodiments, y of -D-(CH$_2$—CH$_2$-G)$_y$-V for $R^{25}$ is 3 to 10. In some embodiments, y of -D-(CH$_2$—CH$_2$-G)$_y$-V for $R^{25}$ is 5 to 10. In some embodiments, y is 0, 1, 2, 3, 4, 5, 6, 7, 8, 9, 10, 11, 12, 13, 14, 15, 16, 17, 18, 19, 20, 25, or 100. In some embodiments, y is 1, 2, 3, 4, 5, 6, 7, 8, 9, 10, 11, 12, 13, 14, 15, 16, 17, 18, 19, 20, 25, or 100.

In some embodiments, for the compound or salt of Formula (X), (XA), (XB), (XC), (XD), (XE), (XF), or (XG), $R^{25}$ of

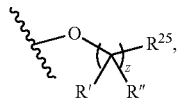

is represented by -D-(CH$_2$—CH$_2$-G)$_y$-V and G of -D-(CH$_2$—CH$_2$-G)$_y$-V at each occurrence is —O—. In some embodiments, $R^4$ is selected from

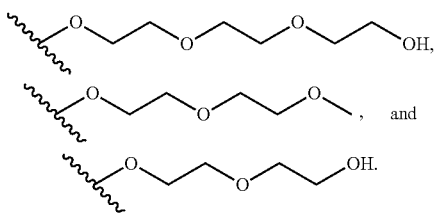

In some embodiments, $R^4$ is selected from

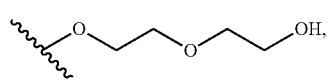

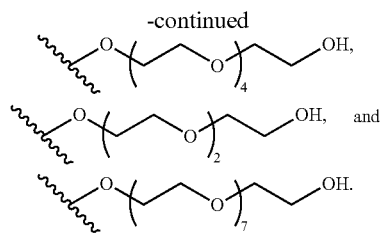

In some embodiments, for the compound or salt of Formula (X), (XA), (XB), (XC), (XD), (XE), (XF), or (XG), $R^{25}$ of

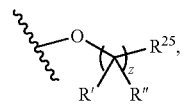

is represented by -D-(CH$_2$—CH$_2$-G)$_y$-V. In some embodiments, D is selected from a bond or —O—. In some embodiments, D is a bond. In some embodiments, D is —O—. In some embodiments, when z is 0, D is a bond. In some embodiments, when z is 1, D is a bond. In some embodiments, when z is 2, D is a bond. In some embodiments, when D is —O—, z is selected from 1, 2, 3, 4, or 5. In some embodiments, when D is —O—, z is selected from 2, 3, 4, or 5.

In some embodiments, for the compound or salt of Formula (X), (XA), (XB), (XC), (XD), (XE), (XF), or (XG), $R^{25}$ of

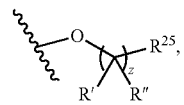

is represented by -D-(CH$_2$—CH$_2$)$_y$—V and G of -D-(CH$_2$—CH$_2$-G)$_y$-V at each occurrence is —NR$^{32}$—. In some embodiments, each R$^{32}$ of —NR$^{32}$— is independently selected from hydrogen; and C$_{1-10}$ alkyl, each of which is optionally substituted with one or more substituents independently selected from halogen, —OH, C$_{1-10}$ alkyl, —C$_{1-10}$ haloalkyl, and —O—C$_{1-10}$ alkyl.

In some embodiments, for the compound or salt of Formula (X), (XA), (XB), (XC), (XD), (XE), (XF), or (XG), $R^{25}$ of

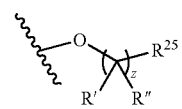

is represented by -D-(CH$_2$—CH$_2$-G)$_y$-V, and V is an optionally substituted C$_1$-C$_6$ alkyl. In some embodiments, the C$_1$-C$_6$ alkyl of V is optionally substituted with one or more substituents independently selected from —(O—CH$_2$—(CH$_2$)$_p$)$_n$—W wherein
each p is selected from 1 or 2; each n is selected from 3 to 7; each W is selected from hydrogen, —OH, —C$_1$-C$_4$ alkyl, and —O(C$_1$-C$_4$ alkyl).

In some embodiments, for the compound or salt of Formula (X), (XA), (XB), (XC), (XD), (XE), (XF), or (XG), $R^{25}$ of

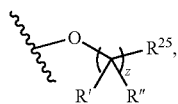

is represented by -D-(CH$_2$—CH$_2$-G)$_y$-V, and V is an optionally substituted C$_1$-C$_6$ alkyl. In some embodiments, the C$_1$-C$_6$ alkyl of V is optionally substituted with one or more substituents independently selected from halogen, —OR$^{30}$, —N(R$^{30}$)$_2$, —SR$^{30}$, —C(O)R$^{30}$, —C(O)N(R$^{30}$)$_2$, —N(R$^{30}$)C(O)R$^{30}$, —C(O)OR$^{30}$, —OC(O)R$^{30}$, —S(O)R$^{30}$, —S(O)$_2$R$^{30}$, —P(O)(OR$^{30}$)$_2$, —OP(O)(OR$^{30}$)$_2$, —NO$_2$, =O, =S, =N(R$^{30}$), and —CN.

In some embodiments, for the compound or salt of Formula (X), (XA), (XB), (XC), (XD), (XE), (XF), or (XG), R$^{25}$ of

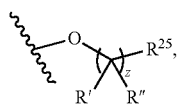

is represented by -D-(CH$_2$—CH$_2$-G)$_y$-V, and V is an optionally substituted C$_1$-C$_6$ alkyl. In some embodiments, the C$_1$-C$_6$ alkyl of V is optionally substituted with one or more substituents independently selected from halogen, —OR$^{30}$, —N(R$^{30}$)$_2$, —(O—CH$_2$—(CH$_2$)$_p$)$_n$—W, —SR$^{30}$, —C(O)R$^{30}$, —C(O)N(R$^{30}$)$_2$, —N(R$^{30}$)C(O)R$^{30}$, —C(O)OR$^{30}$, —OC(O)R$^{30}$, —S(O)R$^{30}$, —S(O)$_2$R$^{30}$, —P(O)(OR$^{30}$)$_2$, —OP(O)(OR$^{30}$)$_2$, —NO$_2$, =O, =S, =N(R$^{30}$), and —CN.

In some embodiments, for the compound or salt of Formula (X), (XA), (XB), (XC), (XD), (XE), (XF), or (XG), R$^{25}$ of

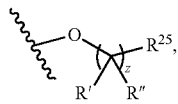

is represented by -D-(CH$_2$—CH$_2$-G)$_y$-V, and V is a substituted C$_1$-C$_6$ alkyl with one or more substituents independently selected from —OR$^{30}$ and —N(R$^{30}$)$_2$. In some embodiments, V is a substituted C$_1$-C$_6$ alkyl with one or more substituents independently selected from —OR$^{30}$ wherein R$^{30}$ is selected from hydrogen; and C$_{1-5}$ alkyl, C$_{3-6}$ carbocycle, and 3- to 6-membered heterocycle, each of which is optionally substituted with one or more substituents independently selected from halogen, —OH, —CN, —NO$_2$, —NH$_2$, =O, =S, C$_{1-10}$ alkyl, —C$_{1-10}$ haloalkyl, and —O—C$_{1-10}$ alkyl.

In some embodiments, for the compound or salt of Formula (X), (XA), (XB), (XC), (XD), (XE), (XF), or (XG), R$^{25}$ of

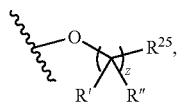

is an optionally substituted 3- to 6-membered heterocycle. In some embodiments, the 3- to 6-membered heterocycle is saturated. In some embodiments, the 3- to 6-membered heterocycle is unsaturated. In some embodiments, the optionally substituted 3- to 6-membered heterocycle comprises at least one heteroatom selected from nitrogen, oxygen, sulfur, and any combination thereof. In some embodiments, the optionally substituted 3- to 6-membered heterocycle comprises at least one heteroatom selected from N and O wherein the 3- to 6-membered heterocycle is optionally substituted with C$_{1-6}$ alkyl. In some embodiments, R$^4$ is selected from

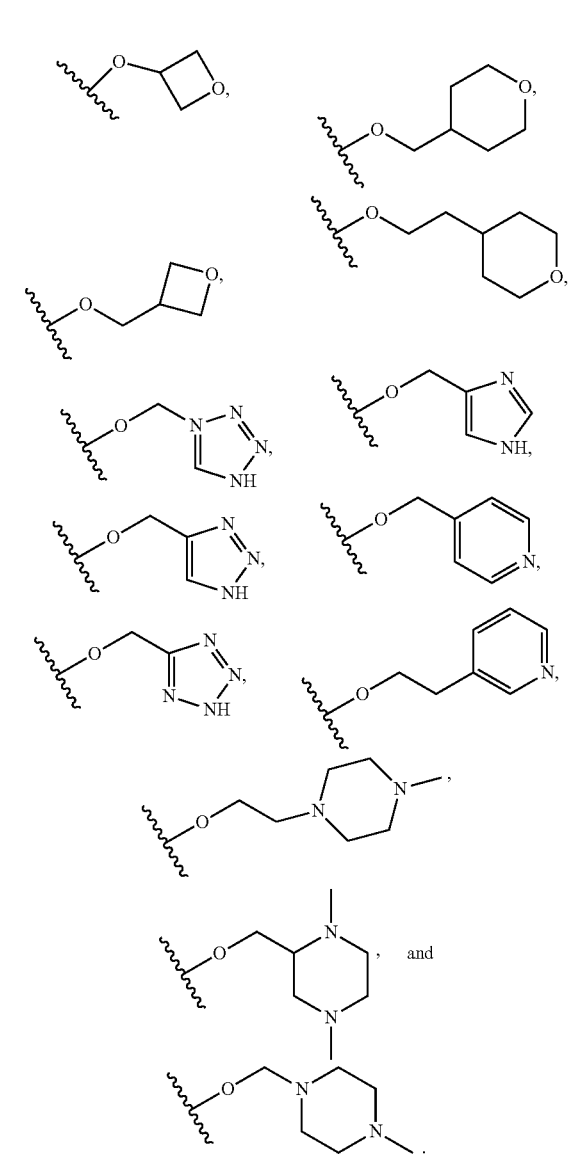

In some embodiments, for the compound or salt of Formula (X), (XA), (XB), (XC), (XD), (XE), (XF), or (XG), R$^{25}$ of

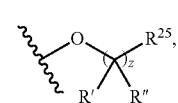

is an optionally substituted C$_{3-10}$ carbocycle. In some embodiments, R$^{25}$ is an optionally substituted C$_{3-6}$ carbocycle. In some embodiments, the C$_{3-6}$ carbocycle is saturated. In some embodiments, $C_{3-6}$ carbocycle is unsaturated. In some embodiments, $R^4$ is selected from:

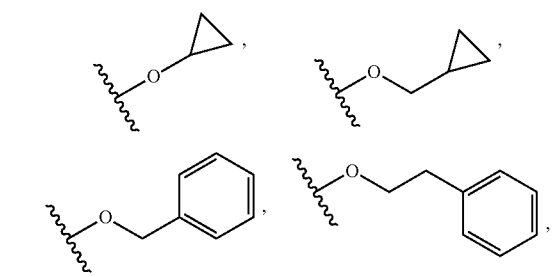

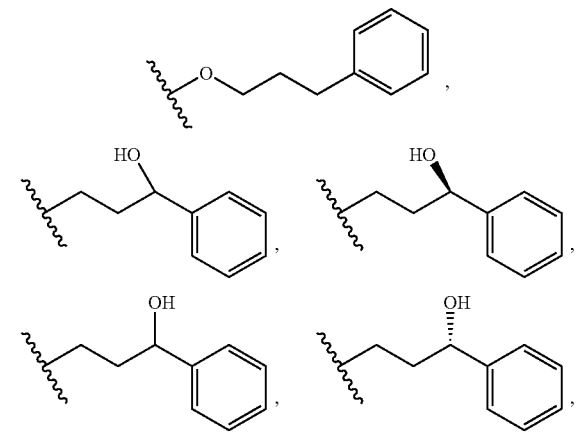

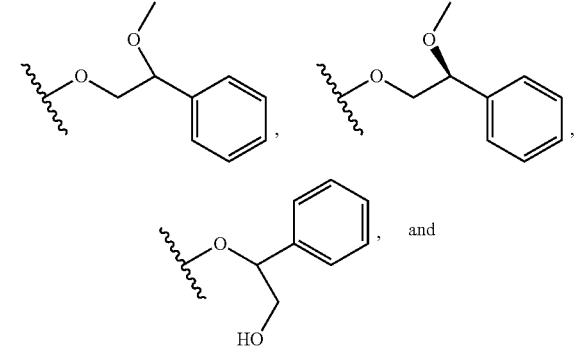

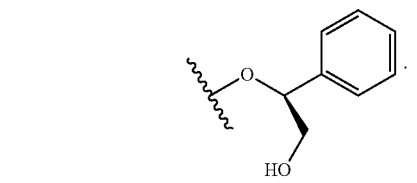

and

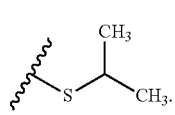

In some embodiments, for the compound or salt of Formula (X), (XA), (XB), (XC), (XD), (XE), (XF), or (XG), $R^4$ is

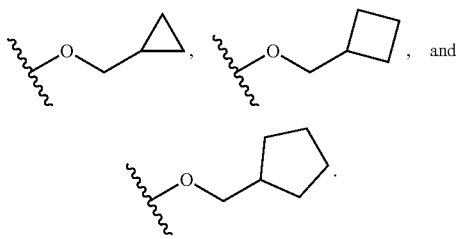

In some embodiments, for the compound or salt of Formula (X), (XA), (XB), (XC), (XD), (XE), (XF), or (XG), $R^4$ is selected from:

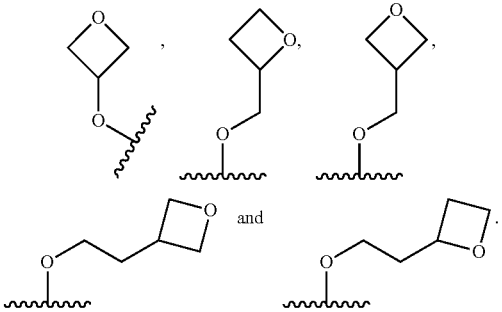

In some embodiments, $R^4$ is

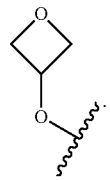

In some embodiments, $R^4$ is

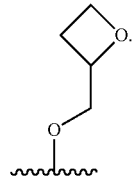 [SMILES: *OCC1CCO1]

In some embodiments, $R^4$ is

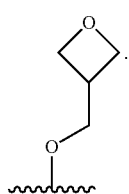 [SMILES: *OCC1COC1]

In some embodiments, $R^4$ is

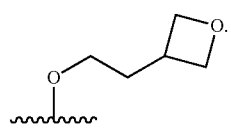 [SMILES: *OCCC1COC1]

In some embodiments, $R^4$ is

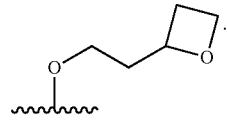 [SMILES: *OCCC1CCO1]

In some embodiments, for the compound or salt of Formula (X), (XA), (XB), (XC), (XD), (XE), (XF), or (XG), $R^4$ is selected from:

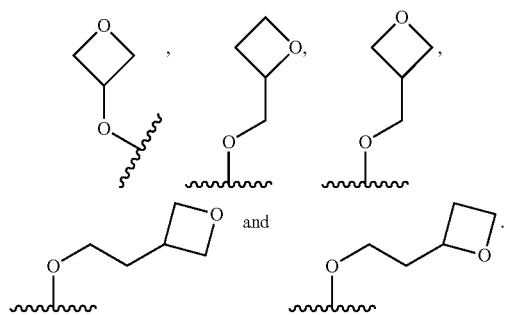

In some embodiments, for the compound or salt of Formula (X), (XA), (XB), (XC), (XD), (XE), (XF), or (XG), $R^4$ is selected from:

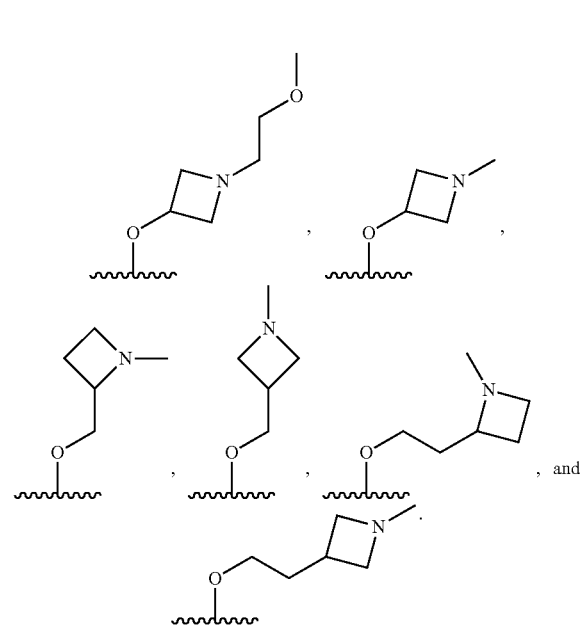

In some embodiments, $R^4$ is

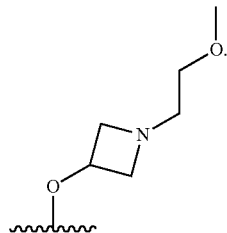 [SMILES: *OC1CN(CCOC)C1]

In some embodiments, $R^4$ is

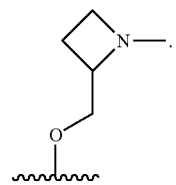 [SMILES: *OCC1CCN1C]

In some embodiments, $R^4$ is

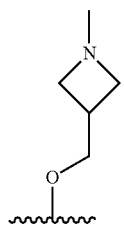

In some embodiments, $R^4$ is

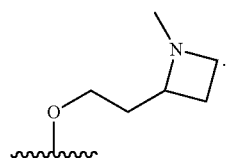 [SMILES: *OCCC1CCN1C]

In some embodiments, $R^4$ is selected from:

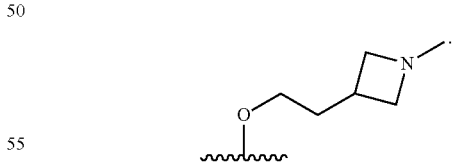

In some embodiments, $R^4$ is

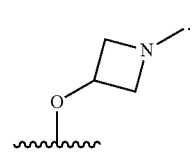 [SMILES: *OC1CN(C)C1]

In some embodiments, for the compound or salt of Formula (X), (XA), (XB), (XC), (XD), (XE), (XF), or (XG), when $R^1$ is hydroxy, $R^4$ is not

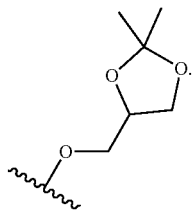 [SMILES: *OCC1COC(C)(C)O1]

In some embodiments, $R^4$ is not

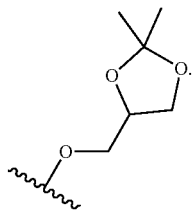 [SMILES: *OCC1COC(C)(C)O1]

In some embodiments, for the compound or salt of Formula (X), (XA), (XB), (XC), (XD), (XE), (XF), or (XG), $R^4$ is selected from:

, , ,

, , , and

.

In some embodiments, $R^4$ is selected from and .

In some embodiments, $R^4$ is

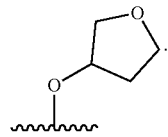 [SMILES: *OC1CCOC1]

In some embodiments, $R^4$ is

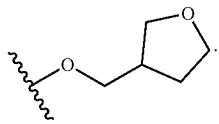 [SMILES: *OCC1CCOC1]

In some embodiments, $R^4$ is

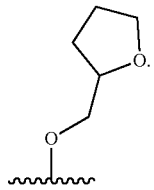 [SMILES: *OCC1CCCO1]

In some embodiments, $R^4$ is

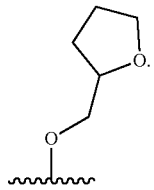 [SMILES: *OCC1CCCO1]

In some embodiments, $R^4$ is

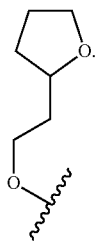

In some embodiments, $R^4$ is

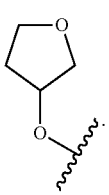

In some embodiments, $R^4$ is

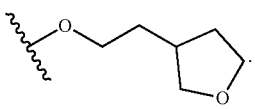 [SMILES: *OCCC1CCOC1]

In some embodiments, for the compound or salt of Formula (X), (XA), (XB), (XC), (XD), (XE), (XF), or (XG), $R^4$ is selected from:

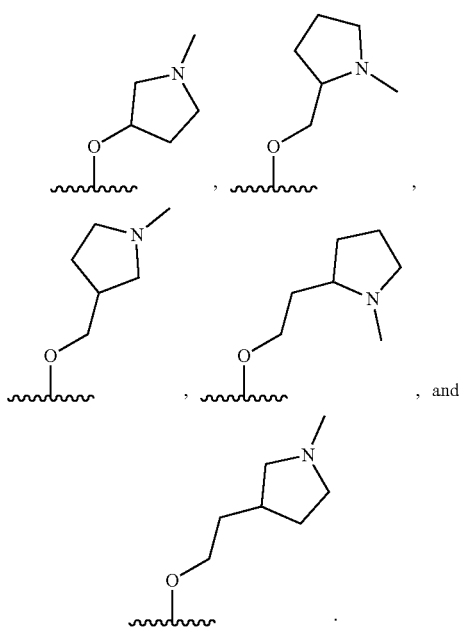, and
In some embodiments, R⁴ is
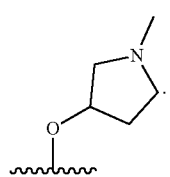 [SMILES: *OC1CCN(C)C1]
In some embodiments, R⁴ is
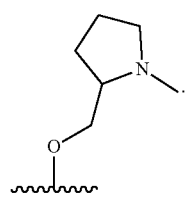 [SMILES: *OCC1CCCN1C]
In some embodiments, R⁴ is
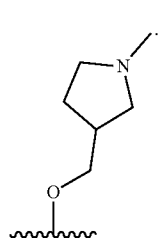 [SMILES: *OCC1CCN(C)C1]
In some embodiments, R⁴ is
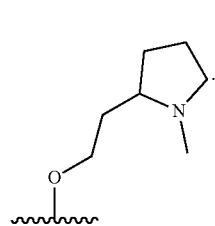 [SMILES: *OCCC1CCCN1C]
In some embodiments, R⁴ is
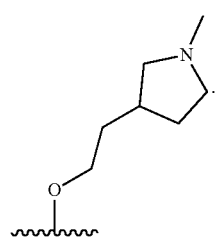 [SMILES: *OCCC1CCN(C)C1]
In some embodiments, for the compound or salt of Formula (X), (XA), (XB), (XC), (XD), (XE), (XF), or (XG), R⁴ is selected from:
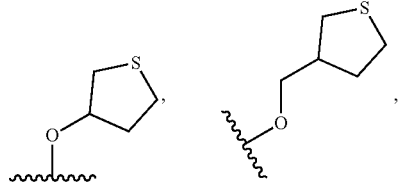
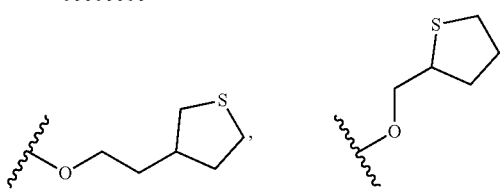
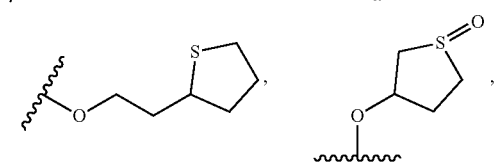
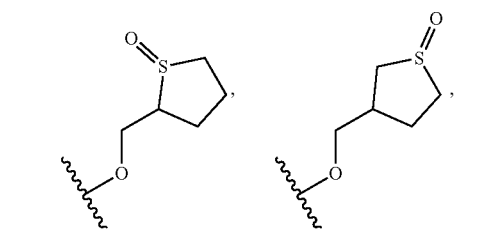
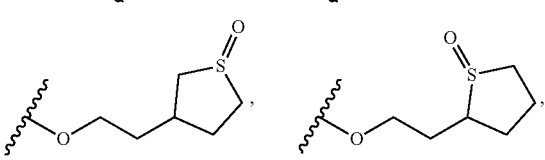

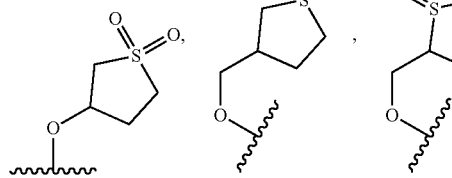, and
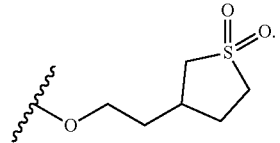
In some embodiments, R⁴ is from
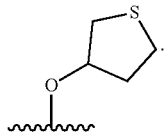 [SMILES: *OC1CCSC1]
In some embodiments, R⁴ is
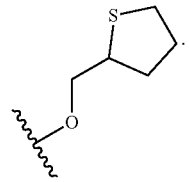 [SMILES: *OCC1CCCS1]
In some embodiments, R⁴ is
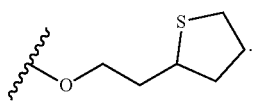
In some embodiments, R⁴ is
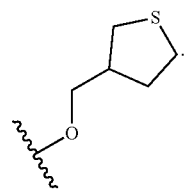 [SMILES: *OCC1CCSC1]
In some embodiments, R⁴ is
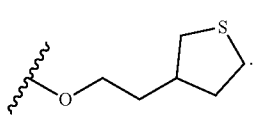 [SMILES: *OCCC1CCSC1]
In some embodiments, R⁴ is
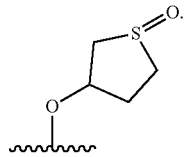 [SMILES: *OC1CCS(=O)C1]
In some embodiments, R⁴ is
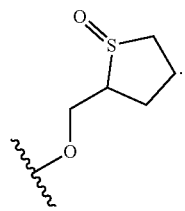 [SMILES: *OCC1CCCS1=O]
In some embodiments, R⁴ is
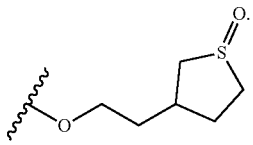 [SMILES: *OCCC1CCS(=O)C1]
In some embodiments, R⁴ is
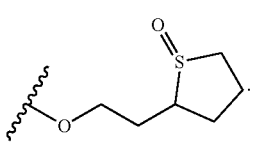 [SMILES: *OCCC1CCCS1=O]
In some embodiments R⁴ is
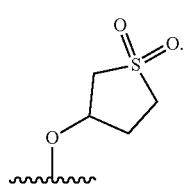 [SMILES: *OC1CCS(=O)(=O)C1]
In some embodiments, R⁴ is In some embodiments, $R^4$ is

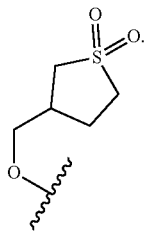

In some embodiments, $R^4$ is

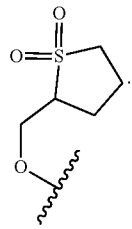

In some embodiments, $R^4$ is

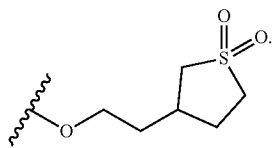 [SMILES: *OCCC1CCS(=O)(=O)C1]

In some embodiments, $R^4$ is

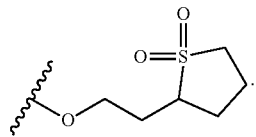 [SMILES: *OCCC1CCCS1(=O)=O]

In some embodiments, for the compound or salt of Formula (X), (XA), (XB), (XC), (XD), (XE), (XF), or (XG), L is selected from optionally substituted $C_{1-6}$ alkylene;
$R^1$ is a sulfone;
$R^2$ is selected from hydrogen and an optionally substituted $C_1$-$C_6$ alkoxy;
$R^3$ is selected from hydrogen and an optionally substituted $C_1$-$C_6$ alkoxy; and
$R^4$ is selected from

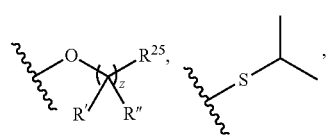

and optionally substituted 3- to 10-membered heterocycle, preferably

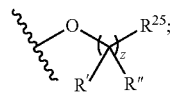

wherein the optionally substituted heterocycle of $R^4$ may be substituted with one or more substituents selected from: hydroxy, halogen, —CN, —NO$_2$, $C_1$-$C_6$ alkyl, $C_1$-$C_6$ haloalkyl, =O, $C_1$-$C_6$ hydroxyalkyl, $C_1$-$C_6$ alkoxy, and $C_1$-$C_6$ alkoxy $C_1$-$C_6$ alkyl;
z is 0, 1, 2, 3, 4 or 5;
$R^5$ is selected from hydrogen, hydroxy, and an optionally substituted $C_1$-$C_6$ alkoxy group;
$R^6$ and $R^7$ are each independently selected from hydrogen, hydroxy, and $C_1$-$C_6$ alkoxy; or $R^6$ and $R^7$ come together to form

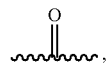

preferably $R^6$ and $R^7$ come together to form

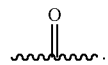

In some embodiments, for the compound or salt of Formula (X), (XA), (XB), (XC), (XD), (XE), (XF), or (XG), L is selected from optionally substituted $C_{1-5}$ alkylene.

In some embodiments, for the compound or salt of Formula (X), (XA), (XB), (XC), (XD), (XE), (XF), or (XG), $R^1$ is selected from a carboxylic acid, an ester, a sulfone, and a sulfonic acid.

In some embodiments, for the compound or salt of Formula (X), (XA), (XB), (XC), (XD), (XE), (XF), or (XG), the ester is represented by —C(O$_2$)(C$_{1-6}$ alkyl), wherein the $C_{1-6}$ alkyl is optionally substituted by one or more substituents selected from halogen, —OH, —NO$_2$, =O, —O—C$_{1-6}$ alkyl and the sulfone is represented by —S(O)$_2$C$_{1-6}$ alkyl, wherein the $C_{1-6}$ alkyl is optionally substituted by one or more substituents selected from halogen, —OH, —NO$_2$, =O, —O—C$_{1-6}$ alkyl.

In some embodiments, for the compound or salt of Formula (X), (XA), (XB), (XC), (XD), (XE), (XF), or (XG), $R^1$ is selected from

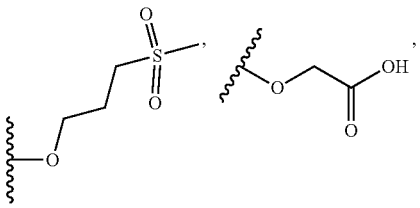

In some embodiments, for the compound or salt of Formula (X), (XA), (XB), (XC), (XD), (XE), (XF), or (XG), $R^1$ is selected from a sulfone and a sulfonic acid. In some embodiments, $R^1$ is selected from

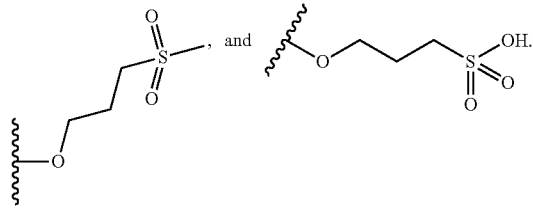

In some cases, $R^1$ is selected from

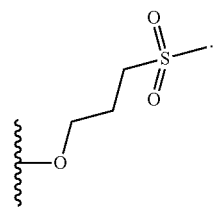 [SMILES: *OCCCS(C)(=O)=O]

In some embodiments, for the compound or salt of Formula (X), (XA), (XB), (XC), (XD), (XE), (XF), or (XG), $R^1$ is selected from

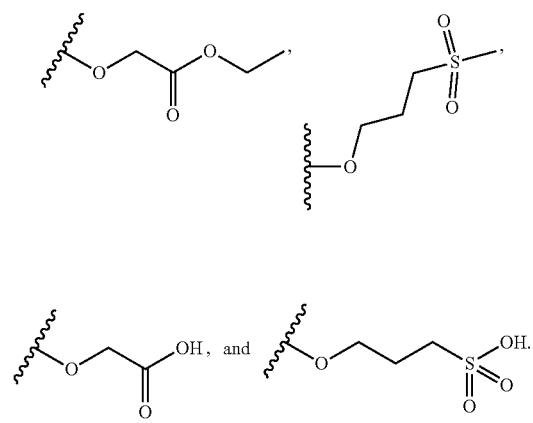

In some embodiments, for the compound or salt of Formula (X), (XA), (XB), (XC), (XD), (XE), (XF), or (XG), $R^1$ is selected from a sulfone and a ester. In some cases, $R^1$ is selected from

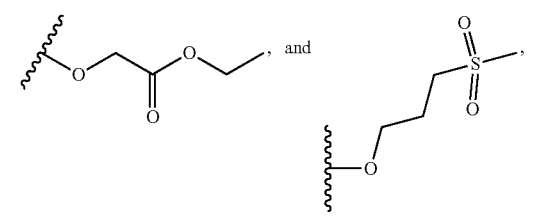

In some embodiments, for the compound or salt of Formula (X), (XA), (XB), (XC), (XD), (XE), (XF), or (XG), $R^4$ is

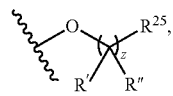

wherein R' and R" are independently selected at each occurrence from hydrogen, hydroxy, and —$OR^{31}$, wherein $R^{31}$ is $C_{1-10}$ alkyl. In some cases, z is selected from 1, 2, and 3.

In some embodiments, for the compound or salt of Formula (X), (XA), (XB), (XC), (XD), (XE), (XF), or (XG), $R^{25}$ is selected from hydrogen, and -D-($CH_2$—$CH_2$-G)$_y$-V, wherein D is —O—, G is —O—, y is 1-3, and V is selected from —$C_1$-$C_6$ alkyl and hydrogen.

In some embodiments, for the compound or salt of Formula (X), (XA), (XB), (XC), (XD), (XE), (XF), or (XG), $R^4$ is methoxy.

In some embodiments, for the compound or salt of Formula (X), (XA), (XB), (XC), (XD), (XE), (XF), or (XG), $R^4$ is selected from

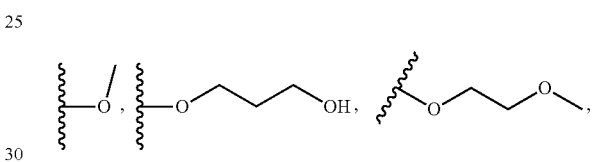

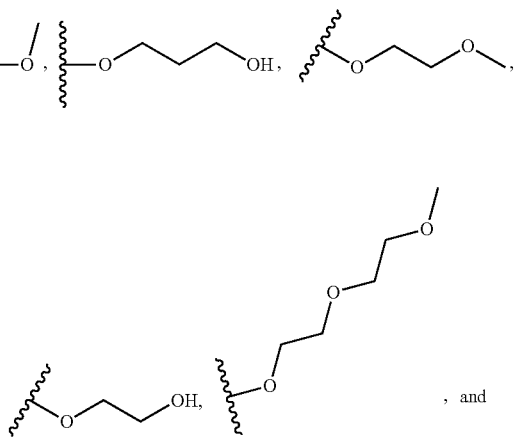

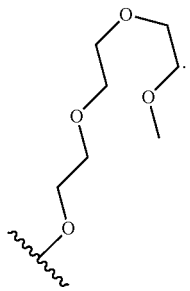

In some embodiments, for the compound or salt of Formula (X), (XA), (XB), (XC), (XD), (XE), (XF), or (XG), $R^4$ is selected from

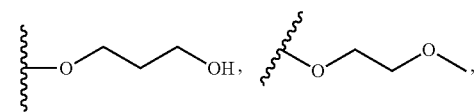

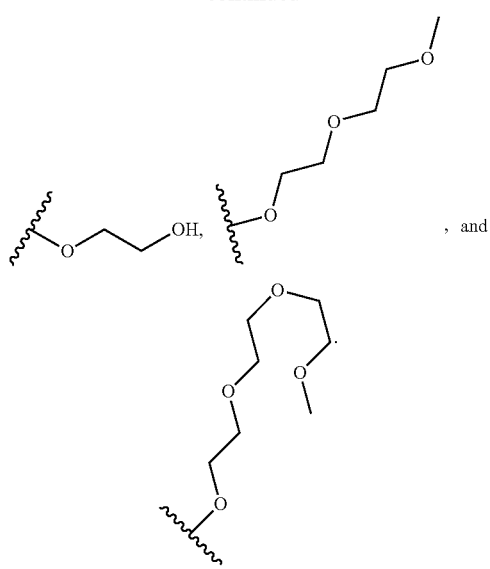

, and

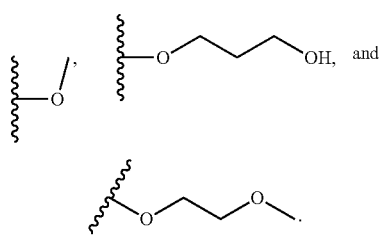

In some embodiments, for the compound or salt of Formula (X), (XA), (XB), (XC), (XD), (XE), (XF), or (XG), $R^4$ is selected from

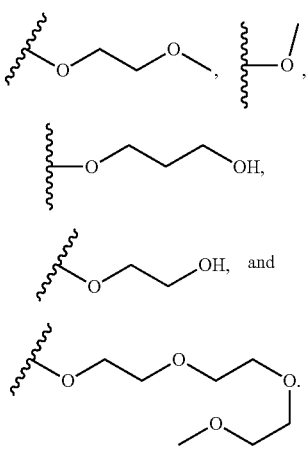

In some embodiments, for the compound or salt of Formula (X), (XA), (XB), (XC), (XD), (XE), (XF), or (XG), $R^4$ is selected from In some embodiments, for the compound or salt of Formula (X), (XA), (XB), (XC), (XD), (XE), (XF), or (XG), $R^4$ is selected from

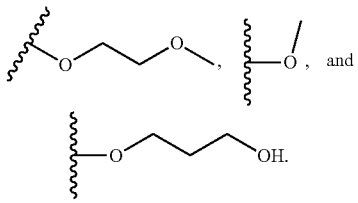

In some cases, $R^4$ is selected from

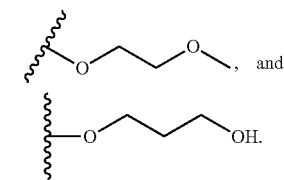

In some embodiments, for the compound or salt of Formula (X), (XA), (XB), (XC), (XD), (XE), (XF), or (XG),

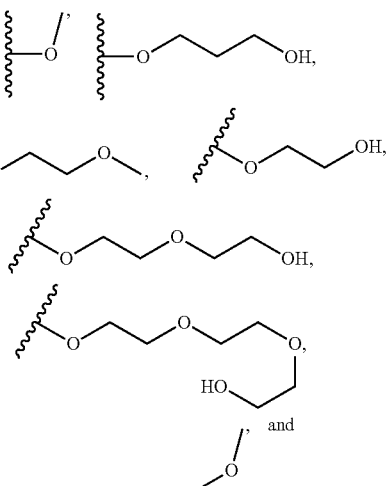

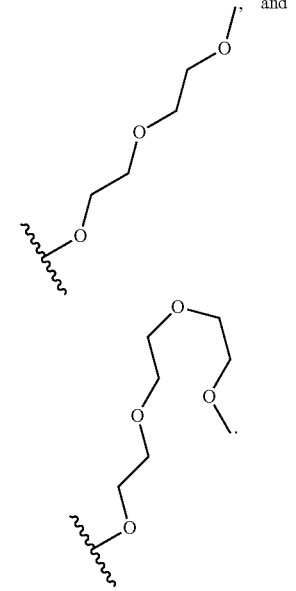

In some embodiments, for the compound or salt of Formula (X), (XA), (XB), (XC), (XD), (XE), (XF), or (XG),

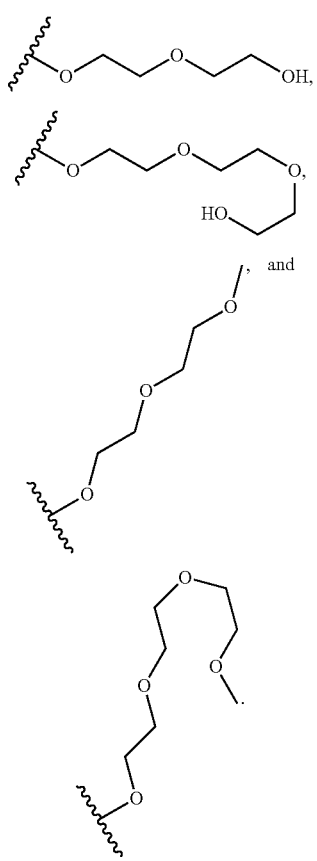
In some embodiments, for the compound or salt of Formula (X), (XA), (XB), (XC), (XD), (XE), (XF), or (XG), $R^4$ is selected from:
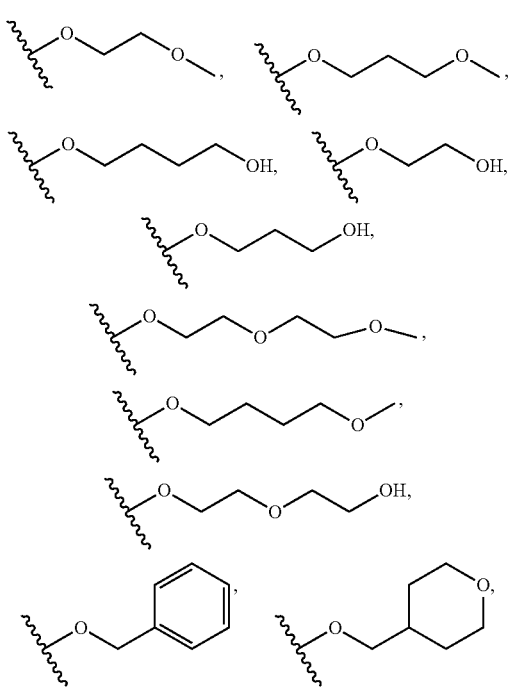
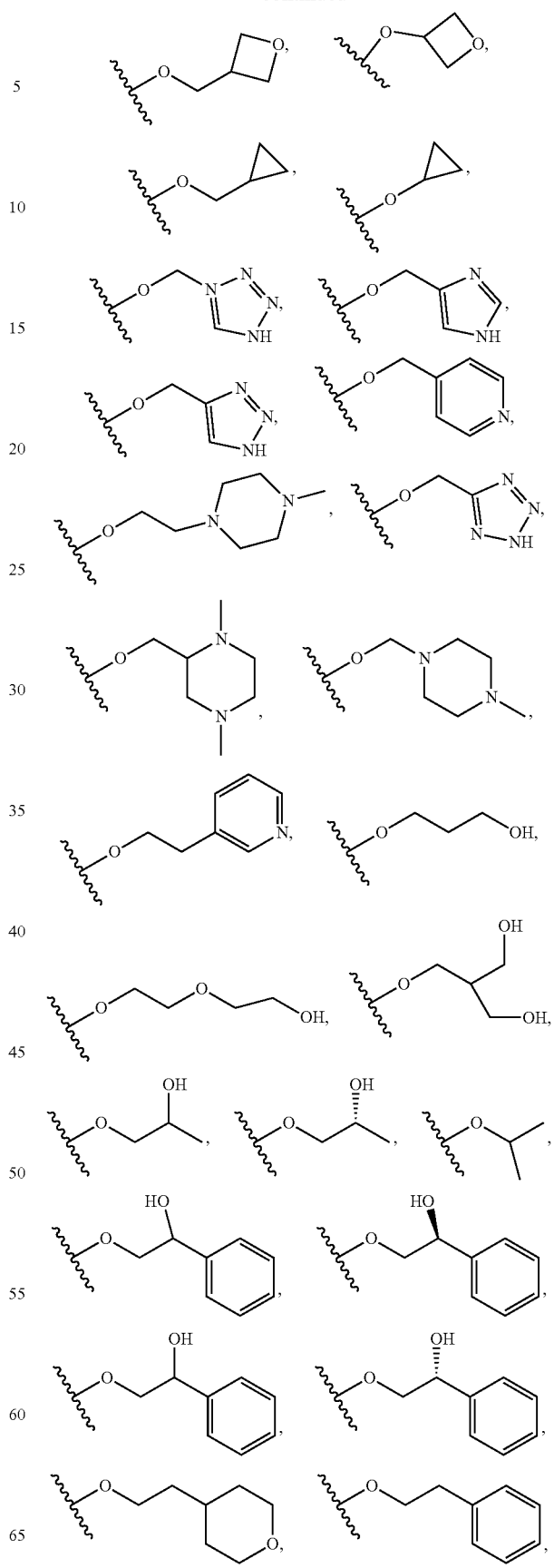

145
-continued
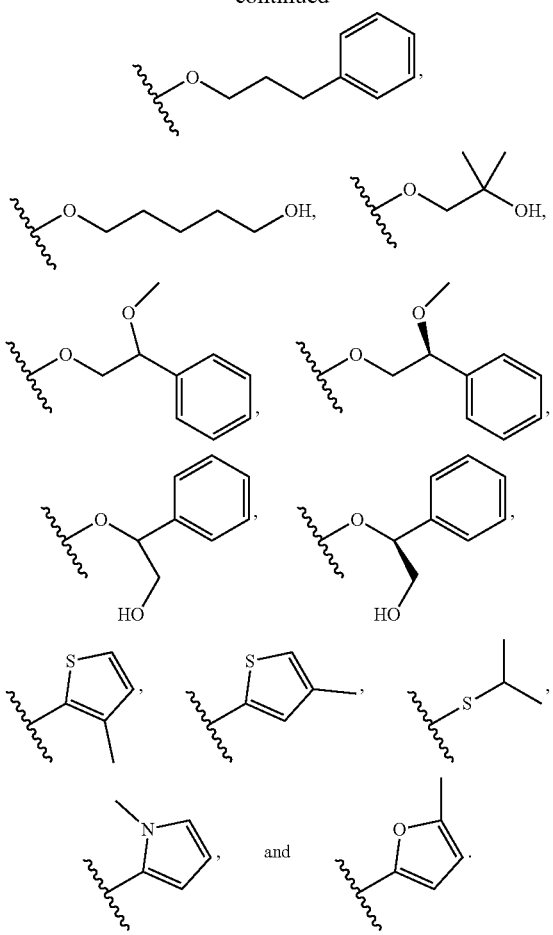
In some embodiments, for the compound or salt of Formula (X), (XA), (XB), (XC), (XD), (XE), (XF), or (XG), $R^4$ is selected from:
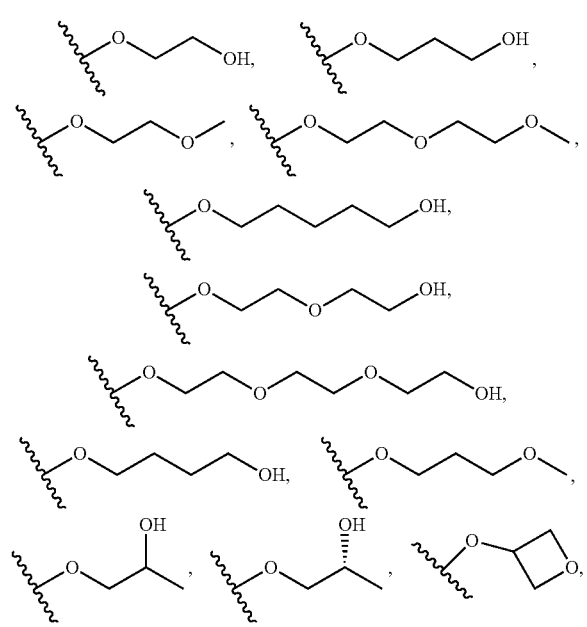
146
-continued
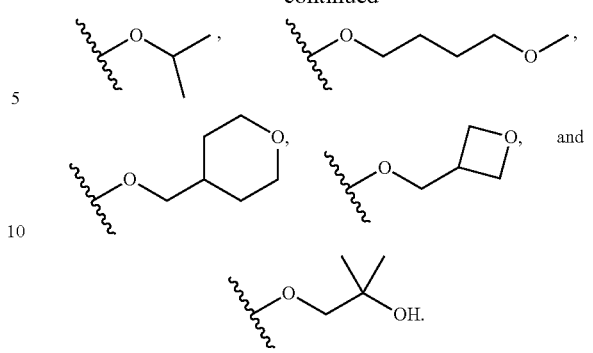
In some embodiments, for the compound or salt of Formula (X), (XA), (XB), (XC), (XD), (XE), (XF), or (XG), $R^4$ is selected from:
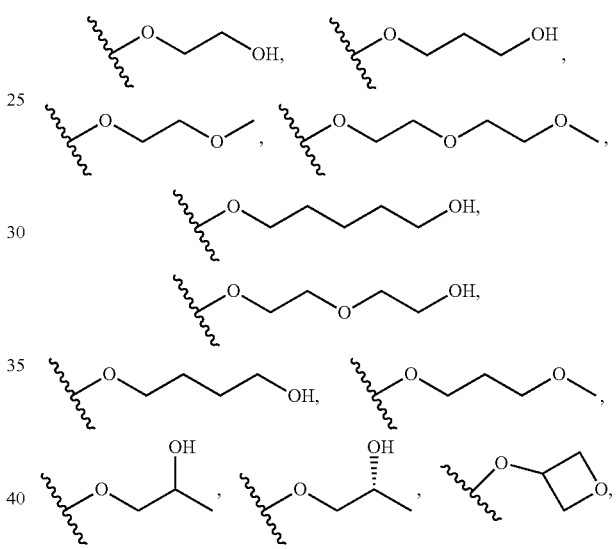
In some embodiments, for the compound or salt of Formula (X), (XA), (XB), (XC), (XD), (XE), (XF), or (XG), $R^4$ is selected from:

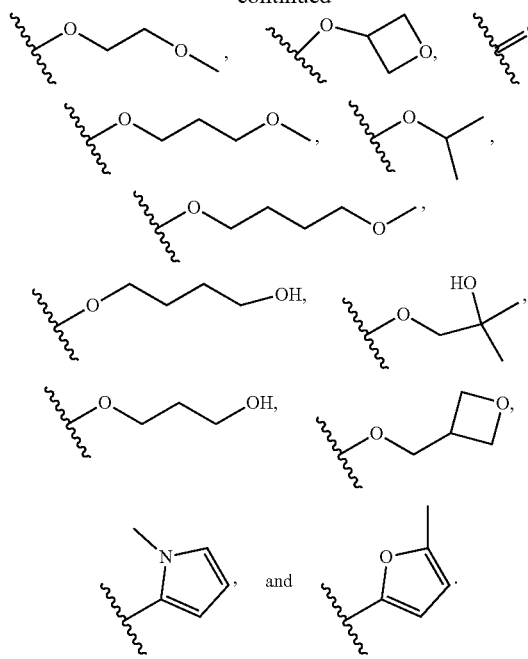
In some embodiments, for the compound or salt of Formula (X), (XA), (XB), (XC), (XD), (XE), (XF), or (XG), $R^4$ is selected from:
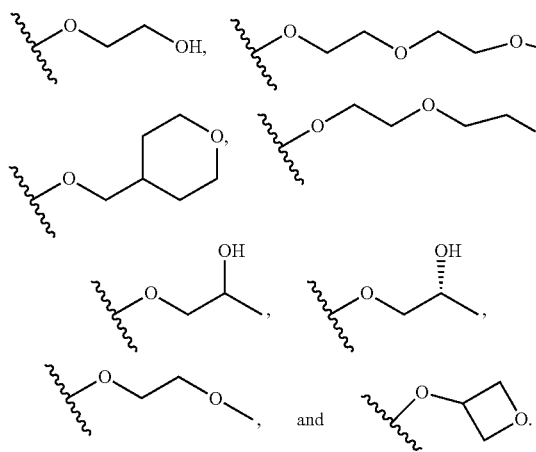
In some embodiments, for the compound or salt of Formula (X), (XA), (XB), (XC), (XD), (XE), (XF), or (XG), $R^4$ is selected from:
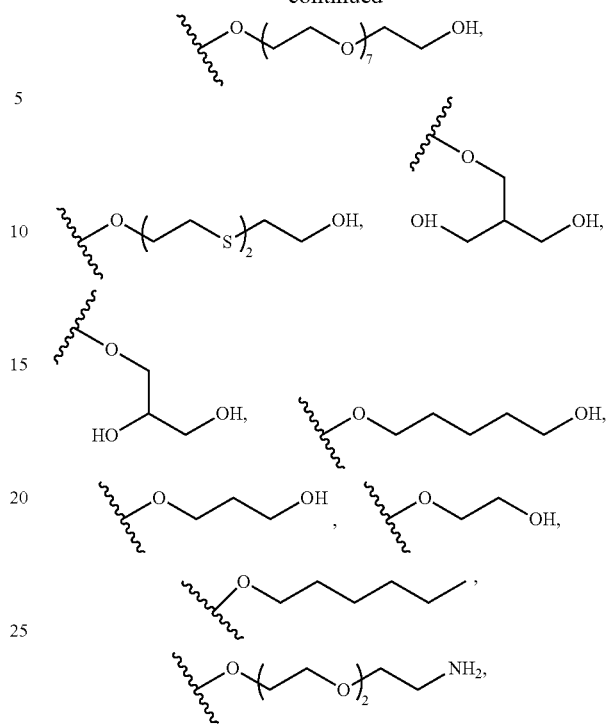
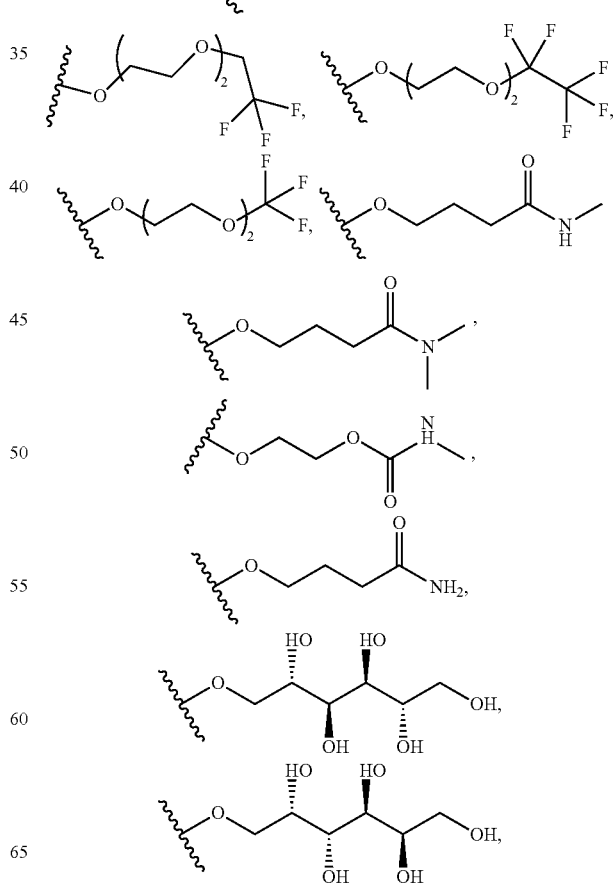

149
-continued
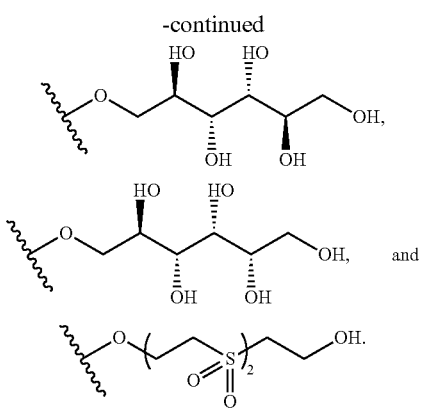
In some embodiments, for the compound or salt of Formula (X), (XA), (XB), (XC), (XD), (XE), (XF), or (XG), R$^4$ is selected from:
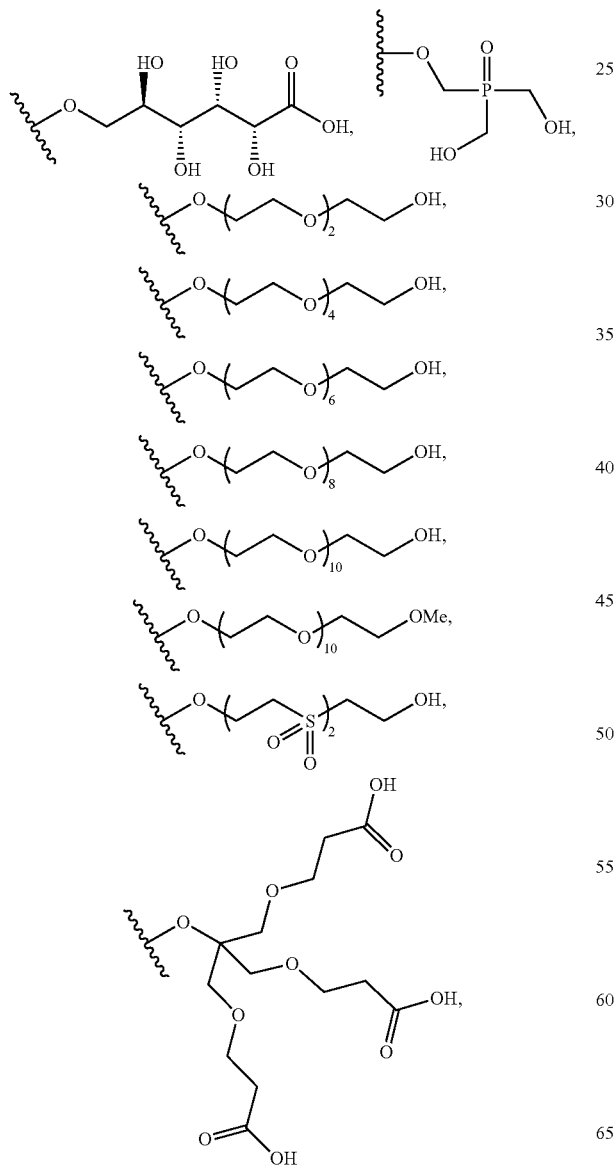
150
-continued
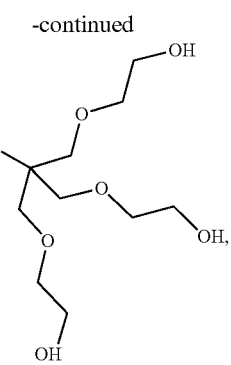
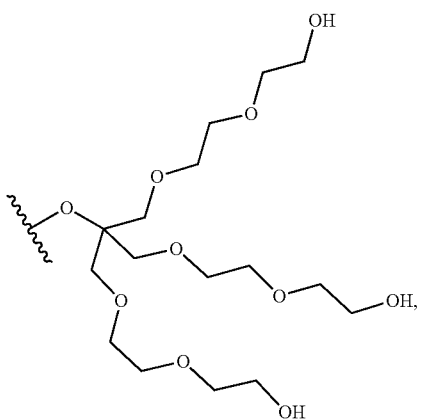
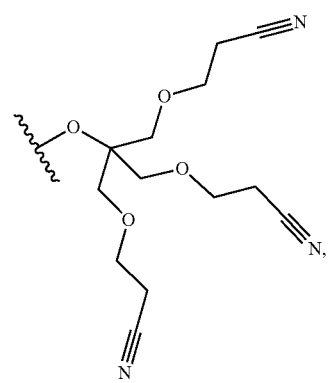
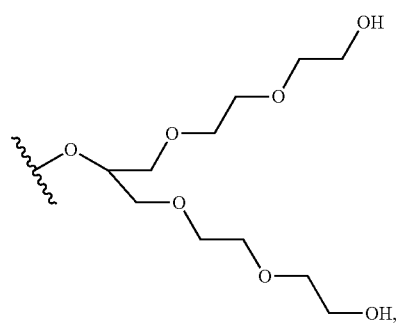

-continued
In some embodiments, for the compound or salt of Formula (X), (XA), (XB), (XC), (XD), (XE), (XF), or (XG), R⁴ is selected from:
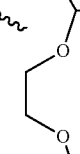
In some embodiments, for the compound or salt of Formula (X), (XA), (XB), (XC), (XD), (XE), (XF), or (XG), R⁴ is selected from:
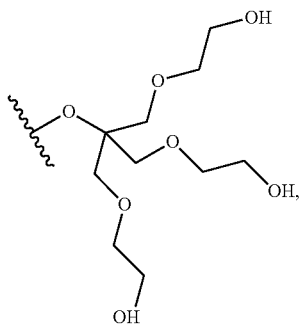

-continued
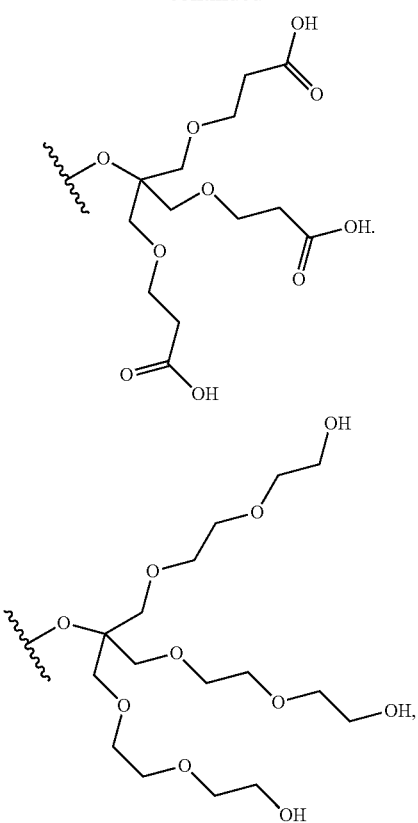
In some embodiments, the compound or salt of Formula (I) is selected from:
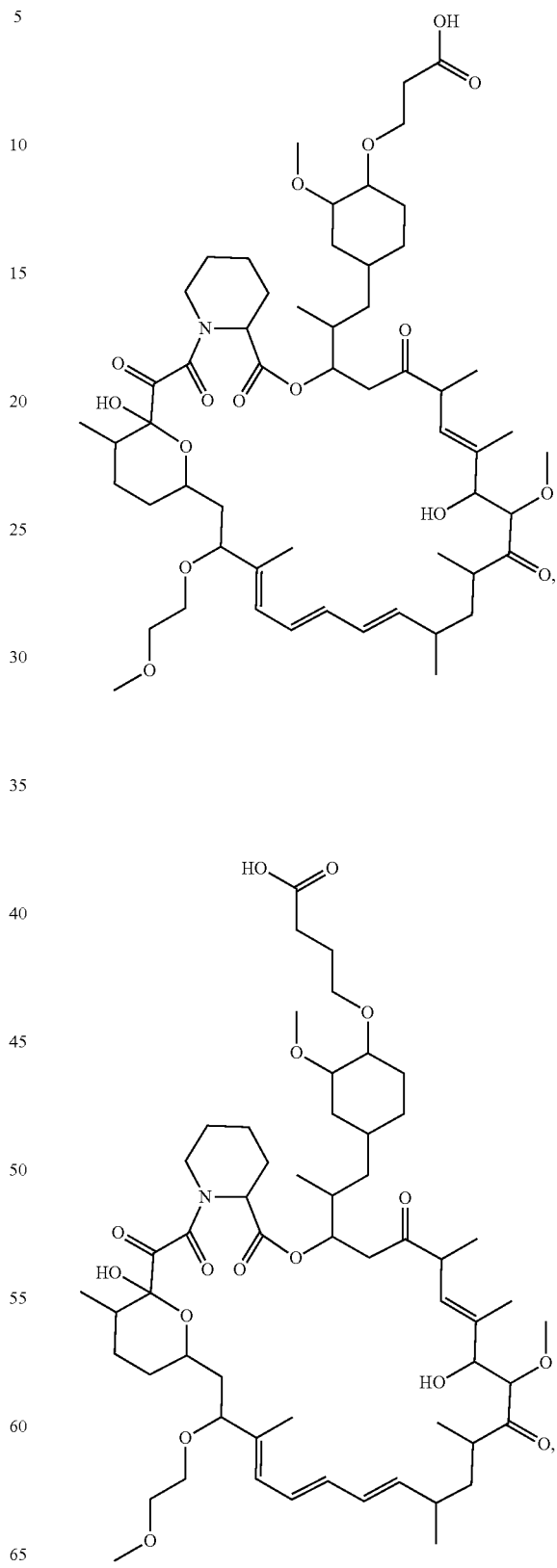

155
-continued
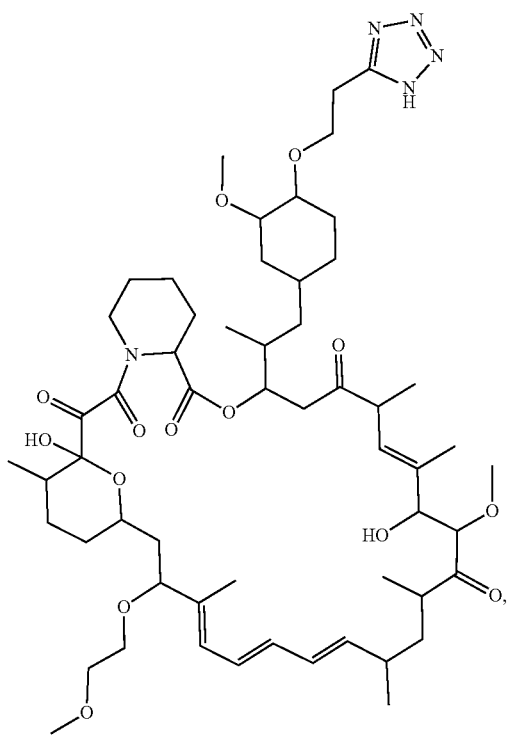
156
-continued
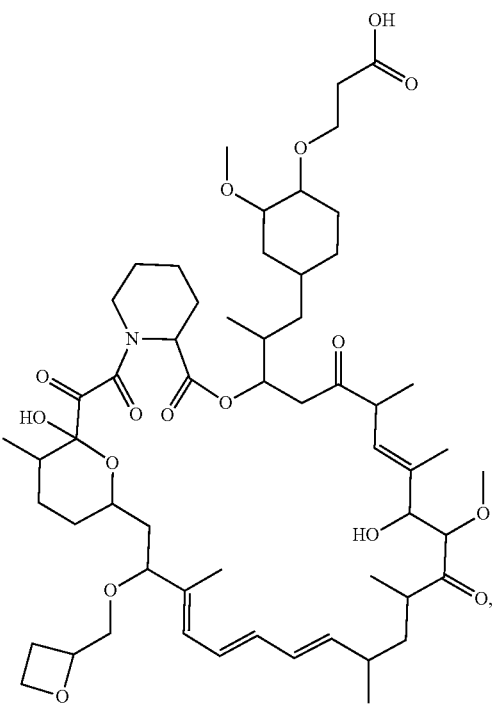
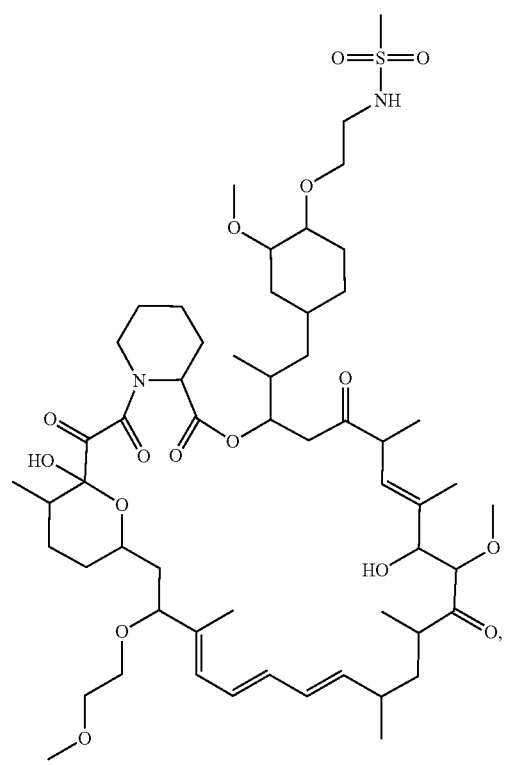
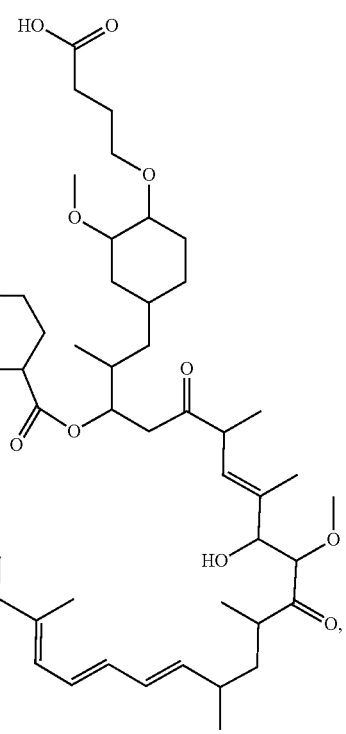

157
-continued

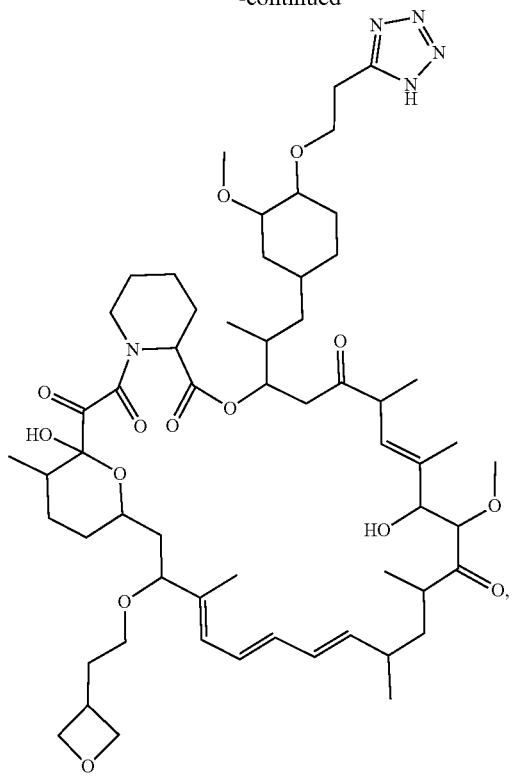

Compound Group 3

In a third aspect, the present disclosure provides a compound represented by the structure of Formula (L):

158

(L)

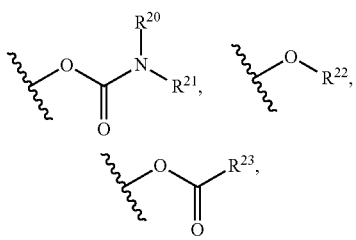

or a pharmaceutically acceptable salt thereof, wherein:

$R^1$ is selected from 3- to 10-membered heterocycle, and $C_{3-10}$ carbocycle, wherein the 3- to 10-membered heterocycle and $C_{3-10}$ carbocycle are each optionally substituted with one or more substituents independently selected from $R^{33}$;

$R^2$ is selected from hydrogen and an optionally substituted $C_1$-$C_6$ alkoxy group, wherein substituents are independently selected at each occurrence from hydroxy, halogen, —CN, —NO$_2$, $C_1$-$C_6$ alkoxy, 3- to 10-membered heterocycle, and $C_{3-10}$ carbocycle, wherein the 3- to 10-membered heterocycle and $C_{3-10}$ carbocycle are each optionally substituted with one or more substituents independently selected from hydroxy, halogen, —CN, —NO$_2$, $C_1$-$C_6$ alkyl, $C_1$-$C_6$ haloalkyl, $C_1$-$C_6$ hydroxyalkyl, $C_1$-$C_6$ alkoxy, and $C_1$-$C_6$ alkoxy $C_1$-$C_6$ alkyl;

$R^3$ is selected from hydrogen and an optionally substituted $C_1$-$C_6$ alkoxy group, wherein the substituents are independently selected at each occurrence from hydroxy, halogen, —CN, —NO$_2$, $C_1$-$C_6$ alkoxy group, 3- to 10-membered heterocycle, and $C_{3-10}$ carbocycle, wherein the 3- to 10-membered heterocycle and $C_{3-10}$ carbocycle, are each optionally substituted with one or more substituents independently selected from hydroxy, halogen, —CN, —NO$_2$, $C_1$-$C_6$ alkyl, $C_1$-$C_6$ haloalkyl, $C_1$-$C_6$ hydroxyalkyl, $C_1$-$C_6$ alkoxy, and $C_1$-$C_6$ alkoxy $C_1$-$C_6$ alkyl; and $R^4$ is

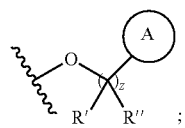

$R^5$ is selected from hydrogen, hydroxy, and an optionally substituted $C_1$-$C_6$ alkoxy group, wherein substituents are independently selected at each occurrence from hydroxy, halogen, —CN, —NO$_2$, $C_1$-$C_6$ alkoxy group, 3- to 10-membered heterocycle, and $C_{3-10}$ carbocycle, wherein the 3- to 10-membered heterocycle, and $C_{3-10}$ carbocycle are each optionally substituted with one or more substituents independently selected from hydroxy, halogen, —CN, —NO$_2$, $C_1$-$C_6$ alkyl, $C_1$-$C_6$ haloalkyl, $C_1$-$C_6$ hydroxyalkyl, $C_1$-$C_6$ alkoxy, and $C_1$-$C_6$ alkoxy $C_1$-$C_6$ alkyl;

$R^6$ and $R^7$ are each independently selected from hydrogen, hydroxy, and $C_{1-6}$ alkoxy; or $R^6$ and $R^7$ come together to form

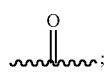

$R^{20}$ is selected from hydrogen and optionally substituted $C_1$-$C_6$ alkyl;

$R^{21}$ is selected from optionally substituted $C_1$-$C_6$ alkyl, and optionally substituted 3 to 7-membered heterocycle;

$R^{22}$ is selected from hydrogen, optionally substituted $C_1$-$C_6$ alkyl, —Si(R$^{24}$)$_3$, and —P(=O)(R$^{24}$)$_2$;

$R^{23}$ is selected from optionally substituted $C_1$-$C_6$ alkyl and optionally substituted 3 to 7-membered heterocycle;

$R^{24}$ is optionally substituted $C_1$-$C_6$ alkyl;

wherein the substituents on $R^{20}$, $R^{21}$, $R^{22}$, $R^{23}$, and $R^{24}$ are independently selected at each occurrence from: halogen, —OR$^{30}$, —N(R$^{30}$)$_2$, —(O—CH$_2$—(CH$_2$)$_p$)$_n$—W, —SR$^{30}$, —N(R$^{30}$)$_2$, —C(O)R$^{30}$, —C(O)N(R$^{30}$)$_2$, —N(R$^{30}$)C(O)R$^{30}$, —C(O)OR$^{30}$, —OC(O)R$^{30}$, —S(O)R$^{30}$, —S(O)$_2$R$^{30}$, —P(O)(OR$^{30}$)$_2$, —OP(O)(OR$^{30}$)$_2$, —NO$_2$, =O, =S, =N(R$^{30}$), and —CN;

$C_{1-10}$ alkyl, $C_{2-10}$ alkenyl, $C_{2-10}$ alkynyl, each of which is optionally substituted with one or more substituents independently selected from halogen, —OR$^{30}$, —SR$^{30}$, —N(R$^{30}$)$_2$, —C(O)R$^{30}$, —C(O)N(R$^{30}$)$_2$, —N(R$^{30}$)C(O)R$^{30}$, —C(O)OR$^{30}$, —OC(O)R$^{30}$, —S(O)R$^{30}$, —S(O)$_2$R$^{30}$, —P(O)(OR$^{30}$)$_2$, —OP(O)(OR$^{30}$)$_2$, —NO$_2$, =O, =S, =N(R$^{30}$), —CN, $C_{3-10}$ carbocycle and 3- to 10-membered heterocycle; and $C_{3-10}$ carbocycle and 3- to 10-membered heterocycle each of which is optionally substituted with one or more substituents independently selected from halogen, —OR$^{30}$, —SR$^{30}$, —N(R$^{30}$)$_2$, —C(O)R$^{30}$, —C(O)N(R$^{30}$)$_2$, —N(R$^{30}$)C(O)R$^{30}$, —C(O)OR$^{30}$, —OC(O)R$^{30}$, —S(O)R$^{30}$, —S(O)$_2$R$^{30}$, —P(O)(OR$^{30}$)$_2$, —OP(O)(OR$^{30}$)$_2$, —NO$_2$, =O, =S, =N(R$^{30}$), —CN, $C_{1-6}$ alkyl, $C_{1-6}$ alkyl-R$^{30}$, $C_{2-6}$ alkenyl, and $C_{2-6}$ alkynyl;

each p is selected from 1 or 2;
each n is selected from 3 to 7;

each W is selected from hydrogen, —OH, —$C_1$-$C_4$ alkyl, and —O($C_1$-$C_4$ alkyl);

$R^{30}$ is independently selected at each occurrence from: hydrogen; and $C_{1-10}$ alkyl, $C_{2-10}$ alkenyl, $C_{2-10}$ alkynyl, $C_{3-12}$ carbocycle, and 3- to 12-membered heterocycle, each of which is optionally substituted with one or more substituents independently selected from halogen, —OH, —OSi($C_1$-$C_6$ alkyl)$_3$, —CN, —NO$_2$, —NH$_2$, =O, =S, $C_{1-10}$ alkyl, —$C_{1-10}$ haloalkyl, —O—$C_{1-10}$ alkyl, $C_{2-10}$ alkenyl, $C_{2-10}$ alkynyl, $C_{3-12}$ carbocycle, 3- to 12-membered heterocycle, and haloalkyl;

z is selected from 0-2;

R' and R" are independently selected from hydrogen, halogen, —OR$^{31}$, and $C_{1-3}$ alkyl optionally substituted with one or more substituents independently selected from halogen and —OR$^{31}$;

Ring A is selected from an optionally substituted $C_3$-$C_5$ carbocycle and optionally substituted 3- to 5-membered heterocycle, wherein substituents on Ring A are independently selected at each occurrence from:
halogen, —OR$^{31}$, —SR$^{31}$, —N(R$^{31}$)$_2$, —C(O)R$^{31}$, —C(O)N(R$^{31}$)$_2$, N(R$^{31}$)C(O)R$^{31}$, —C(O)OR$^{31}$, —OC(O)R$^{31}$, —S(O)R$^{31}$, —S(O)$_2$R$^{31}$, —P(O)(OR$^{31}$)$_2$, —OP(O)(OR$^{31}$)$_2$, —NO$_2$, =O, =S, =N(R$^{31}$), and —CN;

$C_{1-10}$ alkyl, $C_{2-10}$ alkenyl, $C_{2-10}$ alkynyl, each of which is optionally substituted with one or more substituents independently selected from halogen, —OR$^{31}$, —SR$^{31}$, —N(R$^{31}$)$_2$, —C(O)R$^{31}$, —C(O)N(R$^{31}$)$_2$, —N(R$^{31}$)C(O)R$^{31}$, —C(O)OR$^{31}$, —OC(O)R$^{31}$, —S(O)R$^{31}$, —S(O)$_2$R$^{31}$, —P(O)(OR$^{31}$)$_2$, —OP(O)(OR$^{31}$)$_2$, —NO$_2$, =O, =S, =N(R$^{31}$), —CN, $C_{3-10}$ carbocycle and 3- to 10-membered heterocycle; and $C_{3-10}$ carbocycle and 3- to 10-membered heterocycle each of which is optionally substituted with one or more substituents independently selected from halogen, —OR$^{31}$, —SR$^{31}$, —N(R$^{31}$)$_2$, —C(O)R$^{31}$, —C(O)N(R$^{31}$)$_2$, —N(R$^{31}$)C(O)R$^{31}$, —C(O)OR$^{31}$, —OC(O)R$^{31}$, —S(O)R$^{31}$, —S(O)$_2$R$^{31}$, —P(O)(OR$^{31}$)$_2$, —OP(O)(OR$^{31}$)$_2$, —NO$_2$, =O, =S, =N(R$^{31}$), —CN, $C_{1-6}$ alkyl, $C_{2-6}$ alkenyl, $C_{2-6}$ alkynyl;

$R^{31}$ is independently selected at each occurrence from hydrogen; and $C_{1-10}$ alkyl, $C_{2-10}$ alkenyl, $C_{2-10}$ alkynyl, $C_{3-12}$ carbocycle, and 3- to 12-membered heterocycle, each of which is optionally substituted with one or more substituents independently selected from halogen, —OH, —CN, —NO$_2$, —NH$_2$, =O, =S, $C_{1-10}$ alkyl, —$C_{1-10}$ haloalkyl, —O—$C_{1-10}$ alkyl, $C_{2-10}$ alkenyl, $C_{2-10}$ alkynyl, $C_{3-12}$ carbocycle, and 3- to 12-membered heterocycle; and $R^{33}$ is independently selected at each occurrence from hydroxy, halogen, —CN, —NO$_2$, =O, $C_1$-$C_6$ alkyl, $C_1$-$C_6$ haloalkyl, $C_1$-$C_6$ hydroxyalkyl, $C_1$-$C_6$ alkoxy, $C_1$-$C_6$ alkoxy $C_1$-$C_6$ alkyl, 3- to 10-membered heterocycle, and $C_{3-10}$ carbocycle, wherein the 3- to 10-membered heterocycle and $C_{3-10}$ carbocycle are each optionally substituted with one or more substituents independently selected from hydroxy, halogen, —CN, —NO$_2$, $C_1$-$C_6$ alkyl, $C_1$-$C_6$ haloalkyl, $C_1$-$C_6$ hydroxyalkyl, $C_1$-$C_6$ alkoxy, and $C_1$-$C_6$ alkoxy $C_1$-$C_6$ alkyl.

In certain embodiments, the compound of Formula (L) is represented by Formula (LA):

(LA)

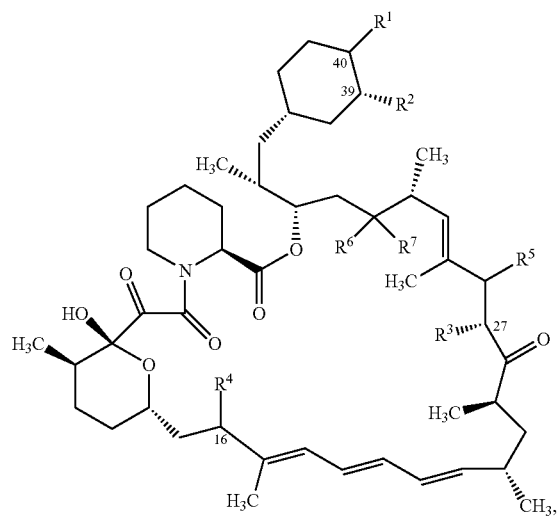

or a salt thereof.

In certain embodiments, the compound of Formula (L) is represented by Formula (LB):

(LB)

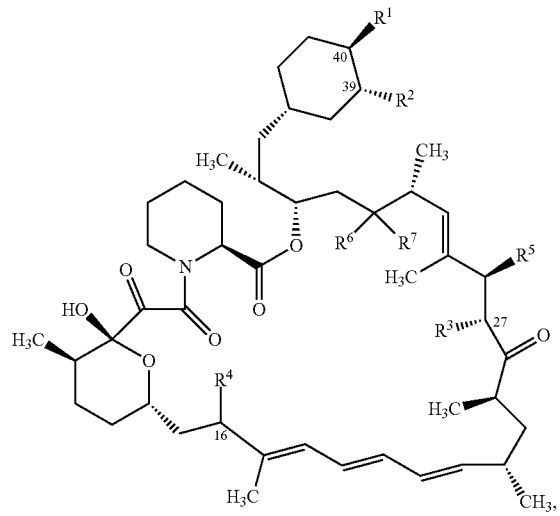

or a salt thereof.

In certain embodiments, the compound of Formula (L) is represented by Formula (LC):

(LC)

or a salt thereof.

In certain embodiments, the compound of Formula (L) is represented by Formula (LD):

(LD)

or a salt thereof.

In certain embodiments, the compound of Formula (L) is represented by Formula (LE):

(LE)

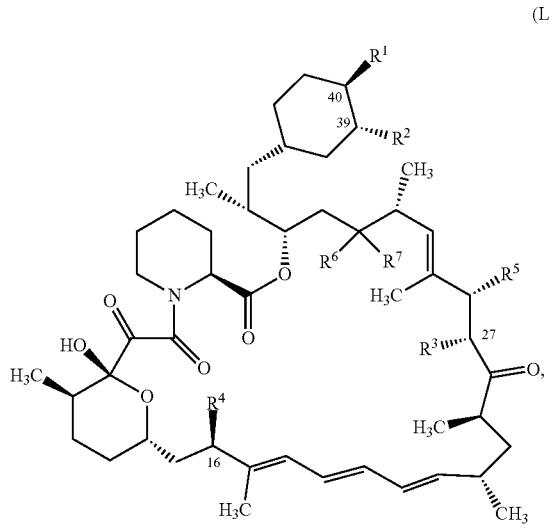

or a salt thereof.

In certain embodiments, the compound of Formula (L) is represented by Formula (LF):

(LF)

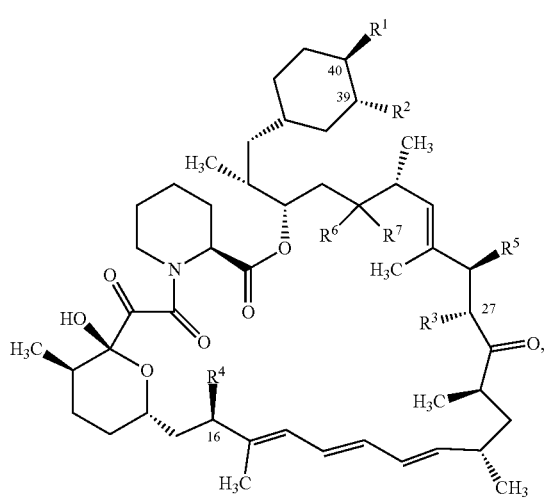

or a salt thereof.

In certain embodiments, the compound of Formula (L) is represented by Formula (LG):

(LG)

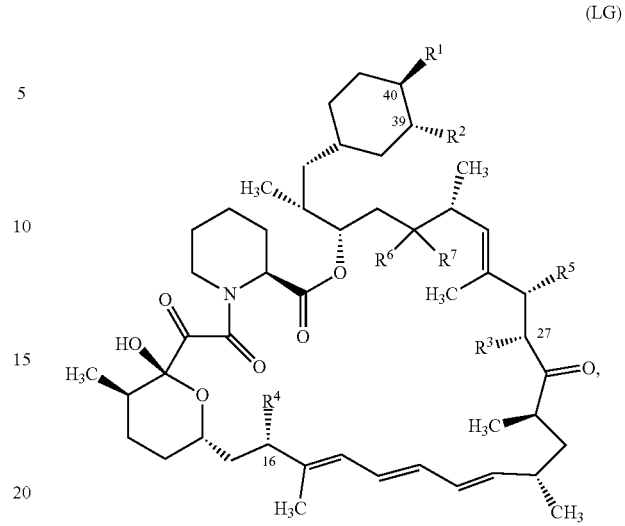

or a salt thereof.

In some embodiments, for the compound or salt of Formula (L), (LA), (LB), (LC), (LD), (LE), (LF), or (LG), z of $R^4$, is selected from 0, 1, or 2. In some embodiments, z is selected from 0 and 1. In some embodiments, z is selected from 0 and 2. In some embodiments, z is selected from 1 and 2. In some embodiments, z is selected from an optionally substituted —$CH_2$— and optionally substituted —$CH_2CH_2$—.

In some embodiments, for the compound or salt of Formula (L), (LA), (LB), (LC), (LD), (LE), (LF), or (LG), z is 0 and $R^4$ is represented by:

In some embodiments, for the compound or salt of Formula (L), (LA), (LB), (LC), (LD), (LE), (LF), or (LG), z is 1 and $R^4$ is represented by:

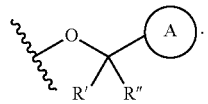

In some embodiments, for the compound or salt of Formula (L), (LA), (LB), (LC), (LD), (LE), (LF), or (LG), z is 2 and $R^4$ is represented by:

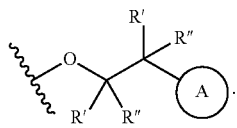

In some embodiments, for the compound or salt of Formula (L), (LA), (LB), (LC), (LD), (LE), (LF), or (LG), each R' and R" of

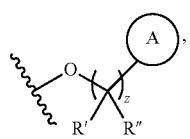

is independently selected from hydrogen, halogen, —OR³¹, and C$_{1-3}$ alkyl optionally substituted with one or more substituents independently selected from halogen and —OR³¹. In some embodiments, z is 1 and R' and R" are the same substitutent, for example R' is methyl and R" is methyl or R' is hydrogen and R" is hydrogen. In some embodiments, z is 1 and R' and R" are independently selected from a different substituent, for example R' is methyl and R" is ethyl. In some embodiments, each R' and R" are independently selected from hydrogen and C$_{1-3}$ alkyl. In some embodiments, each R' and R" are independently selected from hydrogen, halogen, and —OR³¹. In some embodiments, z is 1 and R' and R" are each hydrogen.

In some embodiments, for the compound or salt of Formula (L), (LA), (LB), (LC), (LD), (LE), (LF), or (LG), Ring A is selected from an optionally substituted C$_3$-C$_5$ carbocycle, such as an optionally substituted C$_3$-C$_4$ carbocycle, an optionally substituted C$_3$ carbocycle, an optionally substituted C$_4$ carbocycle, or an optionally substituted C$_5$ carbocycle. In some embodiments, the optionally substituted carbocycle is unsaturated. In some embodiments, the optionally substituted carbocycle is saturated.

In some embodiments, for the compound or salt of Formula (L), (LA), (LB), (LC), (LD), (LE), (LF), or (LG), Ring A is an optionally substituted 3- to 5-membered heterocycle, such as an optionally substituted 3- to 4-membered heterocycle, an optionally substituted 3-membered heterocycle, an optionally substituted 4-membered heterocycle or an optionally substituted 5-membered heterocycle. In some embodiments, the optionally substituted heterocycle is unsaturated. In some embodiments, the optionally substituted heterocycle is saturated.

In some embodiments, for the compound or salt of Formula (L), (LA), (LB), (LC), (LD), (LE), (LF), or (LG), Ring A is selected from optionally substituted C$_3$-C$_5$ carbocycle and optionally substituted 3- to 5-membered heterocycle, wherein each substituent is independently selected from: halogen, —OR³¹, —N(R³¹)$_2$, —C(O)R³¹, —C(O)N(R³¹)$_2$, N(R³¹)C(O)R³¹, —C(O)OR³¹, —OC(O)R³¹, —NO$_2$, and —CN; and C$_{1-3}$ alkyl optionally substituted with one or more substituents independently selected from halogen, —OR³¹, —N(R³¹)$_2$, —C(O)R³¹, —C(O)N(R³¹)$_2$, —N(R³¹)C(O)R³¹, —C(O)OR³¹, —OC(O)R³¹, —NO$_2$, —CN, C$_{3-6}$ carbocycle and 3- to 6-membered heterocycle.

In some embodiments, for the compound or salt of Formula (L), (LA), (LB), (LC), (LD), (LE), (LF), or (LG), Ring A is selected from optionally substituted C$_3$-C$_5$ carbocycle and optionally substituted 3- to 5-membered heterocycle, wherein one or more substituents are independently selected from: C$_{1-3}$ alkyl, which is optionally substituted with one or more —OR³¹ substituents.

In some embodiments, for the compound or salt of Formula (L), (LA), (LB), (LC), (LD), (LE), (LF), or (LG), Ring A is an optionally substituted C$_3$-C$_5$ carbocycle selected from:

, and

, any one of which is optionally substituted by one or more substituents independently selected from halogen, —OR³¹, —N(R³¹)$_2$, —C(O)R³¹, —C(O)N(R³¹)$_2$, N(R³¹)C(O)R³¹, —C(O)OR³¹, —OC(O)R³¹, —NO$_2$, =O, —CN; and C$_{1-6}$ alkyl optionally substituted with one or more substituents independently selected from halogen, —OR³¹, —N(R³¹)$_2$, —C(O)R³¹, —NO$_2$, =O, =S, —CN, C$_{3-6}$ carbocycle and 3- to 6-membered heterocycle.

In some embodiments, for the compound or salt of Formula (L), (LA), (LB), (LC), (LD), (LE), (LF), or (LG), R⁴ is

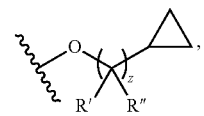

wherein z selected from 1 and 2. In some embodiments, z is selected from 0, 1, and 2. In some embodiments, for the compound or salt of Formula (L), (LA), (LB), (LC), (LD), (LE), (LF), or (LG), R⁴ is

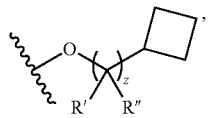

wherein z selected from 0, 1 and 2. In some embodiments, for the compound or salt of Formula (L), (LA), (LB), (LC), (LD), (LE), (LF), or (LG), R⁴ is

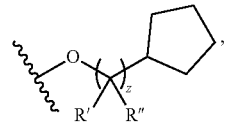

wherein z selected from 0, 1 and 2. In some embodiments, for the compound or salt of Formula (L), (LA), (LB), (LC), (LD), (LE), (LF), or (LG), R⁴ is selected from:

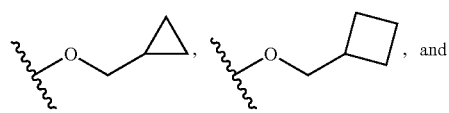

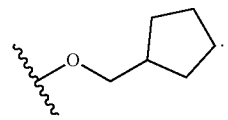

In some embodiments, $R^4$ is

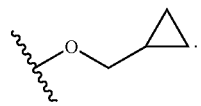 [SMILES: *OCC1CC1]

In some embodiments, $R^4$ is

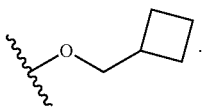 [SMILES: *OCC1CCC1]

In some embodiments, $R^4$ is

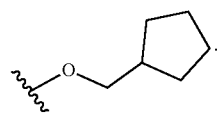 [SMILES: *OCC1CCCC1]

In some embodiments, for the compound or salt of Formula (L), (LA), (LB), (LC), (LD), (LE), (LF), or (LG), the $C_3$-carbocycle is optionally substituted by one or more substituents independently selected from: halogen, $-OR^{31}$, $-N(R^{31})_2$, $-C(O)R^{31}$, $-C(O)N(R^{31})_2$, $N(R^{31})C(O)R^{31}$, $-C(O)OR^{31}$, $-OC(O)R^{31}$, $-NO_2$, $=O$, $-CN$; and $C_{1-10}$ alkyl, $C_{2-10}$ alkenyl, and $C_{2-10}$ alkynyl each of which is optionally substituted with one or more substituents independently selected from halogen, $-OR^{31}$, $-N(R^{31})_2$, $-C(O)R^{31}$, $-NO_2$, $=O$, $=S$, $-CN$, $C_{3-10}$ carbocycle and 3- to 10-membered heterocycle.

In some embodiments, for the compound or salt of Formula (L), (LA), (LB), (LC), (LD), (LE), (LF), or (LG), the $C_3$-carbocycle is substituted by one or more substituents independently selected from: halogen, $-OR^{31}$, $-N(R^{31})_2$, $-C(O)R^{31}$, $-C(O)N(R^{31})_2$, $N(R^{31})C(O)R^{31}$, $-C(O)OR^{31}$, $-OC(O)R^{31}$, $-NO_2$, $=O$, $-CN$; and $C_{1-10}$ alkyl, $C_{2-10}$ alkenyl, and $C_{2-10}$ alkynyl each of which is optionally substituted with one or more substituents independently selected from halogen, $-OR^{31}$, $-N(R^{31})_2$, $-C(O)R^{31}$, $-NO_2$, $=O$, $=S$, $-CN$, $C_{3-10}$ carbocycle and 3- to 10-membered heterocycle.

In some embodiments, for the compound or salt of Formula (L), (LA), (LB), (LC), (LD), (LE), (LF), or (LG), the $C_4$-carbocycle is optionally substituted by one or more substituents independently selected from: halogen, $-OR^{31}$, $-N(R^{31})_2$, $-C(O)R^{31}$, $-C(O)N(R^{31})_2$, $N(R^{31})C(O)R^{31}$, $-C(O)OR^{31}$, $-OC(O)R^{31}$, $-NO_2$, $=O$, $-CN$; and $C_{1-10}$ alkyl, $C_{2-10}$ alkenyl, and $C_{2-10}$ alkynyl each of which is optionally substituted with one or more substituents independently selected from halogen, $-OR^{31}$, $-N(R^{31})_2$, $-C(O)R^{31}$, $-NO_2$, $=O$, $=S$, $-CN$, $C_{3-10}$ carbocycle and 3- to 10-membered heterocycle.

In some embodiments, for the compound or salt of Formula (L), (LA), (LB), (LC), (LD), (LE), (LF), or (LG), the $C_4$-carbocycle is substituted by one or more substituents independently selected from: halogen, $-OR^{31}$, $-N(R^{31})_2$, $-C(O)R^{31}$, $-C(O)N(R^{31})_2$, $N(R^{31})C(O)R^{31}$, $-C(O)OR^{31}$, $-OC(O)R^{31}$, $-NO_2$, $=O$, $-CN$; and $C_{1-10}$ alkyl, $C_{2-10}$ alkenyl, and $C_{2-10}$ alkynyl each of which is optionally substituted with one or more substituents independently selected from halogen, $-OR^{31}$, $-N(R^{31})_2$, $-C(O)R^{31}$, $-NO_2$, $=O$, $=S$, $-CN$, $C_{3-10}$ carbocycle and 3- to 10-membered heterocycle.

In some embodiments, for the compound or salt of Formula (L), (LA), (LB), (LC), (LD), (LE), (LF), or (LG), the $C_5$-carbocycle is optionally substituted by one or more substituents independently selected from: halogen, $-OR^{31}$, $-N(R^{31})_2$, $-C(O)R^{31}$, $-C(O)N(R^{31})_2$, $N(R^{31})C(O)R^{31}$, $-C(O)OR^{31}$, $-OC(O)R^{31}$, $-NO_2$, $=O$, $-CN$; and $C_{1-10}$ alkyl, $C_{2-10}$ alkenyl, and $C_{2-10}$ alkynyl each of which is optionally substituted with one or more substituents independently selected from halogen, $-OR^{31}$, $-N(R^{31})_2$, $-C(O)R^{31}$, $-NO_2$, $=O$, $=S$, $-CN$, $C_{3-10}$ carbocycle and 3- to 10-membered heterocycle.

In some embodiments, for the compound or salt of Formula (L), (LA), (LB), (LC), (LD), (LE), (LF), or (LG), the $C_5$-carbocycle is substituted by one or more substituents independently selected from: halogen, $-OR^{31}$, $-N(R^{31})_2$, $-C(O)R^{31}$, $-C(O)N(R^{31})_2$, $N(R^{31})C(O)R^{31}$, $-C(O)OR^{31}$, $-OC(O)R^{31}$, $-NO_2$, $=O$, $-CN$; and $C_{1-10}$ alkyl, $C_{2-10}$ alkenyl, and $C_{2-10}$ alkynyl each of which is optionally substituted with one or more substituents independently selected from halogen, $-OR^{31}$, $-N(R^{31})_2$, $-C(O)R^{31}$, $-NO_2$, $=O$, $=S$, $-CN$, $C_{3-10}$ carbocycle and 3- to 10-membered heterocycle.

In some embodiments, for the compound or salt of Formula (L), (LA), (LB), (LC), (LD), (LE), (LF), or (LG), Ring A is an optionally substituted 3- to 5-membered heterocycle wherein one or more substituents are independently selected from halogen, $-OR^{31}$, $-N(R^{31})_2$, $-C(O)R^{31}$, $-C(O)N(R^{31})_2$, $N(R^{31})C(O)R^{31}$, $-C(O)OR^{31}$, $-OC(O)R^{31}$, $-NO_2$, $=O$, $-CN$; and $C_{1-10}$ alkyl, $C_{2-10}$ alkenyl, and $C_{2-10}$ alkynyl each of which is optionally substituted with one or more substituents independently selected from halogen, $-OR^{31}$, $-N(R^{31})_2$, $-C(O)R^{31}$, $-NO_2$, $=O$, $=S$, $-CN$, $C_{3-10}$ carbocycle and 3- to 10-membered heterocycle. In some embodiments, the optionally substituted 3- to 5-membered heterocycle is saturated. In some embodiments, the optionally substituted 3- to 5-membered heterocycle is unsaturated.

In some embodiments, for the compound or salt of Formula (L), (LA), (LB), (LC), (LD), (LE), (LF), or (LG), the 3- to 5-membered heterocycle comprises at least one heteroatom selected from oxygen, nitrogen, sulfur, boron, phosphorus, silicon, selenium, and any combination thereof. In some embodiments, the 3- to 5-membered heterocycle comprises at least one heteroatom selected from oxygen, nitrogen, and sulfur.

In some embodiments, for the compound or salt of Formula (L), (LA), (LB), (LC), (LD), (LE), (LF), or (LG), Ring A is a 3-membered heterocycle wherein the heterocycle comprises one heteroatom selected from oxygen, nitrogen, and sulfur. In some embodiments, Ring A is a 3-membered heterocycle optionally substituted by one or more substituents independently selected from halogen, $-OR^{31}$, $-N(R^{31})_2$, $-C(O)R^{31}$, $-C(O)N(R^{31})_2$, $N(R^{31})C(O)R^{31}$, $-C(O)OR^{31}$, $-OC(O)R^{31}$, $-NO_2$, $=O$, $-CN$; and $C_{1-10}$ alkyl, $C_{2-10}$ alkenyl, and $C_{2-10}$ alkynyl each of which is optionally substituted with one or more substituents independently selected from halogen, $-OR^{31}$, $-N(R^{31})_2$, $-C(O)R^{31}$, $-NO_2$, $=O$, $=S$, $-CN$, $C_{3-10}$ carbocycle and 3- to 10-membered heterocycle.

In some embodiments, for the compound or salt of Formula (L), (LA), (LB), (LC), (LD), (LE), (LF), or (LG), Ring A is a 4-membered heterocycle optionally substituted by one or more substituents independently selected from halogen, $-OR^{31}$, $-N(R^{31})_2$, $-C(O)R^{31}$, $-C(O)N(R^{31})_2$, N(R$^{31}$)C(O)R$^{31}$, —C(O)OR$^{31}$, —OC(O)R$^{31}$, —NO$_2$, =O, —CN; and C$_{1-10}$ alkyl, C$_{2-10}$ alkenyl, and C$_{2-10}$ alkynyl each of which is optionally substituted with one or more substituents independently selected from halogen, —OR$^{31}$, —N(R$^{31}$)$_2$, —C(O)R$^{31}$, —NO$_2$, =O, =S, —CN, C$_{3-10}$ carbocycle and 3- to 10-membered heterocycle.

In some embodiments, for the compound or salt of Formula (L), (LA), (LB), (LC), (LD), (LE), (LF), or (LG), Ring A is an optionally substituted 4-membered heterocycle comprising 1 oxygen atom, wherein the 4-membered heterocycle is optionally substituted by one or more substituents independently selected from halogen, —OR$^{31}$, —N(R$^{31}$)$_2$, —C(O)R$^{31}$, —C(O)N(R$^{31}$)$_2$, N(R$^{31}$)C(O)R$^{31}$, —C(O)OR$^{31}$, —OC(O)R$^{31}$, —NO$_2$, =O, —CN; and C$_{1-10}$ alkyl, C$_{2-10}$ alkenyl, and C$_{2-10}$ alkynyl each of which is optionally substituted with one or more substituents independently selected from halogen, —OR$^{31}$, —N(R$^{31}$)$_2$, —C(O)R$^{31}$, —NO$_2$, =O, =S, and —CN. In some embodiments, R$^{31}$ of —OR$^{31}$ is independently selected at each occurrence from C$_{1-6}$ alkyl and hydrogen. In some embodiments, R$^4$ is selected from:

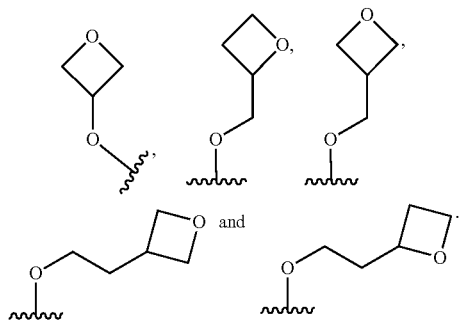

In some embodiments, R$^4$ is

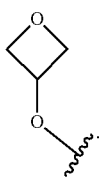 [SMILES: *OC1COC1]

In some embodiments, R$^4$ is

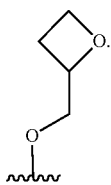 [SMILES: *OCC1CCO1]

In some embodiments, R$^4$ is

In some embodiments, R$^4$ is

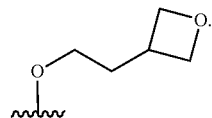 [SMILES: *OCCC1COC1]

In some embodiments, R$^4$ is

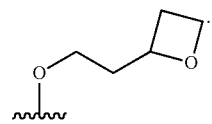

In some embodiments, for the compound or salt of Formula (L), (LA), (LB), (LC), (LD), (LE), (LF), or (LG), Ring A is a substituted 4-membered heterocycle comprising 1 oxygen atom, wherein the 4-membered heterocycle is substituted by one or more substituents independently selected from halogen, —OR$^{31}$, —N(R$^{31}$)$_2$, —C(O)R$^{31}$, —C(O)N(R$^{31}$)$_2$, N(R$^{31}$)C(O)R$^{31}$, —C(O)OR$^{31}$, —OC(O)R$^{31}$, —NO$_2$, =O, —CN; and C$_{1-10}$ alkyl, C$_{2-10}$ alkenyl, and C$_{2-10}$ alkynyl each of which is optionally substituted with one or more substituents independently selected from halogen, —OR$^{31}$, —N(R$^{31}$)$_2$, —C(O)R$^{31}$, —NO$_2$, =O, =S, and —CN. In some embodiments, R$^{31}$ of —OR$^{31}$ is independently selected at each occurrence from C$_{1-10}$ alkyl and hydrogen. In some embodiments, R$^4$ is selected from:

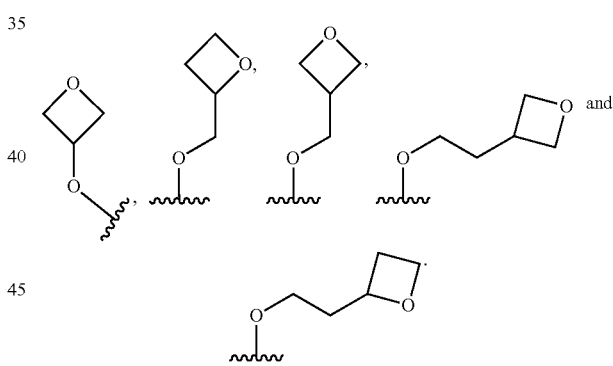

In some embodiments, for the compound or salt of Formula (L), (LA), (LB), (LC), (LD), (LE), (LF), or (LG), the optionally substituted 4-membered heterocycle comprises 1 or 2 heteroatoms selected from nitrogen and sulfur.

In some embodiments, for the compound or salt of Formula (L), (LA), (LB), (LC), (LD), (LE), (LF), or (LG), Ring A is an optionally substituted 4-membered heterocycle comprising 1 or 2 nitrogen atoms. In some embodiments, the optionally substituted 4-membered heterocycle is selected from azetidine, 2,3-dihydroazete, azete, 1,3-diazetidine and 1,4-diazetidine, any one of which is optionally substituted by one or more substituents independently selected from halogen, —OR$^{31}$, —N(R$^{31}$)$_2$, —C(O)R$^{31}$, —C(O)N(R$^{31}$)$_2$, N(R$^{31}$)C(O)R$^{31}$, —C(O)OR$^{31}$, —OC(O)R$^{31}$, —NO$_2$, =O, —CN; and C$_{1-10}$ alkyl, C$_{2-10}$ alkenyl, and C$_{2-10}$ alkynyl each of which is optionally substituted with one or more substituents independently selected from halogen, —OR$^{31}$, —N(R$^{31}$)$_2$, —C(O)R$^{31}$, —NO$_2$, =O, =S, —CN, C$_{3-10}$ carbocycle and 3- to 10-membered heterocycle. In some embodiments, $R^{31}$ of —$OR^{31}$ is independently selected at each occurrence from $C_{1-10}$ alkyl and hydrogen.

In some embodiments, for the compound or salt of Formula (L), (LA), (LB), (LC), (LD), (LE), (LF), or (LG), Ring A is an optionally substituted 4-membered heterocycle selected from azetidine, 1,3-diazetidine and 1,4-diazetidine, any one of which is optionally substituted by one or more substituents independently selected from halogen, —$OR^{31}$, —$N(R^{31})_2$, —$C(O)R^{31}$, —$C(O)N(R^{31})_2$, $N(R^{31})C(O)R^{31}$, —$C(O)OR^{31}$, —$OC(O)R^{31}$, —$NO_2$, =O, —CN; and $C_{1-10}$ alkyl, $C_{2-10}$ alkenyl, and $C_{2-10}$ alkynyl each of which is optionally substituted with one or more substituents independently selected from halogen, —$OR^{31}$, —$N(R^{31})_2$, —$C(O)R^{31}$, —$NO_2$, =O, =S, —CN, $C_{3-10}$ carbocycle and 3- to 10-membered heterocycle. In some embodiments, $R^{31}$ of —$OR^{31}$ is independently selected at each occurrence from $C_{1-10}$ alkyl and hydrogen.

In some embodiments, for the compound or salt of Formula (L), (LA), (LB), (LC), (LD), (LE), (LF), or (LG), Ring A is an optionally substituted 4-membered heterocycle selected from 2,3-dihydroazete and azete, any one of which is optionally substituted by one or more substituents independently selected from halogen, —$OR^{31}$, —$N(R^{31})_2$, —$C(O)R^{31}$, —$C(O)N(R^{31})_2$, $N(R^{31})C(O)R^{31}$, —$C(O)OR^{31}$, —$OC(O)R^{31}$, —$NO_2$, =O, —CN; and $C_{1-10}$ alkyl, $C_{2-10}$ alkenyl, and $C_{2-10}$ alkynyl each of which is optionally substituted with one or more substituents independently selected from halogen, —$OR^{31}$, —$N(R^{31})_2$, —$C(O)R^{31}$, —$NO_2$, =O, =S, —CN, $C_{3-10}$ carbocycle and 3- to 10-membered heterocycle. In some embodiments, $R^{31}$ of —$OR^{31}$ is independently selected at each occurrence from $C_{1-10}$ alkyl and hydrogen.

In some embodiments, for the compound or salt of Formula (L), (LA), (LB), (LC), (LD), (LE), (LF), or (LG), Ring A is an optionally substituted azetidine, which is optionally substituted by one or more substituents independently selected from $C_{1-10}$ alkyl, each of which is optionally substituted with one or more substituents independently selected from —$OR^{31}$. In some embodiments, $R^{31}$ of —$OR^{31}$ is independently selected at each occurrence from $C_{1-10}$ alkyl and hydrogen. In some embodiments, $R^4$ is selected from:

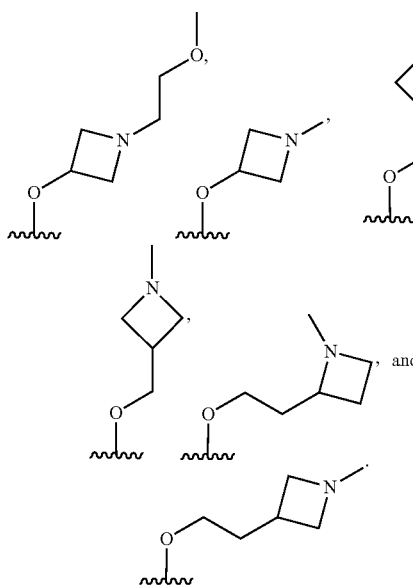

In some embodiments, $R^4$ is

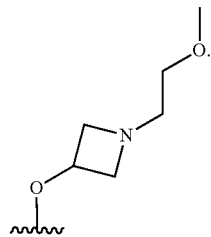 [SMILES: *OC1CN(CCOC)C1]

In some embodiments, $R^4$ is

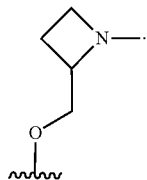

In some embodiments, $R^4$ is

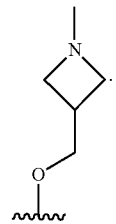

In some embodiments, $R^4$ is

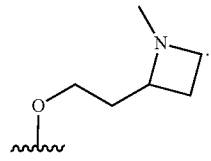 [SMILES: *OCCC1CCN1C]

In some embodiments, $R^4$ is selected from:

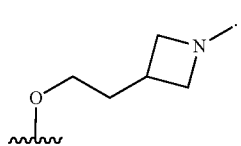

In some embodiments, $R^4$ is

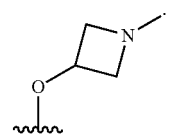

In some embodiments, for the compound or salt of Formula (L), (LA), (LB), (LC), (LD), (LE), (LF), or (LG), Ring A is an optionally substituted 5-membered heterocycle comprising at least one heteroatom selected from nitrogen, oxygen, sulfur, and any combination thereof. In some embodiments, Ring A is an optionally substituted 5-membered heterocycle comprising 4 heteroatoms selected from nitrogen, oxygen, sulfur, and any combination thereof.

In some embodiments, for the compound or salt of Formula (L), (LA), (LB), (LC), (LD), (LE), (LF), or (LG), Ring A is an optionally substituted 5-membered heterocycle comprising 4 nitrogen atoms. In some embodiments, Ring A is an optionally substituted tetrazole, which is optionally substituted by one or more substituents independently selected from halogen, —$OR^{31}$, —$N(R^{31})_2$, —$C(O)R^{31}$, —$C(O)N(R^{31})_2$, $N(R^{31})C(O)R^{31}$, —$C(O)OR^{31}$, —$OC(O)R^{31}$, —$NO_2$, =O, —CN; and $C_{1-10}$ alkyl, $C_{2-10}$ alkenyl, and $C_{2-10}$ alkynyl each of which is optionally substituted with one or more substituents independently selected from halogen, —$OR^{31}$, —$N(R^{31})_2$, —$C(O)R^{31}$, —$NO_2$, =O, =S, —CN, $C_{3-10}$ carbocycle and 3- to 10-membered heterocycle.

In some embodiments, for the compound or salt of Formula (L), (LA), (LB), (LC), (LD), (LE), (LF), or (LG), Ring A is an optionally substituted 5-membered heterocycle comprising 3 heteroatoms selected from nitrogen, oxygen, sulfur, and any combination thereof.

In some embodiments, for the compound or salt of Formula (L), (LA), (LB), (LC), (LD), (LE), (LF), or (LG), Ring A is an optionally substituted 5-membered heterocycle comprising 3 heteroatoms selected from nitrogen, oxygen, and sulfur, wherein the optionally substituted 5-membered heterocycle is selected from 1,2,4-triazole, 1,2,3-triazole, 1,2,5-oxadiazole, 1,2,3-oxadiazole, 1,3,4-thiadiazole, and 1,2,5-thiadiazole, any one of which is optionally substituted by one or more substituents independently selected from halogen, —$OR^{31}$, —$N(R^{31})_2$, —$C(O)R^{31}$, —$C(O)N(R^{31})_2$, $N(R^{31})C(O)R^{31}$, —$C(O)OR^{31}$, —$OC(O)R^{31}$, —$NO_2$, =O, —CN; and $C_{1-10}$ alkyl, $C_{2-10}$ alkenyl, and $C_{2-10}$ alkynyl each of which is optionally substituted with one or more substituents independently selected from halogen, —$OR^{31}$, —$N(R^{31})_2$, —$C(O)R^{31}$, —$NO_2$, =O, =S, —CN, $C_{3-10}$ carbocycle and 3- to 10-membered heterocycle.

In some embodiments, for the compound or salt of Formula (L), (LA), (LB), (LC), (LD), (LE), (LF), or (LG), Ring A is an optionally substituted 5-membered heterocycle comprising 2 heteroatoms selected from nitrogen, oxygen, and sulfur, wherein the optionally substituted 5-membered heterocycle is selected from pyrazolidine, imidazolidine, 2-pyrazoline, 2-imidazoline, pyrazole, imidazole, 1,3-dioxolane, oxazole, isoxazole, thiazole, isothiazole, 1,2-oxathiolane, and 1,3-oxathiolane, any one of which is optionally substituted by one or more substituents independently selected from halogen, —$OR^{31}$, —$N(R^{31})_2$, —$C(O)R^{31}$, —$C(O)N(R^{31})_2$, $N(R^{31})C(O)R^{31}$, —$C(O)OR^{31}$, —$OC(O)R^{31}$, —$NO_2$, =O, —CN; and $C_{1-10}$ alkyl, $C_{2-10}$ alkenyl, and $C_{2-10}$ alkynyl each of which is optionally substituted with one or more substituents independently selected from halogen, —$OR^{31}$, —$N(R^{31})_2$, —$C(O)R^{31}$, —$NO_2$, =O, =S, —CN, $C_{3-10}$ carbocycle and 3- to 10-membered heterocycle.

In some embodiments, for the compound or salt of Formula (L), (LA), (LB), (LC), (LD), (LE), (LF), or (LG), Ring A is a substituted 5-membered heterocycle comprising 2 oxygen atoms, wherein the optionally substituted 5-membered heterocycle is selected at each occurrence from halogen, —$OR^{31}$, —$N(R^{31})_2$, —$C(O)R^{31}$, —$C(O)N(R^{31})_2$, $N(R^{31})C(O)R^{31}$, —$C(O)OR^{31}$, —$OC(O)R^{31}$, —$NO_2$, =O, —CN; and $C_{2-10}$ alkyl, $C_{2-10}$ alkenyl, and $C_{2-10}$ alkynyl each of which is optionally substituted with one or more substituents independently selected from halogen, —$OR^{31}$, —$N(R^{31})_2$, —$C(O)R^{31}$, —$NO_2$, =O, =S, —CN, $C_{3-10}$ carbocycle and 3- to 10-membered heterocycle.

In some embodiments, for the compound or salt of Formula (L), (LA), (LB), (LC), (LD), (LE), (LF), or (LG), when $R^1$ is hydroxy, $R^4$ is not

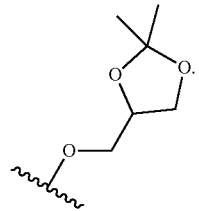

In some embodiments, $R^4$ is not

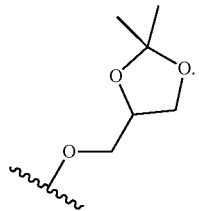 [SMILES: *OCC1COC(C)(C)O1]

In some embodiments, for the compound or salt of Formula (L), (LA), (LB), (LC), (LD), (LE), (LF), or (LG), Ring A is an optionally substituted 5-membered heterocycle comprising 1 heteroatom selected from nitrogen, oxygen, and sulfur. In some embodiments, Ring A is selected from pyrrolidine, 3-pyrroline, 2-pyrroline, 2H-pyrrole, 1H-pyrrole, tetrahydrofuran, furan, tetrahydrothiophene, and thiophene, any one of which is optionally substituted by one or more substituents independently selected from halogen, —$OR^{31}$, —$N(R^{31})_2$, —$C(O)R^{31}$, —$C(O)N(R^{31})_2$, $N(R^{31})C(O)R^{31}$, —$C(O)OR^{31}$, —$OC(O)R^{31}$, —$NO_2$, =O, —CN; and $C_{1-10}$ alkyl, $C_{2-10}$ alkenyl, and $C_{2-10}$ alkynyl each of which is optionally substituted with one or more substituents independently selected from halogen, —$OR^{31}$, —$N(R^{31})_2$, —$C(O)R^{31}$, —$NO_2$, =O, =S, —CN, $C_{3-10}$ carbocycle and 3- to 10-membered heterocycle.

In some embodiments, for the compound or salt of Formula (L), (LA), (LB), (LC), (LD), (LE), (LF), or (LG), Ring A is an optionally substituted 5-membered heterocycle comprising 1 oxygen atom, wherein the optionally substituted 5-membered heterocycle is selected from tetrahydrofuran and furan, any one of which is optionally substituted by one or more substituents independently selected from halogen, —$OR^{31}$, —$N(R^{31})_2$, —$C(O)R^{31}$, —$C(O)N(R^{31})_2$, $N(R^{31})C(O)R^{31}$, —$C(O)OR^{31}$, —$OC(O)R^{31}$, —$NO_2$, =O, —CN; and $C_{1-10}$ alkyl, $C_{2-10}$ alkenyl, and $C_{2-10}$ alkynyl each of which is optionally substituted with one or more substituents independently selected from halogen, —$OR^{31}$, —$N(R^{31})_2$, —$C(O)R^{31}$, —$NO_2$, =O, =S, —CN, $C_{3-10}$ carbocycle and 3- to 10-membered heterocycle.

In some embodiments, for the compound or salt of Formula (L), (LA), (LB), (LC), (LD), (LE), (LF), or (LG), Ring A is an optionally substituted 5-membered heterocycle is selected from tetrahydrofuran and furan which is optionally substituted by one or more substituents independently selected from halogen, —$OR^{31}$, and $C_{1-10}$ alkyl. In some embodiments, the optionally substituted 5-membered heterocycle is tetrahydrofuran which is optionally substituted by one or more substituents independently selected from halogen, —OR$^{31}$, and C$_{1-10}$ alkyl. In some embodiments, R$^{31}$ of —OR$^{31}$ is selected from hydrogen and C$_{1-10}$ alkyl. In some embodiments, R$^4$ is selected from

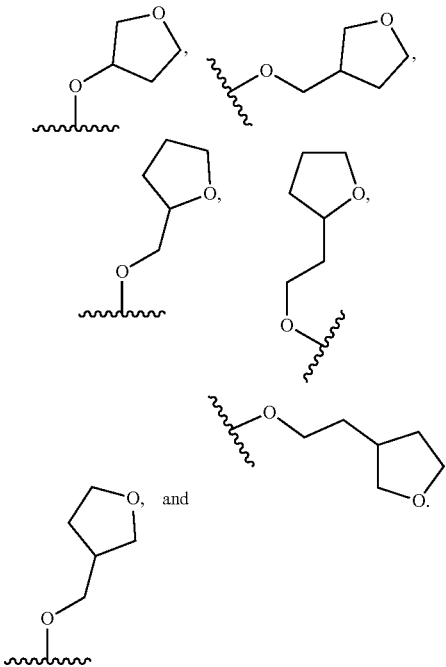

In some embodiments, R$^4$ is selected from

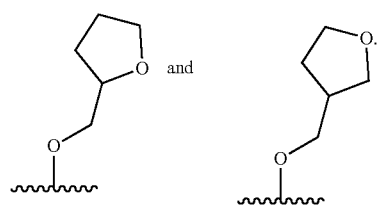 [SMILES: *OCC1CCCO1 ; *OCC1CCOC1]

In some embodiments, R$^4$ is

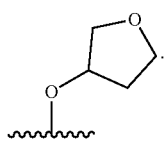 [SMILES: *OC1CCOC1]

In some embodiments, R$^4$ is

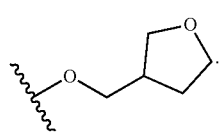 [SMILES: *OCC1CCOC1]

In some embodiments, R$^4$ is

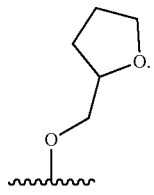

In some embodiments, R$^4$ is

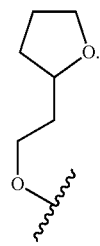

In some embodiments, R$^4$ is

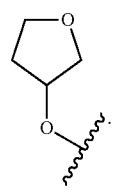

In some embodiments, R$^4$ is

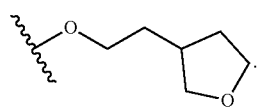

In some embodiments, for the compound or salt of Formula (L), (LA), (LB), (LC), (LD), (LE), (LF), or (LG), Ring A is an optionally substituted 5-membered heterocycle comprising 1 nitrogen atom, wherein the optionally substituted 5-membered heterocycle is selected from pyrrolidine, 3-pyrroline, 2-pyrroline, 2H-pyrrole, and 1H-pyrrole, any one of which is optionally substituted by one or more substituents independently selected from halogen, —OR$^{31}$, —N(R$^{31}$)$_2$, —C(O)R$^{31}$, —C(O)N(R$^{31}$)$_2$, N(R$^{31}$)C(O)R$^{31}$, —C(O)OR$^{31}$, —OC(O)R$^{31}$, —NO$_2$, =O, —CN; and C$_{1-10}$ alkyl, C$_{2-10}$ alkenyl, and C$_{2-10}$ alkynyl each of which is optionally substituted with one or more substituents independently selected from halogen, —OR$^{31}$, —N(R$^{31}$)$_2$, —C(O)R$^{31}$, —NO$_2$, =O, =S, —CN, C$_{3-10}$ carbocycle and 3- to 10-membered heterocycle.

In some embodiments, for the compound or salt of Formula (L), (LA), (LB), (LC), (LD), (LE), (LF), or (LG), the optionally substituted 5-membered heterocycle is is selected from pyrrolidine, 3-pyrroline, 2-pyrroline, 2H-pyrrole, and 1H-pyrrole, any one of which is optionally substituted by one or more substituents independently selected from halogen, —OR$^{31}$; and C$_{1-10}$ alkyl, each of which is optionally substituted with one or more substituents independently selected from $OR^{31}$. In some embodiments, $R^{31}$ of $-OR^{31}$ is independently selected at each occurrence from $C_{1-10}$ alkyl and hydrogen. In some embodiments, $R^4$ is selected from:

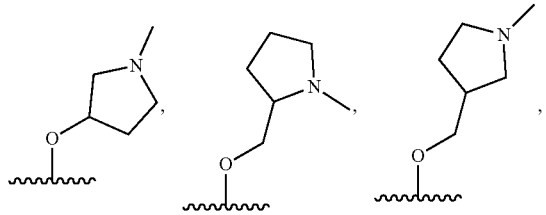

In some embodiments, $R^4$ is

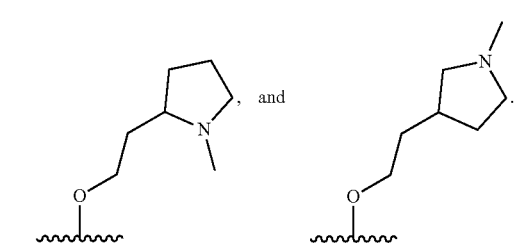

In some embodiments, $R^4$ is

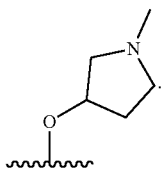 [SMILES: *OC1CCN(C)C1]

In some embodiments, $R^4$ is

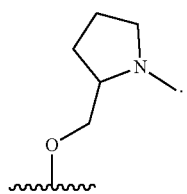 [SMILES: *OCC1CCCN1C]

In some embodiments, $R^4$ is

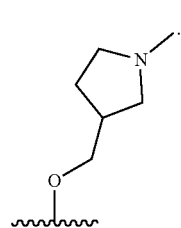 [SMILES: *OCC1CCN(C)C1]

In some embodiments, $R^4$ is

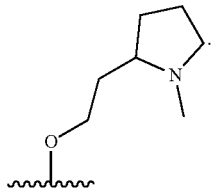 [SMILES: *OCCC1CCCN1C]

In some embodiments, $R^4$ is

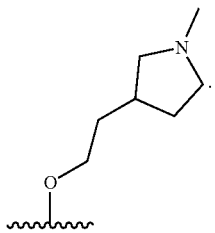

In some embodiments, for the compound or salt of Formula (L), (LA), (LB), (LC), (LD), (LE), (LF), or (LG), Ring A is an optionally substituted 5-membered heterocycle comprising 1 sulfur atom, wherein the optionally substituted 5-membered heterocycle is selected from tetrahydrothiophene and thiophene, any one of which is optionally substituted by one or more substituents independently selected from halogen, $-OR^{31}$, $-N(R^{31})_2$, $-C(O)R^{31}$, $-C(O)N(R^{31})_2$, $N(R^{31})C(O)R^{31}$, $-C(O)OR^{31}$, $-OC(O)R^{31}$, $-NO_2$, $=O$, $-CN$; and $C_{1-10}$ alkyl, $C_{2-10}$ alkenyl, and $C_{2-10}$ alkynyl each of which is optionally substituted with one or more substituents independently selected from halogen, $-OR^{31}$, $-N(R^{31})_2$, $-C(O)R^{31}$, $-NO_2$, $=O$, $=S$, $-CN$, $C_{3-10}$ carbocycle and 3- to 10-membered heterocycle.

In some embodiments, for the compound or salt of Formula (L), (LA), (LB), (LC), (LD), (LE), (LF), or (LG), the optionally substituted 5-membered heterocycle is tetrahydrothiophene which is optionally substituted by one or more substituents independently selected from $-OR^{31}$, $=O$, and $C_{1-10}$ alkyl. In some embodiments, $R^4$ is selected from

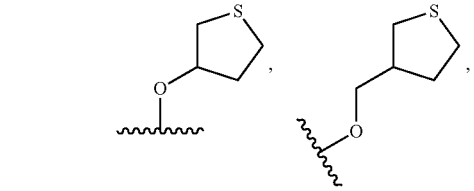

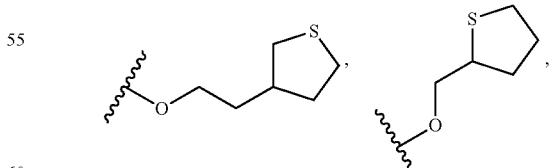

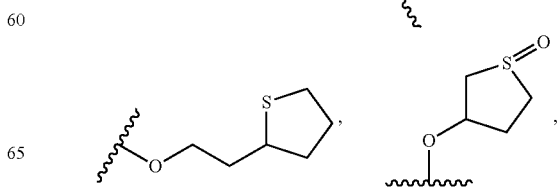

-continued
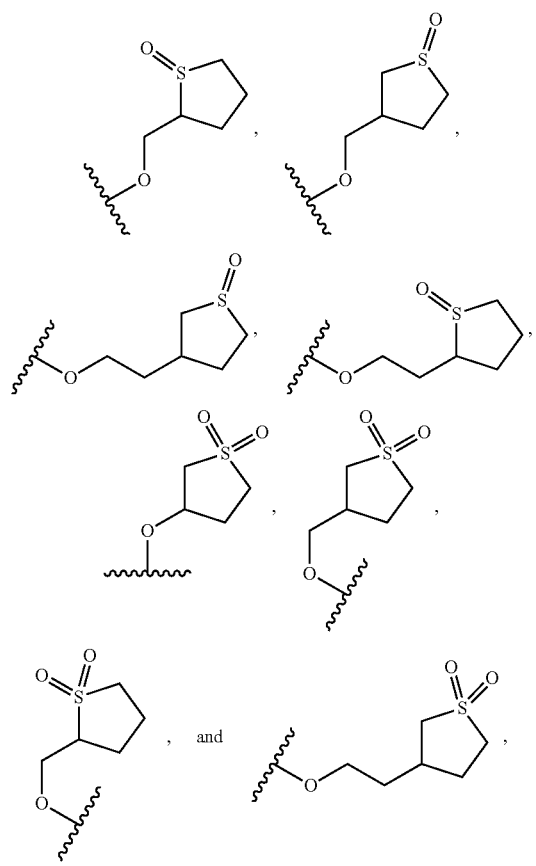
In some embodiments R⁴ is from
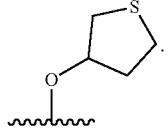
In some embodiments, R⁴ is
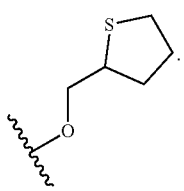 [SMILES: *OCC1CCCS1]
In some embodiments, R⁴ is
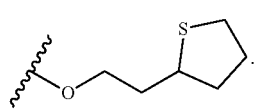 [SMILES: *OCCC1CCCS1]
In some embodiments, R⁴ is
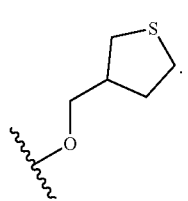 [SMILES: *OCC1CCSC1]
In some embodiments, R⁴ is
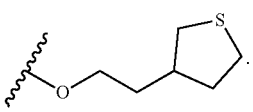 [SMILES: *OCCC1CCSC1]
In some embodiments R⁴ is
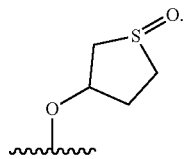 [SMILES: *OC1CCS(=O)C1]
In some embodiments R⁴ is
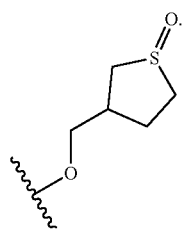 [SMILES: *OCC1CCS(=O)C1]
In some embodiments, R⁴ is
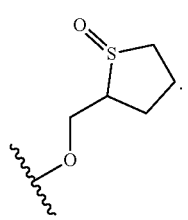 [SMILES: *OCC1CCCS1=O]
In some embodiments, R⁴ is
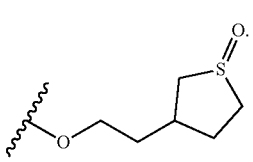 [SMILES: *OCCC1CCS(=O)C1]

In some embodiments, R⁴ is
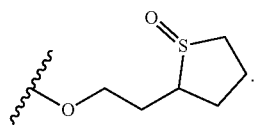 [SMILES: *OCCC1CCCS1=O]
In some embodiments, R⁴ is
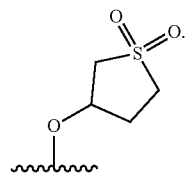 [SMILES: *OC1CCS(=O)(=O)C1]
In some embodiments, R⁴ is
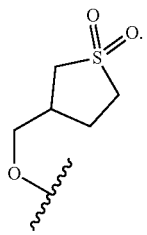 [SMILES: *OCC1CCS(=O)(=O)C1]
In some embodiments, R⁴ is
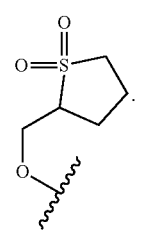 [SMILES: *OCC1CCCS1(=O)=O]
In some embodiments, R⁴ is
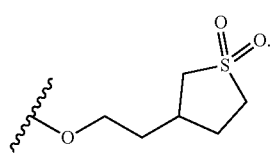 [SMILES: *OCCC1CCS(=O)(=O)C1]
In some embodiments, R⁴ is
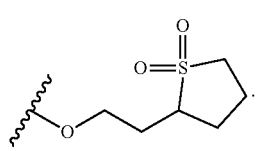 [SMILES: *OCCC1CCCS1(=O)=O]
In some embodiments, for the compound or salt of Formula (L), (LA), (LB), (LC), (LD), (LE), (LF), or (LG), R⁴ is selected from is selected from
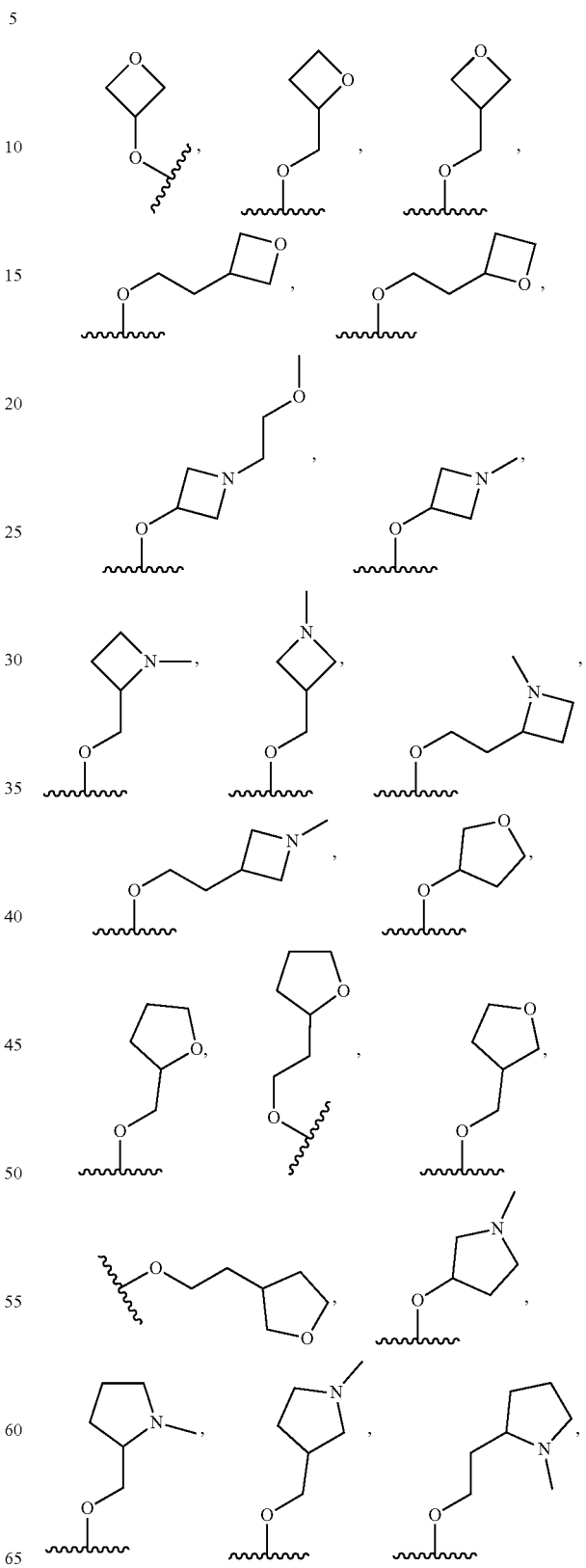

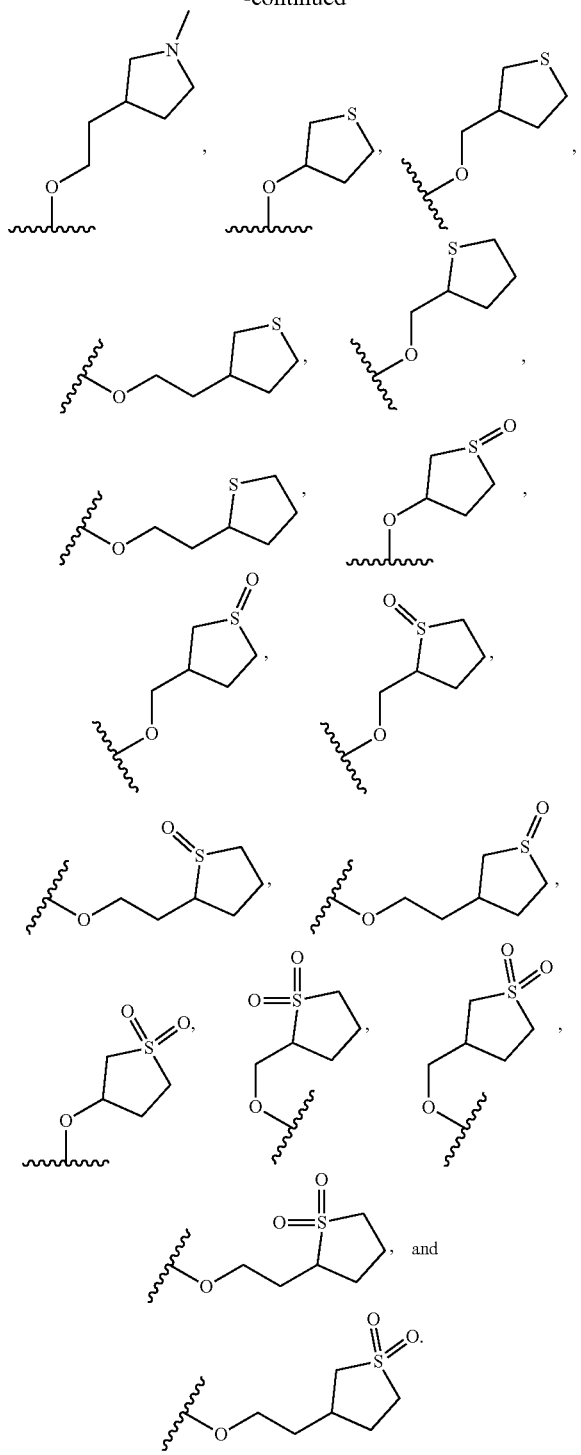

In some embodiments, for the compound or salt of Formula (L), (LA), (LB), (LC), (LD), (LE), (LF), or (LG), $R^2$ is selected from hydrogen and $C_1$-$C_6$ alkoxy. In some embodiments, $R^2$ is selected from hydrogen and —OMe. In some embodiments, $R^2$ is —OMe.

In some embodiments, for the compound or salt of Formula (L), (LA), (LB), (LC), (LD), (LE), (LF), or (LG), $R^3$ is selected from hydrogen and an optionally substituted $C_1$-$C_6$ alkoxy, wherein the substituents are independently selected at each occurrence from hydroxy and $C_1$-$C_6$ alkoxy. In some embodiments, $R^3$ is selected from hydrogen and $C_1$-$C_6$ alkoxy.

In some embodiments, for the compound or salt of Formula (L), (LA), (LB), (LC), (LD), (LE), (LF), or (LG), $R^3$ is selected from $C_1$-$C_6$ alkoxy. In some embodiments, $R^3$ is —OMe.

In some embodiments, for the compound or salt of Formula (L), (LA), (LB), (LC), (LD), (LE), (LF), or (LG), $R^5$ is selected from hydrogen, hydroxy, and an optionally substituted $C_1$-$C_6$ alkoxy group, wherein substituents are independently selected at each occurrence from hydroxy, halogen, —CN, —NO$_2$, and $C_1$-$C_6$ alkoxy.

In some embodiments, for the compound or salt of Formula (L), (LA), (LB), (LC), (LD), (LE), (LF), or (LG), $R^5$ is, hydroxy.

In some embodiments, for the compound or salt of Formula (L), (LA), (LB), (LC), (LD), (LE), (LF), or (LG), $R^6$ and $R^7$ are each independently selected from hydrogen and hydroxy. In some embodiments, $R^6$ and $R^7$ are each hydrogen. In some embodiments, $R^6$ is hydrogen and $R^7$ hydroxy. In some embodiments, $R^6$ and $R^7$ come together to form

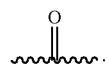

In some embodiments, for the compound or salt of Formula (L), (LA), (LB), (LC), (LD), (LE), (LF), or (LG), $R^1$ is selected from

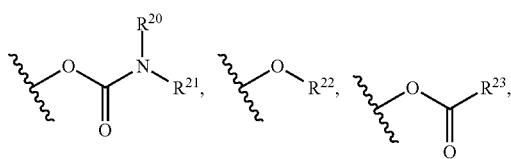

and optionally substituted 3- to 10-membered heterocycle. In some embodiments, for the compound or salt of Formula (L), (LA), (LB), (LC), (LD), (LE), (LF), or (LG), $R^1$ is selected from

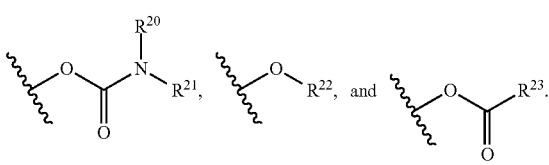

In some embodiments, for the compound or salt of Formula (L), (LA), (LB), (LC), (LD), (LE), (LF), or (LG), $R^1$ is selected from hydroxy.

In some embodiments, for the compound or salt of Formula (L), (LA), (LB), (LC), (LD), (LE), (LF), or (LG), $R^2$ is selected from hydrogen and an optionally substituted $C_1$-$C_6$ alkoxy group, wherein substituents are independently selected at each occurrence from hydroxy, halogen, —CN, —NO$_2$, and $C_1$-$C_6$ alkoxy. In some embodiments, $R^2$ is selected from hydrogen and an optionally substituted $C_1$-$C_6$ alkoxy, wherein substituents are independently selected at each occurrence from hydroxy, halogen, —NO$_2$, and $C_1$-$C_6$ alkoxy.

In some embodiments, for the compound or salt of Formula (L), (LA), (LB), (LC), (LD), (LE), (LF), or (LG), $R^1$ is an optionally substituted 3- to 10-membered heterocycle. In some embodiments, the optionally substituted heterocycle is 3-, 4-, 5-, 6-, 7-, 8-, 9-, or a 10-membered heterocycle. In some embodiments, the optionally substituted 3- to 10-membered heterocycle is a 3- or 4-membered heterocycle, a 5- or 6-membered heterocycle, a 7- or 8-membered heterocycle, or a 9- or 10-membered heterocycle.

In some embodiments, for the compound or salt of Formula (L), (LA), (LB), (LC), (LD), (LE), (LF), or (LG), $R^1$ is an optionally substituted 5- to 6-membered heterocycle comprising at least 1 heteroatom that is selected from oxygen, nitrogen, sulfur, boron, phosphorus, silicon, selenium, and any combination thereof. In some embodiments, the optionally substituted 5- to 6-membered heterocycle comprises at least 1 heteroatom that is selected from oxygen, nitrogen, sulfur, and any combination thereof.

In some embodiments, for the compound or salt of Formula (L), (LA), (LB), (LC), (LD), (LE), (LF), or (LG), the optionally substituted 5- to 6-membered heterocycle of $R^1$ comprises at least 1 heteroatom that is selected from nitrogen. In some embodiments, the optionally substituted 5- to 6-membered heterocycle of $R^1$ is selected from

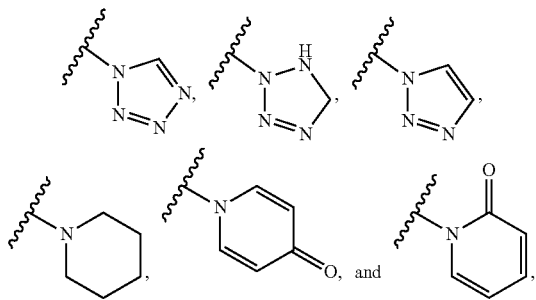

any of which is optionally substituted with one or more substituents independently selected from: hydroxy, halogen, —CN, —NO$_2$, =O, $C_1$-$C_6$ alkyl, $C_1$-$C_6$ haloalkyl, $C_1$-$C_6$ hydroxyalkyl, $C_1$-$C_6$ alkoxy, 3- to 10-membered heterocycle, and $C_{3-10}$ carbocycle, wherein the 3- to 10-membered heterocycle and $C_{3-10}$ carbocycle are each optionally substituted with one or more substituents independently selected from hydroxy, halogen, —CN, —NO$_2$, $C_1$-$C_6$ alkyl, $C_1$-$C_6$ haloalkyl, $C_1$-$C_6$ hydroxyalkyl, and $C_1$-$C_6$ alkoxy. In some embodiments, the one or more substituents are independently hydroxy, =O, $C_1$-$C_6$ alkyl, 3- to 8-membered heterocycle, and $C_{3-8}$ carbocycle, wherein the 3- to 8-membered heterocycle and $C_{3-8}$ carbocycle are each optionally substituted with one or more substituents independently selected from hydroxy, halogen, —CN, —NO$_2$, $C_1$-$C_6$ alkyl, $C_1$-$C_6$ haloalkyl, $C_1$-$C_6$ hydroxyalkyl, and $C_1$-$C_6$ alkoxy.

In some embodiments, for the compound or salt of Formula (L), (LA), (LB), (LC), (LD), (LE), (LF), or (LG), $R^1$ is

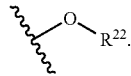

In some embodiments, for the compound or salt of Formula (L), (LA), (LB), (LC), (LD), (LE), (LF), or (LG), $R^{22}$ of $R^1$ is selected from hydrogen, optionally substituted $C_1$-$C_6$ alkyl, and —P(=O)($R^{24}$)$_2$.

In some embodiments, for the compound or salt of Formula (L), (LA), (LB), (LC), (LD), (LE), (LF), or (LG), $R^{22}$ of $R^1$ is hydrogen.

In some embodiments, for the compound or salt of Formula (L), (LA), (LB), (LC), (LD), (LE), (LF), or (LG), $R^{22}$ of $R^1$ is —P(=O)($R^{24}$)$_2$, and $R^{24}$ is selected from optionally substituted $C_{1-10}$ alkyl. In some embodiments, $R^1$ is

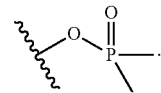

In some embodiments, for the compound or salt of Formula (L), (LA), (LB), (LC), (LD), (LE), (LF), or (LG), $R^{22}$ of $R^1$ is $C_1$-$C_6$ alkyl optionally substituted with one or more substituents selected from —N($R^{30}$)$_2$, —(O—CH$_2$—(CH$_2$)$_p$)$_n$—W, —OR$^{30}$, optionally substituted $C_{3-10}$ carbocycle, and optionally substituted 3- to 10-membered heterocycle, and $R^{30}$ is selected from hydrogen and optionally substituted $C_{1-10}$ alkyl. In some embodiments, $R^{22}$ of $R^1$, is $C_1$-$C_6$ alkyl substituted with one or more substituents selected from —N($R^{30}$)$_2$, —(O—CH$_2$—(CH$_2$)$_p$)$_n$—W, and —OR$^{30}$.

In some embodiments, for the compound or salt of Formula (L), (LA), (LB), (LC), (LD), (LE), (LF), or (LG), $R^{22}$ of $R^1$ is $C_1$-$C_6$ alkyl substituted with one or more substituents selected from —N($R^{30}$)$_2$. In some embodiments, $R^1$ is

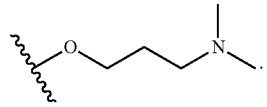 [SMILES: *OCCCN(C)C]

In some embodiments, for the compound or salt of Formula (L), (LA), (LB), (LC), (LD), (LE), (LF), or (LG), $R^{22}$ of $R^1$ is $C_1$-$C_6$ alkyl substituted with one or more substituents selected from —(O—CH$_2$—(CH$_2$)$_p$)$_n$—W, wherein n is 1 to 1000. In some embodiments, n is 1 to 800. In some embodiments, n is 1 to 500. In some embodiments, n is 1 to 300. In some embodiments, n is 1 to 100. In some embodiments, n is 1 to 50. In some embodiments, n is 1 to 25. In some embodiments, n is 3 to 1000. In some embodiments, n is 10 to 1000. In some embodiments, n is 50 to 1000. In some embodiments, n is 100 to 1000. In some embodiments, n is 200 to 1000. In some embodiments, n is 500 to 1000. In some embodiments, n is 1, 2, 3, 4, 5, 6, 7, 8, 9, 10, 11, 12, 13, 14, 15, 16, 17, 18, 19, 20, 25, or 100. In some embodiments, p is 1 to 1000. In some embodiments, p is 1 to 800. In some embodiments, p is 1 to 500. In some embodiments, p is 1 to 300. In some embodiments, p is 1 to 100. In some embodiments, p is 1 to 50. In some embodiments, p is 1 to 25. In some embodiments, p is 3 to 1000. In some embodiments, p is 10 to 1000. In some embodiments, p is 50 to 1000. In some embodiments, p is 100 to 1000. In some embodiments, p is 200 to 1000. In some embodiments, p is 500 to 1000. In some embodiments, p is 1, 2, 3, 4, 5, 6, 7, 8, 9, 10, 11, 12, 13, 14, 15, 16, 17, 18, 19, 20, 25, or 100.

In some embodiments, for the compound or salt of Formula (L), (LA), (LB), (LC), (LD), (LE), (LF), or (LG), $R^{22}$ of $R^1$ is $C_1$-$C_6$ alkyl substituted with one or more substituents selected from —(O—CH$_2$—(CH$_2$)$_p$)$_n$—W, and —OR$^{30}$. In some embodiments, R$^1$ is selected from:

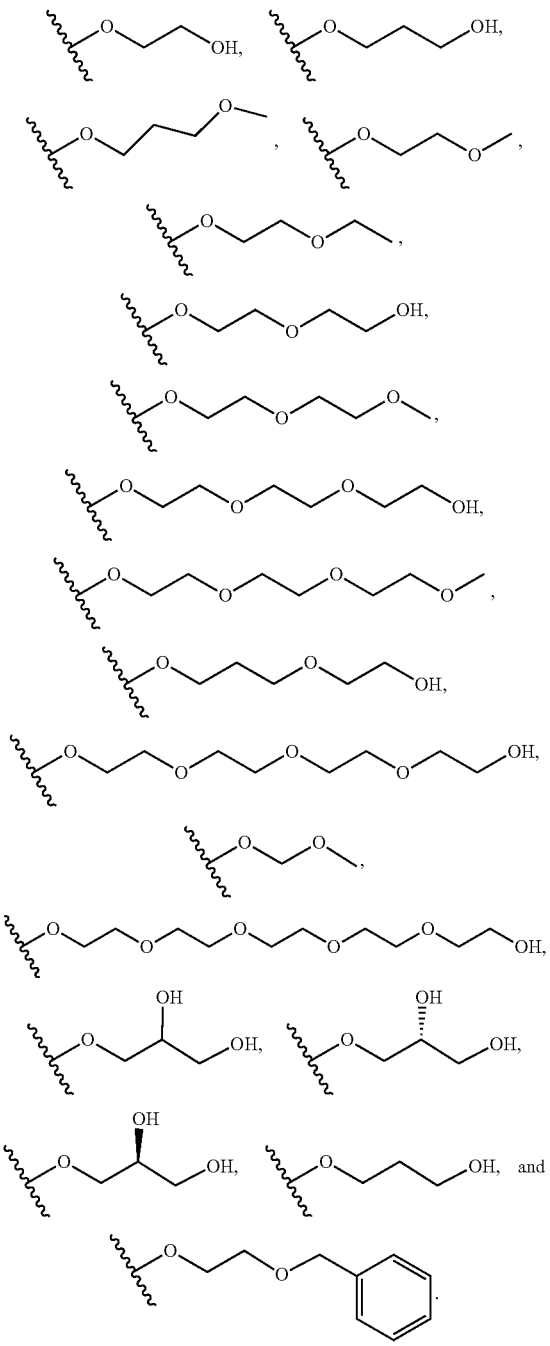

In some embodiments, for the compound or salt of Formula (L), (LA), (LB), (LC), (LD), (LE), (LF), or (LG), R$^{22}$ of R$^1$ is C$_1$-C$_6$ alkyl substituted with substituents selected from an optionally substituted C$_{3-10}$ carbocycle. In some embodiments, the optionally substituted C$_{3-10}$ carbocycle is selected from a C$_{3-6}$ carbocycle. In certain embodiments, the C$_{3-6}$ carbocycle is unsaturated. In certain embodiments, the C$_{3-6}$ carbocycle is saturated. In some embodiments, the optionally substituted C$_{3-6}$ carbocycle is selected from

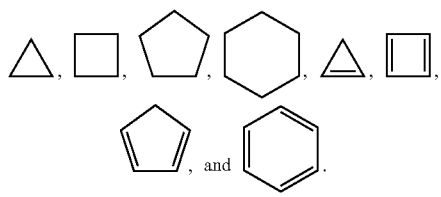

In some embodiments, R$^{22}$ of R$^1$ is C$_1$-C$_6$ alkyl substituted with phenyl. In some embodiments, R$^1$ is selected from:

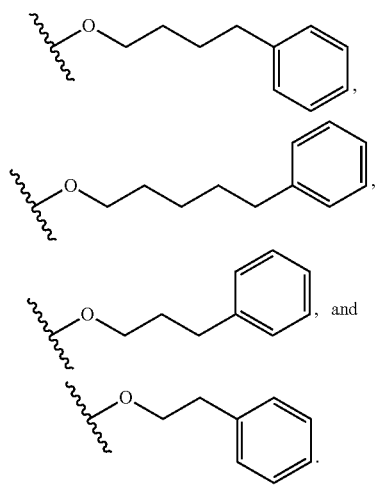

In some embodiments, for the compound or salt of Formula (L), (LA), (LB), (LC), (LD), (LE), (LF), or (LG), R$^{22}$ of R$^1$ is C$_1$-C$_6$ alkyl substituted with one or more substituents selected from an optionally substituted 3- to 6-membered heterocycle. In some embodiments, the optionally substituted 3- to 6-membered heterocycle comprises at least one heteroatom selected from N, O, S, and any combination thereof.

In some embodiments, for the compound or salt of Formula (L), (LA), (LB), (LC), (LD), (LE), (LF), or (LG), R$^{22}$ of R$^1$ is C$_1$-C$_6$ alkyl substituted with one or more substituents selected from an optionally substituted 3- to 6-membered heterocycle wherein the optionally substituted 3- to 6-membered heterocycle comprises at least one heteroatom selected from N and O. In some embodiments, the 3- to 6-membered heterocycle is substituted with one or more substituents selected from optionally substituted C$_{1-6}$ alkyl and —OR$^{30}$. In some embodiments, R$^1$ is selected from:

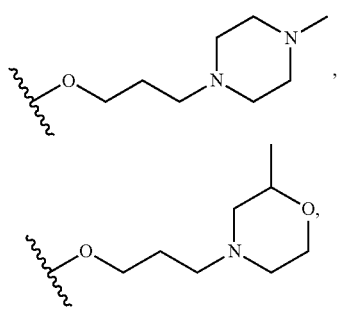

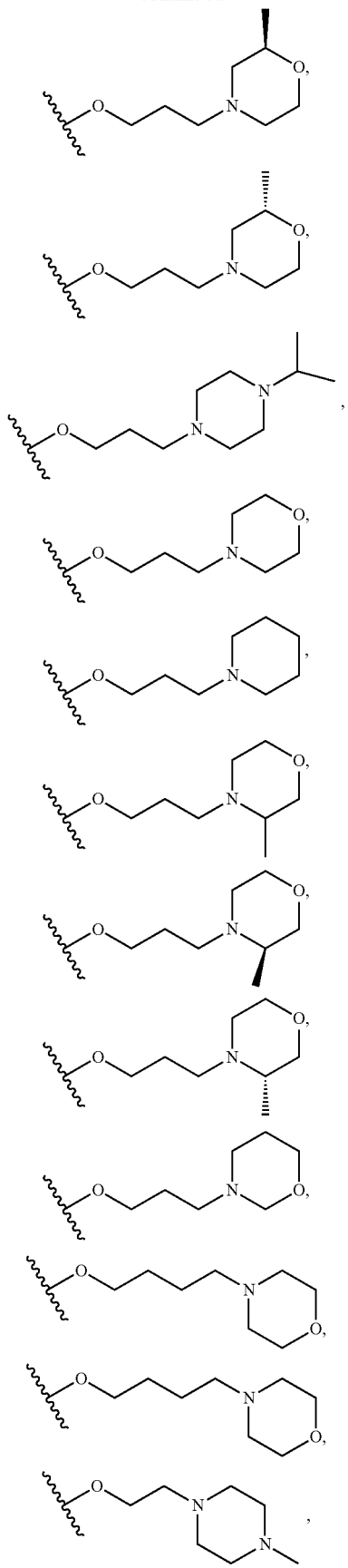
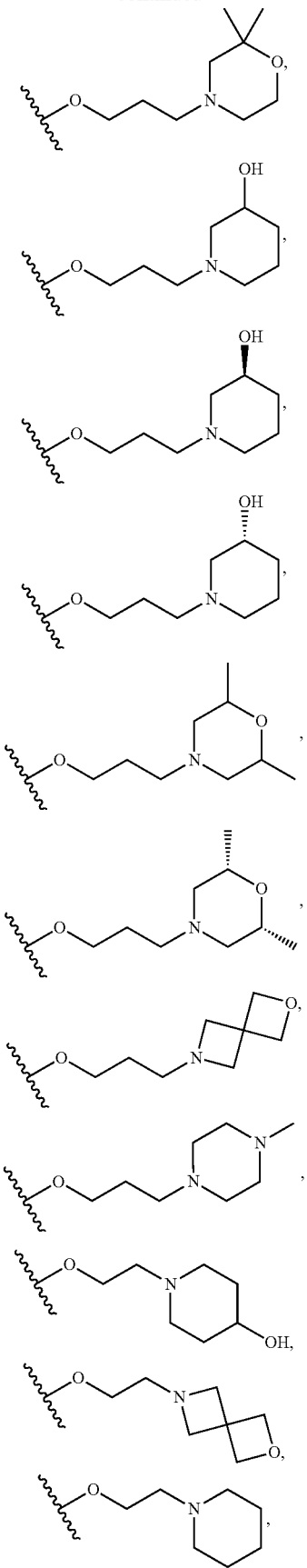

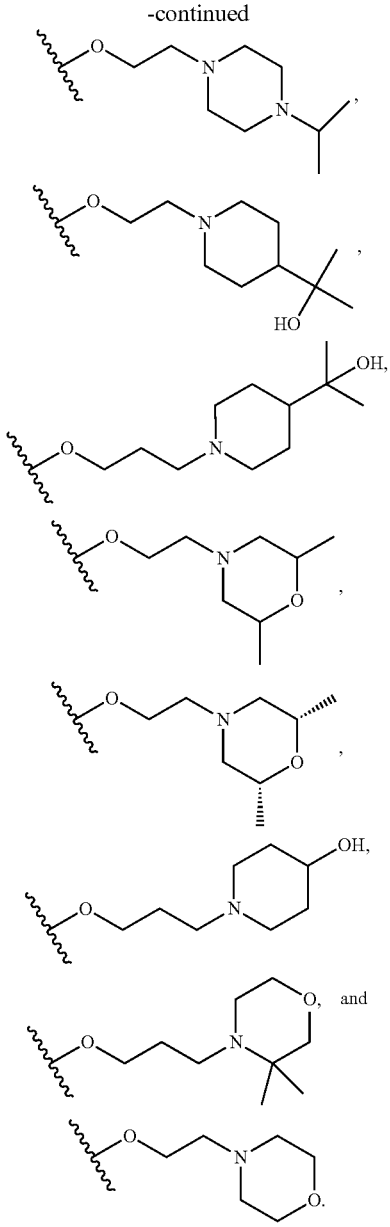
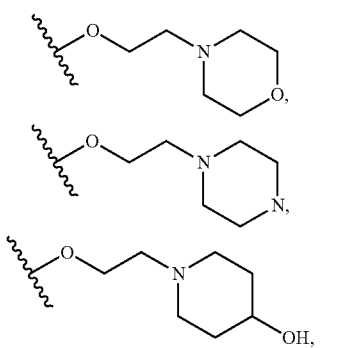
In some embodiments, for the compound or salt of Formula (L), (LA), (LB), (LC), (LD), (LE), (LF), or (LG), $R^1$ is selected from:
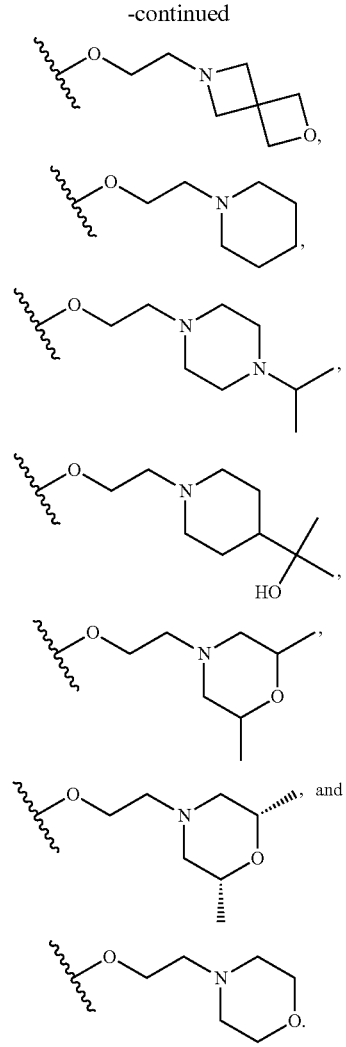
In some embodiments, for the compound or salt of Formula (L), (LA), (LB), (LC), (LD), (LE), (LF), or (LG), $R^1$ is selected from:
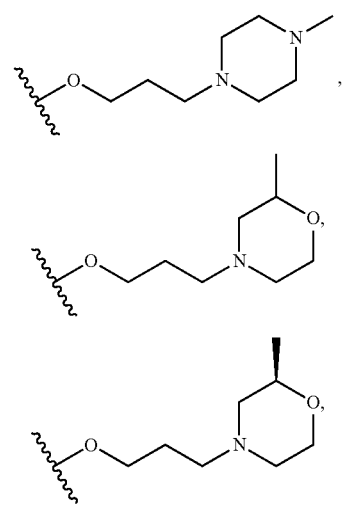

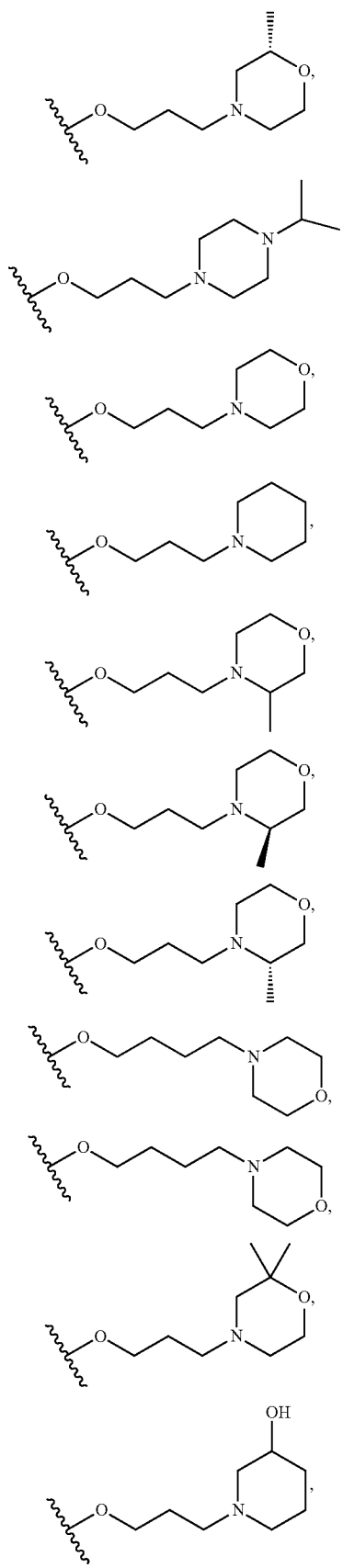
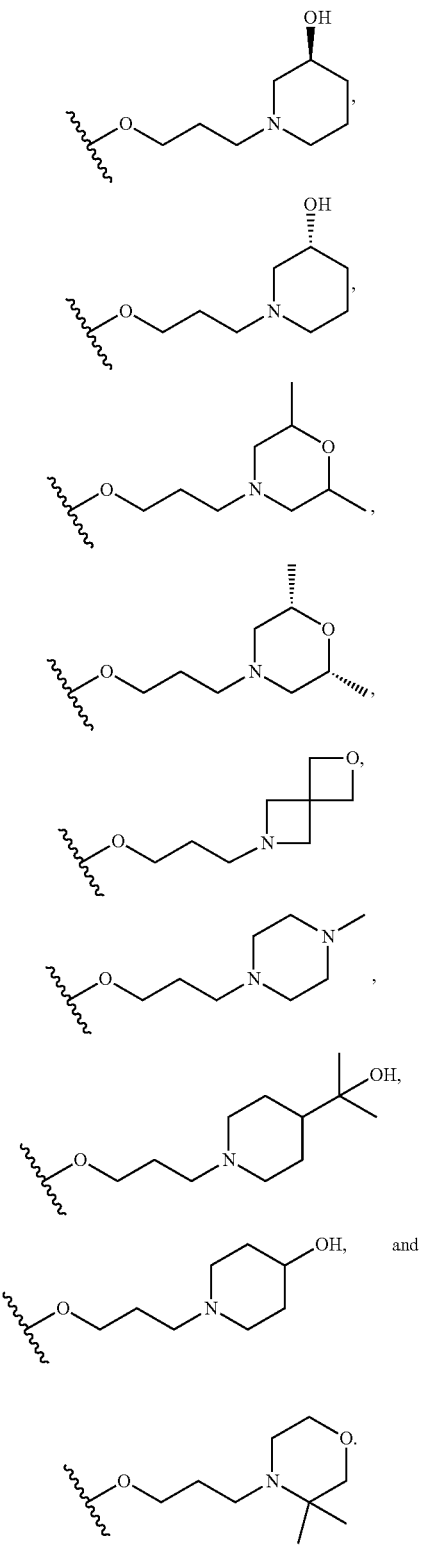
In some embodiments, for the compound or salt of Formula (L), (LA), (LB), (LC), (LD), (LE), (LF), or (LG), $R^1$ is

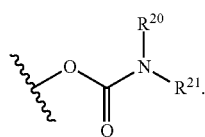

In some embodiments, $R^{20}$ of $R^1$ is selected from hydrogen and optionally substituted $C_1$-$C_3$ alkyl. In some embodiments, $R^{21}$ of $R^1$ is selected from hydrogen and optionally substituted $C_1$-$C_3$ alkyl. In some embodiments, $R^{21}$ of $R^1$ is an optionally substituted $C_{1-10}$ alkyl. In some embodiments, $R^{21}$ of $R^1$ is $C_{1-10}$ alkyl substituted with one or more substituents selected from —$OR^{30}$, —$N(R^{30})_2$, —(O—$CH_2$—$(CH_2)_p)_n$—W, optionally substituted $C_{3-10}$ carbocycle and optionally substituted 3- to 10-membered heterocycle. In some embodiments, $R^1$ is selected from:

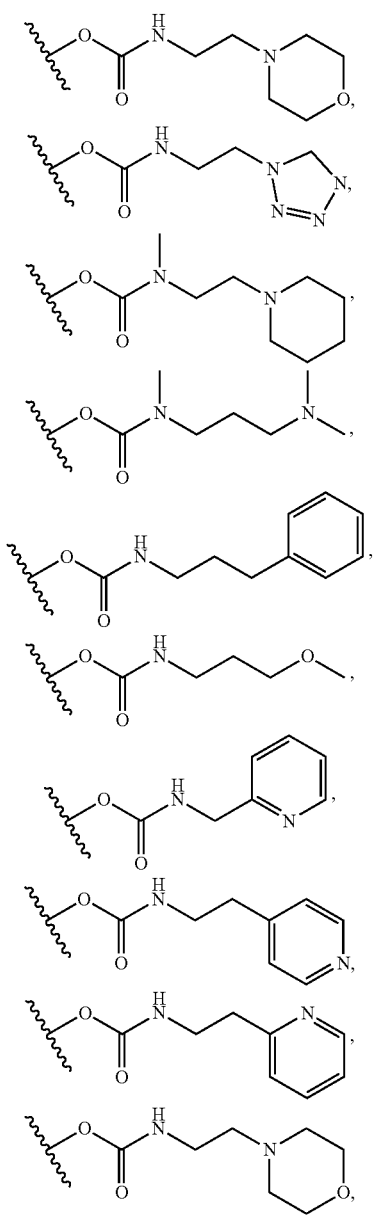

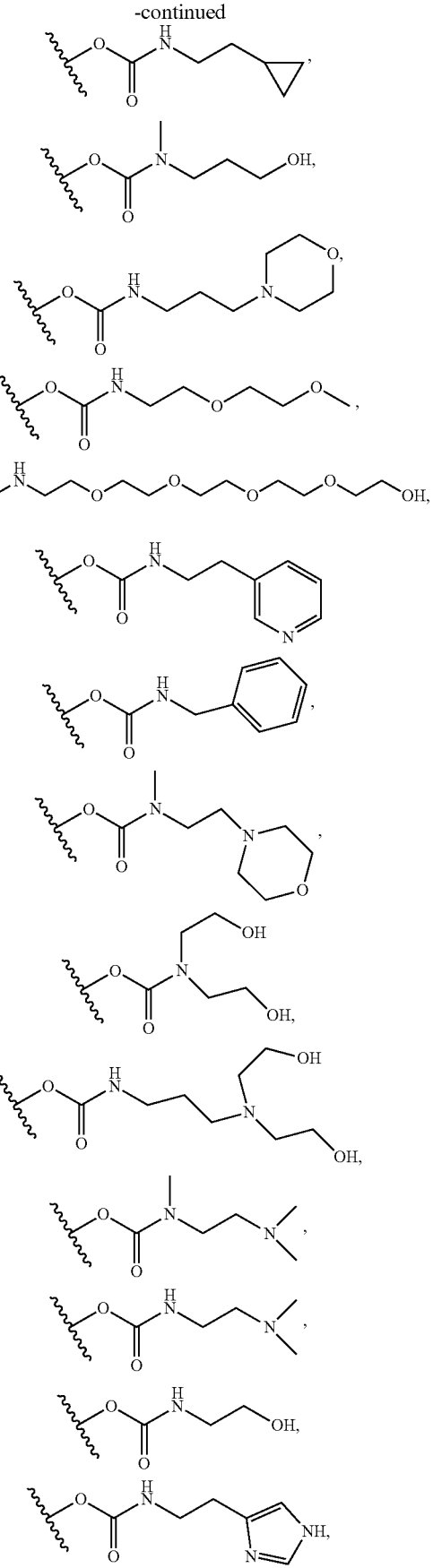

-continued

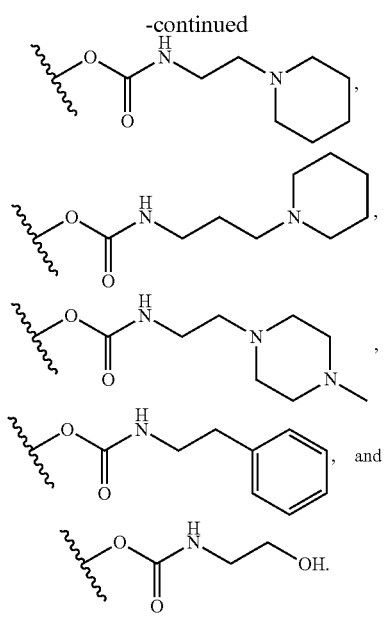

In some embodiments, for the compound or salt of Formula (L), (LA), (LB), (LC), (LD), (LE), (LF), or (LG), $R^1$ is

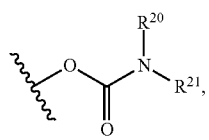

wherein $R^{21}$ of $R^1$ is an optionally substituted 3- to 7-membered heterocycle. In some embodiments, the 3- to 7-membered heterocycle is substituted with one or more substituents selected from —$OR^{30}$ and optionally substituted $C_{1-10}$ alkyl. In some embodiments, $R^1$ is selected from:

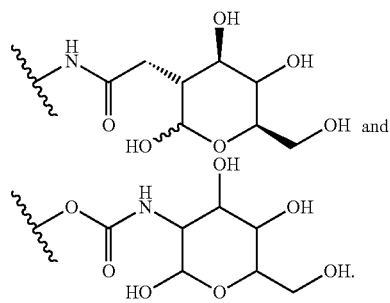

In some embodiments, for the compound or salt of Formula (L), (LA), (LB), (LC), (LD), (LE), (LF), or (LG), $R^1$ is

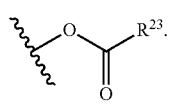

In some embodiments, $R^{23}$ of $R^1$ is an optionally substituted $C_1$-$C_6$ alkyl. In some embodiments, $C_1$-$C_6$ alkyl is substituted with one or more substituents selected from —$OR^{30}$, —$N(R^{30})_2$, optionally substituted $C_{1-10}$ alkyl, optionally substituted $C_{3-10}$ carbocycle and 3- to 10-membered heterocycle. In some embodiments, $R^1$ is selected from:

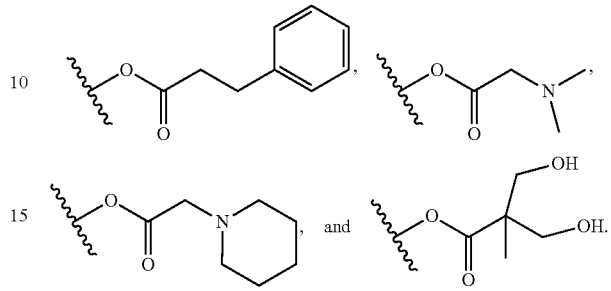

In some embodiments, for the compound or salt of Formula (L), (LA), (LB), (LC), (LD), (LE), (LF), or (LG), $R^{23}$ of $R^1$ is an optionally substituted 3- to 7-membered heterocycle. In some embodiments, the 3- to 7-membered heterocycle is substituted with one or more substituents selected from optionally substituted $C_{1-10}$ alkyl. In some embodiments, $R^1$ is

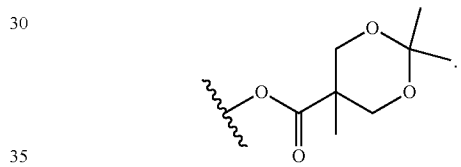

In some embodiments, for the compound or salt of Formula (L), (LA), (LB), (LC), (LD), (LE), (LF), or (LG), $R^1$ is selected from:

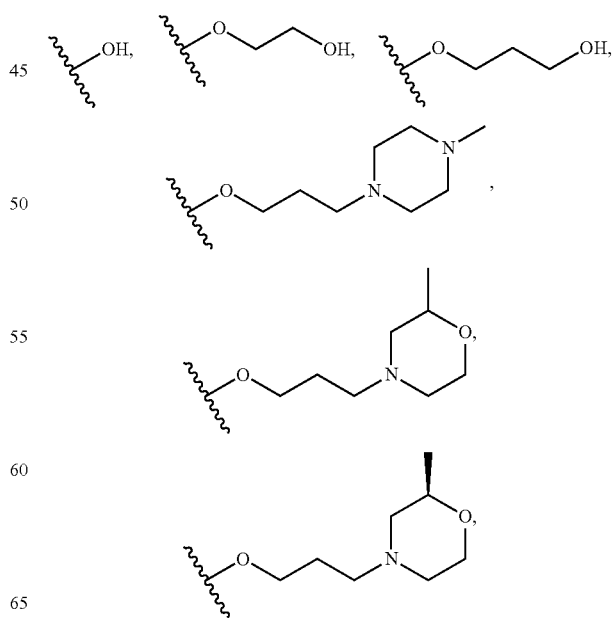

-continued
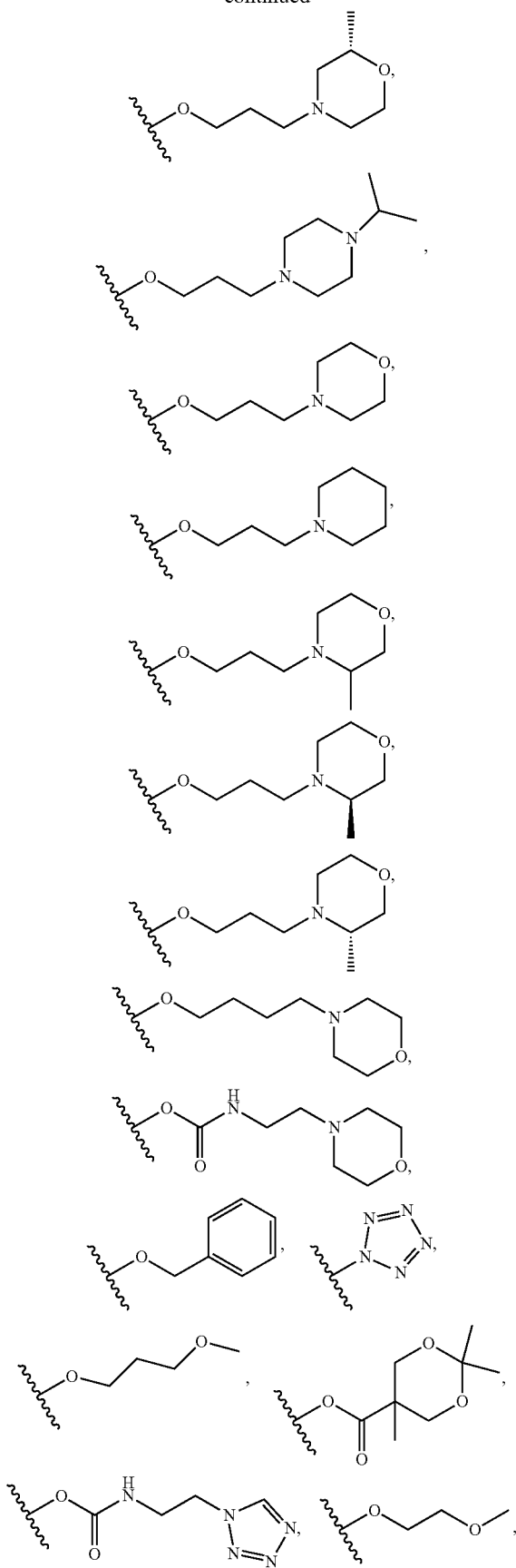
-continued
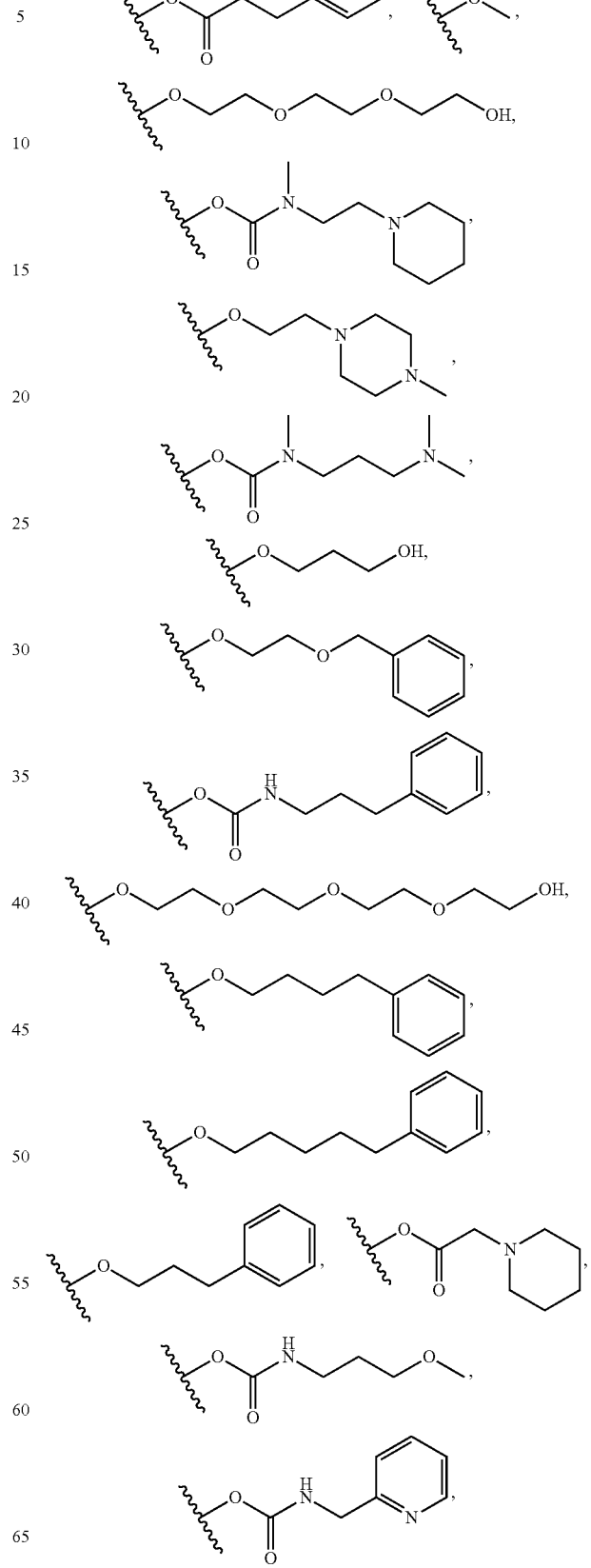

201
-continued
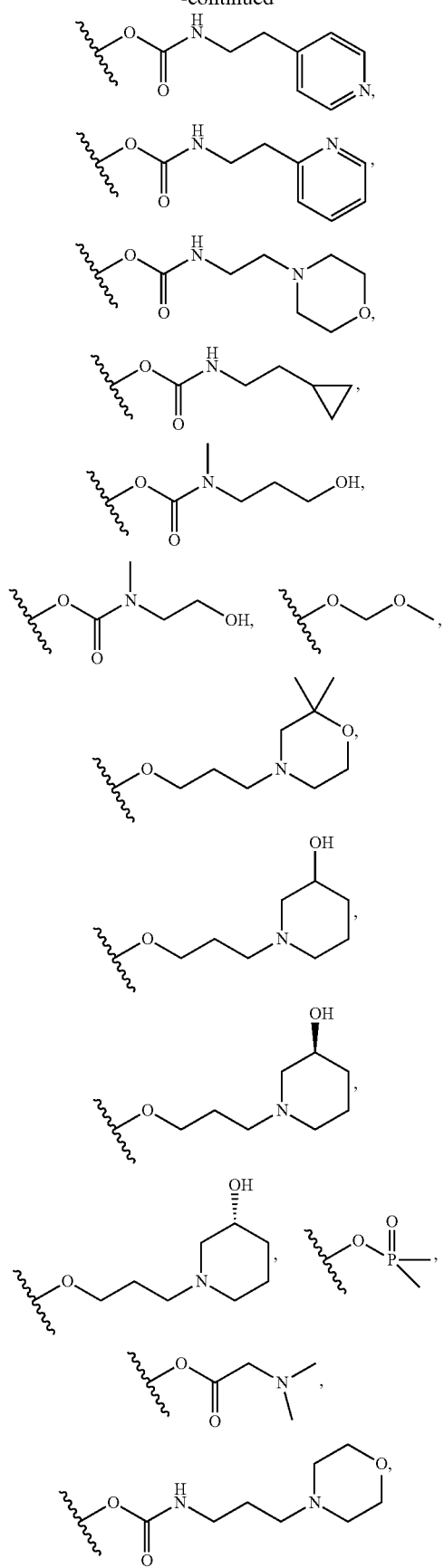
202
-continued
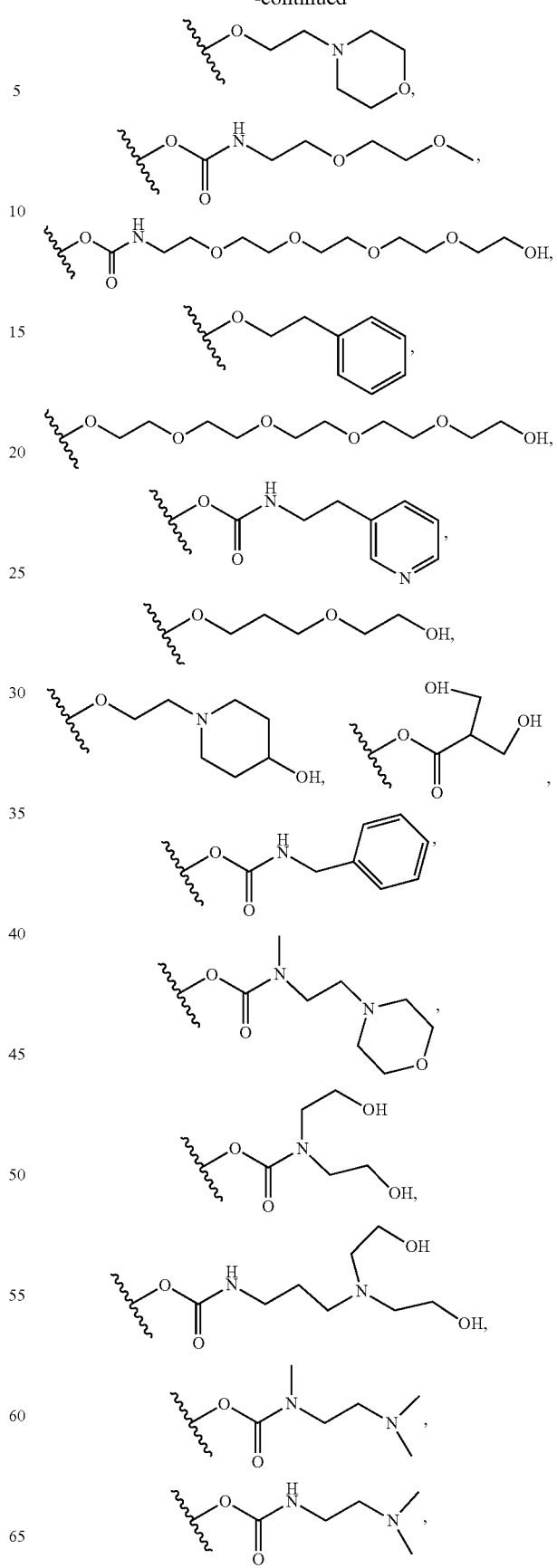

203
-continued
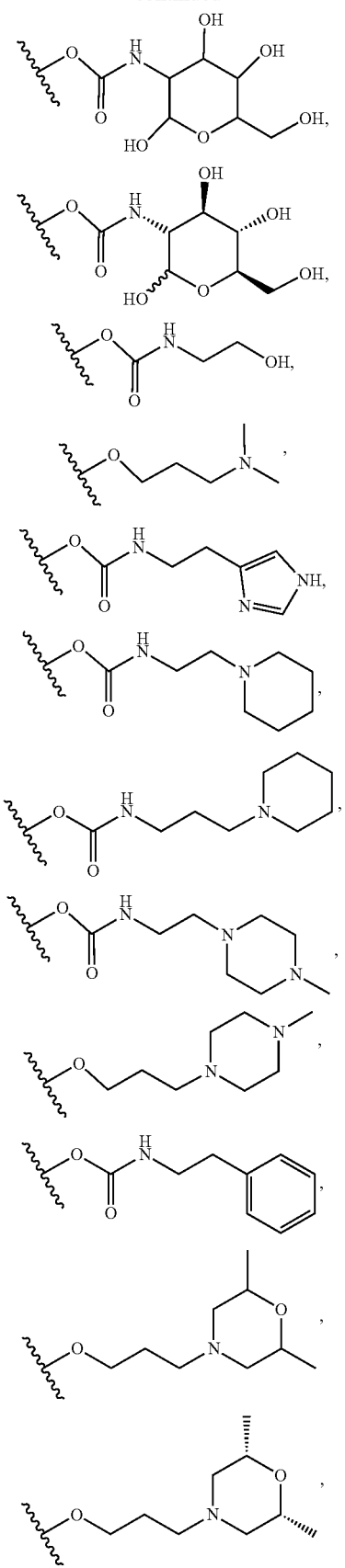
204
-continued
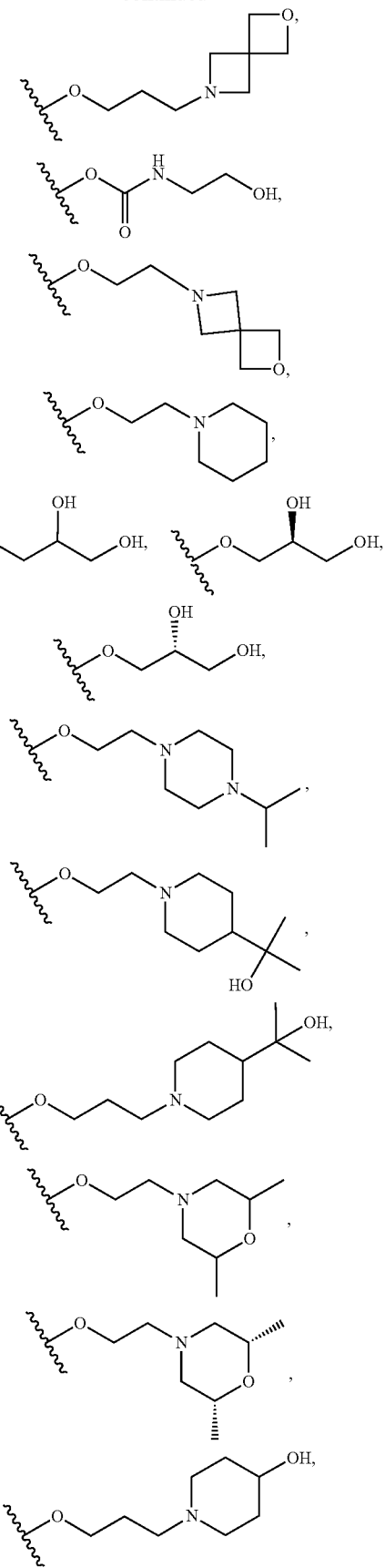

205
-continued
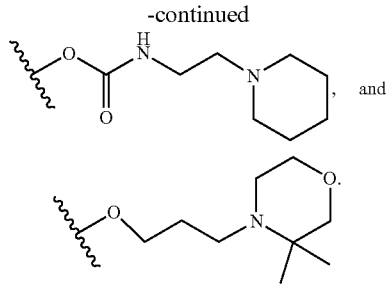
In some embodiments, for the compound or salt of Formula (L), (LA), (LB), (LC), (LD), (LE), (LF), or (LG), R$^1$ is selected from:
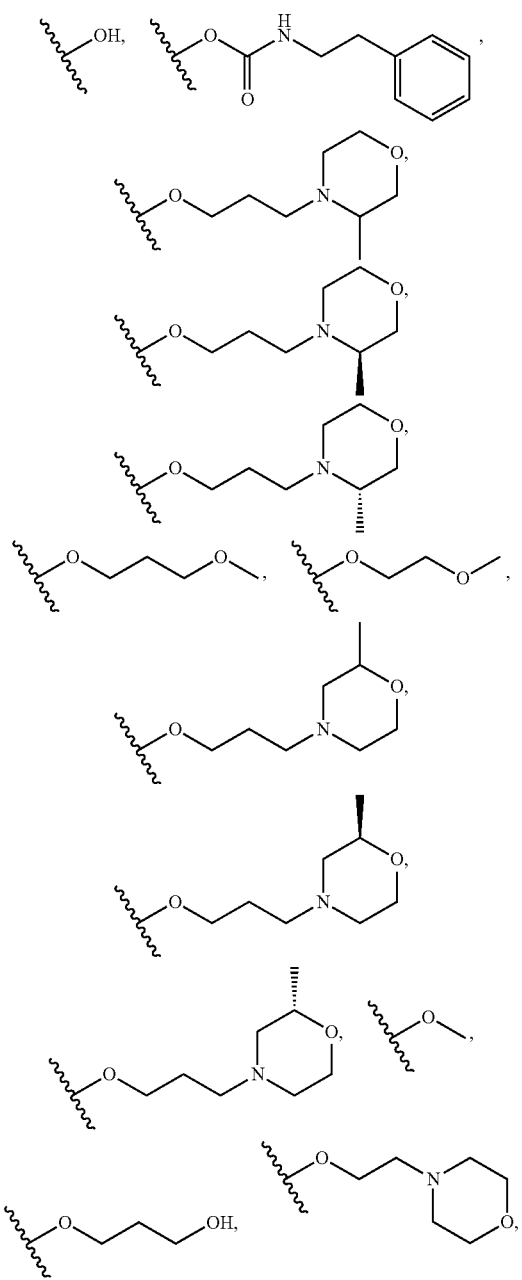
206
-continued
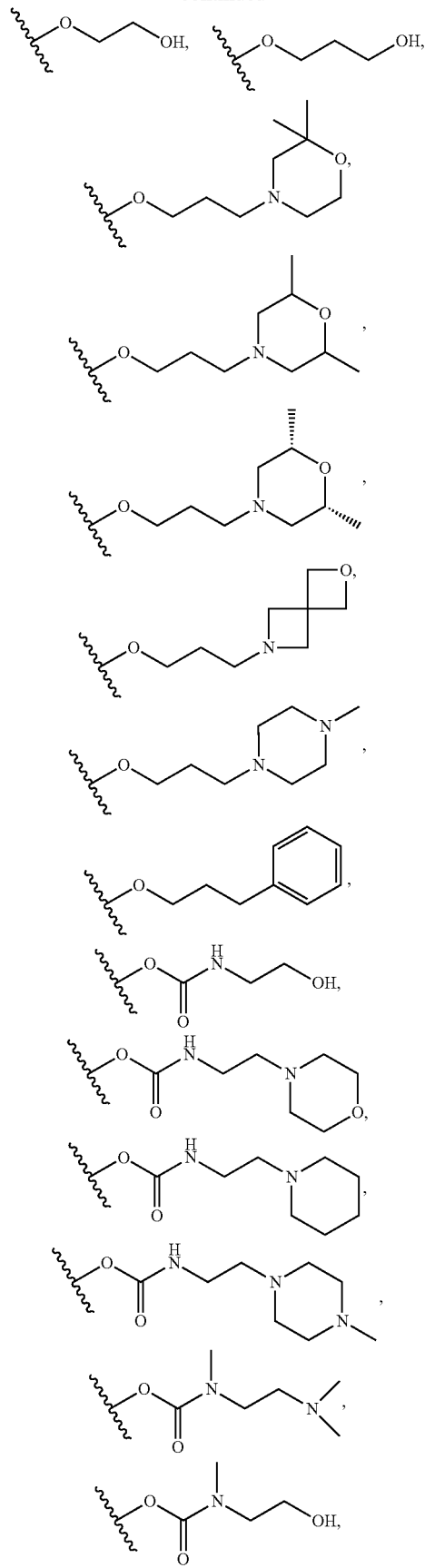

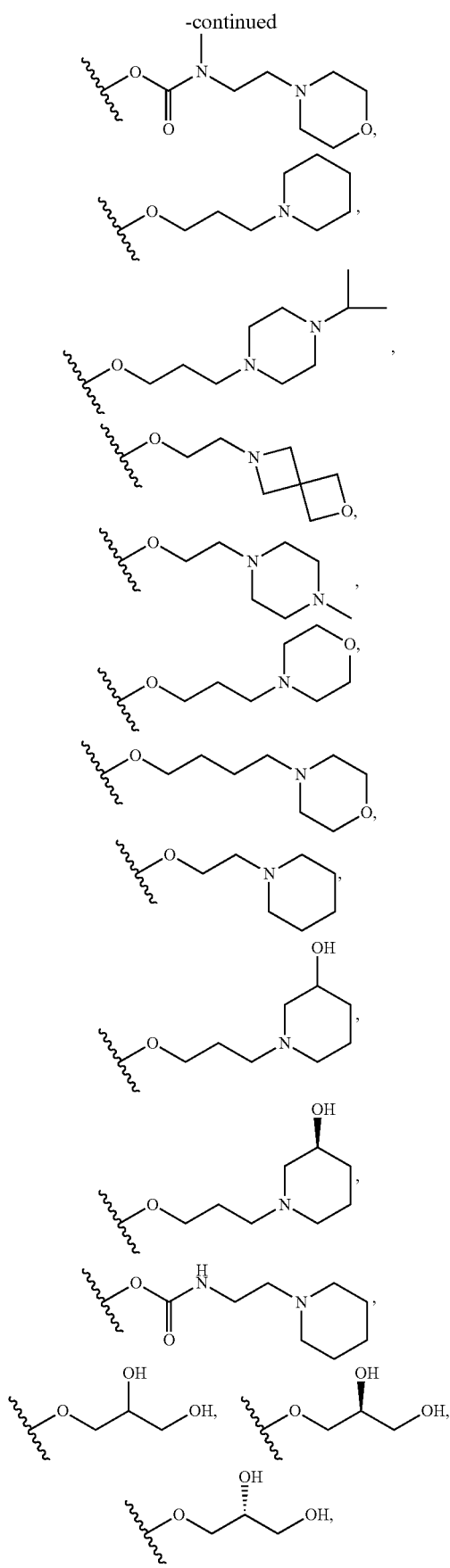
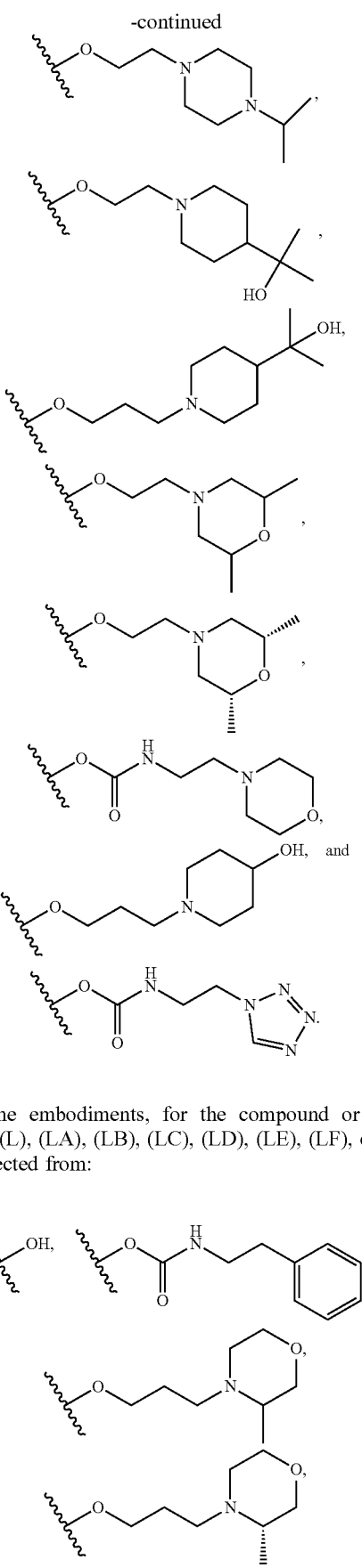
In some embodiments, for the compound or salt of Formula (L), (LA), (LB), (LC), (LD), (LE), (LF), or (LG), $R^1$ is selected from:

-continued
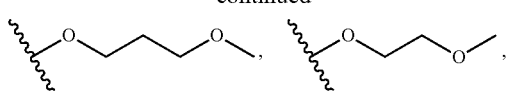
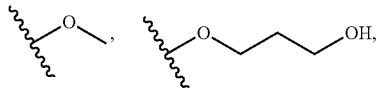
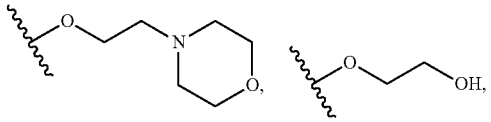
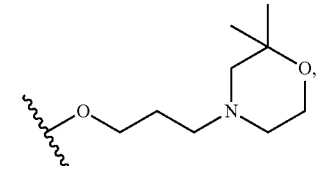
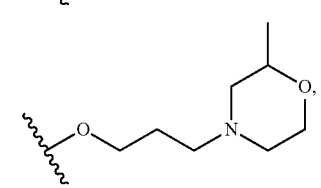
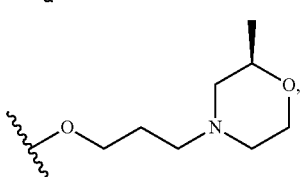
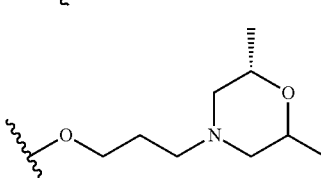
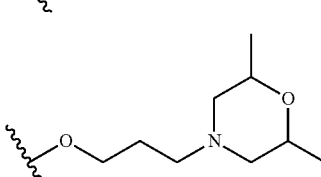
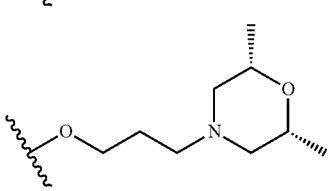
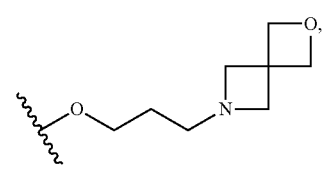
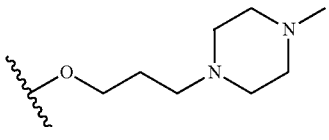
-continued
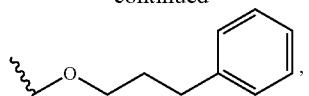
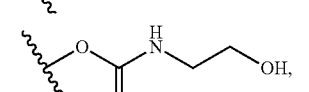
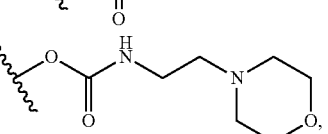
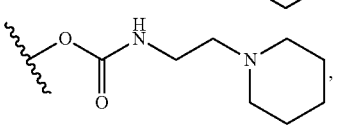
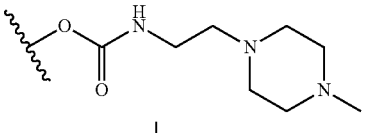
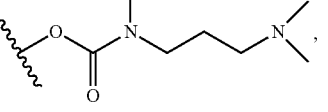
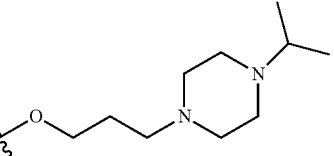
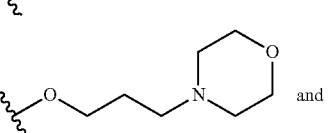
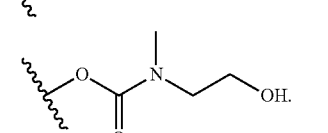 and
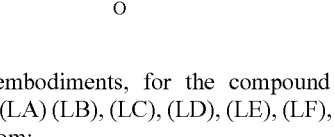
In some embodiments, for the compound or salt of Formula (L), (LA) (LB), (LC), (LD), (LE), (LF), or (LG), $R^1$ is selected from:
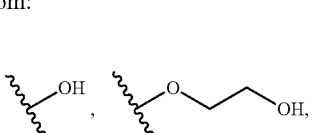
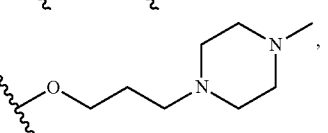
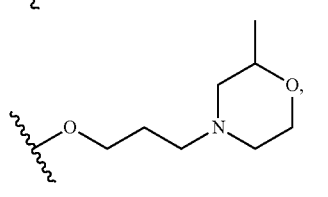

-continued

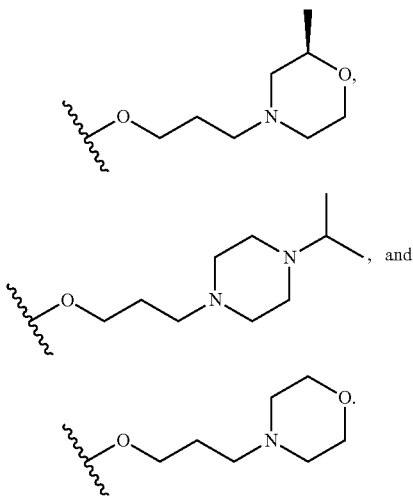

In some embodiments, for the compound or salt of Formula (L), (LA), (LB), (LC), (LD), (LE), (LF), or (LG), $R^1$ is selected from:

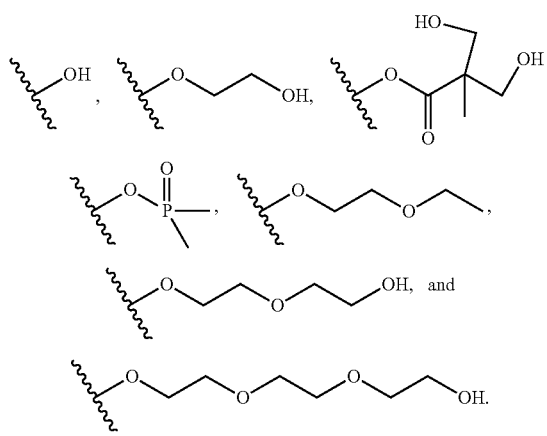

In some embodiments, for the compound or salt of Formula (L), (LA), (LB), (LC), (LD), (LE), (LF), or (LG), $R^1$ is selected from: —OH and

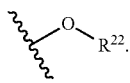

In some cases, $R^1$ is

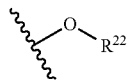

and $R^{22}$ is selected from optionally substituted $C_1$-$C_6$ alkyl, preferably an optionally substituted $C_{2-4}$ alkyl. In some cases, $R^1$ is

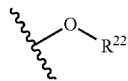

and $R^{22}$ is selected from substituted $C_1$-$C_6$ alkyl, preferably a substituted $C_{2-4}$ alkyl. In some cases, the substituents on $R^{22}$ are independently selected from —$OR^{30}$, —(O—$CH_2$—$(CH_2)_p)_n$—W, —S(O)$R^{30}$, —S(O)$_2R^{30}$, =O, =S, =N($R^{30}$), and —CN. In some cases, the optional substituents on $R^{22}$ are independently selected from —$OR^{30}$, —S(O)$_2R^{30}$, and =O. In some cases, the optional substituents on $R^{22}$ are independently selected from —$OR^{30}$, and —S(O)$_2R^{30}$. In some cases, $R^{30}$ of —$OR^{30}$ and —S(O)$_2R^{30}$, are independently selected from hydrogen and $C_{1-10}$ alkyl, wherein the $C_{1-10}$ alkyl is optionally substituted with one or more substituents independently selected from halogen, —OH, —CN, —$NO_2$, —$NH_2$, =O, =S, —$C_{1-10}$ haloalkyl, —O—$C_{1-10}$ alkyl, $C_{2-10}$ alkenyl, $C_{2-10}$ alkynyl, $C_{3-10}$ carbocycle, and 3- to 10-membered heterocycle. In some cases, $R^{30}$ of —$OR^{30}$ and —S(O)$_2R^{30}$ is independently selected at each occurrence from hydrogen and $C_{1-10}$ alkyl.

In some embodiments, for the compound or salt of Formula (L), (LA), (LB), (LC), (LD), (LE), (LF), or (LG), $R^1$ is selected from

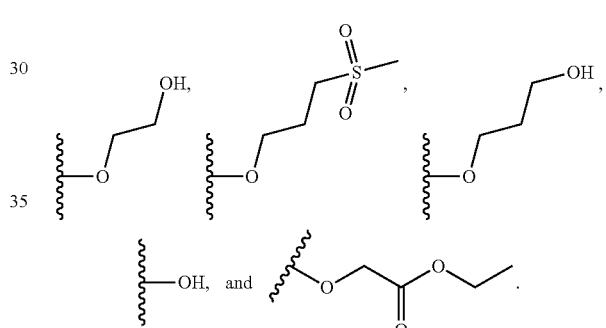

In some cases, $R^1$ is selected from

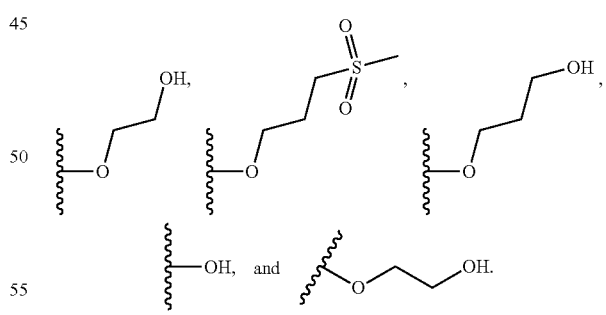

In some embodiments, for the compound or salt of Formula (L), (LA), (LB), (LC), (LD), (LE), (LF), or (LG), R' and R" are independently selected at each occurrence from hydrogen.

In some embodiments, for the compound or salt of Formula (L), (LA), (LB), (LC), (LD), (LE), (LF), or (LG), Ring A is selected from an optionally substituted $C_3$-$C_5$ carbocycle and optionally substituted 4- to 5-membered heterocycle, wherein optional substituents on Ring A are independently selected at each occurrence from halogen, =O, —OH, —O—$C_{1-3}$ alkyl, and —CN. In some cases, Ring A is selected from an optionally substituted saturated $C_3$-$C_5$ carbocycle and optionally substituted saturated 4- to 5-membered heterocycle, wherein optional substituents on Ring A are independently selected at each occurrence from halogen, =O, —OH, —O—$C_{1-3}$ alkyl, and —CN. In some cases, the compound or salt of Formula (L), (LA), (LB), (LC), (LD), (LE), (LF), or (LG), the 4- to 5-membered heterocycle includes at least one heteroatom selected from oxygen and sulfur.

In some embodiments, for the compound or salt of Formula (L), (LA), (LB), (LC), (LD), (LE), (LF), or (LG), $R^4$ is selected from

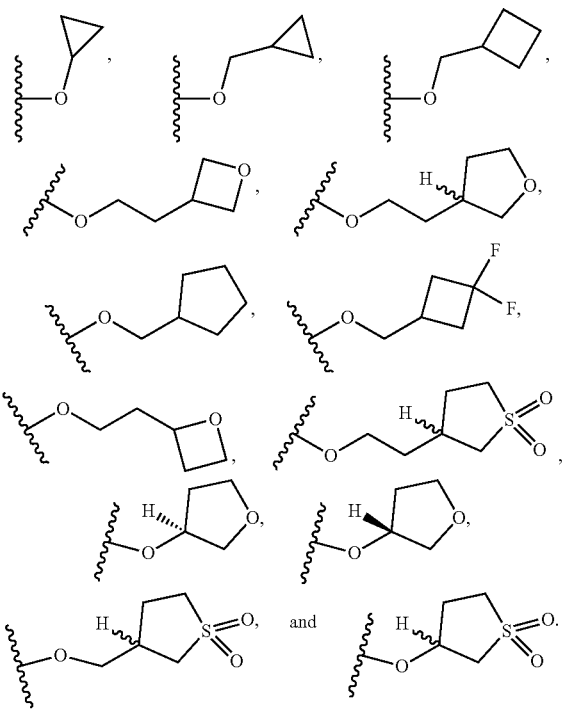

In some embodiments, for the compound or salt of Formula (L), (LA), (LB), (LC), (LD), (LE), (LF), or (LG), $R^4$ is selected from

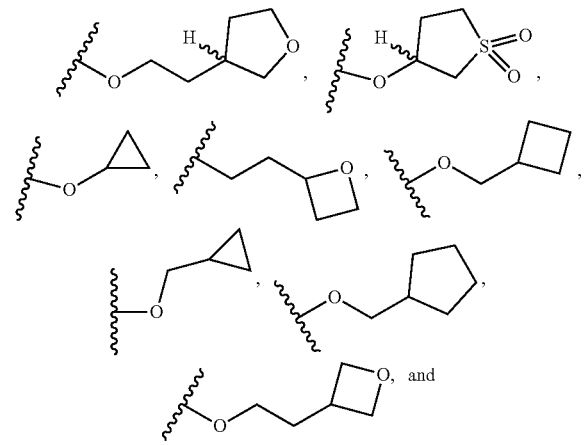

In some embodiments, for the compound or salt of Formula (L), (LA), (LB), (LC), (LD), (LE), (LF), or (LG), $R^4$ is selected from

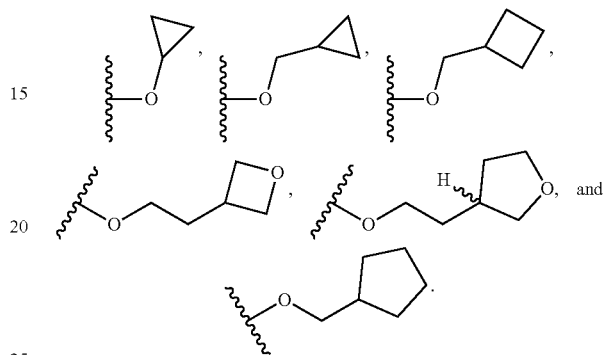

In some embodiments, for the compound or salt of Formula (L), (LA), (LB), (LC), (LD), (LE), (LF), or (LG), Ring A is selected from an unsubstituted $C_3$-$C_5$ carbocycle and optionally substituted 4- to 5-membered heterocycle, wherein optional substituents on the 4- to 5-membered heterocyle are independently selected at each occurrence from halogen, =O, —OH, —O—$C_{1-3}$ alkyl, and —CN.

In some embodiments, for the compound or salt of Formula (L), (LA), (LB), (LC), (LD), (LE), (LF), or (LG), $R^4$ is selected from

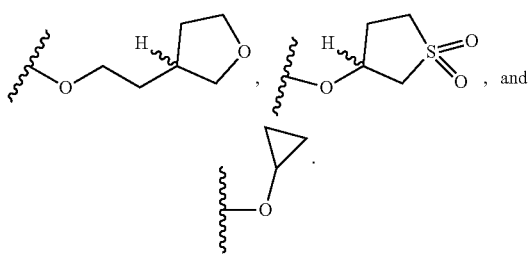

In some embodiments, for the compound or salt of Formula (L), (LA), (LB), (LC), (LD), (LE), (LF), or (LG), Ring A is selected from an optionally substituted $C_3$-$C_5$ carbocycle.

In some embodiments, for the compound or salt of Formula (L), (LA), (LB), (LC), (LD), (LE), (LF), or (LG), Ring A is selected from an unsubstituted $C_3$-$C_5$ carbocycle. In some cases, z is selected from 0 and 1. In some cases, $R^4$ is selected from

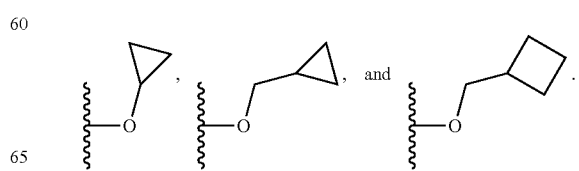

In some embodiments, the compound or salt of Formula (L), (LA), (LB), (LC), (LD), (LE), (LF), or (LG) is selected from:
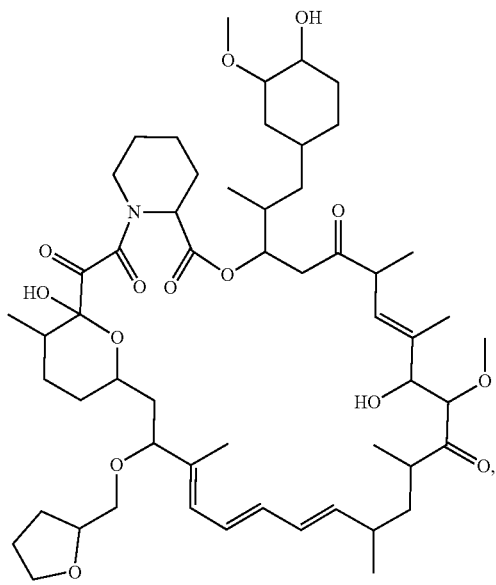
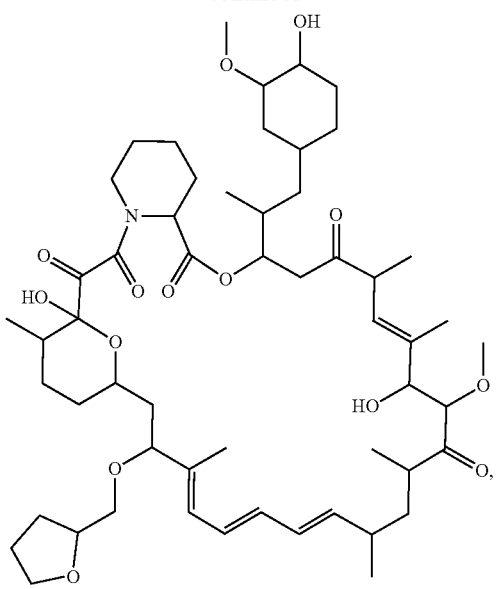
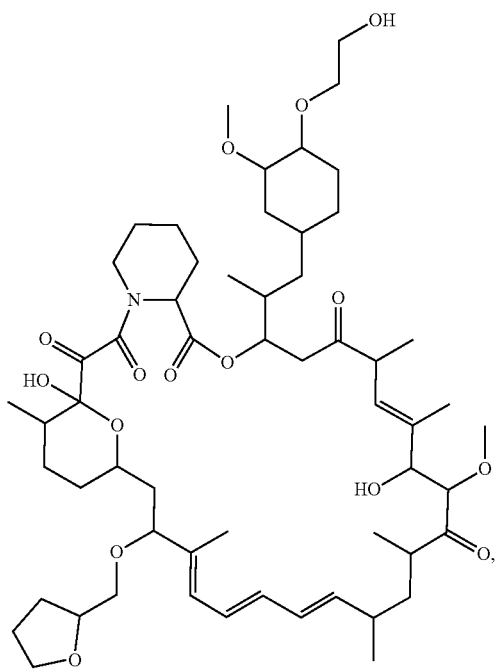
-continued 217
-continued
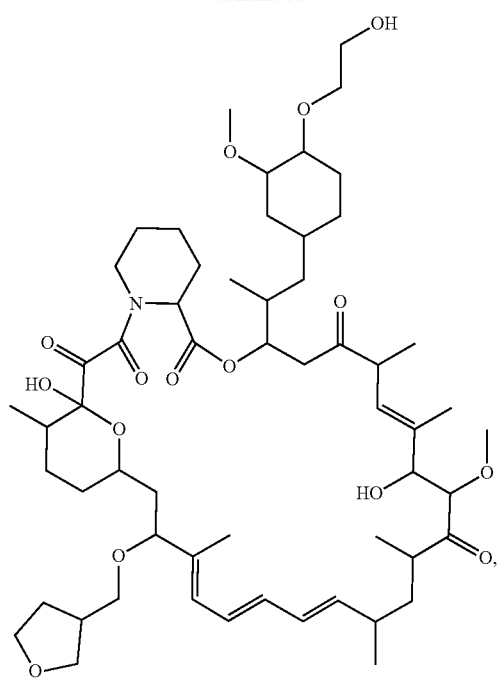
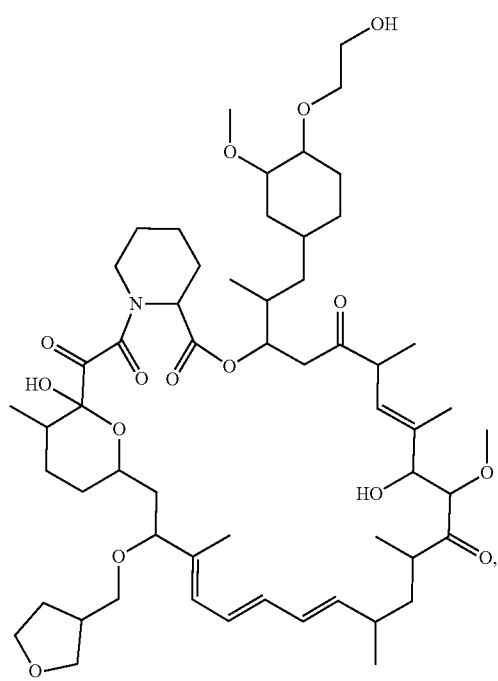
218
-continued
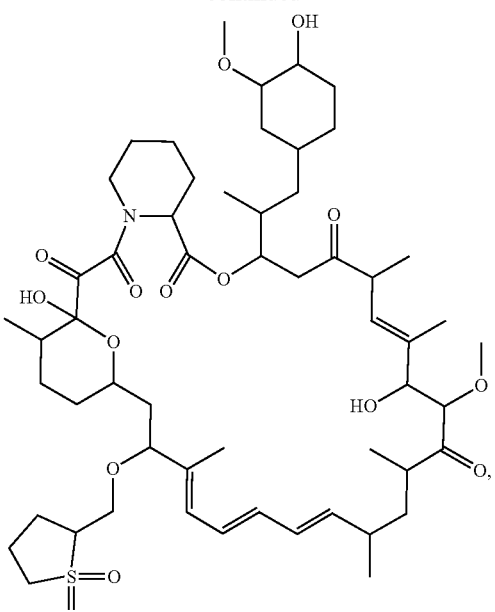
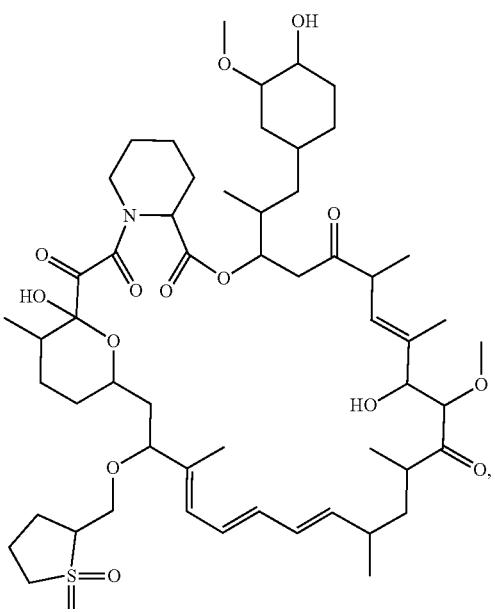

219
-continued
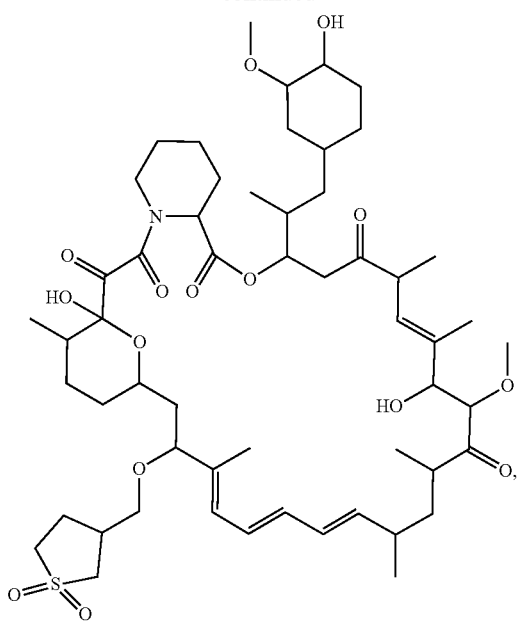
220
-continued
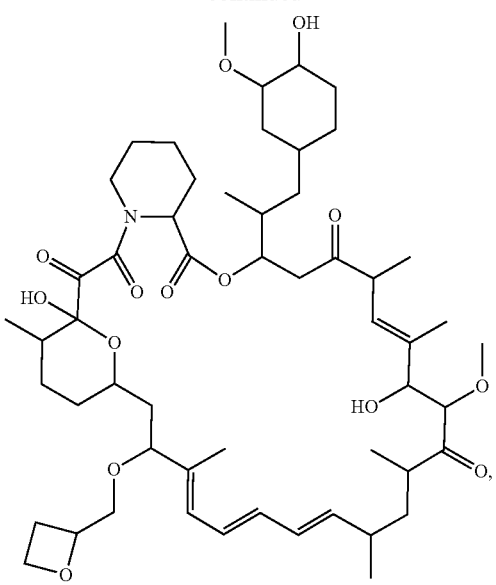
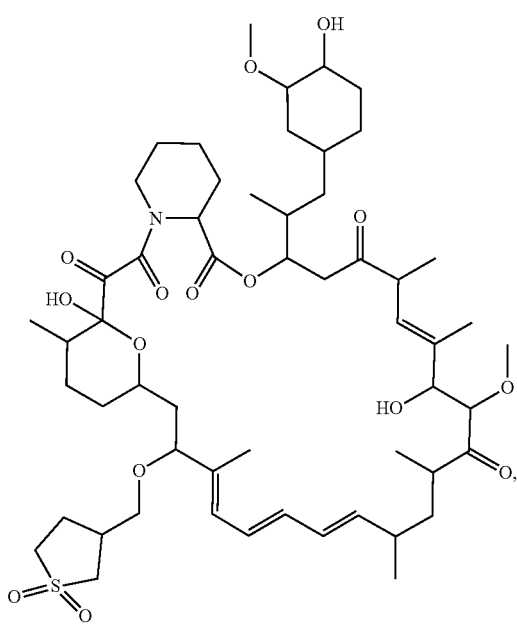
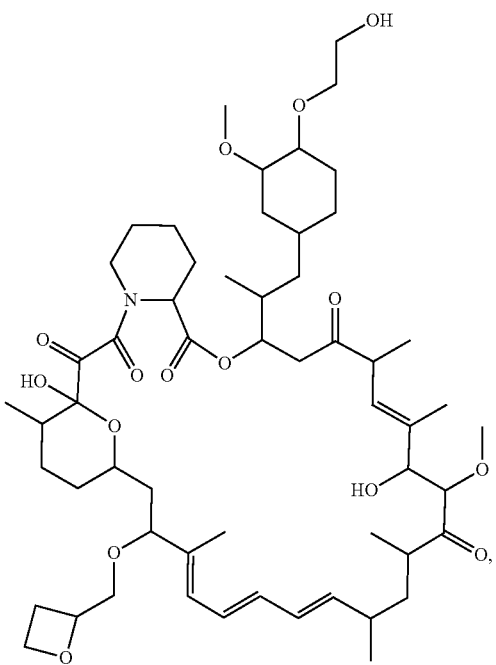

221
-continued
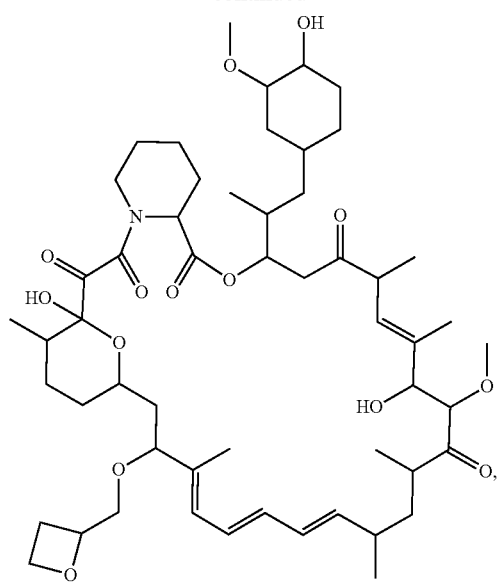
222
-continued
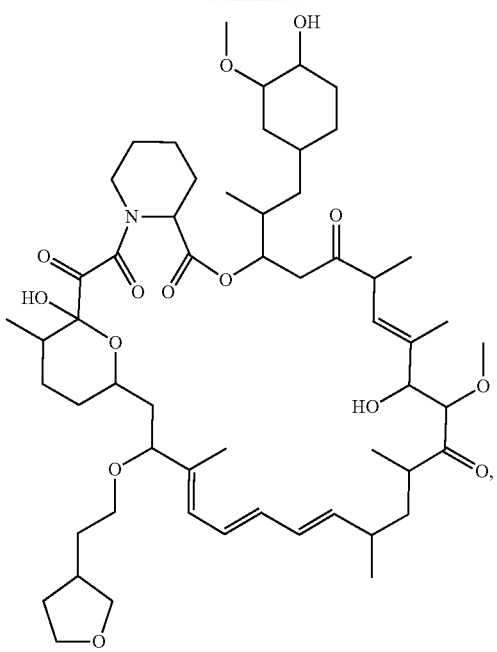
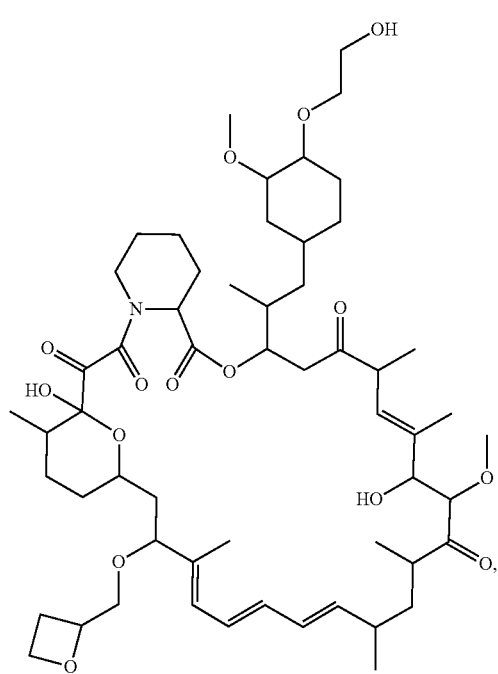
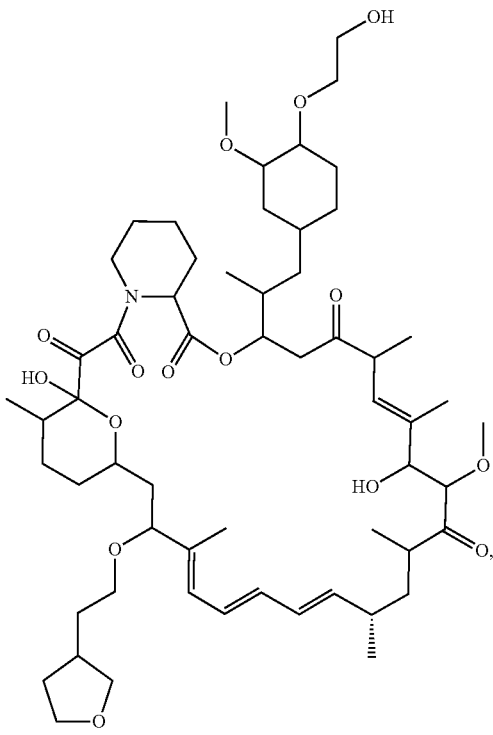

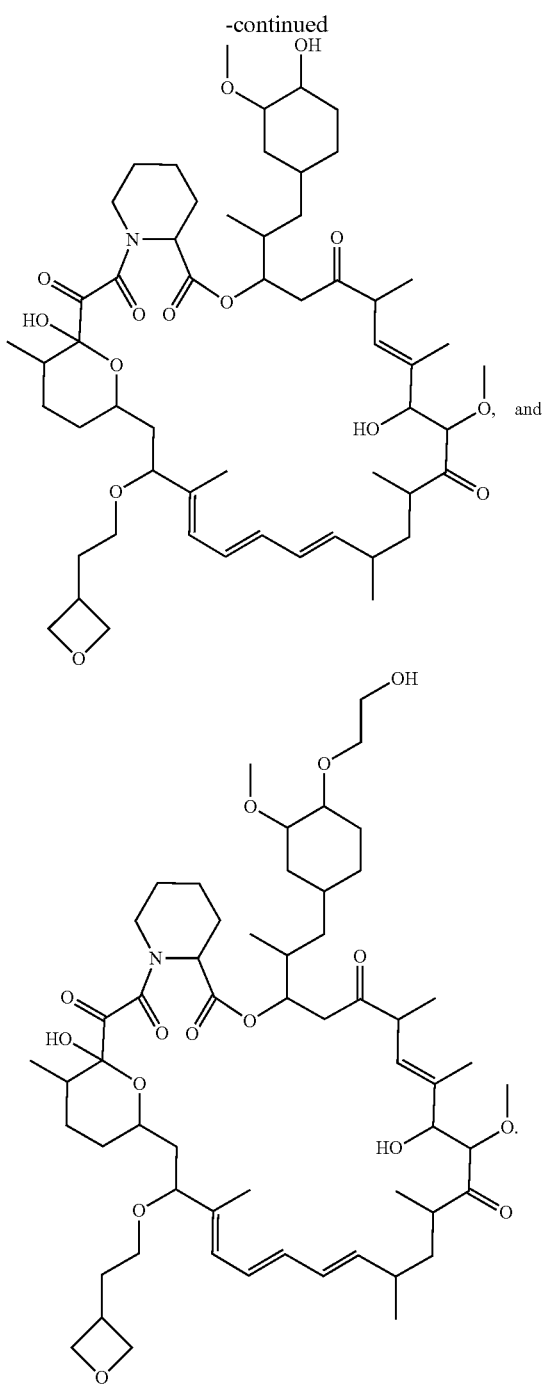

Compound Groups 1, 2, and 3

Chemical entities having carbon-carbon double bonds or carbon-nitrogen double bonds may exist in Z- or E-form (or cis- or trans-form). Furthermore, some chemical entities may exist in various tautomeric forms. Unless otherwise specified, compounds described herein are intended to include all Z-, E- and tautomeric forms as well.

"Isomers" are different compounds that have the same molecular formula. "Stereoisomers" are isomers that differ only in the way the atoms are arranged in space. "Enantiomers" are a pair of stereoisomers that are non-superimposable mirror images of each other. A 1:1 mixture of a pair of enantiomers is a "racemic" mixture. The term "(±)" is used to designate a racemic mixture where appropriate. "Diastereoisomers" or "diastereomers" are stereoisomers that have at least two asymmetric atoms but are not mirror images of each other. The absolute stereochemistry is specified according to the Cahn-Ingold-Prelog R-S system. When a compound is a pure enantiomer, the stereochemistry at each chiral carbon can be specified by either R or S. Resolved compounds whose absolute configuration is unknown can be designated (+) or (−) depending on the direction (dextro- or levorotatory) in which they rotate plane polarized light at the wavelength of the sodium D line. Certain compounds described herein contain one or more asymmetric centers and can thus give rise to enantiomers, diastereomers, and other stereoisomeric forms, the asymmetric centers of which can be defined, in terms of absolute stereochemistry, as (R)- or (S)-. The present chemical entities, pharmaceutical compositions and methods are meant to include all such possible stereoisomers, including racemic mixtures, optically pure forms, mixtures of diastereomers and intermediate mixtures. Optically active (R)- and (S)-isomers can be prepared using chiral synthons or chiral reagents, or resolved using conventional techniques. The optical activity of a compound can be analyzed via any suitable method, including but not limited to chiral chromatography and polarimetry, and the degree of predominance of one stereoisomer over the other isomer can be determined.

When stereochemistry is not specified, molecules with stereocenters described herein include isomers, such as enantiomers and diastereomers, mixtures of enantiomers, including racemates, mixtures of diastereomers, and other mixtures thereof, to the extent they can be made by one of ordinary skill in the art by routine experimentation. In certain embodiments, the single enantiomers or diastereomers, i.e., optically active forms, can be obtained by asymmetric synthesis or by resolution of the racemates or mixtures of diastereomers. Resolution of the racemates or mixtures of diastereomers, if possible, can be accomplished, for example, by conventional methods such as crystallization in the presence of a resolving agent, or chromatography, using, for example, a chiral high-pressure liquid chromatography (HPLC) column. Furthermore, a mixture of two enantiomers enriched in one of the two can be purified to provide further optically enriched form of the major enantiomer by recrystallization and/or trituration.

In certain embodiments, compositions of the disclosure may comprise two or more enantiomers or diastereomers of a compound wherein a single enantiomer or diastereomer accounts for at least about 70% by weight, at least about 80% by weight, at least about 90% by weight, at least about 98% by weight, or at least about 99% by weight or more of the total weight of all stereoisomers. Methods of producing substantially pure enantiomers are well known to those of skill in the art. For example, a single stereoisomer, e.g., an enantiomer, substantially free of its stereoisomer may be obtained by resolution of the racemic mixture using a method such as formation of diastereomers using optically active resolving agents (Stereochemistry of Carbon Compounds, (1962) by E. L. Eliel, McGraw Hill; Lochmuller (1975) J. Chromatogr., 113(3): 283-302). Racemic mixtures of chiral compounds can be separated and isolated by any suitable method, including, but not limited to: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. Another approach for separation of the enantiomers is to use a Diacel chiral column and elution using an organic mobile phase such as done by Chiral Technologies (www.chiraltech.com) on a fee for service basis.

A "tautomer" refers to a molecule wherein a proton shift from one atom of a molecule to another atom of the same molecule is possible. The compounds presented herein, in certain embodiments, exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

In certain embodiments, the compounds disclosed herein have some or all of the $^1H$ atoms replaced with $^2H$ atoms. The methods of synthesis for deuterium-containing compounds are known in the art and include, by way of non-limiting example only, the following synthetic methods.

Deuterium substituted compounds are synthesized using various methods such as described in: Dean, Dennis C.; Editor. Recent Advances in the Synthesis and Applications of Radiolabeled Compounds for Drug Discovery and Development. [In: Curr., Pharm. Des., 2000; 6(10)] 2000, 110 pp; George W.; Varma, Rajender S. The Synthesis of Radiolabeled Compounds via Organometallic Intermediates, Tetrahedron, 1989, 45(21), 6601-21; and Evans, E. Anthony. Synthesis of radiolabeled compounds, J. Radioanal. Chem., 1981, 64(1-2), 9-32.

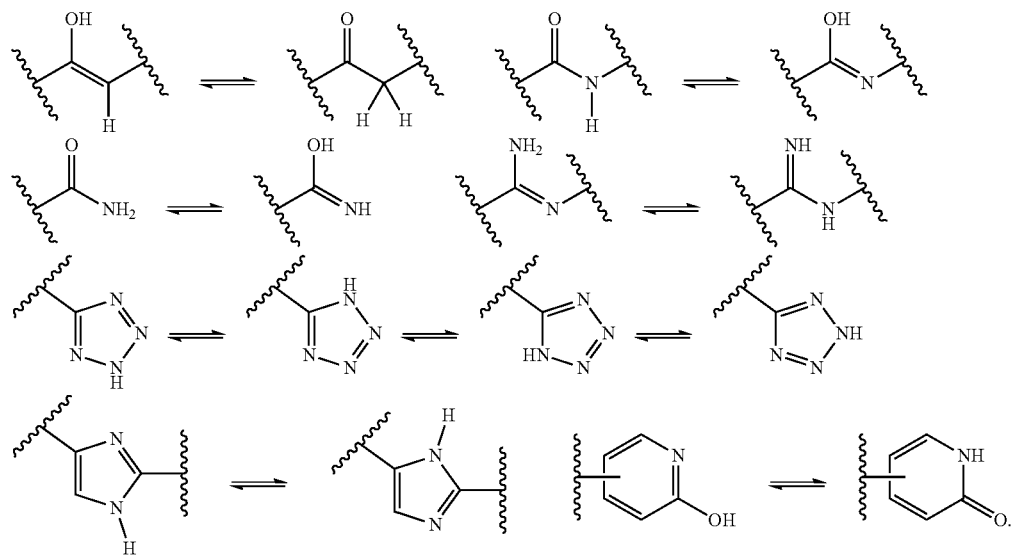

The compounds disclosed herein, in some embodiments, are used in different enriched isotopic forms, e.g., enriched in the content of $^2H$, $^3H$, $^{11}C$, $^{13}C$ and/or $^{14}C$. In one particular embodiment, the compound is deuterated in at least one position. Such deuterated forms can be made by the procedure described in U.S. Pat. Nos. 5,846,514 and 6,334,997. As described in U.S. Pat. Nos. 5,846,514 and 6,334,997, deuteration can improve the metabolic stability and or efficacy, thus increasing the duration of action of drugs.

Unless otherwise stated, compounds described herein are intended to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of the present disclosure.

The compounds of the present disclosure optionally contain unnatural proportions of atomic isotopes at one or more atoms that constitute such compounds. For example, the compounds may be labeled with isotopes, such as for example, deuterium ($^2H$), tritium ($^3H$), iodine-125 ($^{125}I$) or carbon-14 ($^{14}C$). Isotopic substitution with $^2H$, $^{11}C$, $^{13}C$, $^{14}C$, $^{15}C$, $^{12}N$, $^{13}N$, $^{15}N$, $^{16}O$, $^{17}O$, $^{14}F$, $^{15}F$, $^{16}F$, $^{17}F$, $^{18}F$, $^{33}S$, $^{34}S$, $^{35}S$, $^{36}S$, $^{35}Cl$, $^{37}Cl$, $^{79}Br$, $^{81}Br$, and $^{125}I$ are all contemplated. All isotopic variations of the compounds of the present invention, whether radioactive or not, are encompassed within the scope of the present invention.

Deuterated starting materials are readily available and are subjected to the synthetic methods described herein to provide for the synthesis of deuterium-containing compounds. Large numbers of deuterium-containing reagents and building blocks are available commercially from chemical vendors, such as Aldrich Chemical Co.

Compounds of the present invention also include crystalline and amorphous forms of those compounds, pharmaceutically acceptable salts, and active metabolites of these compounds having the same type of activity, including, for example, polymorphs, pseudopolymorphs, solvates, hydrates, unsolvated polymorphs (including anhydrates), conformational polymorphs, and amorphous forms of the compounds, as well as mixtures thereof.

Included in the present disclosure are salts, particularly pharmaceutically acceptable salts, of the compounds described herein. The compounds of the present disclosure that possess a sufficiently acidic, a sufficiently basic, or both functional groups, can react with any of a number of inorganic bases, and inorganic and organic acids, to form a salt. Alternatively, compounds that are inherently charged, such as those with a quaternary nitrogen, can form a salt with an appropriate counterion, e.g., a halide such as bromide, chloride, or fluoride, particularly bromide.

The methods and compositions described herein include the use of amorphous forms as well as crystalline forms (also known as polymorphs). The compounds described herein may be in the form of pharmaceutically acceptable salts. As well, in some embodiments, active metabolites of these compounds having the same type of activity are included in the scope of the present disclosure. In addition, the compounds described herein can exist in unsolvated as well as solvated forms with pharmaceutically acceptable solvents such as water, ethanol, and the like. The solvated forms of the compounds presented herein are also considered to be disclosed herein.

In certain embodiments, compounds or salts of the compounds may be prodrugs, e.g., wherein a hydroxyl in the parent compound is presented as an ester or a carbonate, or carboxylic acid present in the parent compound is presented as an ester. The term "prodrug" is intended to encompass compounds which, under physiologic conditions, are converted into pharmaceutical agents of the present disclosure. One method for making a prodrug is to include one or more selected moieties which are hydrolyzed under physiologic conditions to reveal the desired molecule. In other embodiments, the prodrug is converted by an enzymatic activity of the host animal such as specific target cells in the host animal. For example, esters or carbonates (e.g., esters or carbonates of alcohols or carboxylic acids and esters of phosphonic acids) are preferred prodrugs of the present disclosure.

Prodrugs are often useful because, in some situations, they may be easier to administer than the parent drug. They may, for instance, be bioavailable by oral administration whereas the parent is not. Prodrugs may help enhance the cell permeability of a compound relative to the parent drug. The prodrug may also have improved solubility in pharmaceutical compositions over the parent drug. Prodrugs may be designed as reversible drug derivatives, for use as modifiers to enhance drug transport to site-specific tissues or to increase drug residence inside of a cell.

In some embodiments, the design of a prodrug increases the lipophilicity of the pharmaceutical agent. In some embodiments, the design of a prodrug increases the effective water solubility. See, e.g., Fedorak et al., *Am. J. Physiol.,* 269:G210-218 (1995); McLoed et al., *Gastroenterol,* 106: 405-413 (1994); Hochhaus et al., *Biomed. Chrom.,* 6:283-286 (1992); J. Larsen and H. Bundgaard, *Int. J. Pharmaceutics,* 37, 87 (1987); J. Larsen et al., *Int. J. Pharmaceutics,* 47, 103 (1988); Sinkula et al., *J. Pharm. Sci.,* 64:181-210 (1975); T. Higuchi and V. Stella, *Pro-drugs as Novel Delivery Systems,* Vol. 14 of the A.C.S. Symposium Series; and Edward B. Roche, *Bioreversible Carriers in Drug Design,* American Pharmaceutical Association and Pergamon Press, 1987, all incorporated herein for such disclosure). According to another embodiment, the present disclosure provides methods of producing the above-defined compounds. The compounds may be synthesized using conventional techniques. Advantageously, these compounds are conveniently synthesized from readily available starting materials.

Synthetic chemistry transformations and methodologies useful in synthesizing the compounds described herein are known in the art and include, for example, those described in R. Larock, *Comprehensive Organic Transformations* (1989); T. W. Greene and P. G. M. Wuts, *Protective Groups in Organic Synthesis,* 2d. Ed. (1991); L. Fieser and M. Fieser, *Fieser and Fieser's Reagents for Organic Synthesis* (1994); and L. Paquette, ed., *Encyclopedia of Reagents for Organic Synthesis* (1995).

Pharmaceutical Formulations for Compounds of Groups 1, 2, and 3

A compound or salt of any one of the Formulas or sub Formulas described herein (e.g., Formula (I), Formula (X), Formula (L), etc.) may be formulated in any suitable pharmaceutical formulation. A pharmaceutical formulation of the present disclosure typically contains an active ingredient (e.g., compound or salt of any one of the Formulas described herein) and one or more pharmaceutically acceptable excipients or carriers, including but not limited to: inert solid diluents and fillers, diluents, sterile aqueous solution and various organic solvents, permeation enhancers, antioxidents, solubilizers, and adjuvants.

In certain embodiments, a compound or salt of any one of the Formulas or sub Formulas described herein (e.g., Formula (I) of the first aspect, Formula (X) of the second aspect, Formula (L) of the third aspect, etc.) is formulated with an agent that inhibits degradation of the compound or salt. In certain embodiments, the compound or salt is formulated with one or more antioxidants. Acceptable antioxidants include, but are not limited to, citric acid, d,l-α-tocopherol, BHA, BHT, monothioglycerol, ascorbyl palmitate, ascorbic acid, and propyl gallate. In certain embodiments, the formulation contains from 0.1 to 30%, from 0.5 to 25%, from 1 to 20%, from 5 to 15%, or from 7 to 12% (wt/wt) CCI-779, from 0.5 to 50%, from 1 to 40%, from 5 to 35%, from 10 to 25%, or from 15 to 20% (wt/wt) water soluble polymer, from 0.5 to 10%, 1 to 8%, or 3 to 5% (wt/wt) surfactant, and from 0.001% to 1%, 0.01% to 1%, or 0.1% to 0.5% (wt/wt) antioxidant. In certain embodiments, the antioxidants of the formulations of this invention will be used in concentrations ranging from 0.001% to 3% wt/wt.

In certain embodiments, a compound or salt of any one of the Formulas or sub Formulas described herein (e.g., Formula (I) of the first aspect, Formula (X) of the second aspect, Formula (L) of the third aspect, etc.) is formulated with a pH modifying agent to maintain a pH of about 4 to about 6. Acceptable pH modifying agents include, but are not limited to citric acid, sodium citrate, dilute HCl, and other mild acids or bases capable of buffering a solution containing a compound or a salt of the disclosure to a pH in the range of about 4 to about 6.

In certain embodiments, a compound or salt of any one of the Formulas or sub Formulas described herein (e.g., Formula (I) of the first aspect, Formula (X) of the second aspect, Formula (L) of the third aspect, etc.) is formulated with a chelating agent or other material capable of binding metal ions, such as ethylene diamine tetra acetic acid (EDTA) and its salts are capable of enhancing the stability of a compound or salt of any one of the Formulas described herein (e.g., Formula (I), Formula (X), Formula (L), etc.).

Pharmaceutical formulations may be provided in any suitable form, which may depend on the route of administration. In some embodiments, the pharmaceutical composition disclosed herein can be formulated in dosage form for administration to a subject. In some embodiments, the pharmaceutical composition is formulated for oral, intravenous, intraarterial, aerosol, parenteral, buccal, topical, transdermal, rectal, intramuscular, subcutaneous, intraosseous, intranasal, intrapulmonary, transmucosal, inhalation, and/or intraperitoneal administration. In some embodiments, the dosage form is formulated for oral administration. For example, the pharmaceutical composition can be formulated in the form of a pill, a tablet, a capsule, an inhaler, a liquid suspension, a liquid emulsion, a gel, or a powder. In some embodiments, the pharmaceutical composition can be formulated as a unit dosage in liquid, gel, semi-liquid, semi-solid, or solid form.

The amount of a compound or salt of any one of the Formulas or sub Formulas described herein (e.g., Formula (I), Formula (X), Formula (L), etc.) will be dependent on the mammal being treated, the severity of the disorder or condition, the rate of administration, the disposition of the compound or salt of any one of the Formulas or sub Formulas described herein (e.g., Formula (I), Formula (X), Formula (L), etc.) and the discretion of the prescribing physician.

In some embodiments, pharmaceutically acceptable carriers of a compound or salt of any one of the Formulas or sub Formulas described herein (e.g., Formula (I), Formula (X), Formula (L), Formula (I), Formula (X), Formula (L), etc.) can include a physiologically acceptable compound that is an antioxidant.

In some embodiments, the disclosure provides a pharmaceutical composition for oral administration containing at least one compound or salt of any one of the Formulas or sub Formulas described herein (e.g., Formula (I), Formula (X), Formula (L), etc.) and a pharmaceutical excipient suitable for oral administration. The composition may be in the form of a solid, liquid, gel, semi-liquid, or semi-solid. In some embodiments, the composition further comprises a second agent.

Pharmaceutical compositions of the disclosure suitable for oral administration can be presented as discrete dosage forms, such as hard or soft capsules, cachets, troches, lozenges, or tablets, or liquids or aerosol sprays each containing a predetermined amount of an active ingredient as a powder or in granules, a solution, or a suspension in an aqueous or non-aqueous liquid, an oil-in-water emulsion, or a water-in-oil liquid emulsion, or dispersible powders or granules, or syrups or elixirs. Such dosage forms can be prepared by any of the methods of pharmacy, which typically include the step of bringing the active ingredient(s) into association with the carrier. In general, the composition are prepared by uniformly and intimately admixing the active ingredient(s) with liquid carriers or finely divided solid carriers or both, and then, if necessary, shaping the product into the desired presentation. For example, a tablet can be prepared by compression or molding, optionally with one or more accessory ingredients. Compressed tablets can be prepared by compressing in a suitable machine the active ingredient(s) in a free-flowing form such as powder or granules, optionally mixed with an excipient such as, but not limited to, a binder, a lubricant, an inert diluent, and/or a surface active or dispersing agent. Molded tablets can be made by molding in a suitable machine a mixture of the powdered compound or salt of any one of the Formulas or sub Formulas described herein (e.g., Formula (I), Formula (X), Formula (L), etc.) moistened with an inert liquid diluent.

In some embodiments, the disclosure provides a pharmaceutical composition for injection containing a compound or salt of any one of the Formulas described herein (e.g., Formula (I), Formula (X), Formula (L), etc.) and a pharmaceutical excipient suitable for injection. Components and amounts of agents in the composition are as described herein.

In certain embodiments, the compound or salt of any one of the Formulas or sub Formulas described herein (e.g., Formula (I), Formula (X), Formula (L), etc.) may be formulated for injection as aqueous or oil suspensions, emulsions, with sesame oil, corn oil, cottonseed oil, or peanut oil, as well as elixirs, mannitol, dextrose, or a sterile aqueous solution, and similar pharmaceutical vehicles.

Aqueous solutions in saline are also conventionally used for injection. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, for the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Pharmaceutical compositions may also be prepared from a compound or salt of any one of the Formulas or sub Formulas described herein (e.g., Formula (I), Formula (X), Formula (L), etc.) and one or more pharmaceutically acceptable excipients suitable for transdermal, inhalative, sublingual, buccal, rectal, intraosseous, intraocular, intranasal, epidural, or intraspinal administration. Preparations for such pharmaceutical composition are well-known in the art. See, e.g., Anderson, Philip O.; Knoben, James E.; Troutman, William G, eds., Handbook of Clinical Drug Data, Tenth Edition, McGraw-Hill, 2002; Pratt and Taylor, eds., Principles of Drug Action, Third Edition, Churchill Livingston, N.Y., 1990; Katzung, ed., Basic and Clinical Pharmacology, Ninth Edition, McGraw Hill, 2003; Goodman and Gilman, eds., The Pharmacological Basis of Therapeutics, Tenth Edition, McGraw Hill, 2001; Remingtons Pharmaceutical Sciences, 20th Ed., Lippincott Williams & Wilkins., 2000; Martindale, The Extra Pharmacopoeia, Thirty-Second Edition (The Pharmaceutical Press, London, 1999).

The disclosure also provides kits. The kits may include a compound or salt of any one of the Formulas or sub Formulas described herein (e.g., Formula (I), Formula (X), Formula (L), etc.) and one or more additional agents in suitable packaging with written material that can include instructions for use, discussion of clinical studies, listing of side effects, and the like. Such kits may also include information, such as scientific literature references, package insert materials, clinical trial results, and/or summaries of these and the like, which indicate or establish the activities and/or advantages of the composition, and/or which describe dosing, administration, side effects, drug interactions, or other information useful to the health care provider. Such information may be based on the results of various studies, for example, studies using experimental animals involving in vivo models and studies based on human clinical trials. The kit may further contain another agent. In some embodiments, a compound or salt of any one of the Formulas or sub Formulas described herein (e.g., Formula (I), Formula (X), Formula (L), etc.) and the agent are provided as separate compositions in separate containers within the kit. In some embodiments, a compound or salt of any one of the Formulas or sub Formulas described herein (e.g., Formula (I), Formula (X), Formula (L), etc.) and the agent are provided as a single composition within a container in the kit. Suitable packaging and additional articles for use (e.g., measuring cup for liquid preparations, foil wrapping to minimize exposure to air, and the like) are known in the art and may be included in the kit. Kits described herein can be provided, marketed and/or promoted to health providers, including physicians, nurses, pharmacists, formulary officials, and the like. Kits may also, in some embodiments, be marketed directly to the consumer.

Therapeutic Applications for Compounds of Groups 1, 2, and 3

In one aspect, the present disclosure provides a method of inhibiting mTORC1, comprising administering a compound or salt of any one of the Formulas or sub Formulas described herein (e.g., Formula (I), Formula (X), Formula (L), etc.). In one aspect, the present disclosure provides a method of inhibiting mTORC1 without appreciably modulating mTORC2, comprising administering a compound or salt of any one of the Formulas described herein (e.g., Formula (I), Formula (X), Formula (L), etc.). In certain embodiments, the compounds and salts of the disclosure do not appreciably inhibit mTORC2.

While not being bound to any particular mechanism, a compound or salt of any one of the Formulas or sub Formulas described herein (e.g., Formula (I), Formula (X), Formula (L), etc.) may show reduced side effects relative to rapamycin. In particular, compounds or salts of the disclosure may not appreciably impact the gastrointestinal and/or cardiac systems. In certain embodiments the compounds of the disclosure may be administered in larger dosing amounts or over longer periods of time than the prescribed dosing amounts or timeframes for rapamycin. For example of the intended timeframes, a compound or salt of any one of the Formulas or sub Formulas described herein (e.g., Formula (I), Formula (X), Formula (L), etc.) may be administered daily, every other day, once a week, once every two weeks over a period of time, such as 2 months or more, 4 months or more, 6 months or more, 1 year or more, or even two years or more. For example of the intended dosing, a compound or salt of any one of the Formulas or sub Formulas described herein (e.g., Formula (I), Formula (X), Formula (L), etc.) may be administered in dose, 30% or greater, 50% greater, 80% or greater than rapamycin indicated dosing for the same indication.

In certain embodiments, a compound or salt of any one of the Formulas or sub Formulas described herein (e.g., Formula (I), Formula (X), Formula (L), etc.) is administered to a subject in need thereof for the treatment and/or prevention of a tauopathy (including but not limited to Alzheimer's disease, Parkinson's disease, progressive supranuclear palsy (PSP), corticobasal degeneration, corticobasal syndrome, frontotemporal dementia, frontotemporal lobar degeneration (FTLD) including but not limited to FTLD-17, behavior variant FTD, primary progressive aphasia (semantic, agrammatic or logopenic variants), argyrophilic grain disease, Pick's disease, globular glial tauopathies, primary age-related tauopathy (including neurofibrillary tangle dementia), chronic traumatic encephalopathy (CTE)-traumatic brain injury and aging-related tau astrogliopathy), an mTORopathy (including but not limited to tuberous sclerosis complex (TSC)), an mTORopathy associated with epileptic seizures, focal cortical dysplasia (FCD), ganglioglioma, hemimegalencephaly, neurofibromatosis 1, Sturge-Weber syndrome, Cowden syndrome, PMSE (Polyhydramnios, Megalencephaly, Symptomatic Epilepsy)), familial multiple discoid fibromas (FMDF), an epilepsy/epileptic seizures (both genetic and acquired forms of the disease such as familial focal epilepsies, epileptic spasms, infantile spasms (IS), status epilepticus (SE), temporal lobe epilepsy (PLE) and absence epilepsy), rare diseases associated with a dysfunction of mTORC1 activity (e.g., lymphangioleiomyomatosis (LAM), Leigh's syndrome, Friedrich's ataxia, Diamond-Blackfan anemia, etc.), metabolic diseases (e.g., obesity, Type II diabetes, etc.), autoimmune and inflammatory diseases (e.g., Systemic Lupus Erythematosus (SLE), multiple sclerosis (MS) psoriasis, etc.), cancer, a fungal infection, a proliferative disease, the maintenance of immunosuppression, transplant rejection, traumatic brain injury, autism, lysosomal storage diseases and neurodegenerative diseases associated with an mTORC1 hyperactivity (e.g., Parkinson's, Huntington's disease, etc.), aberrant compound accumulation, dysfunction of the autophagy mechanisms, and generally including but not limited to disorders that can be modulated by selective inhibition of the mTORC1 pathway.

In certain embodiments, a compound or salt of any one of the Formulas or sub Formulas described herein (e.g., Formula (I), Formula (X), Formula (L), etc.) is administered to a subject in need thereof for treatment and/or prevention of a tauopathy selected from the group consisting of: progressive supranuclear palsy, dementia pugilistica (chronic traumatic encephalopathy), frontotemporal dementia, lytico-bodig disease (parkinson-dementia complex of guam), tangle-predominant dementia (with nfts similar to Alzheimer's disease, but without plaques), ganglioglioma and gangliocytoma, meningioangiomatosis, subacute sclerosing panencephalitis, lead encephalopathy, tuberous sclerosis, Pick's disease, corticobasal degeneration (tau proteins are deposited in the form of inclusion bodies within swollen or "ballooned" neurons), Alzheimer's disease, Parkinson's disease, Huntington's disease, frontotemporal dementia, and frontotemporal lobar degeneration.

In certain embodiments, a compound or salt of any one of the Formulas or sub Formulas described herein (e.g., Formula (I), Formula (X), Formula (L), etc.) is administered to a subject in need thereof for the treatment and/or prevention of a tauopathy selected from the group consisting of: Alzheimer's disease, Parkinson's disease, progressive supranuclear palsy (PSP), corticobasal degeneration, corticobasal syndrome, frontotemporal dementia, frontotemporal lobar degeneration (FTLD) including but not limited to FTLD-17, behavior variant FTD, primary progressive aphasia (semantic, agrammatic or logopenic variants), argyrophilic grain disease, Pick's disease, globular glial tauopathies, primary age-related tauopathy (including neurofibrillary tangle dementia), chronic traumatic encephalopathy (CTE)-traumatic brain injury and aging-related tau astrogliopathy.

In certain embodiments, a compound or salt of any one of the Formulas or sub Formulas described herein (e.g., Formula (I), Formula (X), Formula (L), etc.) is administered to a subject in need thereof for the treatment and/or prevention of a mTORopathy. The mTORopathy may be, for example, Tuberous Sclerosis, Focal Cortical Dysplasia, or a PTEN (Phosphatase and tensin homolog) disease, etc. The mTORopathy may be a disease or disorder described elsewhere herein.

In certain embodiments, a compound or salt of any one of the Formulas or sub Formulas described herein (e.g., Formula (I), Formula (X), Formula (L), etc.) is administered to a subject in need thereof for the treatment and/or prevention of cancer. Non-limiting examples of cancers can include Acute lymphoblastic leukemia (ALL); Acute myeloid leukemia; Adrenocortical carcinoma; Astrocytoma, childhood cerebellar or cerebral; Basal-cell carcinoma; Bladder cancer; Bone tumor, osteosarcoma/malignant fibrous histiocytoma; Brain cancer; Brain tumors, such as, cerebellar astrocytoma, malignant glioma, ependymoma, medulloblastoma, visual pathway and hypothalamic glioma; Brainstem glioma; Breast cancer; Bronchial adenomas/carcinoids; Burkitt's lymphoma; Cerebellar astrocytoma; Cervical cancer; Cholangiocarcinoma; Chondrosarcoma; Chronic lymphocytic leukemia; Chronic myelogenous leukemia; Chronic myeloproliferative disorders; Colon cancer; Cutaneous T-cell lymphoma; Endometrial cancer; Ependymoma; Esophageal cancer; Eye cancers, such as, intraocular melanoma and retinoblastoma; Gallbladder cancer; Glioma; Hairy cell leukemia; Head and neck cancer; Heart cancer; Hepatocellular (liver) cancer; Hodgkin lymphoma; Hypopharyngeal cancer; Islet cell carcinoma (endocrine pancreas); Kaposi sarcoma;

Kidney cancer (renal cell cancer); Laryngeal cancer; Leukemia, such as, acute lymphoblastic, acute myeloid, chronic lymphocytic, chronic myelogenous and, hairy cell; Lip and oral cavity cancer; Liposarcoma; Lung cancer, such as, non-small cell and small cell; Lymphoma, such as, AIDS-related, Burkitt; Lymphoma, cutaneous T-Cell, Hodgkin and Non-Hodgkin, Macroglobulinemia, Malignant fibrous histiocytoma of bone/osteosarcoma; Melanoma; Merkel cell cancer; Mesothelioma; Multiple myeloma/plasma cell neoplasm; Mycosis fungoides; Myelodysplastic syndromes; Myelodysplastic/myeloproliferative diseases; Myeloproliferative disorders, chronic; Nasal cavity and paranasal sinus cancer; Nasopharyngeal carcinoma; Neuroblastoma; Oligodendroglioma; Oropharyngeal cancer; Osteosarcoma/malignant fibrous histiocytoma of bone; Ovarian cancer; Pancreatic cancer; Parathyroid cancer; Pharyngeal cancer; Pheochromocytoma; Pituitary adenoma; Plasma cell neoplasia; Pleuropulmonary blastoma; Prostate cancer; Rectal cancer; Renal cell carcinoma (kidney cancer); Renal pelvis and ureter, transitional cell cancer; Rhabdomyosarcoma; Salivary gland cancer; Sarcoma, Ewing family of tumors; Sarcoma, Kaposi; Sarcoma, soft tissue; Sarcoma, uterine; Sezary syndrome; Skin cancer (non-melanoma); Skin carcinoma; Small intestine cancer; Soft tissue sarcoma; Squamous cell carcinoma; Squamous neck cancer with occult primary, metastatic; Stomach cancer; Testicular cancer; Throat cancer; Thymoma and thymic carcinoma; Thymoma; Thyroid cancer; Thyroid cancer, childhood; Uterine cancer; Vaginal cancer; Waldenström macroglobulinemia; Wilms tumor and any combination thereof.

In certain embodiments, a compound or salt of any one of the Formulas or sub Formulas described herein (e.g., Formula (I) of the first aspect, Formula (X) of the second aspect, Formula (L) of the third aspect, etc.) is administered to a subject in need thereof for the treatment and/or prevention of seizures and/or seizure related disorders. The seizure related disorders may include but not limited to: West syndrome, Focal Cortical Dysplasia (FCD), tuberous sclerosis complex (TSC), childhood absence epilepsy, benign focal epilepsies of childhood, juvenile myoclonic epilepsy (JME), temporal lobe epilepsy, frontal lobe epilepsy, refractory epilepsy, Lennox-Gastaut syndrome, occipital lobe epilepsy, 5 Proteus syndrome, hemi-megalencephaly syndrome (HMEG), megalencephaly syndrome (MEG), megalencephaly-capillary malformation (MCAP), megalencephalypolymicrogyria-polydactyly-hydrocephalus syndrome (MPPH) and PTEN disorders.

A compound according any therapeutic compound disclosed herein for use in the treatment and/or prevention of disorders that include the processes of fibrosis and/or inflammation (e.g., liver and kidney disorders). The disorders may include but not limited to liver fibrosis (which may occur in end-stage liver disease); liver cirrhosis; liver failure due to toxicity; non-alcohol-associated hepatic steatosis or NASH; and alcohol-associated steatosis. Another example may be kidney fibrosis, which may occur as a result of acute kidney injury, chronic kidney disease, or diabetic nephropathy can induce kidney fibrosis and inflammation. The disorder may include polycystic kidney disease, ischemia/reperfusion injury, transplantation, adriamycin nephropathy, unilateral ureteral obstruction (UUO), glomerulopathy, IgA nephropathy, focal segmental glomerulosclerosis (FSGS), Lupus mesangial proliferative nephritis.

A compound according any therapeutic compound disclosed herein for use in the treatment and/or prevention of acute or chronic organ or tissue transplant rejection, for example, heart, lung, combined heart-lung, liver, kidney, pancreatic, skin or corneal transplants, prevention of graft-versus-host disease, such as following bone marrow transplantation, etc.

A compound according any therapeutic compound disclosed herein for use in the treatment and/or prevention of autoimmune diseases and/or and inflammatory conditions include in particular inflammatory conditions with an etiology that may include an autoimmune component such as arthritis (for example rheumatoid arthritis, arthritis chronica progrediente and arthritis deformans) and rheumatic diseases. Examples may include autoimmune hematological disorders (including e. g. hemolytic anemia, aplastic anemia, pure red cell anaemia and idiopathic thrombocytopenia), systemic lupus erythematosus, polychondritis, scleroderma, Wegener granulamatosis, dermatomyositis, chronic active hepatitis, myasthenia gravis, psoriasis, Steven-Johnson syndrome, idiopathic sprue, autoimmune inflammatory bowel disease (including e. g. ulcerative colitis and Crohn's disease) endocrine ophthalmopathy, Graves disease, sarcoidosis, multiple sclerosis, primary biliary cirrhosis, juvenile diabetes (diabetes mellitus type I), uveitis (anterior and posterior), keratoconjunctivitis sicca and vernal keratoconjunctivitis, interstitial lung fibrosis, psoriatic arthritis, glomerulonephritis (with and without nephrotic syndrome, e.g. including idiopathic nephrotic syndrome or minimal change nephropathy) and juvenile dermatomyositis.

A compound according any therapeutic compound disclosed herein for use in the treatment and/or prevention of mitochondrial diseases or disorders.

A compound according any therapeutic compound disclosed herein for use in the treatment and/or prevention of smooth muscle cell proliferation migration leading to vessel intimal thickening, blood vessel obstruction, obstructive coronary atherosclerosis, or restenosis.

In certain embodiments, the disclosure provides a method of treating disease characterized by hyperactivation of mTORC1. The following references include methods for evaluating mTORC (e.g., mTORC1) activity: T. O'Reilly et al., *Translational Oncology*, v3, i2, p 65-79, (2010); J. Peralba, *Clinical Cancer Research*, v9, i8, p 2887-2892 (2003); D. R. Moore et al., *Acta Physiologica*, v201, i3, p 365-372 (2010); M. Dieterlen, Clinical Cytometry, v82B, i3, p 151-157, (2012); the contents of each of which are incorporated by reference herein.

In certain embodiments, the disclosure provides a method of treating age-related diseases. It may be established that modulation of mTORC1 signaling may prolong lifespan and may delay the onset of age-related diseases across a wide array of organisms, ranging from flies to mammals, thus possibly providing therapeutic options for preventing or treating age-related diseases in humans. In a recent clinical study Mannick et al. (mTOR inhibition improves immune function in the elderly, Sci Transl Med. 2014 Dec. 24; 6(268):268ra179. doi: 10.1126/scitranslmed.3009892) may have showed that mTOR inhibition improves the immune function in the elderly.

In certain embodiments, the disclosure provides a method of treating mitochondrial diseases. Mitochondrial myopathy and mitochondrial stress may be mitochondrial disorders as described in Chinnery, P. F. (2015); EMBO Mol. Med. 7, 1503-1512; Koopman, W. J. et al., 10 (2016); EMBO Mol. Med. 8, 311-327 and Young, M. J., and Yound and Copeland, W. C. (2016); Curr. Opin. Genet. Dev. 38, 52-62.

In certain embodiments, the disclosure provides a method of treating diseases of impaired autophagy. In some cases they may include impaired autophagies that result in mitochondrial damage, lysosomal storage diseases, cancer, Crohn's disease, etc. In some cases the impaired autophagies may be as described in Jiang P. & Mizushima, N., Autophagy and human diseases, *Cell Research* volume 24, p. 69-79 (2014).

In certain embodiments, a compound or salt of the disclosure is used to induce heterodimerization of FKBP12 and the FRB domain of mTOR. Chemical Induction of Dimerization (CID) can be employed as a biological tool to spatially manipulate specific molecules, e.g., peptides and polypeptides, within cells at precise times to control a particular activity. Uses of CID include experimental investigations to elucidate cellular systems and therapeutic uses to regulate cell-based therapies. Exemplary uses include activation of cells used to promote engraftment, to treat diseases or conditions, or to control or modulate the activity of therapeutic cells that express chimeric antigen receptors or recombinant T cell receptors. Compounds of the disclosure may be used in the development of inducible systems or molecular switches to control cell signaling.

In certain embodiments, a compound or salt of any one of the Formulas or sub Formulas described herein (e.g., Formula (I), Formula (X), Formula (L), etc.) is administered to a subject in need thereof for the treatment and/or prevention of diabetic nephropathy, kidney-related complications of type 1 diabetes and type 2 diabetes, autosomal dominant polycystic kidney disease (ADPKD), autosomal recessive polycystic kidney disease (ARPKD), kidney diseases associated with cyst formation or cystogenesis, focal segmental glomerulosclerosis (FSGS) and other diseases associated with sclerosis of the kidney (glomerulopathy, IgA nephropathy, Lupus mesangial proliferative nephritis), laminopathies, age-related macular degeneration (AMD), diabetic macular edema, diabetic retinopathy, glaucoma, age related retinal disease, immune system senescence, respiratory tract infections, urinary tract infections, heart failure, osteoarthritis, pulmonary arterial hypertension (PAH), and/or chronic obstructive pulmonary disease (COPD).

In certain embodiments, a compound or salt of any one of the Formulas or sub Formulas described herein (e.g., Formula (I), Formula (X), Formula (L), etc.) is administered to a subject in need thereof for the treatment and/or prevention of Lymphangioleiomyomatosis (LAM) and/or polycystic kidney disease.

The use of rapamycin as a dimerizing agent is limited by side effects associated with mTOR inhibition. mTOR inhibition can lead to reductions in cell growth and proliferation as well as possible immunosuppression. In contrast, compounds of the present disclosure may present an advantage over rapamycin due to the high selectivity for mTOR1 over mTOR2. mTOR2 inhibition is associated with the negative side effects affiliated with rapamycin. As the presently described compounds are selective from mTOR1 and have minimal impact on mTOR2.

The term "multimerize" or multimerization refers to the dimerization of two peptides or polypeptides, or the multimerization of more than two peptides or polypeptides, for example, the dimerization of FKBP12 and the FRB domain of mTOR.

Inducible FKBP12/FRB-based multimerization systems can also be incorporated into chimeric antigen receptor (CAR) T cells which can be used, for example, in immunotherapy applications. One type of immunotherapy is adoptive cell transfer in which a subject's immune cells are collected and modified ex vivo, e.g., CAR-modified T cells, to provide for specific and targeted tumor cell killing when the modified cells are returned to the body. T Cells from a patient's blood may be extracted and genetically engineered to express CARs on the cell surface. The components of a CAR typically include an extracellular, antibody-derived single chain variable fragment (scFv), which specifically recognizes a target tumor cell antigen, and one or more multicellular T-cell-derived signaling sequences fused to the scFv. Binding of the scFv region to an antigen results in activation of the T cell through the signaling domains of the CAR. In certain embodiments, a compound of the disclosure may be administered to a cell to activate a CAR-T cell with an FKBP12/FRB-based multimerization system. In certain embodiments, the disclosure provides a method of activating the growth of a cell, e.g., CAR-T cell, containing an FKBP protein fusion and an FRB fusion protein by contacting the cell with a compound or salt of any one of the Formulas described herein (e.g., Formula (I), Formula (X), Formula (L), etc.).

In some instances, it is beneficial to increase the activity of a therapeutic cell. For example, co-stimulating polypeptides may be used to enhance the activation of T Cells, and of CAR-expressing T cells against antigens, which would increase the potency of the adoptive immunotherapy. These treatments are used, for example, to treat tumors for elimination, and to treat cancer and blood disorders, but these therapies may have negative side effects. Overzealous on-target effects, such as those directed at large tumor masses, can lead to cytokine storms associated with tumor lysis syndrome (TLS), cytokine release syndrome (CRS) or macrophage activation syndrome (MAS). In some instances of therapeutic cell-induced adverse events, there is a need for rapid and near complete elimination of the therapeutic cells. If there is a need to reduce the number of transferred CAR-T cells, an inducing ligand may be administered to the subject being treated, thereby inducing apoptosis specifically of the modified T cells. For example, multimeric versions of the ligand binding domains FRB and/or FKBP12 or variants thereof, such as those described in WO 2020/076738, fused to caspase proteins and expressed in a modified therapeutic cell can serve as scaffolds that permit the spontaneous dimerization and activation of the caspase units upon recruitment through the FRB and/or FKBP12 with a chemical inducing agent such as a compound or salt of any one of the Formulas described herein (e.g., Formula (I), Formula (X), Formula (L), etc.). In certain embodiments, the disclosure provides a method of inhibiting the growth of a cell containing an FKBP protein fusion and an FRB fusion protein by contacting the cell with a compound a compound or salt of any one of the Formulas described herein (e.g., Formula (I), Formula (X), Formula (L), etc.).

EXAMPLES

The following examples are offered to illustrate, but not to limit the claimed invention. It will be recognized that these preparation methods are illustrative and not limiting. Using the teaching provided herein, numerous other methods of producing the rapamycin analogs described herein will be available to one of skill in the art.

Where designated the absolute stereochemistry is assigned by analogy based upon on the analytical data for rapamycin (e.g., at C16 and C28 for the compounds described elsewhere herein).

Example 1: NMR Spectroscopy $^1$H NMR spectra were recorded at 400 MHz on a Bruker Avance III NMR spectrometer. Samples were prepared in deuterated chloroform ($CDCl_3$) or dimethylsulfoxide (DMSO-$d_6$) and the raw data were processed using the MNova NMR software.

Example 2: UPLC-MS Analysis

LCMS analysis was conducted on a Waters Acquity UPLC system consist of an Acquity i-Class Sample Manager-FL, Acquity i-Class Binary Solvent Manager and Acquity i-Class UPLC Column Manager. UV detection was achieved using an Acquity i-Class UPLC PDA detector (scanning from 210-400 nm), whereas mass detection was achieved using an Acquity QDa detector (mass scanning from 100-1250 Da; positive and negative modes simultaneously). A Waters Acquity UPLC CSH C18 Column (2.1×100 mm); particle size 1.7 μm was used to achieve the separation of the analytes.

Samples were prepared by dissolving (with or without sonication) into 1 mL of MeOH or MeCN. The resulting solutions were filtered through a 0.2 μm syringe filter before being submitted for analysis. All of the solvents (including formic acid) used were used as the HPLC grade.

Details of the analytical method used for this work are presented below.

Method 1: 0.1% v/v Formic acid in water [Eluent A]; 0.1% v/v Formic acid in MeCN [Eluent B]; Flow rate 0.8 mL/min; injection volume 2 μL and 1.5 min equilibration time between samples.

TABLE 1

| UPLC-MS parameters | | |
| --- | --- | --- |
| Time (min) | Eluent A (%) | Eluent B (%) |
| 0.00 | 50 | 50 |
| 10 | 0 | 100 |
| 10.10 | 50 | 50 |
| 12 | 5 | 95 |

Example 3: Prep HPLC

Method 1: Compounds were purified via reverse phase column chromatography on a Gemini NX C18 (30 mm×150 mm, 5 μm) cartridge eluting with a $H_2O$ (0.2% formic acid): MeCN gradient. Gradients were selected based on analytical separation.

Example 4: SFC

SFC was carried out using the following method:
Method 1: Greensep 2EP (19 mm×100 mm, 5 μm); $CO_2$/MeCN. Gradients were selected based on analytical separation.

Synthesis of Intermediates

Example 5: Synthesis of 2-[2-(2-methoxyethoxy)ethoxy]ethane-1-sulfonyl chloride

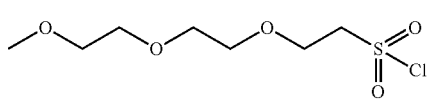

A stirred mixture of 1-bromo-2-[2-(2-methoxyethoxy)ethoxy]ethane (2.50 g, 11.0 mmol) and sodium sulfite [$Na_2SO_3$](1.39 g, 11.0 mmol) in $H_2O$ (13.4 mL) was heated at reflux for 18 h. The mixture was concentrated under reduced pressure, then taken up in ethanol (20 mL) and concentrated to dryness. A 1:1 mixture of TBME/hexanes (20 mL) was added, and again the mixture was concentrated to dryness. This final step was repeated to give sodium 2-[2-(2-methoxyethoxy)ethoxy]ethane-1-sulfonate as a solid (as a mixture with sodium bromide) which was used without analysis or purification. $POCl_3$ (6.8 mL, 74.1 mmol) was added, and the mixture heated at 70° C. for 4 h, then stirred at rt overnight. The mixture was added carefully to ice-$H_2O$ (50 mL), then the product extracted with EtOAc (3×50 mL). The combined organic extracts were dried ($Na_2SO_4$) and concentrated under reduced pressure to give 2-[2-(2-methoxyethoxy)ethoxy]ethane-1-sulfonyl chloride) (1.90 g, 70%) as an oil. $^1$H NMR (400 MHz, $CDCl_3$) δ 4.14-4.04 (m, 2H), 3.99 (t, J=6.0 Hz, 2H), 3.78-3.69 (m, 2H), 3.69-3.61 (m, 4H), 3.55 (dd, J=5.7, 3.4 Hz, 2H), 3.38 (s, 3H).

Example 6: Synthesis of N-tert-butyl-2-[2-(2-methoxyethoxy)ethoxy]ethane-1-sulfonamide

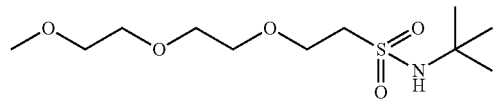 [SMILES: COCCOCCOCCS(=O)(=O)NC(C)(C)C]

To a solution of tert-butylamine (0.70 mL, 4.43 mmol) in THF (4.4 mL) at −20° C. was added 2-[2-(2-methoxyethoxy)ethoxy]ethane-1-sulfonyl chloride (0.84 g, 2.21 mmol) dropwise. The mixture was allowed to warm tort, and stirred overnight. The resulting precipitate was filtered, the filter cake was washed with THF (10 mL), and the combined filtrate was concentrated under reduced pressure. The residue was purified by silica gel column chromatography (20-100% EtOAc in hexanes; staining with acidic vanillin solution) to give N-tert-butyl-2-[2-(2-methoxyethoxy)ethoxy]ethane-1-sulfonamide (0.144 g, 23%) as an oil. $^1$H NMR (400 MHz, $CDCl_3$) δ 4.77 (s, 1H), 3.90 (t, J=5.8 Hz, 2H), 3.64 (d, J=11.5 Hz, 6H), 3.59-3.54 (m, 2H), 3.38 (s, 3H), 3.30 (t, J=5.8 Hz, 2H), 1.37 (s, 9H).

Example 7: Synthesis of 2-[2-(2-methoxyethoxy)ethoxy]ethane-1-sulfonamide

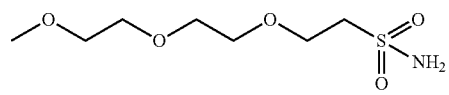

To N-tert-butyl-2-[2-(2-methoxyethoxy)ethoxy]ethane-1-sulfonamide (144 mg, 0.51 mmol) in DCM (2 mL) was added TFA (0.39 mL, 5.1 mmol) and the mixture stirred at rt for 18 h. The mixture was concentrated under reduced pressure, followed by azeotroping with toluene (2×10 mL) and DCM (10 mL) to give 2-[2-(2-methoxyethoxy)ethoxy]ethane-1-sulfonamide as an oil which still contained some TFA, but was used without further purification. $^1$H NMR (400 MHz, $CDCl_3$) δ 4.06-3.95 (m, 2H), 3.75-3.58 (m, 9H), 3.43 (s, 3H), 3.40-3.34 (m, 2H).

Example 8: Synthesis of 3-methanesulfonylpropyl trifluoromethanesulfonate

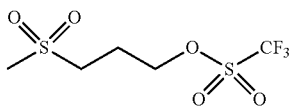

3-methanesulfonylpropan-1-ol (2.00 g, 14.5 mmol) and 2,6-dimethylpyridine (1.80 mL, 15.2 mmol) were dissolved in anhydrous DCM (25 mL) and cooled to −30° C. Trifluoromethanesulfonyl trifluoromethanesulfonate (2.3 mL, 13.9 mmol) was added dropwise and the mixture allowed to warm to −10° C. over 50 min. The mixture was quenched with $H_2O$ (25 mL), and the layers separated. The organic layer was washed with $H_2O$ (25 mL) and brine (25 mL), and the organic layer was dried ($Na_2SO_4$), filtered, and concentrated under reduced pressure to give 3-methanesulfonylpropyl trifluoromethanesulfonate (3.05 g, 78%) as an oil. $^1$H NMR (400 MHz, DMSO-$d_6$) δ 4.36 (t, J=6.0 Hz, 2H), 3.25-3.15 (m, 2H), 3.02 (s, 3H), 2.22-2.06 (m, 2H). $^{19}$F NMR (376 MHz, DMSO-$d_6$) δ−77.7 (s).

Example 9: Synthesis of 3-[(tert-butyldimethylsilyl)oxy]propyl trifluoromethanesulfonate

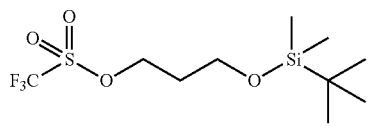 [SMILES: CC(C)(C)[Si](C)(C)OCCCOS(=O)(=O)C(F)(F)F]

To a solution of 3-[(tert-butyldimethylsilyl)oxy]propan-1-ol (5.21 g, 27.4 mmol) and DIPEA (6.0 mL, 34.2 mmol) in pentane (26 mL) at 0° C. was added triflic anhydride (5.1 mL, 30.5 mmol), and the reaction mixture stirred at this temperature for 2 h, then filtered through a plug of Celite. The residue was dissolved in hexane (20 mL), filtered through a plug of Celite, then concentrated under reduced pressure to give 3-[(tert-butyldimethylsilyl)oxy]propyl trifluoromethanesulfonate (7.56 g, 86%) as an oil.

Example 10: Synthesis of Intermediate A

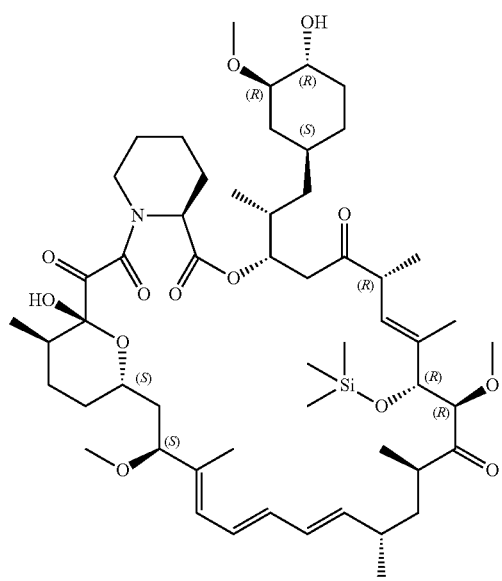

To a solution of rapamycin (4.00 g, 4.4 mmol) in EtOAc (120 mL) was added 1H-imidazole (1.30 g, 19.0 mmol), then the reaction mixture was cooled to 0° C. TMSCl (2.2 mL, 17.5 mmol) was added over 10 min, then the reaction stirred for 50 min. 0.5M $H_2SO_4$ (8.0 mL, 4.0 mmol) was added dropwise over 10 min, then the mixture stirred for 20 min. The mixture was washed sequentially with brine (120 mL), saturated sodium bicarbonate solution (120 mL), $H_2O$ (120 mL) and brine (120 mL). The organic layer was dried ($Na_2SO_4$), filtered, and concentrated under reduced pressure, and the resultant solid was purified by silica gel column chromatography (30-60% EtOAc in heptane) to give Intermediate A (3.74 g, 87%) as a solid. $^1$H NMR (400 MHz, DMSO-$d_6$) δ 6.52-6.32 (m, 2H), 6.31-6.07 (m, 3H), 5.48 (dd, J=12.6, 10.1 Hz, 1H), 5.21-4.86 (m, 3H), 4.67-4.56 (m, 1H), 4.17-3.95 (m, 3H), 3.70-3.60 (m, 1H), 3.54-3.41 (m, 1H), 3.36-3.33 (m, 3H), 3.31-3.26 (m, 1H), 3.24-3.14 (m, 4H), 3.13-2.98 (m, 4H), 2.87-2.78 (m, 1H), 2.76-2.66 (m, 1H), 2.49-2.42 (m, 1H), 2.41-2.30 (m, 1H), 2.29-2.18 (m, 1H), 2.17-2.08 (m, 1H), 2.07-2.02 (m, 1H), 1.97-1.73 (m, 6H), 1.72-1.47 (m, 11H), 1.46-1.22 (m, 6H), 1.16-0.94 (m, 7H), 0.93-0.69 (m, 13H), 0.64-0.54 (m, 1H), 0.00 (s, 9H). UPLC-MS (Method 1): rt 6.47 min, m/z (ES+) 1003.8 $[M+NH_4]^+$

Example 11: Synthesis of Intermediate B

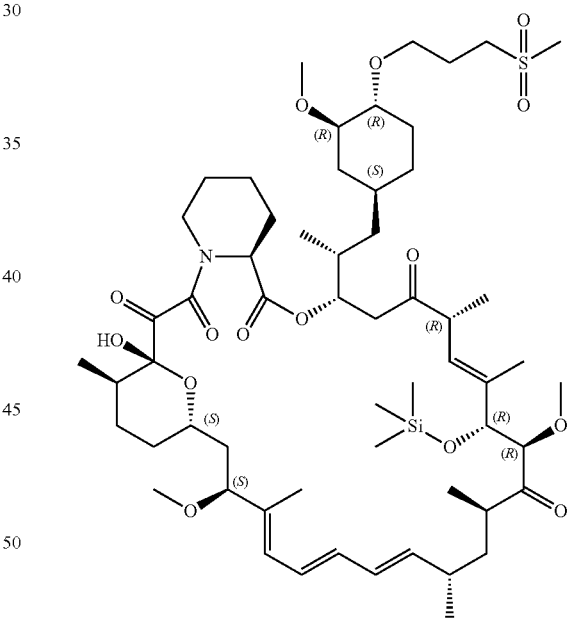

To a solution of Intermediate A (2.00 g, 2.0 mmol) and DIPEA (3.4 mL, 19.0 mmol) in anhydrous DCM (25 mL) was added a solution of 3-methanesulfonylpropyl trifluoromethanesulfonate (4.93 g, 18.3 mmol) in anhydrous DCM (7.2 mL) and the mixture was stirred for 18 h. Amberlyst basic resin (15 g) was added and stirring continued for 10 min, then the mixture filtered and the resin washed with DCM (50 mL). The combined organic layers were washed with $H_2O$ (2×50 mL) and brine (50 mL), then dried ($Na_2SO_4$), filtered, and concentrated under reduced pressure. The residue was purified by silica gel column chromatography (40-80% EtOAc in heptane) to give Intermediate B (1.15 g, 51%) as a solid. $^1$H NMR (400 MHz, DMSO-$d_6$) δ

6.52-6.33 (m, 2H), 6.29-6.08 (m, 3H), 5.48 (dd, J=12.6, 10.1 Hz, 1H), 5.19-4.90 (m, 3H), 4.16-3.96 (m, 3H), 3.69-3.53 (m, 3H), 3.52-3.44 (m, 1H), 3.34-3.30 (s, 4H) 3.22-2.93 (m, 14H), 2.77-2.65 (m, 1H), 2.49-2.42 (m, 1H), 2.41-2.30 (m, 1H), 2.29-2.18 (m, 1H), 2.17-2.09 (m, 1H), 2.08-2.02 (m, 1H), 2.00-1.74 (m, 8H), 1.73-1.47 (m, 11H), 1.46-1.22 (m, 6H), 1.16-0.95 (m, 7H), 0.94-0.71 (m, 13H), 0.69-0.57 (m, 1H), 0.00 (s, 9H). UPLC-MS (Method 1): rt 6.56 min, m/z (ES+) 1123.8 [M+NH$_4$]$^+$ Example 12: Synthesis of Intermediate C

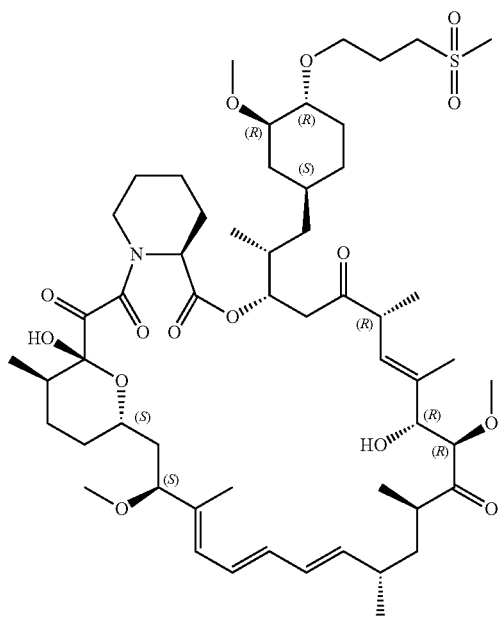

To a solution of Intermediate B (1.12 g, 1.00 mmol) in acetone (47 mL) at 0° C. was added 0.5M sulfuric acid (1.8 mL, 0.90 mmol) and the mixture stirred for 2 h. The mixture was diluted with EtOAc (120 mL) and washed sequentially with saturated aqueous sodium bicarbonate solution (2×80 mL), H$_2$O (2×80 mL) and brine (80 mL). The organic layer was dried (Na$_2$SO$_4$) then concentrated under reduced pressure and the residue purified by silica gel column chromatography (20-100% EtOAc in hexanes) to give Intermediate C [also known as Compound 59] (0.91 g, 88%) as a solid. $^1$H NMR (400 MHz, DMSO-d$_6$) δ 6.52-6.34 (m, 2H), 6.29-6.06 (m, 3H), 5.47 (dd, J=12.6, 9.6 Hz, 1H), 5.30-5.24 (m, 1H), 5.18-4.89 (m, 3H), 4.06-3.92 (m, 3H), 3.66-3.51 (m, 3H), 3.49-3.38 (m, 1H), 3.35-3.32 (m, 4H), 3.30-3.24 (m, 1H), 3.18-3.09 (m, 5H), 3.07-2.90 (m, 8H), 2.76-2.67 (m, 1H), 2.47-2.30 (m, 2H), 2.28-2.15 (m, 1H), 2.14-2.01 (m, 2H), 1.96-1.77 (m, 6H), 1.76-1.47 (m, 11H), 1.46-1.20 (m, 7H), 1.15-0.93 (m, 8H), 0.91-0.71 (m, 13H), 0.69-0.60 (m, 1H). UPLC-MS (Method 1): rt 4.02 min, m/z (ES+) 1051.7 [M+NH$_4$]$^+$ Example 13: Synthesis of Intermediate D

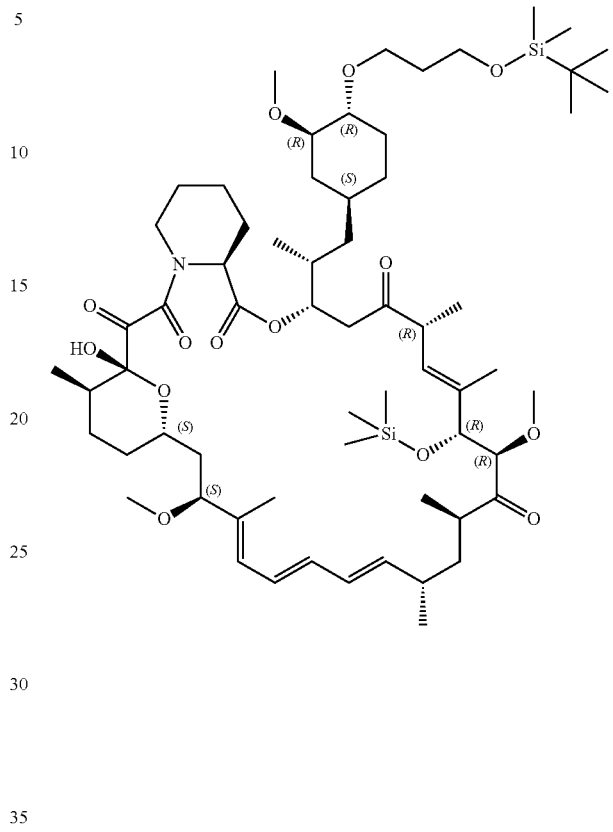

To a solution of Intermediate A (2.65 g, 2.69 mmol) in chlorobenzene (14 mL) was added DIPEA (2.1 mL, 11.8 mmol). The mixture was heated to 60° C., then a solution of 3-[(tert-butyldimethylsilyl)oxy]propyl trifluoromethanesulfonate) (1.73 g, 5.4 mmol) in chlorobenzene (1 mL) was added over 1 h. The mixture was maintained at 60° C. for 1 h then further 3-[(tert-butyldimethylsilyl)oxy]propyl trifluoromethanesulfonate) (1.73 g, 5.4 mmol) in chlorobenzene (1 mL) was added dropwise over 1 h. The mixture was stirred at 60° C. for 1 h then allowed to cool and stirred at rt for 18 h. Saturated aqueous sodium bicarbonate solution (5 mL) was added and the mixture was extracted with EtOAc (3×15 mL). The combined organic layers were each washed with brine (15 mL), then combined, dried (Na$_2$SO$_4$), concentrated under reduced pressure, and the residue was purified by silica gel column chromatography (EtOAc in hexanes, 10-100%) to yield Intermediate D (2.35 g, 72%) as a gum. $^1$H NMR (400 MHz, DMSO-d$_6$) δ 6.50-6.32 (m, 2H), 6.26-6.08 (m, 3H), 5.45 (dd, J=14.7, 9.5 Hz, 1H), 5.10 (d, J=10.4 Hz, 1H), 5.04-4.90 (m, 2H), 4.14-3.97 (m, 3H), 3.70-3.38 (m, 7H), 3.30-3.19 (m, 3H), 3.21-2.85 (m, 9H), 2.72-2.62 (m, 1H), 2.49-2.38 (m, 1H), 2.38-1.47 (m, 28H), 1.44-0.55 (m, 31H), 0.02 (s, 9H), −0.02 (s, 6H). UPLC-MS (Method 1): rt 9.73 min, m/z (ES+) 1176.0 [M+NH$_4$]$^+$

Example 14: Synthesis of Intermediate E

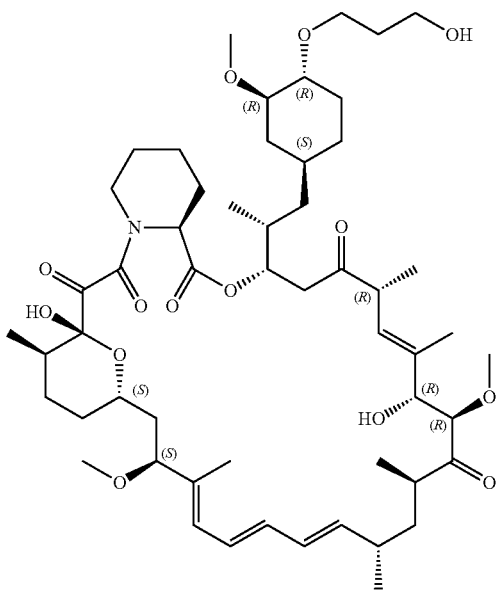

A solution of Intermediate D (2.34 g, 1.84 mmol) in 0.2 M HCl (2.0 mL, 0.40 mmol) and THF (18 mL) was stirred at rt for 7 h. Saturated aqueous sodium bicarbonate solution (5 mL) and brine (10 mL) were added and the mixture was extracted with EtOAc (3×10 mL). The combined organic layers were washed with brine (10 mL), dried ($Na_2SO_4$), concentrated under reduced pressure and the residue was purified by silica gel column chromatography (EtOAc in hexanes, 60-100%, then 4% MeOH in EtOAc) to give Intermediate E (1.54 g, 82%) as a gum. $^1$H NMR (400 MHz, DMSO-$d_6$) δ 6.49-6.34 (m, 2H), 6.28-6.04 (m, 3H), 5.46 (dd, J=14.7, 9.6 Hz, 1H), 5.36-5.19 (m, 1H), 5.14-5.05 (m, 1H), 5.03-4.90 (m, 2H), 4.38-4.22 (m, 1H), 4.09-3.90 (m, 4H), 3.68-3.38 (m, 5H), 3.30-3.20 (m, 1H), 3.19-2.91 (m, 10H), 2.80-2.64 (m, 1H), 2.47-1.77 (m, 12H), 1.77-1.45 (m, 12H), 1.45-0.90 (m, 15H), 0.90-0.57 (m, 14H). UPLC (Method 1): rt 3.93 min, m/z (ES+) 989.9 [M+NH$_4$]$^+$

Example 15: Synthesis of Intermediate F

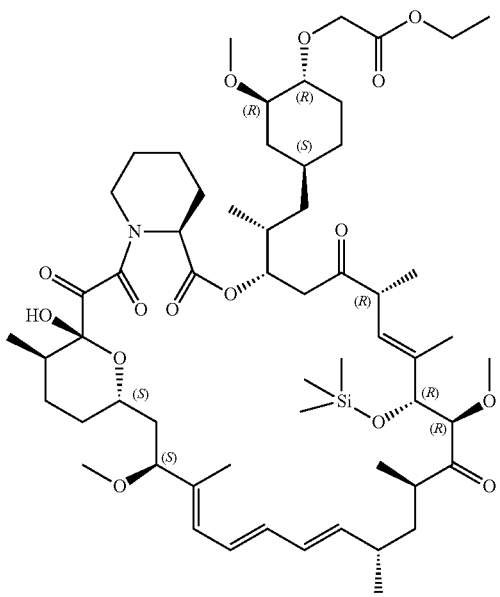

To a mixture of Intermediate A (1.00 g, 1.0 mmol) and dirhodium tetraacetate (19 mg, 0.04 mmol) in DCM (9.3 mL) was added ethyl 2-diazoacetate (87% solution in DCM, 0.94 mL, 7.76 mmol) in three portions over 2 h, and the mixture stirred for 18 h. The mixture was purified directly by silica gel column chromatography (0-50% EtOAc in hexanes) to give Intermediate F (0.82 g, 0.77 mmol, 76%) as an oil. $^1$H NMR (400 MHz, DMSO-$d_6$) δ 6.47 (d, J=1.6 Hz, 1H), 6.45-6.32 (m, 1H), 6.28-6.08 (m, 3H), 5.46 (dd, J=14.6, 9.5 Hz, 1H), 5.11 (d, J=10.3 Hz, 1H), 5.03-4.97 (m, 1H), 4.95 (d, J=5.3 Hz, 1H), 4.32-4.25 (m, 1H), 4.25-4.19 (m, 2H), 4.19-4.07 (m, 4H), 3.64 (d, J=12.3 Hz, 1H), 3.45 (d, J=14.2 Hz, 1H), 3.28-3.08 (m, 9H), 3.08-3.04 (m, 3H), 3.02 (s, 1H), 2.78-2.65 (m, 1H), 2.50-2.41 (m, 1H), 2.36 (d, J=12.7 Hz, 1H), 2.23 (s, 1H), 2.18-2.09 (m, 1H), 2.09-2.01 (m, 1H), 1.99-1.95 (m, 1H), 1.91-1.80 (m, 2H), 1.77 (s, 2H), 1.64 (s, 4H), 1.62-1.52 (m, 5H), 1.43-1.32 (m, 3H), 1.32-1.14 (m, 10H), 1.10-0.91 (m, 6H), 0.91-0.70 (m, 13H), 0.60 (q, J=11.9 Hz, 1H), -0.01 (s, 9H). UPLC-MS (Method 1): rt 7.34 min, m/z 1089.9 [M+NH$_4$]$^+$

Example 16: Synthesis of Intermediate G

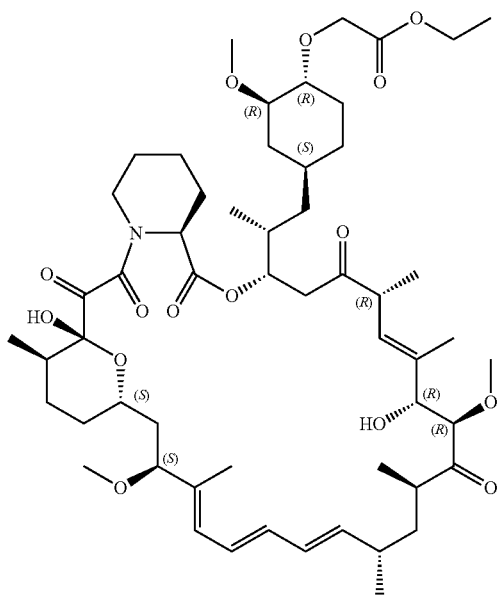

To a solution of Intermediate F (820 mg, 0.75 mmol) in acetone (35 mL) at 0° C. was added 0.5M sulfuric acid (1.3 mL, 0.67 mmol) and the mixture stirred for 1.5 h. The mixture was diluted with EtOAc (150 mL) and washed sequentially with saturated aqueous sodium bicarbonate solution (2×75 mL), H$_2$O (2×75 mL) and brine (75 mL). The organic layer was dried (Na$_2$SO$_4$), then concentrated under reduced pressure and the residue was purified by silica gel column chromatography (10-90% EtOAc in hexanes) to give Intermediate G (0.62 g, 83%) as a solid. $^1$H NMR (400 MHz, DMSO-$d_6$) δ 6.48-6.35 (m, 2H), 6.27-6.07 (m, 3H), 5.46 (dd, J=14.7, 9.6 Hz, 1H), 5.26 (dd, J=8.9, 4.6 Hz, 1H), 5.09 (d, J=10.1 Hz, 1H), 4.95 (dd, J=14.5, 7.0 Hz, 2H), 4.30-4.14 (m, 3H), 4.12-3.92 (m, 3H), 3.62 (d, J=11.4 Hz, 1H), 3.43 (d, J=14.1 Hz, 1H), 3.31-3.25 (m, 5H), 3.18-3.06 (m, 5H), 3.06-2.98 (m, 4H), 2.83-2.68 (m, 1H), 2.40 (d, J=8.2 Hz, 1H), 2.29-2.19 (m, 1H), 2.13-2.06 (m, 1H), 1.95 (s, 1H), 1.87-1.79 (m, 2H), 1.76-1.71 (m, 2H), 1.62 (s, 3H), 1.61-1.56 (m, 2H), 1.56-1.50 (m, 3H), 1.45-1.30 (m, 3H), 1.29-1.19 (m, 11H), 1.08-1.03 (m, 2H), 1.03-0.89 (m, 6H), 0.89-0.70 (m, 13H), 0.61 (q, J=12.1 Hz, 1H).

UPLC-MS (Method 1): rt 5.04 min, m/z 1017.9 $[M+NH_4]^+$

Example 17: Synthesis of Intermediate H

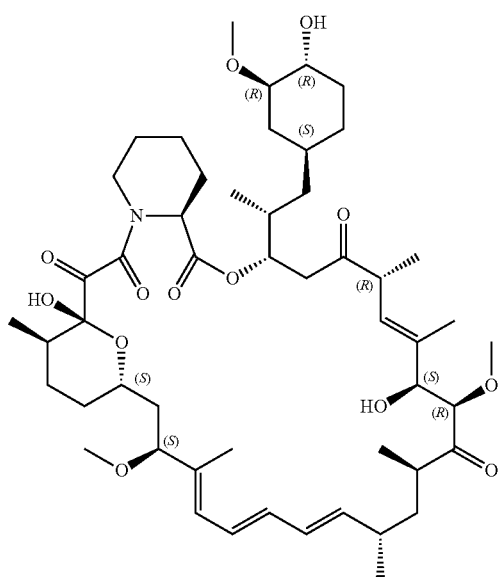

To a solution of rapamycin (197 mg, 0.22 mmol) in DCM (5.5 mL) in the dark was added titanium(IV) isopropoxide and the mixture stirred for 0.5 h, then poured onto a mixture of EtOAc (20 mL) and 1M HCl (15 mL). The layers were separated, and the aqueous layer extracted with EtOAc (20 mL). The combined organic layers were washed sequentially with saturated aqueous sodium bicarbonate solution (10 mL), water (10 mL) and brine (10 mL), then dried ($Na_2SO_4$) and concentrated under reduced pressure. TBME was added and the solution reconcentrated under reduced pressure to give Intermediate H (162 mg, 82%) as a foam. $^1$H NMR (400 MHz, DMSO-$d_6$) δ 6.50-6.33 (m, 2H), 6.34-6.07 (m, 3H), 5.45 (dd, J=14.3, 9.7 Hz, 1H), 5.10-4.88 (m, 4H), 4.68-4.52 (m, 1H), 4.08-3.94 (m, 2H), 3.90-3.78 (m, 1H), 3.62 (dd, J=11.3, 2.5 Hz, 1H), 3.45-2.96 (m, 12H), 2.86-2.62 (m, 3H), 2.46-2.10 (m, 3H), 2.10-1.80 (m, 2H), 1.94-1.36 (m, 17H), 1.42-0.91 (m, 13H), 0.90-0.70 (m, 13H), 0.64-0.47 (m, 1H). UPLC-MS (Method 1): rt 3.87 min, m/z 931.6 $[M+NH_4]^+$ Example 18: Synthesis of Intermediate I

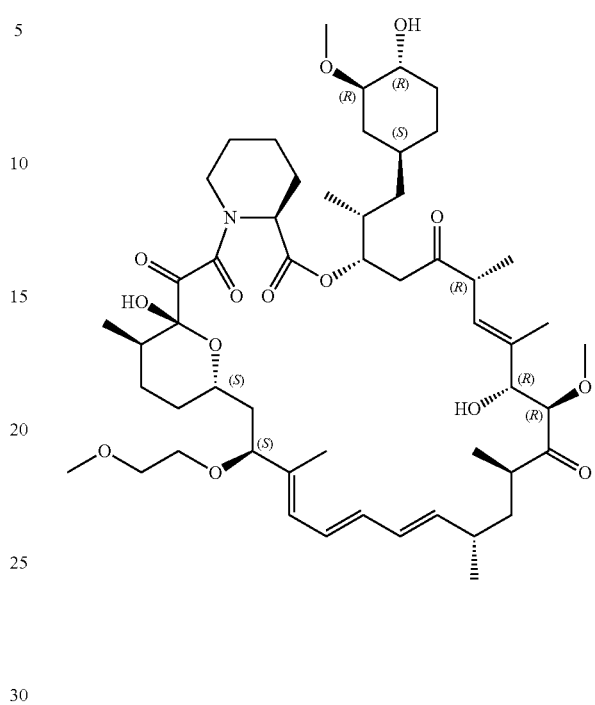

To a suspension of rapamycin (1.00 g, 1.09 mmol) in 2-methoxyethanol (2.0 mL) was added para-toluenesulfonic acid monohydrate (21 mg; 0.11 mmol). The reaction mixture was stirred in the dark for 20 h, then diluted with EtOAc (20 ml). Saturated sodium bicarbonate solution that had been adjusted to pH 7 with 30% $H_2SO_4$ in water (10 mL) was added, and the mixture stirred for 10 min. The layers were separated and the aqueous layer extracted with EtOAc (3×10 mL). The combined organics were washed with water (10 mL), passed through a plug of silica, and concentrated under reduced pressure. The residue was taken up in DME (20 mL) and concentrated under reduced pressure, then the residue was recrystallised from DME to give Intermediate I (0.330 g, 32%) as white crystals. $^1$H NMR (400 MHz, DMSO-$d_6$) δ 6.47 (d, J=1.6 Hz, 1H), 6.45-6.34 (m, 1H), 6.27-6.07 (m, 3H), 5.47 (dd, J=14.7, 9.6 Hz, 1H), 5.27 (d, J=4.5 Hz, 1H), 5.13-5.06 (m, 1H), 4.96 (dd, J=17.7, 7.3 Hz, 2H), 4.60 (d, J=4.5 Hz, 1H), 4.10-3.99 (m, 2H), 3.98-3.93 (m, 1H), 3.83-3.73 (m, 1H), 3.50-3.35 (m, 4H), 3.31-3.11 (m, 12H), 2.89-2.70 (m, 3H), 2.44-2.33 (m, 2H), 2.30-2.16 (m, 1H), 2.16-1.99 (m, 2H), 1.95-1.81 (m, 3H), 1.77-1.72 (m, 3H), 1.71-1.60 (m, 6H), 1.60-1.55 (m, 2H), 1.55-1.51 (m, 2H), 1.47-1.36 (m, 2H), 1.33-1.14 (m, 5H), 1.09-0.91 (m, 6H), 0.90-0.71 (m, 14H), 0.60 (q, J=12.0 Hz, 1H). UPLC-MS (Method 1): rt 4.28 min, m/z 975.8 $[M+NH_4]^+$.

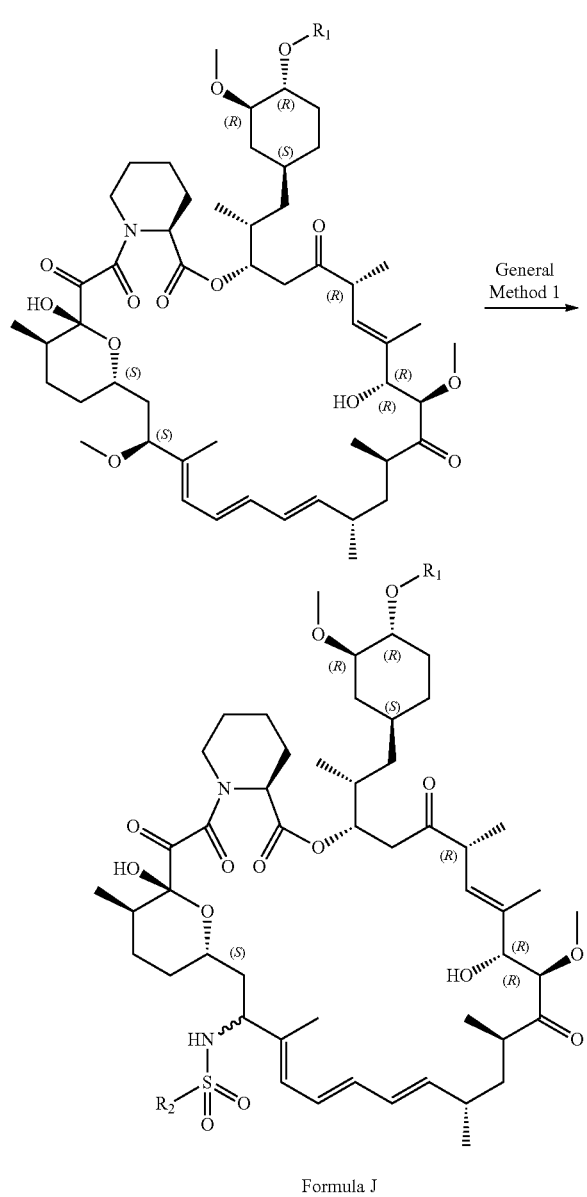

Formula J

General Method 1 (C16 Sulfonamides)

Example 19: Synthesis of Compounds 8 and 9

To a stirred suspension of rapamycin (600 mg; 0.66 mmol) and 2-(2-methoxyethoxy)ethane-1-sulfonamide (1293 mg; 6.6 mmol) in DCM (6.6 mL) was added para-toluenesulfonic acid monohydrate (12.5 mg; 0.066 mmol). The reaction mixture was stirred at room temperature for 2 h. Amberlyst A21 free base (50 mg) was added, and after stirring for 5 min was filtered and washed with DCM (10 mL). The combined filtrate and washings were washed with water (5×10 mL), then dried ($Na_2SO_4$), filtered, and concentrated under reduced pressure. The residue was purified by silica gel column chromatography (EtOAc in hexanes, 20-100%), then by HPLC (Method 1). Isomers were separated by SFC chromatography to give Compound 8 (18.0 mg, 2.6%) and Compound 9 (16.0 mg, 2.3%) as flocculent solids.

General Method 2 (C16 Sulfonamides)

Example 20: Synthesis of Compound 25

To a solution of rapamycin (220 mg, 0.24 mmol) and 2-methoxyethane-1-sulfonamide (109 mg, 0.48 mmol) in DCM (4.4 mL) at rt was added a 0.1M solution of $FeCl_3$ in $Et_2O$ (0.24 mL, 0.024 mmol) and the mixture stirred for 1 h. Amberlyst A21 free base (20 mg) was added, and after stirring for 5 min was filtered and washed with DCM (10 mL). The combined DCM fractions were washed with water (3×20 mL), then dried ($Na_2SO_4$) and concentrated under reduced pressure. The residue was purified by silica gel column chromatography (20-100% EtOAc in hexanes), then by HPLC (Method 1) to give Compound 25 (5.5 mg, 2.1%) as a flocculent solid.

TABLE 2

Compounds of Formula J with corresponding $R^1$ and $R^2$ substituents. Compounds of Table 2 were synthesized using methods described herein, e.g., the procedures of Examples 5-20, and employing the appropriate reagents.

| Compound | $R^1$ | $R^2$ | C16 stereochemical configuration R/S | SFC Purification (Yes/No) | RT/ mins | t/h (reaction time) |
|---|---|---|---|---|---|---|
| 1 | H | (cyclopropylmethyl) | Mix[p] | N | 2.28 | 1 |
| 2[b] | (propyl-OH) | (-CH2CH2OCH2CH2OCH3) | S | N | 2.38 | 2 |

TABLE 2-continued

Compounds of Formula J with corresponding $R^1$ and $R^2$ substituents. Compounds of Table 2 were synthesized using methods described herein, e.g., the procedures of Examples 5-20, and employing the appropriate reagents.

| Compound | $R^1$ | $R^2$ | C16 stereochemical configuration R/S | SFC Purification (Yes/No) | RT/ mins | t/h (reaction time) |
|---|---|---|---|---|---|---|
| 3[b] | ~~~OH (butanol chain) | ~~~O~O~ | R | N | 2.40 | 2 |
| 4 | ~~~S(=O)(=O)CH₃ (butyl sulfone) | ~~~O~O~ | Mix[p] | N | 2.43 | 1 |
| 5 | H | ~~~CH₂-tetrahydropyran | R | Y | 2.10 | 2 |
| 6 | H | ~~~CH₂-tetrahydropyran | S | Y | 2.10 | 2 |
| 7[a] | ~~~OH (propanol chain) | ~~~O~O~ | Mix[p] | N | 2.24 | 1 |
| 8 | H | ~~~O~O~ | R | Y | 2.18 | 2 |
| 9 | H | ~~~O~O~ | S | Y | 2.17 | 2 |
| 10[b,d] | ~~~OH (propanol chain) | ~~~cyclopropyl | R | Y | 2.25 | 2 |
| 11[b,d] | ~~~OH (propanol chain) | ~~~cyclopropyl | S | Y | 2.26 | 2 |
| 12[a,d] | ~~~C(=O)OEt | ~~~cyclopropyl | S | N | 3.54 | 2 |
| 13 | ~~~OH (butanol chain) | ~~~O~ (methoxyethyl) | Mix[p] | N | 2.27 | 1 |
| 14 | ~~~C(=O)OEt | ~~~O~ (methoxyethyl) | Mix[p] | N | 3.29 | 1 |

TABLE 2-continued

Compounds of Formula J with corresponding $R^1$ and $R^2$ substituents. Compounds of Table 2 were synthesized using methods described herein, e.g., the procedures of Examples 5-20, and employing the appropriate reagents.

| Compound | $R^1$ | $R^2$ | C16 stereochemical configuration R/S | SFC Purification (Yes/No) | RT/ mins | t/h (reaction time) |
|---|---|---|---|---|---|---|
| 15 | 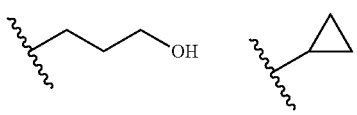 |  | Mix[p] | N | 2.41 | 1 |
| 16 | 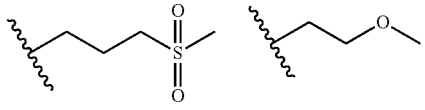 | 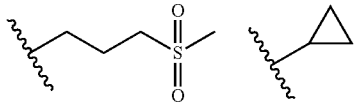 | Mix[p] | N | 2.13 | 1 |
| 17 | 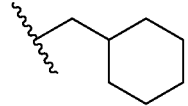 [SMILES: *CC1CCCCC1] | 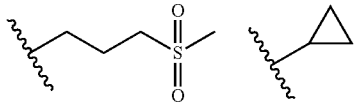 | Mix[p] | N | 2.42 | 2.5 |
| 18[b,d] | 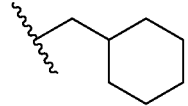 [SMILES: *CC1CCCCC1] |  | Mix[p] | N | 2.76 | 2 |
| 19 | H | 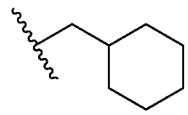 | R | N | 4.04 | 0.2 |
| 20[e] | H | 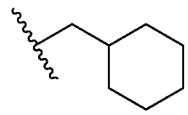 | S[g] | N | 4.02 | 0.2 |
| 21[c] | H | 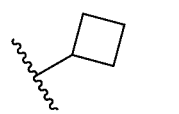 [SMILES: *C1CCC1] | Mix[p] | N | 3.19 | 2 |
| 22[e] | H | 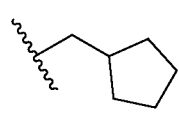 [SMILES: *CC1CCCC1] | R | N | 3.55 | 0.3 |
| 23[e] | H | 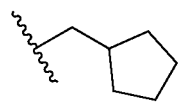 [SMILES: *CC1CCCC1] | S | N | 3.60 | 0.3 |
| 24 | H | 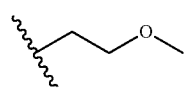 [SMILES: *CCOC] | Mix[p] | N | 2.15 | 1 |
| 25[f] | H | 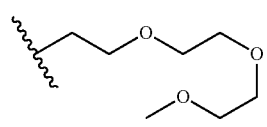 [SMILES: *CCOCCOCCOC] | S | N | 2.12 | 1 |

TABLE 3

| | Characterization of compounds of Table 2 | | |
|---|---|---|---|
| Compound | NMR $^1$H NMR (400 MHz, DMSO-$d_6$)$^h$ | Yield/% | [M + NH$_4$]$^+$ |
| 1 | δ 7.69-7.26 (m, 1H), 6.57-6.03 (m, 5H), 5.65-5.48 (m, 1H), 5.35-5.04 (m, 3H), 5.03-4.92 (m, 1H), 4.64 (t, J = 6.5 Hz, 1H), 4.11-3.73 (m, 4H), 3.65-3.39 (m, 2H), 3.34-3.07 (m, 9H), 2.87-2.60 (m, 3H), 2.46-1.95 (m, 8H), 1.84-1.47 (m, 12H), 1.46-1.13 (m, 7H), 1.12-0.67 (m, 18H), 0.66-0.53 (m, 1H). 75 out of 82 protons observed. | 5.1 | 1020.7 |
| 2 $^b$ | δ 7.54 (d, J = 9.3 Hz, 1H), 6.55-6.00 (m, 5H), 5.48 (dd, J = 15.0, 9.2 Hz, 1H), 5.33-5.15 (m, 1H), 5.07 (d, J = 10.1 Hz, 1H), 4.98-4.91 (m, 2H), 4.38-4.14 (m, 2H), 4.11-3.79 (m, 4H), 3.76-3.39 (m, 14H), 3.29-2.89 (m, 10H), 2.86-2.62 (m, 2H), 2.49-2.33 (m, 1H), 2.31-1.81 (m, 8H), 1.81-1.18 (m, 22H), 1.17-0.59 (m, 20H). | 2.4 | 1140.9 |
| 3 $^b$ | δ 7.37 (d, J = 8.0 Hz, 1H), 6.46 (s, 1H), 6.46-6.31 (m, 1H), 6.23-6.03 (m, 3H), 5.60 (dd, J = 14.2, 8.6 Hz, 1H), 5.28-5.18 (m, 2H), 5.16-5.06 (m, 1H), 5.01-4.91 (m, 1H), 4.37-4.22 (m, 2H), 4.09-3.84 (m, 3H), 3.79-3.61 (m, 4H), 3.59-3.38 (m, 10H), 3.29-3.07 (m, 8H), 3.08-2.89 (m, 3H), 2.86-2.63 (m, 2H), 2.48-2.36 (m, 1H), 2.35-1.81 (m, 8H), 1.81-1.16 (m, 22H), 1.19-0.88 (m, 9H), 0.90-0.52 (m, 11H). | 1.7 | 1140.9 |
| 4 | δ 7.54-7.34 (m, 1H), 6.71-5.99 (m, 5H), 5.64-5.44 (m, 1H), 5.42-4.90 (m, 4H), 4.32-3.79 (m, 3H), 3.76-3.38 (m, 8H), 3.37-3.22 (m, 11H), 3.21-3.09 (m, 5H), 3.08-2.88 (m, 5H), 2.87-2.63 (m, 2H), 2.47-2.28 (m, 2H), 2.27-1.80 (m, 8H), 1.79-1.48 (m, 11H), 1.47-0.72 (m, 21H), 0.71-0.60 (m, 1H). 88H out of 96 protons observed. | 2.6 | 1202.8 |
| 5 | δ 7.42 (d, J = 8.2 Hz, 1H), 6.58-6.01 (m, 5H), 5.58 (dd, J = 14.2, 8.6 Hz, 1H), 5.30-4.86 (m, 4H), 4.67-4.51 (m, 1H), 4.16-3.63 (m, 6H), 3.61-3.37 (m, 2H), 3.36-3.06 (m, 9H), 3.04-2.65 (m, 6H), 2.45-1.86 (m, 7H), 1.82-1.45 (m, 14H), 1.46-1.09 (m, 8H), 1.08-0.67 (m, 14H), 0.67-0.46 (m, 1H). 79 out of 88 protons observed. | 5.8 | 1078.8 |
| 6 | δ 7.55 (d, J = 9.4 Hz, 1H), 6.54-5.71 (m, 5H), 5.41 (dd, J = 14.9, 9.5 Hz, 1H), 5.19 (d, J = 4.6 Hz, 1H), 5.00 (d, J = 10.1 Hz, 1H), 4.88 (m, 1H), 4.67-4.51 (m, 1H), 4.27-3.64 (m, 6H), 3.47-3.31 (m, 1H), 3.28-3.00 (m, 10H), 2.85-2.53 (m, 6H), 2.39-2.22 (m, 1H), 2.22-2.07 (m, 1H), 2.05-1.78 (m, 5H), 1.76-1.39 (m, 12H), 1.39-1.06 (m, 7H), 1.03-0.62 (m, 14H), 0.53 (q, J = 11.9 Hz, 1H). 75 out of 88 protons observed. | 4.2 | 1078.9 |
| 7 $^a$ | δ 7.64-7.35 (m, 1H), 6.57-5.97 (m, 4H), 5.65-5.36 (m, 1H), 5.34-4.99 (m, 2H), 4.99-4.85 (m, 1H), 4.60-4.17 (m, 1H), 4.17-3.78 (m, 2H), 3.78-3.53 (m, 3H), 3.53-3.39 (m, 9H), 3.33-3.26 (m, 7H), 3.25-3.20 (m, 4H), 3.20-3.10 (m, 4H), 3.07-2.90 (m, 3H), 2.83-2.68 (m, 1H), 2.46-2.34 (m, 1H), 2.31-2.10 (m, 2H), 2.10-1.45 (m, 19H), 1.45-1.17 (m, 6H), 1.17-0.70 (m, 20H), 0.65 (q, J = 12.7 Hz, 1H). | 10.1 | 1126.8 |
| 8 | δ 7.39 (d, J = 8.1 Hz, 1H), 6.57-5.99 (m, 5H), 5.60 (dd, J = 14.1, 8.7 Hz, 1H), 5.33-4.89 (m, 4H), 4.72-4.58 (m, 1H), 4.11-3.81 (m, 4H), 3.79-3.62 (m, 3H), 3.56-3.38 (m, 5H), 3.32-3.22 (m, 6H), 3.21-3.10 (m, 5H), 3.07-2.95 (m, 1H), 2.91-2.64 (m, 3H), 2.45-1.84 (m, 6H), 1.83-1.13 (m, 19H), 1.13-0.69 (m, 18H), 0.66-0.47 (m, 1H). 83 of 88 protons observed. | 2.3 | 1082.8 |
| 9 | δ 7.56 (d, J = 9.3 Hz, 1H), 6.65-5.79 (m, 5H), 5.62-4.82 (m, 5H), 4.73-4.55 (m, 1H), 4.30-3.77 (m, 4H), 3.75-3.58 (m, 3H), 3.56-3.08 (m, 16H), 3.06-2.62 (m, 4H), 2.44-2.28 (m, 1H), 2.27-2.16 (m, 1H), 2.12-1.84 (m, 4H), 1.82-1.11 (m, 17H), 1.11-0.69 (m, 14H), 0.61 (q, J = 11.9 Hz, 1H). 77 out of 88 protons observed. | 2.6 | 1082.8 |

TABLE 3-continued

Characterization of compounds of Table 2

| Compound | NMR $^1$H NMR (400 MHz, DMSO-d$_6$)$^h$ | Yield/% | [M + NH$_4$]$^+$ |
|---|---|---|---|
| 10 $^{b, d}$ | δ 7.37-7.28 (m, 1H), 6.48-6.03 (m, 5H), 5.71-5.55 (m, 1H), 5.32-4.90 (m, 4H), 4.49-4.39 (m, 1H), 4.10-3.89 (m, 3H), 3.85-3.74 (m, 1H), 3.62-3.40 (m, 6H), 3.31-2.92 (m, 9H), 2.84-2.65 (m, 2H), 2.49-2.37 (m, 1H), 2.13-1.86 (m, 6H), 1.76-1.23 (m, 21H), 1.15-0.74 (m, 24H), 0.69-0.57 (m, 1H). | 2.2 | 1064.8 |
| 11 $^{b, d}$ | δ 7.56 (d, J = 7.5 Hz, 1H), 6.52-6.00 (m, 5H), 5.55-5.43 (m, 1H), 5.26 (d, J = 3.5 Hz, 1H), 5.21-4.89 (m, 3H), 4.51-4.40 (m, 1H), 4.08-3.76 (m, 4H), 3.67-3.39 (m, 6H), 3.36-3.33 (m, 3H), 3.31-3.22 (m, 1H), 3.18-2.93 (m, 5H), 2.82-2.64 (m, 2H), 2.49-2.34 (m, 2H), 2.27-2.15 (m, 2H), 2.13-1.82 (m, 6H), 1.80-1.46 (m, 12H), 1.45-0.71 (m, 30H), 0.70-0.59 (m, 1H). | 1.5 | 1064.8 |
| 12 $^{a, d}$ | δ 7.53 (d, J = 9.5 Hz, 1H), 6.53-5.98 (m, 5H), 5.67-4.83 (m, 5H), 4.38-3.63 (m, 9H), 3.50-3.36 (m, 1H), 3.31-3.25 (m, 4H), 3.23-2.90 (m, 6H), 2.93-2.62 (m, 1H), 2.48-1.82 (m, 9H), 1.77-1.49 (m, 13H), 1.48-1.13 (m, 8H), 1.13-0.71 (m, 25H), 0.63 (q, J = 11.9 Hz, 1H). | 8.0 | 1106.8 |
| 13 | δ 7.63-7.43 (m, 1H), 6.52-6.01 (m, 5H), 5.64-5.47 (m, 1H), 5.39-5.02 (m, 3H), 4.95 (t, J = 5.9 Hz, 1H), 4.34-4.25 (m, 2H), 4.10-3.68 (m, 4H), 3.68-3.36 (m, 8H), 3.30 (s, 3H), 3.25-3.07 (m, 8H), 3.06-2.86 (m, 2H), 2.86-2.64 (m, 1H), 2.48-2.34 (m, 1H), 2.34-1.81 (m, 8H), 1.81-1.48 (m, 17H), 1.47-1.20 (m, 5H), 1.15-0.56 (m, 20H). | 16.2 | 1096.8 |
| 14 | δ 7.67-7.33 (m, 1H), 6.52-6.44 (m, 1H), 6.40-5.97 (m, 4H), 5.67-5.43 (m, 1H), 5.29-5.22 (m, 1H), 5.06 (d, J = 10.2 Hz, 1H), 5.00-4.87 (m, 2H), 4.24-4.17 (m, 3H), 4.12-4.03 (m, 2H), 4.03-3.89 (m, 1H), 3.84 (d, J = 5.3 Hz, 1H), 3.68-3.50 (m, 3H), 3.48-3.42 (m, 1H), 3.30-3.25 (m, 4H), 3.24-2.92 (m, 11H), 2.85-2.62 (m, 1H), 2.45-2.12 (m, 2H), 2.10-1.80 (m, 3H), 1.79-1.46 (m, 15H), 1.45-1.12 (m, 8H), 1.10-0.74 (m, 16H), 0.59 (q, J = 12.2 Hz, 1H). 83 out of 90 protons observed. | 12.9 | 1124.8 |
| 15 | δ 7.56-7.31 (m, 1H), 6.55-5.99 (m, 5H), 5.62-5.44 (m, 1H), 5.33-5.15 (m, 2H), 5.12-5.02 (m, 1H), 5.02-4.91 (m, 1H), 4.37-4.21 (m, 1H), 4.10-3.70 (m, 4H), 3.64-3.37 (m, 6H), 3.32-3.21 (m, 4H), 3.21-3.07 (m, 4H), 3.07-2.90 (m, 2H), 2.82-2.64 (m, 1H), 2.48-2.34 (m, 1H), 2.34-1.81 (m, 8H), 1.81-1.17 (m, 20H), 1.17-0.57 (m, 26H). | 11.8 | 1078.9 |
| 16 | δ 7.71-7.46 (m, 1H), 6.60-6.49 (m, 1H), 6.42-6.03 (m, 4H), 5.63-5.39 (m, 2H), 5.38-4.89 (m, 5H), 4.54-4.46 (m, 1H), 4.12-3.77 (m, 4H), 3.76-3.66 (m, 1H), 3.65-3.40 (m, 7H), 3.34-2.92 (m, 13H), 2.82-2.65 (m, 2H), 2.47-2.31 (m, 2H), 2.30-1.85 (m, 7H), 1.82-1.20 (m, 17H), 1.18-0.71 (m, 18H), 0.68-0.59 (m, 1H). 86 out of 88 protons observed. | 3.6 | 1082.9 |
| 17 | δ 7.70-7.41 (m, 1H), 6.57-6.48 (m, 1H), 6.47-6.05 (m, 4H), 5.64-5.01 (m, 4H), 4.95 (d, J = 5.9 Hz, 1H), 4.12-3.67 (m, 4H), 3.68-3.40 (m, 7H), 3.32-2.91 (m, 18H), 2.84-2.62 (m, 1H), 2.47-2.30 (m, 2H), 2.27-2.10 (m, 2H), 2.12-1.82 (m, 7H), 1.78-1.46 (m, 12H), 1.47-1.17 (m, 4H), 1.17-0.89 (m, 11H), 0.89-0.70 (m, 13H), 0.64 (q, J = 12.4 Hz, 1H). | 10.5 | 1158.9 |
| 18 $^{b, d}$ | δ 7.60-7.37 (m, 1H), 6.60-6.04 (m, 5H), 5.64-5.38 (m, 1H), 5.32-4.90 (m, 4H), 4.11-3.72 (m, 4H), 3.66-3.39 (m, 4H), 3.33-2.91 (m, 14H), 2.84-2.63 (m, 2H), 2.47-1.81 (m, 10H), 1.78-1.48 (m, 11H), 1.47-1.19 (m, 5H), 1.18-0.69 (m, 19H), 0.68-0.54 (m, 1H). 81 out of 90 protons observed. | 5.7 | 1140.7 |

TABLE 3-continued

Characterization of compounds of Table 2

| Compound | NMR $^1$H NMR (400 MHz, DMSO-$d_6$)$^h$ | Yield/% | [M + NH$_4$]$^+$ |
|---|---|---|---|
| 19 | δ 7.41 (d, J = 8.2 Hz, 1H), 6.52-5.98 (m, 5H), 5.62-4.86 (m, 5H), 4.62 (d, J = 4.4 Hz, 1H), 4.19-3.47 (m, 7H), 3.31-2.60 (m, 11H), 2.41-1.84 (m, 8H), 1.81-1.45 (m, 20H), 1.45-0.65 (m, 31H), 0.56 (q, J = 12.6 Hz, 1H). | 3.0 | 1076.9 |
| 20 $^e$ | δ 7.62 (d, J = 9.4 Hz, 1H), 6.59-6.00 (m, 5H), 5.54-5.40 (m, 1H), 5.29 (dd, J = 8.9, 4.4 Hz, 1H), 5.06 (d, J = 10.2 Hz, 1H), 5.01-4.90 (m, 2H), 4.68-4.60 (m, 1H), 4.12-3.76 (m, 4H), 3.73-3.42 (m, 1H), 3.35-3.08 (m, 10H), 3.04-2.57 (m, 4H), 2.46-1.84 (m, 6H), 1.83-1.10 (m, 17H), 1.10-0.70 (m, 21H), 0.60 (q, J = 12.1 Hz, 1H). 76 out of 90 protons observed. | 20.0 | 1076.9 |
| 21 $^e$ | δ 7.62-7.22 (m, 1H), 6.57-5.96 (m, 5H), 5.67-5.01 (m, 4H), 4.98-4.93 (m, 2H), 4.71-4.64 (m, 1H), 4.11-3.62 (m, 4H), 3.31-3.06 (m, 9H), 3.05-2.60 (m, 4H), 2.48-2.15 (m, 3H), 2.12-1.08 (m, 29H), 1.08-0.69 (m, 21H), 0.68-0.50 (m, 1H). 84 out of 86 protons observed. | 8.3 | 1048.9 |
| 22 $^e$ | δ 7.45-7.26 (m, 1H), 6.75-5.99 (m, 5H), 5.76-5.53 (m, 1H), 5.35-4.90 (m, 4H), 4.69-4.55 (m, 1H), 4.14-3.51 (m, 5H), 3.33-3.06 (m, 8H), 3.05-2.88 (m, 2H), 2.87-2.63 (m, 3H), 2.46-1.97 (m, 6H), 1.95-1.34 (m, 23H), 1.33-1.04 (m, 8H), 1.03-0.66 (m, 14H), 0.66-0.49 (m, 1H). 82 out of 88 protons observed. | 6.8 | 1063.0 |
| 23 $^e$ | δ 7.62-7.30 (m, 1H), 6.73-6.05 (m, 5H), 5.54-5.44 (m, 1H), 5.41-5.17 (m, 2H), 5.16-5.00 (m, 1H), 4.98-4.89 (m, 1H), 4.69-4.55 (m, 1H), 4.14-3.65 (m, 4H), 3.52-3.39 (m, 1H), 3.34-3.08 (m, 9H), 2.99-2.66 (m, 4H), 2.46-2.32 (m, 2H), 2.25-1.81 (m, 8H), 1.80-1.35 (m, 19H), 1.34-0.68 (m, 23H), 0.66-0.54 (m, 1H). 83 out of 88 protons observed. | 11.1 | 1062.9 |
| 24 | δ 7.73-7.44 (m, 1H), 6.60-5.96 (m, 5H), 5.64-5.03 (m, 4H), 5.00-4.92 (m, 1H), 4.68-4.57 (m, 1H), 4.12-3.67 (m, 4H), 3.65-3.47 (m, 3H), 3.45-3.37 (m, 1H), 3.34-3.06 (m, 11H), 3.04-2.92 (m, 1H), 2.91-2.63 (m, 3H), 2.46-2.28 (m, 7H), 1.81-1.46 (m, 12H), 1.45-1.12 (m, 7H), 1.10-0.70 (m, 15H), 0.66-0.52 (m, 1H). 77 out of 84 protons observed. | 10.9 | 1038.9 |
| 25 $^f$ | δ 7.58 (d, J = 9.3 Hz, 1H), 6.61-5.97 (m, 5H), 5.57-5.36 (m, 1H), 5.31-5.22 (m, 1H), 5.08 (d, J = 10.0 Hz, 1H), 5.01-4.86 (m, 2H), 4.60 (d, J = 4.8 Hz, 1H), 4.27-3.91 (m, 2H), 3.86 (d, J = 5.6 Hz, 1H), 3.65 (q, J = 6.1 Hz, 3H), 3.55-3.38 (m, 11H), 3.33-3.10 (m, 24H), 3.05-2.94 (m, 1H), 2.90-2.64 (m, 3H), 2.45-2.30 (m, 1H), 2.27-1.84 (m, 5H), 1.81-1.03 (m, 13H), 1.01-0.68 (m, 15H), 0.61 (q, J = 11.9 Hz, 1H). | 2.1 | 1126.7 |

For Table 2 and Table 3: [a]Addition carried out at −40° C., then allowed to warm to RT; [b]Addition carried out at 0° C. then allowed to warm to RT; [c]MeCN solvent; [d]40 equivalents of sulfonamide and 5 equivalents of pTSA used; [e]Isomers separable by normal phase column chromatography; [f]Prepared following General Method 2; [g]6:4 C16 S:R isomeric ratio; [h]The NMR characterization data shown for the compounds correspond only to the major equilibrium form observed in the deuterated solvent conditions; [P]Mix refers to a mixture of diastereomers of an undetermined amount.

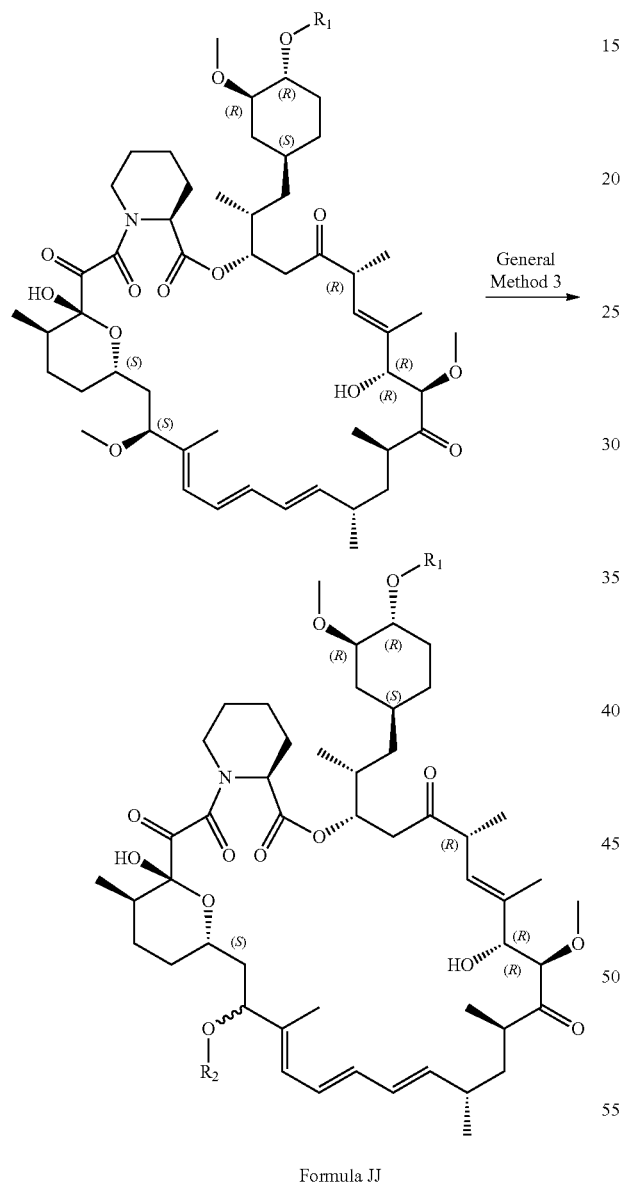

Formula JJ

General Method 3 (C-16 Ethers)

Example 21: Synthesis of Compounds 50 and 51

To a stirred suspension of Intermediate G (600 mg; 0.60 mmol) and cyclopropylmethanol (1.76 g; 24.4 mmol) in DCM (24 mL) at −40° C. was added para-toluenesulfonic acid monohydrate (570 mg; 3.00 mmol). The reaction mixture was allowed to warm to 0° C., and stirred at this temperature for 0.5 h. Amberlyst A21 free base (2.7 g) was added, and after stirring for 5 min, the mixture was filtered and washed with DCM (100 mL). The combined filtrate and washings were washed with water (5×25 mL), then dried ($Na_2SO_4$), filtered, and concentrated under reduced pressure. The residue was purified by silica gel column chromatography (EtOAc in hexanes, 20-100%), then by HPLC (Method 1) to give Compound 50 (41.5 mg, 6.7%) and Compound 51 (14.0 mg, 2.2%) as flocculent solids.

Example 22: Synthesis of Compound 56

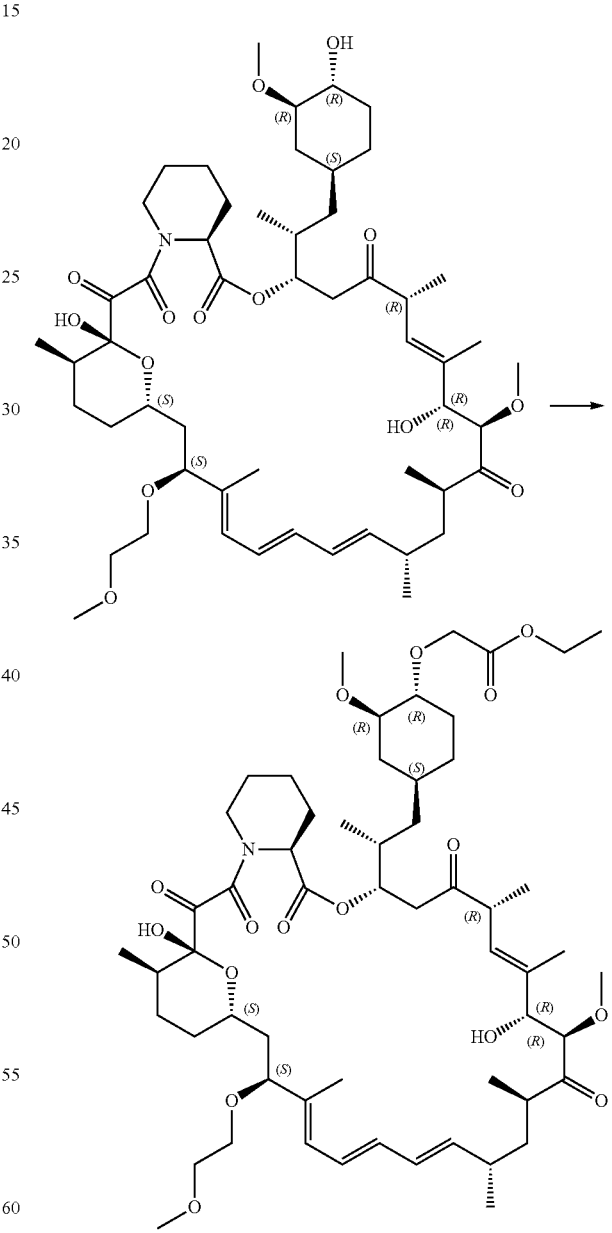

To a mixture of Intermediate I (0.50 g, 0.52 mmol) and dirhodium tetraacetate (9.5 mg, 0.022 mmol) in DCM (5 mL) was added 15% solution of ethyl diazoacetate (0.76 g, 1.00 mmol) and the reaction mixture stirred for 16 h. Further 15% solution of ethyl diazoacetate (0.76 g, 1.00 mmol) was added and stirring continued for 3 h. Further 15% solution of ethyl diazoacetate (0.76 g, 1.00 mmol) was added and stirring continued for 48 h. The reaction mixture was concentrated and purified by silica gel chromatography (0-60% EtOAc in hexanes) to give Compound 56 as an impure oil which was used in subsequent steps without further purification. A small sample was purified by HPLC (Method 1) to give Compound 56 as a flocculent solid.

Example 23: Synthesis of Compound 57

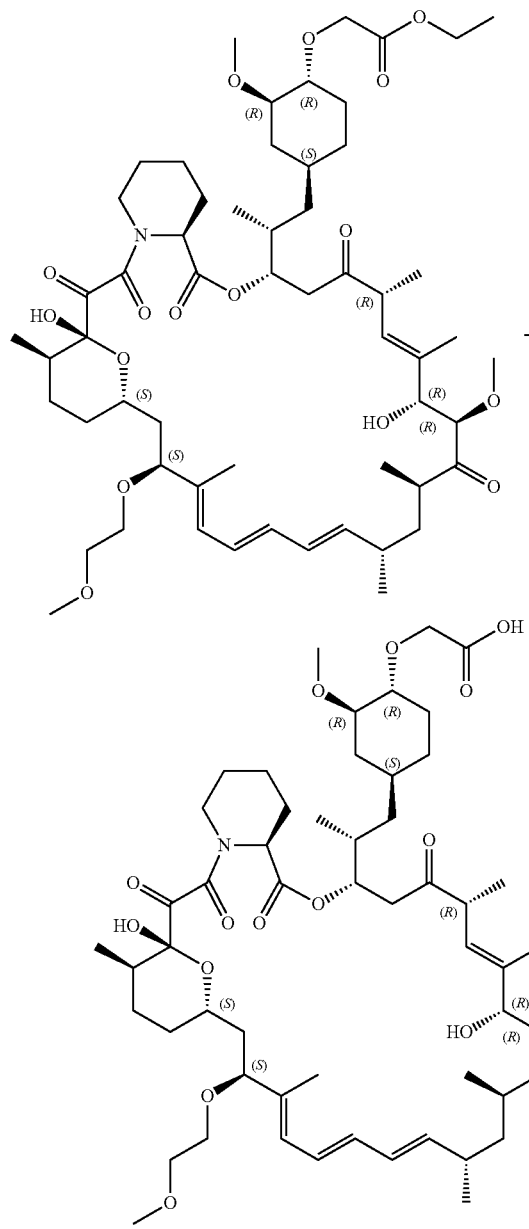

To a stirred mixture of Compound 56 (0.32 g, 0.31 mmol), 2-{2-[2-(2-hydroxyethoxy)ethoxy]ethoxy}ethan-1-ol) (3 mL) and Tween80 (0.78 mL) in water (16 mL) was added esterase from porcine liver lyophilized powder, ≥15 units/mg solid (20 mg). The mixture was stirred for 48 h at rt, then further 2-{2-[2-(2-hydroxyethoxy)ethoxy]ethoxy}ethan-1-ol) (0.5 mL) was added. The mixture was stirred for 432 h at rt, then further 2-{2-[2-(2-hydroxyethoxy)ethoxy]ethoxy}ethan-1-ol) (1 mL), Tween80 (0.26 mL) and esterase from porcine liver lyophilized powder, ≥15 units/mg solid (25 mg) was added. The mixture was stirred for 48 h at rt, then purified directly by reverse phase column chromatography (5-95% MeCN in water, with 0.1% formic acid) followed by HPLC (Method 1) to give Compound 57 as a solid (76 mg, 24%).

Example 24: Synthesis of Compound 58

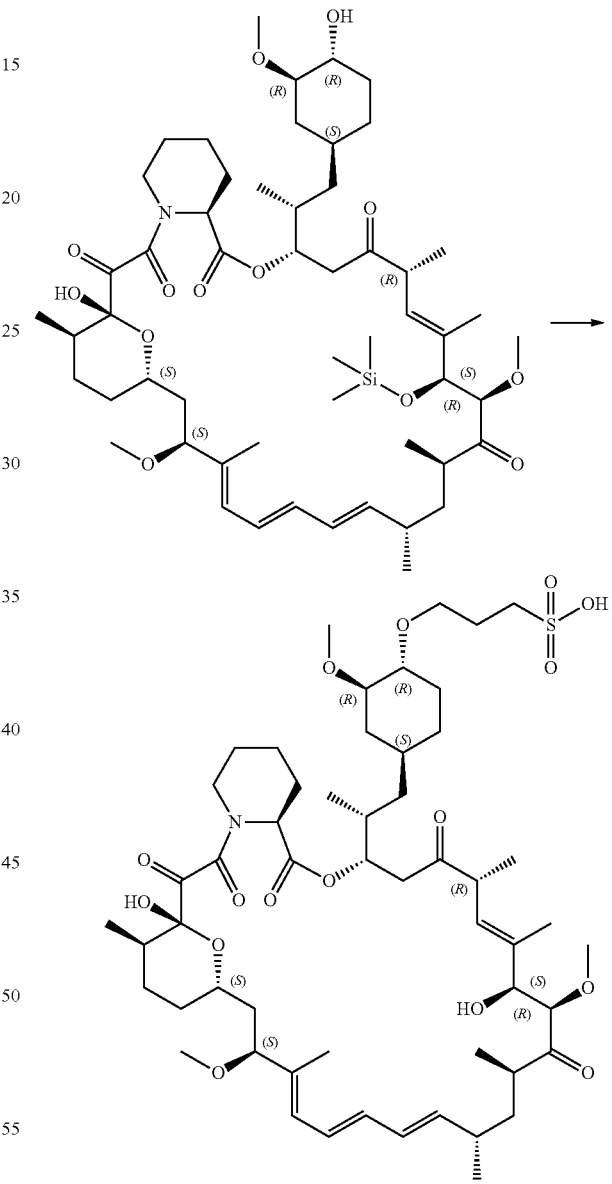

To a mixture of Intermediate A (1.00 g, 1.01 mmol) and Cs$_2$CO$_3$ (0.69 g, 2.13 mmol) in DMF (28 mL) was added 1,3-propanesultone (0.26 g, 2.13 mmol), and the reaction mixture was stirred at rt for 18 h. EtOAc (250 mL) was added, and the mixture washed sequentially with 0.1M HCl (250 mL) and brine (250 mL), then dried (Na$_2$SO$_4$) and concentrated under reduced pressure, and the residue purified by silica gel column chromatography (0-20% MeOH in DCM) to give Compound 58 (0.78 g, 71%) as a solid.

TABLE 4
Compounds of Formula JJ with corresponding $R^1$ and $R^2$ substituents. Compounds of Table 4 were synthesized using the methods described herein, e.g., procedures of Examples 21-24, and employing the appropriate reagents.
| Compound | t/h$^a$ | R$_1$ | R$_2$ | C16$^\&$ R/S | RT/ mins |
|---|---|---|---|---|---|
| 26 | 1.5 | H | 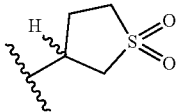 [SMILES: *C1CCS(=O)(=O)C1] | S$^d$ | 2.21 |
| 27 | 1.5 | H | 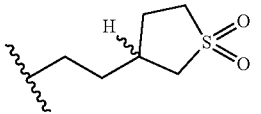 [SMILES: *CCC1CCS(=O)(=O)C1] | S$^d$ | 2.59 |
| 28 | 5 | H | 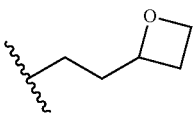 [SMILES: *CCC1CCO1] | S$^d$ | 3.42 |
| 29 | 3 | H | 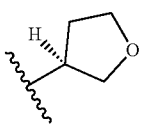 | S$^d$ | 3.21 |
| 30 | 0.5 | H | 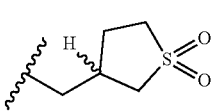 [SMILES: *CC1CCS(=O)(=O)C1] | S$^d$ | 2.38 |
| 31 | 1 | H | 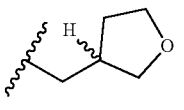 [SMILES: *CC1CCOC1] | S$^d$ | 3.55 |
| 32 | 3 | H | 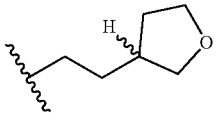 [SMILES: *CCC1CCOC1] | S$^d$ | 3.86 |
| 33 | 2.5 | H | 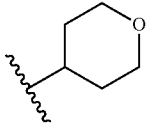 [SMILES: *C1CCOCC1] | S$^d$ | 3.42 |
| 34 | 2.5 | H | 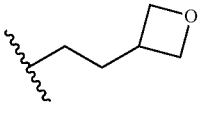 [SMILES: *CCC1COC1] | S$^d$ | 3.61 |
| 35 | 1 | H | 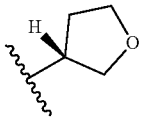 [SMILES: *[C@@H]1CCOC1] | S$^d$ | 3.13 |
| 36 | 4 | H | 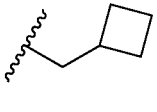 [SMILES: *CC1CCC1] | S | 5.88 |
| 37 | 4 | H | 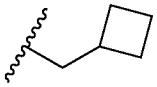 [SMILES: *CC1CCC1] | R | 5.62 |

TABLE 4-continued

Compounds of Formula JJ with corresponding R[1] and R[2] substituents. Compounds of Table 4 were synthesized using the methods described herein, e.g., procedures of Examples 21-24, and employing the appropriate reagents.

| Compound | t/h[a] | R₁ | R₂ | C16[&] R/S | RT/ mins |
|---|---|---|---|---|---|
| 38 | 168[b] | ~~~CH₂CH₂CH₂OH | ~~~CH₂CH₂-oxetanyl | S[d] | 3.59 |
| 39 | 4 | H | ~~~CH₂-cyclopropyl | S[d] | 4.69 |
| 40 | 5 | H | ~~~CH₂-cyclopentyl | S[d] | 6.27 |
| 41 | 0.5 | H | ~~~CH₂-(3,3-difluorocyclobutyl) | S[d] | 4.74 |
| 42 | 4 | ~~~CH₂CH₂CH₂CH₂OH | ~~~CH₂-cyclopropyl | S | 4.89 |
| 43 | 4 | ~~~CH₂CH₂CH₂CH₂OH | ~~~CH₂-cyclopropyl | R | 4.75 |
| 44 | 6 | ~~~CH₂CH₂CH₂CH₂OH | ~~~CH₂-cyclobutyl | S[d] | 6.02 |
| 45 | 9 | ~~~CH₂CH₂CH₂OH | ~~~CH₂-cyclobutyl | S[d] | 5.89 |
| 46 | 2 | ~~~CH₂CH₂CH₂OH | ~~~CH₂-cyclopropyl | S | 4.33 |
| 47 | 2 | ~~~CH₂CH₂CH₂OH | ~~~CH₂-cyclopropyl | R | 4.15 |
| 48 | 1 | ~~~CH₂C(O)OCH₂CH₃ | ~~~CH₂-cyclopropyl | S[d] | 5.60 |
| 49 | 5.5 | ~~~CH₂C(O)OCH₂CH₃ | ~~~CH₂-cyclobutyl | S[d] | 6.81 |
| 50 | 3.5 | ~~~CH₂C(O)OCH₂CH₃ | ~~~CH₂-cyclopropyl | S | 6.00 |

TABLE 4-continued

Compounds of Formula JJ with corresponding $R^1$ and $R^2$ substituents. Compounds of Table 4 were synthesized using the methods described herein, e.g., procedures of Examples 21-24, and employing the appropriate reagents.

| Compound | t/h$^a$ | R$_1$ | R$_2$ | C16$^\&$ R/S | RT/mins |
|---|---|---|---|---|---|
| 51 | 3.5 | ethyl ester group | cyclopropyl | R | 5.61 |
| 52 | 1.5 | propanol group | cyclopropyl | S | 4.62 |
| 53 | 1.5 | propanol group | cyclopropyl | R | 4.32 |
| 54 | 2 | ethanol group | cyclopropyl | S$^d$ | 4.57 |
| 55$^c$ C28 isomer (C28 S configuration) | 5 | H | oxetane-ethyl group | S$^d$ | 3.78 |
| 56$^e$ | | ethyl ester group | methoxyethyl | S$^d$ | 4.87 |
| 57$^e$ | | carboxylic acid | methoxyethyl | S$^d$ | 3.51 |
| 58$^e$ | | propyl sulfonic acid | isopropyl | S$^d$ | 4.20 |

TABLE 5

Characterization of compounds of Table 4

| Compound | NMR $^1$H NMR (400 MHz, DMSO-d$_6$)$^f$ | Yield (%) | [M + NH$_4$]$^+$ |
|---|---|---|---|
| 26 | δ 6.56-6.33 (m, 2H), 6.31-6.04 (m, 3H), 5.48 (dd, J = 14.7, 9.6 Hz, 1H), 5.25 (d, J = 4.5 Hz, 1H), 5.08 (d, J = 10.2 Hz, 1H), 5.02-4.89 (m, 2H), 4.59 (d, J = 4.5 Hz, 1H), 4.18-3.84 (m, 5H), 3.49-3.37 (m, 1H), 3.37-3.04 (m, 12H), 2.88-2.60 (m, 3H), 2.45-1.80 (m, 8H), 1.81-1.08 (m, 23H), 1.09-0.90 (m, 6H), 0.90-0.68 (m, 13H), 0.60 (q, J = 11.9 Hz, 1H). | 11.4 | 1035.9 |
| 27 | δ 6.51-6.34 (m, 2H), 6.27-6.02 (m, 3H), 5.46 (dd, J = 14.6, 9.6 Hz, 1H), 5.26 (d, J = 4.4 Hz, 1H), 5.09 (d, J = 10.2 Hz, 1H), 5.04-4.92 (m, 2H), 4.63-4.54 (m, 1H), 4.09-3.88 (m, 3H), 3.83-3.65 (m, 1H), 3.48-3.38 (m, 1H), 3.30-3.07 (m, 10H), 3.06-2.93 (m, 2H), 2.90-2.62 (m, 5H), 2.46-2.33 (m, 3H), 2.31-2.14 (m, 2H), 2.15-1.94 (m, 2H), 1.95-1.45 (m, 20H), 1.46-1.10 (m, 7H), 1.10-0.89 (m, 6H), 0.90-0.69 (m, 13H), 0.60 (q, J = 11.6 Hz, 1H). | 38.5 | 1063.9 |

TABLE 5-continued

Characterization of compounds of Table 4

| Compound | NMR $^1$H NMR (400 MHz, DMSO-d$_6$)$^f$ | Yield (%) | [M + NH$_4$]$^+$ |
|---|---|---|---|
| 28 | δ 6.52-6.31 (m, 2H), 6.31-6.06 (m, 3H), 5.45 (dd, J = 14.6, 9.6 Hz, 1H), 5.31-5.18 (m, 1H), 5.08 (d, J = 10.3 Hz, 1H), 5.01-4.91 (m, 2H), 4.84-4.71 (m, 1H), 4.59 (d, J = 4.6 Hz, 1H), 4.55-4.44 (m, 1H), 4.41-4.29 (m, 1H), 4.11-3.89 (m, 4H), 3.79-3.64 (m, 1H), 3.49-3.36 (m, 1H), 3.31-2.98 (m, 9H), 2.89-2.54 (m, 4H), 2.44-2.15 (m, 4H), 2.15-1.46 (m, 21H), 1.47-1.10 (m, 7H), 1.12-0.92 (m, 6H), 0.88-0.70 (m, 13H), 0.60 (q, J = 12.0 Hz, 1H). | 4.0 | 1002.0 |
| 29 | δ 6.52-6.32 (m, 2H), 6.30-6.00 (m, 3H), 5.60-5.37 (m, 1H), 5.37-5.18 (m, 1H), 5.14-5.04 (m, 1H), 5.01-4.82 (m, 2H), 4.61-4.57 (m, 1H), 4.09-3.45 (m, 10H), 3.49-3.35 (m, 1H), 3.28-3.13 (m, 8H), 2.91-2.63 (m, 2H), 2.47-2.16 (m, 3H), 2.14-1.95 (m, 2H), 1.95-1.47 (m, 17H), 1.46-0.92 (m, 15H), 0.91-0.69 (m, 13H), 0.67-0.53 (m, 1H). | 3.5 | 987.9 |
| 30 | δ 6.67-6.34 (m, 2H), 6.32-5.89 (m, 3H), 5.70-5.42 (m, 1H), 5.38-4.85 (m, 4H), 4.65-4.50 (m, 1H), 4.14-3.65 (m, 4H), 3.58-3.40 (m, 1H), 3.32-3.06 (m, 12H), 2.95-2.55 (m, 5H), 2.47-1.95 (m, 5H), 1.94-1.47 (m, 15H), 1.45-0.66 (m, 22H), 0.65-0.54 (m, 1H). 76H out of 85H observed. | 8.0 | 1049.9 |
| 31 | δ 6.64-6.31 (m, 2H), 6.29-5.88 (m, 3H), 5.47 (dd, J = 12.2, 9.8 Hz, 1H), 5.32-5.19 (m, 1H), 5.17-4.85 (m, 3H), 4.71-4.50 (m, 1H), 4.32-3.82 (m, 3H), 3.81-3.37 (m, 6H), 3.33-2.96 (m, 10H), 2.91-2.59 (m, 3H), 2.46-2.31 (m, 2H), 2.29-1.81 (m, 6H), 1.80-1.36 (m, 15H), 1.34-0.69 (m, 20H), 0.61 (q, J = 11.5 Hz, 1H). 77H out of 85H observed. | 21.5 | 1002.0 |
| 32 | δ 6.66-6.31 (m, 2H), 6.28-5.88 (m, 3H), 5.52-5.39 (m, 1H), 5.36-4.83 (m, 4H), 4.61 (d, J = 4.4 Hz, 2H), 4.15-3.85 (m, 3H), 3.85-3.50 (m, 5H), 3.47-3.38 (m, 1H), 3.33-3.24 (m, 4H), 3.25-2.97 (m, 6H), 2.87-2.65 (m, 3H), 2.44-2.31 (m, 1H), 2.27-1.79 (m, 7H), 1.77-1.48 (m, 15H), 1.47-1.36 (m, 3H), 1.33-1.10 (m, 5H), 1.09-0.65 (m, 19H), 0.65-0.53 (m, 1H). 85 out of 87 protons observed. | 23.0 | 1015.9 |
| 33 | δ 6.48 (d, J = 1.6 Hz, 1H), 6.39 (dd, J = 14.3, 11.2 Hz, 1H), 6.27-6.05 (m, 3H), 5.46 (dd, J = 14.7, 9.6 Hz, 1H), 5.26 (d, J = 4.5 Hz, 1H), 5.12-5.03 (m, 1H), 5.03-4.90 (m, 2H), 4.58 (dd, J = 4.5, 1.8 Hz, 1H), 4.12-3.85 (m, 4H), 3.81-3.68 (m, 2H), 3.48-3.37 (m, 1H), 3.37-3.10 (m, 12H), 2.91-2.66 (m, 2H), 2.45-2.32 (m, 2H), 2.31-1.95 (m, 3H), 1.95-1.48 (m, 21H), 1.48-0.90 (m, 13H), 0.87-0.69 (m, 13H), 0.60 (q, J = 11.7 Hz, 1H). | 13.5 | 1001.9 |
| 34 | δ 6.50-6.45 (m, 1H), 6.45-6.34 (m, 1H), 6.27-6.01 (m, 3H), 5.51-5.41 (m, 1H), 5.29-5.23 (m, 1H), 5.12-5.05 (m, 1H), 5.02-4.90 (m, 2H), 4.66-4.52 (m, 1H), 4.07-3.98 (m, 2H), 3.97-3.87 (m, 1H), 3.84-3.50 (m, 5H), 3.47-3.36 (m, 2H), 3.31-3.25 (m, 4H), 3.22-2.97 (m, 6H), 2.88-2.60 (m, 2H), 2.43-2.17 (m, 4H), 2.13-1.97 (m, 2H), 1.96-1.78 (m, 4H), 1.76-1.60 (m, 10H), 1.57-1.13 (m, 11H), 1.13-0.94 (m, 7H), 0.91-0.70 (m, 13H), 0.66-0.53 (m, 1H). | 19.6 | 1001.9 |
| 35 | δ 6.54-6.32 (m, 2H), 6.30-6.00 (m, 3H), 5.60-5.37 (m, 1H), 5.37-5.18 (m, 1H), 5.14-5.01 (m, 1H), 5.01-4.82 (m, 2H), 4.61-4.54 (m, 1H), 4.09-3.80 (m, 4H), 3.73-3.59 (m, 4H), 3.51-3.37 (m, 2H), 3.28-3.10 (m, 9H), 2.91-2.63 (m, 2H), 2.47-2.16 (m, 2H), 2.14-1.95 (m, 3H), 1.95-1.47 (m, 19H), 1.46-0.92 (m, 13H), 0.91-0.69 (m, 13H), 0.67-0.53 (m, 1H). | 3.8 | 987.9 |
| 36 | δ 6.51-6.34 (m, 2H), 6.29-6.04 (m, 3H), 5.46 (dd, J = 13.6, 9.6 Hz, 1H), 5.31-5.23 (m, 1H), 5.16-4.86 (m, 3H), 4.65-4.54 (m, 1H), 4.13-3.85 (m, 3H), 3.81-3.67 (m, 1H), 3.51-3.39 (m, 1H), 3.33-3.04 (m, 11H), 2.86-2.69 (m, 2H), 2.49-2.16 (m, 4H), 2.15-1.47 (m, 25H), 1.46-1.12 (m, 7H), 1.11-0.68 (m, 19H), 0.67-0.57 (m, 1H). | 20.4 | 986.0 |
| 37 | δ 6.61-6.39 (m, 2H), 6.21-5.89 (m, 3H), 5.70-5.54 (m, 1H), 5.37-5.28 (m, 1H), 5.27-5.07 (m, 2H), 5.03-4.91 (1H), 4.67-4.58 (m, 1H), 4.12-3.88 (m, 3H), 3.84-3.70 (m, 1H), 3.64-3.49 (m, 1H), 3.33-2.99 (m, 11H), 2.85-2.69 (m, 2H), 2.59-2.54 (m, 1H), 2.47-2.40 (m, 1H), 2.35-2.12 (m, 2H), 2.05-1.78 (m, | 3.0 | 985.9 |

TABLE 5-continued

Characterization of compounds of Table 4

| Compound | NMR ¹H NMR (400 MHz, DMSO-$d_6$)$^f$ | Yield (%) | [M + NH$_4$]$^+$ |
|---|---|---|---|
|  | 6H), 1.77-1.46 (m, 17H), 1.45-1.06 (m, 9H), 1.05-0.67 (m, 19H), 0.64-0.53 (m, 1H). |  |  |
| 38 | δ 6.50 (s, 1H), 6.45-6.34 (m, 1H), 6.29-6.07 (m, 2H), 5.46 (dd, J = 14.7, 9.6 Hz, 1H), 5.33-5.16 (m, 1H), 5.14-5.04 (m, 1H), 5.01-4.90 (m, 2H), 4.52-4.44 (m, 1H), 4.08-3.90 (m, 2H), 3.82-3.53 (m, 5H), 3.53-3.40 (m, 5H), 3.31-3.20 (m, 5H), 3.20-2.92 (m, 8H), 2.86-2.61 (m, 2H), 2.43-2.31 (m, 2H), 2.30-2.16 (m, 1H), 2.16-2.00 (m, 2H), 2.00-1.78 (m, 5H), 1.78-1.34 (m, 16H), 1.34-1.18 (m, 4H), 1.18-0.90 (m, 8H), 0.90-0.54 (m, 14H). | 8.7 | 1046.0 |
| 39 | δ 6.54-6.31 (m, 2H), 6.30-6.05 (m, 3H), 5.46 (dd, J = 12.4, 10.2 Hz, 1H), 5.31-5.24 (m, 1H), 5.14-4.86 (m, 3H), 4.65-4.54 (m, 1H), 4.20-3.92 (m, 3H), 3.83-3.74 (m, 1H), 3.52-3.40 (m, 1H), 3.34-3.32 (m, 3H), 3.30-2.91 (m, 7H), 2.90-2.64 (m, 3H), 2.45-2.05 (m, 5H), 2.04-1.82 (m, 3H), 1.80-1.47 (m, 11H), 1.46-1.13 (m, 7H), 1.11-0.69 (m, 19H), 0.66-0.55 (m, 1H), 0.52-0.31 (m, 2H), 0.18-0.00 (m, 2H). 79H out of 83H observed. | 8.2 | 971.9 |
| 40 | δ 6.48-6.44 (m, 1H), 6.39 (dd, J = 14.4, 11.2 Hz, 1H), 6.27-6.14 (m, 1H), 6.14-6.06 (m, 2H), 5.45 (dd, J = 14.6, 9.7 Hz, 1H), 5.26 (d, J = 4.6 Hz, 1H), 5.11 5.05 (m, 1H), 5.01-4.90 (m, 2H), 4.59 (d, J = 4.5 Hz, 1H), 4.11-3.98 (m, 2H), 3.95 (d, J = 4.5 Hz, 1H), 3.75 3.69 (m, 1H), 3.48 3.41 (m, 1H), 3.32 (s, 3H), 3.25-3.05 (m, 7H), 2.95 (dd, J = 9.2, 6.8 Hz, 1H), 2.88-2.78 (m, 1H), 2.78-2.65 (m, 1H), 2.43-2.29 (m, 2H), 2.29-2.15 (m, 1H), 2.14-1.94 (m, 3H), 1.94-1.78 (m, 3H), 1.77-1.71 (m, 3H), 1.71-1.59 (m, 9H), 1.58-1.34 (m, 9H), 1.32-1.09 (m, 7H), 1.08-0.90 (m, 7H), 0.90-0..69 (m, 13H), 0.60 (q, J = 12.0 Hz, 1H). | 7.6 | 1000.0 |
| 41 | δ 6.53-6.34 (m, 2H), 6.28-6.05 (m, 3H), 5.46 (dd, J = 12.4, 9.0 Hz, 1H), 5.32-5.24 (m, 1H), 5.09 (d, J = 10.2 Hz, 1H), 5.05-4.87 (m, 2H), 4.65-4.55 (m, 1H), 4.09-3.68 (m, 4H), 3.51-3.39 (m, 1H), 3.35-3.32 (m, 3H), 3.26-3.12 (m, 7H), 2.95-2.55 (m, 5H), 2.46-1.96 (m, 8H), 1.95-1.13 (m, 23H), 1.12-0.68 (m, 19H), 0.61 (dd, J = 12.4, 10.0 Hz, 1H). 82H out of 83H observed.<br>¹⁹F NMR (376 MHz, DMSO-$d_6$) δ −81.3 (d, J = 203 Hz), −91.3 (d, J = 203 Hz). | 22.1 | 1022.0 |
| 42 | δ 6.51 (d, J = 1.4 Hz, 1H), 6.38 (dd, J = 14.5, 11.2 Hz, 1H), 6.27-6.05 (m, 3H), 5.45 (dd, J = 14.6, 9.6 Hz, 1H), 5.36-5.24 (m, 1H), 5.07 (d, J = 10.1 Hz, 1H), 5.01-4.87 (m, 2H), 4.38-4.30 (m, 1H), 4.13-3.95 (m, 3H), 3.83-3.71 (m, 1H), 3.63-3.39 (m, 6H), 3.33-3.09 (m, 6H), 3.06-2.90 (m, 4H), 2.85-2.62 (m, 1H), 2.44-2.30 (m, 2H), 2.30-2.14 (m, 1H), 2.15-1.77 (m, 6H), 1.77-1.46 (m, 14H), 1.46-1.13 (m, 7H), 1.13-0.89 (m, 9H), 0.89-0.69 (m, 13H), 0.64 (q, J = 11.9 Hz, 1H), 0.52-0.37 (m, 2H), 0.18-0.02 (m, 2H). | 22.3 | 1029.9 |
| 43 | δ 6.57 (s, 1H), 6.51-6.36 (m, 1H), 6.25-6.07 (m, 2H), 6.07-5.96 (m, 1H), 5.66-5.53 (m, 1H), 5.34-5.05 (m, 3H), 5.02-4.95 (m, 1H), 4.41-4.22 (m, 1H), 4.07-3.87 (m, 3H), 3.79 (dd, J = 9.6, 2.2 Hz, 1H), 3.75-3.66 (m, 1H), 3.59-3.40 (m, 6H), 3.30-2.88 (m, 7H), 2.83-2.66 (m, 2H), 2.55 (d, J = 9.4 Hz, 1H), 2.38-1.79 (m, 7H), 1.79 (s, 23H), 1.18-0.54 (m, 23H), 0.42 (dt, J = 7.4, 2.2 Hz, 2H), 0.19--0.04 (m, 2H). | 9.0 | 1029.8 |
| 44 | δ 6.49 (d, J = 1.5 Hz, 1H), 6.46-6.33 (m, 1H), 6.27-6.06 (m, 3H), 5.45 (dd, J = 14.6, 9.7 Hz, 1H), 5.28 (d, J = 13.6 Hz, 1H), 5.08 (d, J = 10.2 Hz, 1H), 5.01-4.89 (m, 2H), 4.39-4.30 (m, 1H), 4.10-3.93 (m, 3H), 3.79-3.66 (m, 1H), 3.62-3.39 (m, 7H), 3.32-2.89 (m, 10H), 2.79-2.62 (m, 1H), 2.49-2.31 (m, 5H), 2.31-2.16 (m, 1H), 2.15-1.48 (m, 26H), 1.46-0.90 (m, 12H), 0.89-0.57 (m, 14H). | 7.6 | 1043.9 |
| 45 | δ 6.50 (s, 1H), 6.47-6.32 (m, 1H), 6.27-6.07 (m, 3H), 5.45 (dd, J = 14.4, 9.9 Hz, 1H), 5.35-5.24 (m, 1H), 5.07 (d, J = 10.1 Hz, 1H), 5.01-4.89 (m, 2H), 4.56-4.44 (m, 1H), 4.10-3.90 (m, 2H), 3.78-3.66 (m, 1H), 3.55-3.42 (m, 5H), 3.34-3.22 (m, 4H), 3.22-2.91 (m, 8H), 2.87-2.58 (m, 2H), 2.49-2.16 (m, 4H), 2.15-1.77 (m, 9H), 1.75 (s, 2H), 1.73-1.46 (m, 14H), 1.46- | 11.4 | 1029.9 |

TABLE 5-continued

Characterization of compounds of Table 4

| Compound | NMR $^1$H NMR (400 MHz, DMSO-$d_6$)$^f$ | Yield (%) | [M + NH$_4$]$^+$ |
|---|---|---|---|
| | 1.35 (m, 2H), 1.35-0.91 (m, 11H), 0.89-0.69 (m, 13H), 0.69-0.57 (m, 1H). | | |
| 46 | δ 6.55-6.33 (m, 2H), 6.29-6.06 (m, 3H), 5.46 (dd, J = 12.3, 10.1 Hz, 1H), 5.36-5.27 (m, 1H), 5.16-4.86 (m, 3H), 4.49 (d, J = 2.0 Hz, 1H), 4.08-3.76 (m, 4H), 3.56-3.38 (m, 5H), 3.34-2.93 (m, 11H), 2.77-2.67 (m, 1H), 2.45-2.32 (m, 2H), 2.28-2.16 (m, 1H), 2.14-1.87 (m, 4H), 1.86-1.46 (m, 15H), 1.45-1.10 (m, 8H), 1.09-0.91 (m, 7H), 0.90-0.68 (m, 11H), 0.67-0.59 (m, 1H), 0.54-0.24 (m, 4H). | 12.7 | 1001.9 |
| 47 | δ 6.69-6.36 (m, 2H), 6.32-5.92 (m, 3H), 5.68-5.41 (m, 1H), 5.35-5.04 (m, 3H), 5.02-4.87 (m, 1H), 4.52-4.44 (m, 1H), 4.11-3.75 (m, 4H), 3.63-3.37 (m, 5H), 3.34-3.28 (m, 4H), 3.21-3.10 (m, 3H), 3.09-2.90 (m, 3H), 2.84-2.64 (m, 2H), 2.57-2.52 (m, 1H), 2.41-2.04 (m, 3H), 2.03-1.82 (m, 3H), 1.81-1.17 (m, 20H), 1.16-0.68 (m, 19H), 0.67-0.54 (m, 1H), 0.52-0.15 (m, 4H). 83H out of 85H observed. | 2.8 | 1001.9 |
| 48 | δ 6.57-5.93 (m, 5H), 5.58-5.36 (m, 1H), 5.33-4.86 (m, 4H), 4.35-3.68 (m, 13H), 3.20-2.95 (m, 7H), 2.83-2.62 (m, 1H), 2.45-2.32 (m, 2H), 2.16-1.45 (m, 19H), 1.45-0.68 (m, 30H), 0.62 (q, J = 11.8 Hz, 1H), 0.54-0.23 (m, 4H). | 10.0 | 1043.9 |
| 49 | δ 6.52 (s, 1H), 6.47-6.34 (m, 1H), 6.29-6.07 (m, 3H), 5.55 (dd, J = 12.4, 10.2 Hz, 1H), 5.36-5.28 (m, 1H), 5.14-4.89 (m, 3H), 4.28-3.94 (m, 7H), 3.78-3.68 (m, 1H), 3.42 (d, J = 7.0 Hz, 1H), 3.32-2.96 (m, 12H), 2.83-2.64 (m, 2H), 2.47-2.16 (m, 4H), 2.15-1.90 (m, 6H), 1.89-1.47 (m, 18H), 1.46-1.12 (m, 11H), 1.11-0.68 (m, 18H), 0.65-0.54 (m, 1H). | 10.4 | 1071.9 |
| 50 | δ 6.48 (s, 1H), 6.41-6.33 (m, 1H), 6.26-6.05 (m, 3H), 5.47 (dd, J = 12.4, 10.2 Hz, 1H), 5.29-5.23 (m, 1H), 5.12-4.89 (m, 3H), 4.28-3.92 (m, 7H), 3.82-3.75 (m, 1H), 3.49-3.39 (m, 1H), 3.31-3.07 (m, 9H), 3.06-2.94 (m, 3H), 2.76-2.66 (m, 1H), 2.45-2.29 (m, 2H), 2.27-2.16 (m, 1H), 2.13-1.82 (m, 6H), 1.78-1.51 (m, 13H), 1.45-1.15 (m, 10H), 1.09-0.68 (m, 20H), 0.67-0.55 (m, 1H), 0.49-0.36 (m, 2H), 0.20-0.04 (m, 2H). | 6.7 | 1057.9 |
| 51 | δ 6.58-6.34 (m, 2H), 6.27-5.97 (m, 3H), 5.68-5.55 (m, 1H), 5.29-5.23 (m, 1H), 5.17-5.06 (m, 2H), 5.02-4.90 (m, 1H), 4.24-3.90 (m, 7H), 3.79 (d, J = 7.8 Hz, 1H), 3.56 (d, J = 8.0 Hz, 1H), 3.29-2.92 (m, 12H), 2.81-2.73 (m, 1H), 2.59-2.52 (m, 1H), 2.34-2.20 (m, 1H), 2.19-1.85 (m, 5H), 1.76-1.45 (m, 14H), 1.43-1.06 (m, 12H), 1.04-0.69 (m, 19H), 0.68-0.54 (m, 1H), 0.49-0.34 (m, 2H), 0.20-0.00 (m, 2H). | 2.2 | 1057.9 |
| 52 | δ 6.48-6.35 (m, 2H), 6.31-6.06 (m, 3H), 5.47 (dd, J = 14.8, 9.6 Hz, 1H), 5.27 (d, J = 4.4 Hz, 1H), 5.09 (d, J = 10.2 Hz, 1H), 5.01-4.89 (m, 2H), 4.36-4.23 (m, 1H), 4.06-3.77 (m, 4H), 3.62-3.37 (m, 7H), 3.27-3.11 (m, 5H), 3.10-2.87 (m, 4H), 2.78-2.65 (m, 1H), 2.45-1.84 (m, 5H), 1.84-1.16 (m, 23H), 1.16-0.90 (m, 10H), 0.91-0.57 (m, 13H), 0.55-0.24 (m, 4H). | 28.6 | 1015.9 |
| 53 | δ 6.64 (s, 1H), 6.56-6.38 (m, 1H), 6.31-6.03 (m, 3H), 5.71-5.58 (m, 1H), 5.44-5.10 (m, 3H), 5.01-4.83 (m, 1H), 4.35-4.20 (m, 1H), 4.11-3.97 (m, 1H), 3.97-3.77 (m, 3H), 3.59-3.37 (m, 6H), 3.22-3.11 (m, 9H), 2.87-2.58 (m, 2H), 2.59-2.51 (m, 1H), 2.42-2.21 (m, 1H), 2.21-1.81 (m, 5H), 1.80-1.18 (m, 24H), 1.17-0.60 (m, 20H), 0.53-0.20 (m, 4H). | 5.4 | 1015.9 |

TABLE 5-continued

Characterization of compounds of Table 4

| Compound | NMR ¹H NMR (400 MHz, DMSO-d₆)$^f$ | Yield (%) | [M + NH₄]⁺ |
|---|---|---|---|
| 54 | δ 6.77-6.52 (m, 1H), 6.44-6.32 (m, 1H), 6.27-6.01 (m, 2H), 5.45 (dd, J = 14.7, 9.7 Hz, 1H), 5.37-5.20 (m, 1H), 5.10-5.00 (m, 1H), 5.00-4.89 (m, 2H), 4.52 (t, J = 5.3 Hz, 1H), 4.12-3.96 (m, 3H), 3.82-3.68 (m, 1H), 3.58-3.39 (m, 5H), 3.35-3.21 (m, 4H), 3.22-3.09 (m, 4H), 3.09-2.89 (m, 4H), 2.79-2.68 (m, 1H), 2.41-2.28 (m, 2H), 2.28-2.14 (m, 1H), 2.14-1.79 (m, 6H), 1.75 (s, 2H), 1.72-1.45 (m, 11H), 1.45-1.33 (m, 2H), 1.33-0.87 (m, 14H), 0.87-0.56 (m, 13H), 0.48-0.36 (m, 2H), 0.18-0.00 (m, 2H). | 19.1 | 1015.8 |
| 55 $^c$ C28 isomer (C28 S configuration) | δ 6.46-6.34 (m, 2H), 6.30-6.05 (m, 3H), 5.44 (dd, J = 14.3, 9.8 Hz, 1H), 5.02 (d, J = 4.7 Hz, 2H), 4.94 (d, J = 7.6 Hz, 1H), 4.58 (d, J = 4.4 Hz, 1H), 4.09-3.96 (m, 2H), 3.88-3.55 (m, 5H), 3.31 (s, 13H), 2.86-2.60 (m, 3H), 2.45-2.21 (m, 3H), 2.19-1.98 (m, 2H), 1.98-1.38 (m, 20H), 1.38-1.07 (m, 7H), 1.07-0.87 (m, 6H), 0.87-0.66 (m, 13H), 0.66-0.47 (m, 1H). | 14.5 | 1001.8 |
| 56 $^e$ | δ 6.50 (s, 1H), 6.45-6.34 (m, 1H), 6.27-6.07 (m, 3H), 5.46 (dd, J = 14.7, 9.7 Hz, 1H), 5.33-5.22 (m, 1H), 5.08 (d, J = 10.2 Hz, 1H), 5.00-4.90 (m, 2H), 4.32-4.15 (m, 2H), 4.15-4.04 (m, 2H), 4.05-3.93 (m, 2H), 3.82-3.71 (m, 1H), 3.47-3.29 (m, 7H), 3.28-3.19 (m, 6H), 3.19-3.09 (m, 5H), 3.08-2.98 (m, 1H), 2.77-2.68 (m, 1H), 2.42-2.30 (m, 2H), 2.28-2.16 (m, 1H), 2.14-2.06 (m, 1H), 2.03-1.81 (m, 4H), 1.74 (s, 3H), 1.70-1.47 (m, 10H), 1.45-1.35 (m, 2H), 1.34-1.09 (m, 9H), 1.08-0.87 (m, 6H), 0.89-0.70 (m, 13H), 0.61 (q, J = 12.1 Hz, 1H). | | 1062.0 |
| 57 $^e$ | δ 12.68 (s, 1H), 6.65 (ddd, J = 15.7, 8.1, 1.8 Hz, 1H), 6.60-6.33 (m, 2H), 6.33-6.01 (m, 3H), 5.55 (dd, J = 14.6, 8.6 Hz, 1H), 5.26 (d, J = 4.6 Hz, 1H), 5.23-5.15 (m, 1H), 4.38-4.03 (m, 3H), 3.94 (dd, J = 7.0, 4.4 Hz, 1H), 3.81-3.67 (m, 3H), 3.66-3.55 (m, 1H), 3.55-3.45 (m, 1H), 3.43-3.35 (m, 2H), 3.31-3.17 (m, 8H), 3.15 (s, 3H), 3.13-3.07 (m, 1H), 3.06-2.94 (m, 1H), 2.80-2.68 (m, 2H), 2.42-2.34 (m, 1H), 2.31-2.20 (m, 1H), 2.18-1.89 (m, 5H), 1.77-1.38 (m, 14H), 1.38-1.07 (m, 8H), 1.06-0.87 (m, 16H), 0.87-0.75 (m, 1H), 0.74-0.65 (m, 3H). | 24.4 | 1033.9 |
| 58 $^e$ | δ 6.66 (dd, J = 15.6, 8.0 Hz, 1H), 6.48 (dd, J = 17.2, 1.6 Hz, 1H), 6.41 (d, J = 12.1 Hz, 1H), 6.29-6.05 (m, 4H), 5.65-5.51 (m, 1H), 5.27-5.17 (m, 2H), 4.57 (d, J = 4.3 Hz, 1H), 4.52-4.46 (m, 1H), 4.33-4.07 (m, 3H), 3.99-3.91 (m, 1H), 3.75 (d, J = 7.0 Hz, 2H), 3.67-3.53 (m, 2H), 3.32-3.27 (m, 3H), 3.21-3.11 (m, 4H), 3.09-3.01 (m, 3H), 2.86-2.71 (m, 3H), 2.47-2.19 (m, 3H), 2.18-1.85 (m, 5H), 1.79-1.41 (m, 18H), 1.37-1.09 (m, 8H), 1.06-0.94 (m, 10H), 0.91 (d, J = 6.6 Hz, 3H), 0.88-0.78 (m, 1H), 0.76-0.62 (m, 4H) | 71 | 1106.6 |

For Table 4 and Table 5: [a]Reaction performed according to General Method 3 unless otherwise noted. Time reported is the time stirred at 0° C. Where reaction was incomplete at end of working day, reaction was stored at −20° C. overnight, then stirring at 0° C. continued, as excessive stirring at 0° C. could lead to degradation; [b]Addition carried out at −40° C., then stored at −20° C. for 7 days, after which reaction was complete; [c]C-28 epimer, from Intermediate H; [d]R-isomer not isolated; [e]See specific example for synthetic details; [f]The NMR characterization data shown in the examples correspond only to the major equilibrium form observed under the reported deutero solvent conditions; [&]denotes the stereochemical configuration at C16.

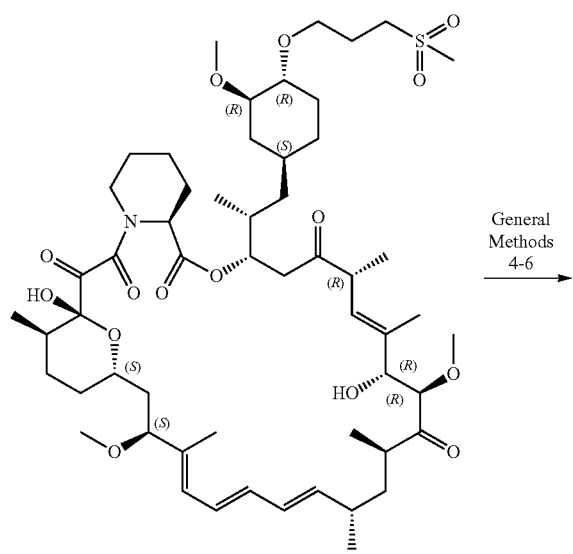

General Methods 4-6

JJJ

General Method 4 (C-16 Ethers)

Example 25: Synthesis of Compound 60

To a stirred solution of Intermediate C (600 mg; 0.60 mmol) and cyclopropylmethanol (1.76 g; 24.4 mmol) in DCM (24 mL) at −40° C. was added para-toluenesulfonic acid monohydrate (570 mg; 3.00 mmol). The reaction mixture was allowed to warm to 0° C. and stirred at this temperature for 0.5 h. Amberlyst A21 free base (2.7 g) was added, and after stirring for 5 min, the mixture was filtered and washed with DCM (100 mL). The combined filtrate and washings were washed with water (5×25 mL), then dried ($Na_2SO_4$), filtered, and concentrated under reduced pressure. The residue was purified by silica gel column chromatography (EtOAc in hexanes, 20-100%), then by HPLC (method 1) to give Compound 60 (41.5 mg, 10.9%) as a flocculent solid.

General Method 5 (C-16 Ethers)

Example 26: Synthesis of Compound 61

To a stirred solution of Intermediate C (150 mg; 0.15 mmol) in 2-methoxyethanol (3 mL) at room temperature was added para-toluenesulfonic acid monohydrate (2.8 mg; 0.015 mmol). The reaction mixture was stirred for 4.5 h., then diluted with EtOAc (5 mL) and saturated sodium bicarbonate solution that had been adjusted to pH 7 with 30% $H_2SO_4$ in water (4 mL). After stirring for 5 min, the layers were separated and the aqueous layer extracted with ethyl acetate (2×4 mL). The combined organics were washed with water (4 mL) and brine (4 mL), then dried ($Na_2SO_4$), and concentrated under reduced pressure. The residue was purified by HPLC (method 1) to give Compound 61 (31.1 mg, 19.9%) as a flocculent solid.

General Method 6 (C-16 Ethers)

Example 27: Synthesis of Compound 66

To a stirred solution of Intermediate C (150 mg; 0.15 mmol) and 2-[2-(2-methoxyethoxy)ethoxy]ethan-1-ol (242 mg, 1.47 mmol) in DCM (3.5 mL) at rt was added a 0.1M solution of $FeCl_3$ in $Et_2O$ (140 µL, 0.015 mmol) and the mixture stirred for 5 h. After storing overnight at −20° C. further 0.1M $FeCl_3$ in $Et_2O$ (193 µL, 0.015 mmol) was added, and stirring continued for 5 h. Saturated sodium bicarbonate solution (3 mL) was added, and the mixture extracted with DCM (3×5 mL). The combined organics were washed with water (3 mL) and brine (3 mL) and purified by silica gel column chromatography (50-100% EtOAc in hexanes then 0-2% MeOH in EtOAc) followed by HPLC (method 1) to give Compound 66 (16.0 mg, 9.50) as a flocculent solid.

TABLE 6
Compounds of Formula JJJ with corresponding R substituents. Compounds of Table 6 were synthesized using the methods described herein, e.g., the procedures of Examples 25-27, and employing the appropriate reagents.
| Compound | Method | R | C16 R/S | RT/ mins | t/h[a] |
|---|---|---|---|---|---|
| 59 [Int C] | Int C |  | S | | |
| 60 | 4 | 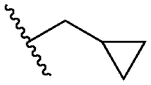 | S[b] | 4.98 | 3 |
| 61 | 5 | 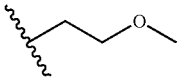 [SMILES: *CCOC] | S[b] | 3.69 | 4.5 |
| 62 | 4 | 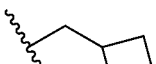 | S | 5.89 | 4 |
| 63 | 4 | 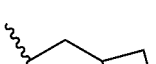 | R | 5.72 | 4 |
| 64 | 4 |  | S[b] | 4.69 | 1.5 |
| 65 | 6 | 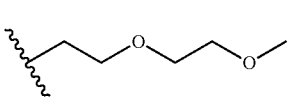 [SMILES: *CCOCCOC] | S[e] | 3.33 | 9 |
| 66 | 6 | 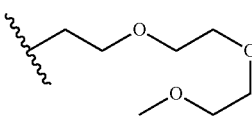 | S[e] | 3.28 | 10 |
| 67[c,d] | 7 | 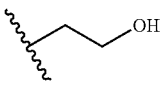 | S | 2.22 | 24 |
| 68[d] | 6 | 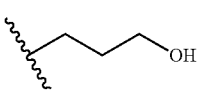 | S | 2.47 | 16 |
| 69[d] | 6 | 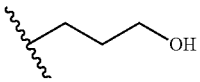 | R | 2.77 | 16 |
| 70 | 6 | 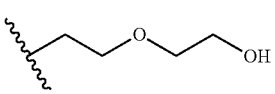 [SMILES: *CCOCCO] | S | 2.26 | 13 |
| 71 | 6 | 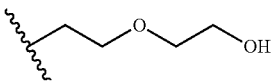 | R[f] | 2.44 | 13 |
| 72 | 6 | 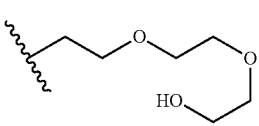 [SMILES: *CCOCCOCCO] | S | 2.25 | 13 |

TABLE 6-continued

Compounds of Formula JJJ with corresponding R substituents. Compounds of Table 6 were synthesized using the methods described herein, e.g., the procedures of Examples 25-27, and employing the appropriate reagents.

| Compound | Method | R | C16 R/S | RT/ mins | t/h[a] |
|---|---|---|---|---|---|
| 73 | 6 | (structure: ~~CH2CH2-O-CH2CH2-O-CH2CH2-OH) | R[f] | 2.44 | 13 |

TABLE 7

Characterization data for compounds of Table 6

| Compound | NMR ¹H NMR (400 MHz, DMSO-d$_6$)[g] | Yield (%) | [M + NH$_4$]$^+$ |
|---|---|---|---|
| 60 | δ 6.49 (d, J = 1.6 Hz, 1H), 6.41-6.33 (m, 1H), 6.28-5.99 (m, 3H), 5.45 (dd, J = 12.6, 10.1 Hz, 1H), 5.32-5.23 (m, 1H), 5.12-4.84 (m, 3H), 4.15-3.92 (m, 3H), 3.82-3.74 (m, 1H), 3.62-3.37 (m, 3H), 3.34-3.22 (m, 4H), 3.19-3.05 (m, 5H), 3.04-2.91 (m, 6H), 2.84-2.62 (m, 2H), 2.43-2.29 (m, 2H), 2.22-1.78 (m, 8H), 1.72-1.45 (m, 12H), 1.44-1.07 (m, 7H), 1.06-0.69 (m, 19H), 0.69-0.58 (m, 1H), 0.52-0.34 (m, 2H), 0.17-0.00 (m, 2H). 87H out of 91H observed. | 10.9 | 1091.9 |
| 61 | δ 6.50 (d, J = 1.5 Hz, 1H), 6.45-6.35 (m, 1H), 6.31-6.00 (m, 3H), 5.46 (dd, J = 14.7, 9.6 Hz, 1H), 5.35-5.24 (m, 1H), 5.15-4.89 (m, 3H), 4.11-3.89 (m, 3H), 3.85-3.75 (m, 1H), 3.66-3.50 (m, 2H), 3.48-3.36 (m, 3H), 3.32-3.06 (m, 13H), 3.05-2.94 (m, 5H), 2.87-2.64 (m, 2H), 2.45-1.81 (m, 9H), 1.80-1.45 (m, 13H), 1.44-1.18 (m, 6H), 1.17-0.71 (m, 19H), 0.68-0.57 (m, 1H). 87H out of 91H observed. | 19.9 | 1096.0 |
| 62 | δ 6.50 (d, J = 1.6 Hz, 1H), 6.46-6.32 (m, 1H), 6.29-6.03 (m, 3H), 5.45 (dd, J = 14.7, 9.7 Hz, 1H), 5.30 (dd, J = 8.7, 4.7 Hz, 1H), 5.08 (d, J = 10.3 Hz, 1H), 4.99-4.89 (m, 2H), 4.10-3.93 (m, 3H), 3.77-3.66 (m, 1H), 3.65-3.38 (m, 5H), 3.29-2.90 (m, 14H), 2.80-2.58 (m, 2H), 2.47-2.16 (m, 3H), 2.16-1.47 (m, 29H), 1.45-0.90 (m, 12H), 0.89-0.55 (m, 14H). | 8.2 | 1106.0 |
| 63 | δ 6.62 (s, 1H), 6.51-6.37 (m, 1H), 6.25-5.98 (m, 3H), 5.66-5.53 (m, 1H), 5.35-5.27 (m, 1H), 5.24 (d, J = 10.2 Hz, 1H), 5.15-5.07 (m, 1H), 5.01-4.95 (m, 1H), 4.08-3.89 (m, 4H), 3.81-3.73 (m, 1H), 3.64-3.49 (m, 4H), 3.30-2.89 (m, 15H), 2.81-2.64 (m, 2H), 2.52-2.40 (m, 2H), 2.33-2.11 (m, 2H), 2.04-1.19 (m, 33H), 1.18-0.55 (m, 20H). | 4.9 | 1106.0 |
| 64 | δ 6.62-6.27 (m, 2H), 6.21-5.92 (m, 3H), 5.47 (dd, J = 12.6, 10.1 Hz, 1H), 5.33-4.89 (m, 4H), 4.18-3.78 (m, 4H), 3.67-3.39 (m, 3H), 3.34-2.90 (m, 16H), 2.78-2.66 (m, 1H), 2.45-2.05 (m, 4H), 2.04-1.45 (m, 18H), 1.44-1.09 (m, 7H), 1.08-0.58 (m, 18H), 0.54-0.19 (m, 4H). 85H out of 89H observed. | 14.2 | 1077.9 |
| 65 | δ 6.49-6.33 (m, 2H), 6.29-6.02 (m, 4H), 5.46 (dd, J = 14.5, 9.6 Hz, 1H), 5.30-5.17 (m, 2H), 5.14-5.04 (m, 1H), 5.01-4.91 (m, 2H), 4.11-3.90 (m, 3H), 3.84-3.74 (m, 1H), 3.65-3.39 (m, 10H), 3.29-3.20 (m, 5H), 3.20-3.07 (m, 6H), 3.08-2.92 (m, 6H), 2.84-2.61 (m, 1H), 2.47-1.81 (m, 8H), 1.79-1.46 (m, 12H), 1.46-0.90 (m, 17H), 0.90-0.57 (m, 14H). | 10.5 | 1139.8 |
| 66 | δ 6.49-6.33 (m, 2H), 6.31-6.01 (m, 3H), 5.46 (dd, J = 14.6, 9.6 Hz, 1H), 5.30-5.21 (m, 1H), 5.15-5.06 (m, 1H), 5.01-4.91 (m, 2H), 4.12-3.89 (m, 3H), 3.86-3.71 (m, 1H), 3.67-3.38 (m, 16H), 3.27-3.09 (m, 11H), 3.08-2.91 (m, 5H), 2.85-2.63 (m, 2H), 2.44-1.80 (m, 9H), 1.81-1.48 (m, 16H), 1.44-0.90 (m, 12H), 0.90-0.56 (m, 14H). | 9.5 | 1183.7 |
| 67 [c, d] | δ 6.82-6.44 (m, 1H), 6.44-6.35 (m, 1H), 6.30-6.06 (m, 3H), 5.46 (dd, J = 14.7, 9.5 Hz, 1H), 5.30-5.24 (m, 1H), 5.13-5.06 (m, 1H), 5.00-4.90 (m, 2H), 4.54-4.49 (m, 1H), 4.10-3.98 (m, 2H), 4.00-3.93 (m, 1H), 3.81-3.70 (m, 1H), 3.65-3.52 (m, 2H), 3.48-3.40 (m, 3H), 3.30-3.08 (m, 12H), 3.07-2.98 (m, 2H), 2.96 (s, 3H), 2.83- | 1.2 | 1081.8 |

TABLE 7-continued

Characterization data for compounds of Table 6

| Compound | NMR $^1$H NMR (400 MHz, DMSO-d$_6$)$^g$ | Yield (%) | [M + NH$_4$]$^+$ |
|---|---|---|---|
| | 2.69 (m, 1H), 2.55-2.51 (m, 1H), 2.44-2.33 (m, 1H), 2.28-2.17 (m, 1H), 2.14-2.06 (m, 1H), 2.06-1.83 (m, 6H), 1.74 (s, 3H), 1.71-1.46 (m, 11H), 1.45-0.92 (m, 13H), 0.91-0.59 (m, 14H). | | |
| 68 $^d$ | δ 6.48-6.41 (m, 1H), 6.41-6.34 (m, 1H), 6.27-6.02 (m, 3H), 5.45 (dd, J = 14.5, 9.6 Hz, 1H), 5.30-5.23 (m, 1H), 5.12-5.05 (m, 1H), 5.00-4.96 (m, 1H), 4.96-4.90 (m, 1H), 4.39-4.32 (m, 1H), 4.05-3.99 (m, 2H), 3.99-3.93 (m, 1H), 3.76-3.68 (m, 1H), 3.66-3.52 (m, 3H), 3.48-3.38 (m, 3H), 3.29-3.22 (m, 3H), 3.18-3.08 (m, 8H), 3.07-2.94 (m, 5H), 2.87-2.69 (m, 1H), 2.43-2.30 (m, 2H), 2.27-2.15 (m, 1H), 2.14-2.00 (m, 2H), 1.99-1.78 (m, 6H), 1.75 (s, 3H), 1.71-1.47 (m, 12H), 1.47-1.35 (m, 2H), 1.34-0.89 (m, 11H), 0.89-0.53 (m, 14H). | 4.9 | 1095.8 |
| 69 $^d$ | δ 6.60-6.51 (m, 1H), 6.51-6.35 (m, 1H), 6.31-6.00 (m, 3H), 5.64 (dd, J = 14.3, 7.9 Hz, 1H), 5.35-5.07 (m, 3H), 5.03-4.93 (m, 1H), 4.54-4.33 (m, 1H), 4.08-3.94 (m, 2H), 3.91 (d, J = 4.7 Hz, 1H), 3.83-3.66 (m, 1H), 3.65-3.51 (m, 3H), 3.50-3.40 (m, 2H), 3.38-3.32 (m, 4H), 3.27-3.00 (m, 9H), 3.00-2.95 (m, 4H), 2.84-2.70 (m, 1H), 2.60-2.53 (m, 1H), 2.31-2.21 (m, 1H), 2.20-2.07 (m, 1H), 2.06-1.81 (m, 6H), 1.78-1.46 (m, 16H), 1.46-1.20 (m, 6H), 1.19-0.91 (m, 11H), 0.91-0.57 (m, 11H). | 8.8 | 1095.8 |
| 70 | 6.48-6.33 (m, 2H), 6.27-6.08 (m, 3H), 5.46 (dd, J = 14.8, 9.5 Hz, 1H), 5.30-5.23 (m, 1H), 5.13-5.06 (m, 1H), 5.01-4.91 (m, 2H), 4.59-4.51 (m, 1H), 4.09-3.98 (m, 2H), 3.98-3.92 (m, 1H), 3.83-3.72 (m, 1H), 3.64-3.37 (m, 11H), 3.27-3.09 (m, 9H), 3.07-2.92 (m, 6H), 2.82-2.69 (m, 1H), 2.44-2.35 (m, 1H), 2.28-2.15 (m, 1H), 2.14-1.80 (m, 8H), 1.76-1.46 (m, 12H), 1.46-1.34 (m, 2H), 1.34-1.19 (m, 4H), 1.19-0.91 (m, 9H), 0.91-0.53 (m, 14H). | 9.9 | 1125.8 |
| 71 | 6.94-6.62 (m, 2H), 6.55-6.26 (m, 3H), 5.94-5.70 (m. 1H), 5.63-5.47 (m, 2H), 5.47-5.34 (m, 1H), 5.31-5.19 (m, 1H), 4.89-4.78 (m, 1H), 4.38-4.17 (m, 3H), 4.15-4.02 (m, 1H), 3.94-3.81 (m, 3H), 3.81-3.73 (m, 4H), 3.73-3.62 (m, 4H), 3.51-3.37 (m, 7H), 3.39-3.20 (m, 7H), 3.19-2.89 (m, 2H), 2.73-2.38 (m, 1H), 2.35-2.09 (m, 6H), 2.09-1.74 (m, 15H), 1.74-1.47 (m, 6H), 1.47-1.19 (m, 9H), 1.19-0.83 (m, 14H). | 9.5 | 1125.8 |
| 72 | 6.96-6.34 (m, 2H), 6.31-6.07 (m, 3H), 5.47 (dd, J = 14.6, 9.6 Hz, 1H), 5.31-5.25 (m, 1H), 5.13-5.06 (m, 1H), 5.03-4.91 (m, 2H), 4.59-4.55 (m, 1H), 4.10-3.99 (m, 2H), 3.99-3.93 (m, 1H), 3.84-3.73 (m, 1H), 3.67-3.56 (m, 2H), 3.56-3.46 (m, 10H), 3.46-3.39 (m, 3H), 3.26-3.09 (m, 9H), 3.08-2.98 (m, 2H), 2.98-2.95 (m, 4H), 2.84-2.69 (m, 1H), 2.44-2.33 (m, 2H), 2.30-2.18 (m, 1H), 2.14-2.01 (m, 2H), 2.01-1.85 (m, 5H), 1.75 (s, 3H), 1.72-1.51 (m, 9H), 1.46-1.36 (m, 2H), 1.35-1.20 (m, 4H), 1.20-1.10 (m, 2H), 1.10-0.92 (m, 7H), 0.92-0.72 (m, 13H), 0.65 (q, J = 11.9 Hz, 1H). | 11.3 | 1169.9 |
| 73 | 6.59-6.52 (m, 1H), 6.50-6.33 (m, 1H), 6.28-6.01 (m, 3H), 5.67-5.42 (m, 1H), 5.29-5.06 (m, 3H), 5.04-4.92 (m, 1H), 4.61-4.50 (m, 2H), 4.10-3.90 (m, 3H), 3.89-3.74 (m, 1H), 3.74-3.38 (m, 15H), 3.33-3.22 (m, 1H), 3.24-3.08 (m, 7H), 3.10-2.91 (m, 5H), 2.81-2.63 (m, 2H), 2.58-2.52 (m, 1H), 2.43-1.81 (m, 9H), 1.81-1.47 (m, 16H), 1.46-1.19 (m, 3H), 1.19-0.90 (m, 8H), 0.90-0.54 (m, 14H). | 8.1 | 1169.9 |

For Table 6 and Table 7: [a]Time stirred at 0° C. (Method 1) or room temperature (Methods 3 and 4). Where reaction was incomplete at end of working day, reaction was stored at 20° C. overnight, then stirring at listed temperature continued; [b]Isolated S-isomer contained up to 1000 C-16 R isomer; [c]A third addition of $FeCl_3$ solution was required for complete conversion. [d]Reaction mixture cooled in ice bath for first addition of $FeCl_3$ solution; [e]~3:1 mix S:R at C-16; [f]~2:3 mix S: Rat C-16; [g]The NMR characterization data shown in the examples correspond only to the major equilibrium form observed under the reported deuterated solvent conditions.

Differential pharmacology of compounds described herein may be observed in different cell or tissue types depending on (1) the relative abundance of FKBP homologs in these cells/tissues and (2) the specificity of binding to these different FKBP homologs (Mol. Cell Biol. (2013) 33: 1357-1367). Various FKBP homologs are used in the following examples.

Example 28

SPR Assay to Determine Binding Affinity to FKBP12.

Biotinylated avi-FKBP12 was immobilized on a streptavidin chip (Cytiva Series S SA) using a Biacore 8K or 8 k+ (Cytiva). To achieve an immobilization level of 1000 RU, 2 μg/ml biotinylated avi-FKBP12 were injected for 100 sec at a flow rate of 10 μl/min. Rapalogs were diluted in DMSO to 100× working concentration. Each Rapalog was 100-fold diluted in 50 mM HEPES pH 7.5, 150 mM NaCl, 2 mM $MgCl_2$, 1 mM DTT, 0.05% Tween-20 and a serial dilution prepared (9 concentrations, 3-fold dilutions, 0.08-500 nM). Rapamycin was used as reference sample (9 concentrations, 3-fold dilutions, 0.02-100 nM). The compound dilutions were then injected at 100 uL/min for 120 seconds contact time in sequence with increasing concentrations. Dissociation was monitored for 3600 seconds. 50 mM HEPES pH 7.5, 150 mM NaCl, 2 mM $MgCl_2$, 1 mM DTT, 0.05% Tween-20, 1% DMSO was used as running buffer. The single-cycle kinetics data were fit to a 1:1 binding model to measure the association rate ka (1/Ms), the dissociation rate kd (1/s) and the affinity Kd (M). Table 8 includes FKBP12 direct binding $K_d$ (nM) values of selected compounds; with compounds having a FKBP12 direct binding $K_d$ of less than 0.3 nM as A, 0.3 nM to 1.0 nM as B, and greater than 1.0 nM as C.

Example 29: SPR Assay to Determine Binding Affinity to FKBP51

Biotinylated avi-FKBP51 was immobilized on a streptavidin chip (Cytiva Series S SA) using a Biacore 8K or 8 k+ (Cytiva). To achieve an immobilization level of 2000 RU, 3 μg/ml biotinylated avi-FKBP51 were injected for 360 sec at a flow rate of 10 μl/min. Rapalogs were diluted in DMSO to 100× working concentration. Each Rapalog was 100-fold diluted in 50 mM HEPES pH 7.5, 150 mM NaCl, 2 mM $MgCl_2$, 1 mM DTT, 0.05% Tween-20 and a serial dilution prepared (8 concentrations, 3-fold dilutions, 0.5-1000 nM). Rapamycin was used as reference sample (8 concentrations, 3-fold dilutions, 0.5-1000 nM). The compound dilutions were then injected at 100 uL/min for 120 seconds contact time and with 3600 seconds dissociation time with increasing concentrations. 50 mM HEPES pH 7.5, 150 mM NaCl, 2 mM $MgCl_2$, 1 mM DTT, 0.05% Tween-20, 1% DMSO was used as running buffer. Multi-cycle kinetics data were fit to a 1:1 binding model to measure the association rate ka (1/Ms), the dissociation rate kd (1/s) and the affinity Kd (M).

Table 8 includes FKBP51 direct binding $K_d$ (nM) values of selected compounds; with compounds having a FKBP51 direct binding $K_d$ of less than 10 nM as A, 10 nM to 100 nM as B, and greater than 100 nM as C.

Example 30: SPR Assay to Characterize Ternary Complex Formation with FKBP12

Biotinylated avi-FKBP12 was immobilized on a streptavidin chip (Cytiva Series S SA) using a Biacore 8K or 8 k+ (Cytiva). To achieve an immobilization level of 100 RU, 0.3 μg/ml biotinylated avi-FKBP12 were injected for 80 sec at a flow rate of 10 μl/min. Serial dilution of FRB was prepared (12 concentrations, 3-fold dilutions, 0.00011-20 μM) and supplemented with 100 nM of rapalog. A-B-A injection mode was used to ensure saturation immobilized FKBP12 with respective rapalog. 100 nM solution of the respective rapalog was injected before FRB injection for 120 sec and during dissociation for 420 sec. The FRB dilutions were then injected 120 seconds contact time with increasing concentrations. Rapamycin was used as reference sample. 50 mM HEPES pH 7.5, 150 mM NaCl, 2 mM $MgCl_2$, 1 mM DTT, 0.05% Tween-20, 1% DMSO was used as running buffer at a flow rate of 30 μl/min. The multi-cycle kinetics data were fit to a 1:1 binding model to measure the association rate ka (1/Ms), the dissociation rate kd (1/s) and the affinity Kd (M). In case of fast association and dissociation, steady state affinity analysis following the law of mass action was used to determine the affinity Kd (M).

Table 9 includes FKBP12 ternary complex $K_d$ (nM) values of selected compounds; with compounds having a FKBP12 ternary complex $K_d$ of less than 300 nM as A, 300 nM to 800 nM as B, and greater than 800 nM as C.

Example 31: SPR Assay to Characterize Ternary Complex Formation with FKBP51

Biotinylated avi-FKBP51 was immobilized on a streptavidin chip (Cytiva Series S SA) using a Biacore 8K or 8 k+ (Cytiva). To achieve an immobilization level of 200 RU, 0.6 μg/ml biotinylated avi-FKBP51 were injected for 150 sec at a flow rate of 10 μl/min. Serial dilution of FRB was prepared (12 concentrations, 3-fold dilutions, 0.00011-20 μM) and supplemented with 100 nM of rapalog. A-B-A injection mode was used to ensure saturation immobilized FKBP12 with respective rapalog. 100 nM solution of the respective rapalog was injected before FRB injection for 120 sec and during dissociation for 420 sec. The FRB dilutions were then injected 120 seconds contact time with increasing concentrations. Rapamycin was used as reference sample. 50 mM HEPES pH 7.5, 150 mM NaCl, 2 mM $MgCl_2$, 1 mM DTT, 0.05% Tween-20, 1% DMSO was used as running buffer at a flow rate of 30 μl/min. The multi-cycle kinetics data were fit to a 1:1 binding model to measure the association rate ka (1/Ms), the dissociation rate kd (1/s) and the affinity $K_d$ (M). In case of fast association and dissociation, steady state affinity analysis following the law of mass action was used to determine the affinity Kd (M).

Table 9 includes FKBP51 ternary complex $K_d$ (nM) values of selected compounds; with compounds having a FKBP51 ternary complex $K_d$ of less than 300 nM as A, 300 nM to 800 nM as B, and greater than 800 nM as C.

Example 32: mTORC1 Inhibition, mTORC2 Inhibition, Cell Lysis, AlphaLISA Experiments, and Data Analysis mTORC1 inhibition was determined via analysis of phosphorylation levels of Phospho-p70 S6 kinase (p70S6K pT389) and Phospho-S6 Ribosomal Protein (pRPS6 pS240/pS244) with the corresponding AlphaLISA kits (PerkinElmer Alpha SF Ultra™ Multiplex phospho (Thr389)/total p70 S6K Assay Kit (Eu/Tb) and AlphaLISA SF Ultra™ p-Ribosomal Protein S6 (Ser240/244) Assay Kit). Thus, PC-3 cells were plated on 96 well Corning clear bottom plates (Cat #3997) in growth medium (DMEM: Ham's F12, basic (CLS Cell Lines Service GmbH, Cat #820400a), supplemented with additional 5% fetal bovine serum (FBS; Gibco, Cat #10500064) at 1.20E+06 cells/mL and incubated overnight at 37° C., 5% $CO_2$. On the following day, cells were treated with growth medium containing increasing compound concentrations (12 points at 3-fold dilutions) and incubated for further 24 hours at 37° C., 5% $CO_2$ before cell lysis.

mTORC2 inhibition was determined via analysis of phosphorylation level of Phospho-AKT (pAKT pS473) with the corresponding AlphaLISA kit (PerkinElmer, Alpha SF Ultra™ Multiplex p-AKT1/2/3(Ser473)/Total AKT1). PC3 cells were plated on 96 well plates in assay medium (DMEM: Ham's F12, basic (CLS Cell Lines Service GmbH, Cat #820400a), supplemented with additional 10% FBS at 1.20E+06 cells/mL and incubated over-night at 37° C., 5% $CO_2$. On the following day, cells were treated with assay medium (10% FBS) containing increasing compound concentrations (12 points at 3-fold dilutions) and incubated for 6 hours at 37° C., 5% $CO_2$. Thereafter, medium was aspirated and cells were rinsed with PBS. In the following, cells were treated with compound dilutions in starvation medium (DMEM: Ham's F12, basic; without FBS) for further 18 h at 37° C., 5% $CO_2$. Then, immediately prior to cell lysis, cells were treated with 12% FBS for 15 min.

After performing experiments according to mTORC1 and mTORC2 protocols, cells were harvested in lysis buffer supplied with the AlphaLISA kits, additionally enriched with Roche cOmplete™ Protease Inhibitor Cocktail (Cat #CO-RO). Thus, cells were lysed using 50 μL of the lysis buffer and incubated for 60 min at 4° C. while shaking. After centrifugation at 4000 rpm for 5 min, experiments were performed according to the AlphaLISA manufacturer's protocol.

Ten microliters of cell lysates were mixed with the acceptor mix. After incubation for 2 h at room temperature, the donor mix was added. After additional incubation at room temperature for 2 hours, AlphaLISA signal was read on PHERAstar® FSX (BMG Labtech) with AlphaPLEX module. Percent inhibition was calculated via ExcelFit standard algorithm, based on high control (cells incubated with vehicle/DMSO) and low control (mTORC1: cells incubated with 0.1 μM rapamycin; mTORC2: cells incubated with 1 μM rapamycin). All IC50 experiments were conducted in triplicates with rapamycin and vehicle controls.

Data Analysis

Percentaged activity/inhibition was calculated via application of the equations:

%-activity=100*((Sample−Low control)/(High control−Low control))

%-inhibition=100*(1−((Sample−Low control)/(High control−Low control)))

Sample=Assay signal (phospho-protein normalized to total protein) at respective compound concentration
High Control=Assay signal in presence of vehicle/DMSO
Low Control=Assay signal cells in presence of 0.1 μM (mTORC1) or 1 μM rapamycin (mTORC2)

EC50 values were calculated by ExcelFit standard algorithm. All IC50 experiments were conducted in triplicates with rapamycin and vehicle controls (six high/low controls per plate).

Table 10 includes $IC_{50}$ (nM) values for mTORC1 as measured by inhibition of p70S6K pT389 levels by selected compounds; with compounds having an $IC_{50}$ for mTORC1 of <0.1 nM as A, 0.1 nM to 0.8 nM as B, and greater than 0.8 as C. Table 10 also includes mTORC2% inhibition at 1 uM. For mTORC2: A ≤20% inhibition at 1 micro Molar (uM), B>20% and less than 40% inhibition at 1 uM, C≥40% and less than 60% inhibition at 1 uM, D≥60% inhibition at 1 uM.

TABLE 8

FKBP12 and FKBP51 direct binding $K_d$ values

| Compound | FKBP12 $K_d$ (nM) | FKBP51 $K_d$ (nM) |
|---|---|---|
| 1 | C | B |
| 2 | A | B |
| 3 | B | C |
| 4 | A | B |
| 5 | A | B |
| 6 | A | A |
| 7 | A | B |
| 8 | A | B |
| 9 | A | A |
| 10 | B | B |
| 11 | B | B |
| 12 | B | B |
| 13 | A | B |
| 14 | B | B |
| 15 | A | B |
| 16 | A | B |
| 17 | A | B |
| 18 | B | B |
| 19 | B | C |
| 20 | A | C |
| 21 | A | B |
| 22 | A | C |
| 23 | A | B |
| 24 | A | B |
| 25 | A | B |
| 26 | A | C |
| 27 | A | B |
| 28 | A | B |
| 29 | A | C |
| 30 | A | B |
| 31 | A | B |
| 32 | A | B |
| 33 | A | B |
| 34 | A | B |
| 35 | A | A |
| 36 | A | C |
| 37 | C | |
| 38 | B | B |
| 39 | B | C |
| 40 | C | C |
| 41 | B | C |
| 42 | C | C |
| 43 | C | C |
| 44 | C | C |
| 45 | C | C |
| 46 | C | C |
| 47 | C | C |
| 48 | C | C |
| 49 | A | C |
| 50 | C | C |
| 51 | C | C |
| 52 | B | C |
| 53 | B | C |
| 54 | C | C |
| 55 | A | C |
| 56 | A | C |
| 57 | C | B |
| 58 | B | |

TABLE 8-continued

FKBP12 and FKBP51 direct binding $K_d$ values

| Compound | FKBP12 $K_d$ (nM) | FKBP51 $K_d$ (nM) |
|---|---|---|
| 59 | A | B |
| 60 | C | C |
| 61 | A | C |
| 62 | C | C |
| 63 | C | |
| 64 | B | C |
| 65 | A | B |
| 66 | B | B |
| 67 | A | B |
| 68 | A | B |
| 69 | B | B |
| Rapamycin | A | A |

TABLE 9

FKBP12 and FKBP51 ternary complex formation $K_d$ values

| Compound # | FKBP12 ternary complex $K_d$ (nM) | FKBP51 ternary complex $K_d$ (nM) |
|---|---|---|
| 1 | B | A |
| 2 | A | B |
| 3 | C | C |
| 4 | A | B |
| 5 | C | C |
| 6 | C | C |
| 7 | A | B |
| 8 | B | B |
| 9 | A | A |
| 10 | B | B |
| 11 | B | B |
| 12 | B | B |
| 13 | B | C |
| 14 | C | C |
| 15 | A | C |
| 16 | B | C |
| 17 | B | C |
| 18 | B | B |
| 19 | C | C |
| 20 | B | C |
| 21 | C | C |
| 22 | C | C |
| 23 | C | C |
| 24 | B | B |
| 25 | B | C |
| 26 | C | C |
| 27 | C | C |
| 28 | C | C |
| 29 | C | C |
| 30 | C | C |
| 31 | C | C |
| 32 | B | C |
| 33 | C | C |
| 34 | C | C |
| 35 | C | C |
| 36 | B | C |
| 37 | B | C |
| 38 | C | C |
| 39 | B | C |
| 40 | B | C |
| 41 | C | C |
| 42 | B | C |
| 43 | A | A |
| 44 | A | C |
| 45 | A | A |
| 46 | B | B |
| 47 | A | C |
| 48 | B | C |
| 49 | B | C |
| 50 | B | C |
| 51 | B | C |
| 52 | A | C |
| 53 | A | C |

TABLE 9-continued

FKBP12 and FKBP51 ternary complex formation $K_d$ values

| Compound # | FKBP12 ternary complex $K_d$ (nM) | FKBP51 ternary complex $K_d$ (nM) |
|---|---|---|
| 54 | A | C |
| 55 | B | C |
| 56 | B | C |
| 57 | B | C |
| 58 | B | A |
| 59 | A | B |
| 60 | A | C |
| 61 | A | C |
| 62 | A | C |
| 63 | B | C |
| 64 | A | A |
| 65 | B | C |
| 66 | C | C |
| 67 | B | C |
| 68 | A | C |
| 69 | B | C |

TABLE 10 mTORC 1 and mTORC 2

| Compound | mTORC1 IC50 (nM) | mTORC2 % inhibition at 1 uM |
|---|---|---|
| 1 | B | A |
| 2 | A | A |
| 3 | C | A |
| 4 | A | A |
| 5 | B | A |
| 6 | B | A |
| 7 | B | B |
| 8 | B | B |
| 9 | A | C |
| 10 | B | A |
| 11 | B | A |
| 12 | C | A |
| 13 | B | A |
| 14 | C | A |
| 15 | B | A |
| 16 | B | B |
| 17 | B | A |
| 18 | B | A |
| 19 | C | B |
| 20 | B | B |
| 21 | C | A |
| 22 | B | A |
| 23 | C | A |
| 24 | B | A |
| 25 | B | A |
| 26 | C | A |
| 27 | C | A |
| 28 | B | B |
| 29 | C | A |
| 30 | C | A |
| 31 | B | A |
| 32 | B | A |
| 33 | C | A |
| 34 | C | A |
| 35 | C | A |
| 36 | B | B |
| 37 | C | B |
| 38 | B | A |
| 39 | B | B |
| 40 | B | A |
| 41 | C | A |
| 42 | C | A |
| 43 | C | C |
| 44 | B | C |
| 45 | C | B |
| 46 | B | B |
| 47 | C | B |
| 48 | C | A |
| 49 | C | B |

TABLE 10-continued mTORC 1 and mTORC 2

| Compound | mTORC1 IC50 (nM) | mTORC2 % inhibition at 1 uM |
|---|---|---|
| 50 | C | B |
| 51 | C | A |
| 52 | B | B |
| 53 | B | C |
| 54 | B | B |
| 55 | B | B |
| 56 | B | C |
| 57 | C | B |
| 58 | C | B |
| 59 | A | D |
| 60 | B | B |
| 61 | A | B |
| 62 | C | C |
| 63 | C | C |
| 64 | B | C |
| 65 | B | A |
| 66 | B | A |
| 67 | B | B |
| 68 | A | C |
| 69 | B | B |
| Rapamycin | A | D |

The invention claimed is:

1. A compound represented by the structure of Formula X:

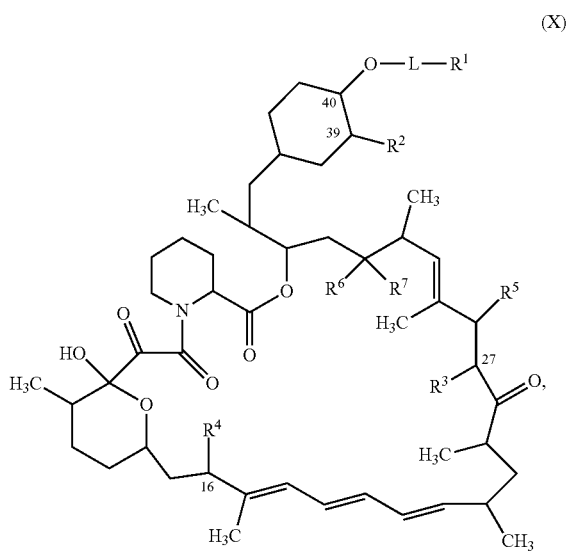

(X)

or a pharmaceutically acceptable salt thereof, wherein:
L is selected from an unsubstituted $C_{2-4}$ alkylene;
$R^1$ is selected from —S(O)OH, —S(O)$_2$OH, and —S(O)$_2C_{1-6}$ alkyl, wherein the $C_{1-6}$ alkyl is optionally substituted by one or more substituents selected from halogen, —OH, —NO$_2$, =O, —O—$C_{1-6}$ alkyl;
$R^2$ is selected from hydrogen and a $C_1$-$C_3$ alkoxy group;
$R^3$ is selected from hydrogen and a $C_1$-$C_3$ alkoxy group; and
$R^4$ is selected from

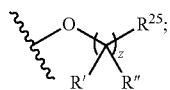

z is 0, 1, 2, 3, 4 or 5;
$R^5$ is selected from hydrogen, hydroxy, and an optionally substituted $C_1$-$C_6$ alkoxy group, wherein substituents are independently selected at each occurrence from hydroxy, halogen, —CN, —NO$_2$, $C_1$-$C_6$ alkoxy group, 3- to 10-membered heterocycle, and $C_{3-10}$ carbocycle, wherein the 3- to 10-membered heterocycle, and $C_{3-10}$ carbocycle are each optionally substituted with one or more substituents independently selected from hydroxy, halogen, —CN, —NO$_2$, $C_1$-$C_6$ alkyl, $C_1$-$C_6$ haloalkyl, $C_1$-$C_6$ hydroxyalkyl, $C_1$-$C_6$ alkoxy, and $C_1$-$C_6$ alkoxy $C_1$-$C_6$ alkyl;
$R^6$ and $R^7$ come together to form

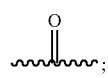

$R^{25}$ is independently selected at each occurrence from hydrogen, optionally substituted $C_1$-$C_6$ alkyl, -D-(CH$_2$—CH$_2$-G)$_y$-V, optionally substituted $C_{3-20}$ carbocycle, and optionally substituted 3- to 20-membered heterocycle,
wherein when $R^{25}$ is optionally substituted $C_1$-$C_6$ alkyl, the substituents on $C_1$-$C_6$ alkyl are independently selected at each occurrence from halogen, —OH, —CN, —NO$_2$, —NH$_2$, =O, =S, —C(O)N(R$^{31}$)$_2$, —OC(O)N(R$^{31}$)$_2$, —C(O)OR$^{31}$, —P(O)(R$^{31}$)$_2$, —O—$C_{1-10}$ alkyl, —O—$C_{1-10}$ alkyl-CN, —O—$C_{1-10}$ alkyl-C(O)OR$^{31}$, $C_{2-10}$ alkenyl, $C_{2-10}$ alkynyl, $C_{3-20}$ carbocycle, and 3- to 20-membered heterocycle;
wherein when $R^{25}$ is optionally substituted $C_{3-20}$ carbocycle or optionally substituted 3- to 20-membered heterocycle, the substituents on $C_{3-20}$ carbocycle and 3- to 20-membered heterocycle are independently selected at each occurrence from halogen, —OR$^{31}$, —SR$^{31}$, —N(R$^{31}$)$_2$, —C(O)R$^{31}$, —C(O)N(R$^{31}$)$_2$, —N(R$^{31}$)C(O)R$^{31}$, —C(O)OR$^{31}$, —OC(O)R$^{31}$, —S(O)R$^{31}$, —S(O)$_2$R$^{31}$, —P(O)(OR$^{31}$)$_2$, —OP(O)(OR$^{31}$)$_2$, —NO$_2$, =O, =S, =N(R$^{31}$), —CN, $C_{1-6}$ alkyl, $C_{1-6}$ haloalkyl, $C_{2-6}$ alkenyl, and $C_{2-6}$ alkynyl;
wherein D is selected from a bond and —O—;
each G is independently selected from —O—, —NR$^{32}$—, —S—, and —SO$_2$—;
each y is selected from 1-20;
each V is selected from hydrogen and optionally substituted —$C_1$-$C_6$ alkyl;
$R^{30}$ is independently selected at each occurrence from hydrogen; $C_{1-10}$ alkyl, $C_{2-10}$ alkenyl, $C_{2-10}$ alkynyl, $C_{3-10}$ carbocycle, and 3- to 10-membered heterocycle, each of which is optionally substituted with one or more substituents independently selected from halogen, —OH, —OSi($C_1$-$C_6$ alkyl)$_3$, —CN, —NO$_2$, —NH$_2$, =O, =S, $C_{1-10}$ alkyl, haloalkyl, —O—$C_{1-10}$ alkyl, $C_{2-10}$ alkenyl, $C_{2-10}$ alkynyl, $C_{3-10}$ carbocycle, and 3- to 10-membered heterocycle;
R' and R" are independently selected at each occurrence from hydrogen, halogen, —OR$^{31}$, and $C_{1-8}$ alkyl optionally substituted with one or more substituents independently selected from halogen and —OR$^{31}$;
$R^{31}$ is independently selected at each occurrence from: hydrogen; and $C_{1-10}$ alkyl, $C_{2-10}$ alkenyl, $C_{2-10}$ alkynyl, $C_{3-12}$ carbocycle, and 3- to 12-membered heterocycle, each of which is optionally substituted with one or more substituents independently selected from halogen, —OH, —OSi($C_1$-$C_6$ alkyl)$_3$, —CN, —NO$_2$, —NH$_2$, =O, =S, $C_{1-10}$ alkyl, haloalkyl, —O—$C_{1-10}$ alkyl, —O—$C_{1-10}$ alkyl-OH, $C_{2-10}$ alkenyl, $C_{2-10}$ alkynyl, $C_{3-12}$ carbocycle, and 3- to 12-membered heterocycle;

$R^{32}$ is independently selected at each occurrence from: hydrogen; and $C_{1-10}$ alkyl, $C_{2-10}$ alkenyl, $C_{2-10}$ alkynyl, $C_{3-10}$ carbocycle, and 3- to 10-membered heterocycle, each of which is optionally substituted with one or more substituents independently selected from halogen, —OH, —CN, —NO$_2$, —NH$_2$, =O, =S, $C_{1-10}$ alkyl, —$C_{1-10}$ haloalkyl, —O—$C_{1-10}$ alkyl, $C_{2-10}$ alkenyl, $C_{2-10}$ alkynyl, $C_{3-10}$ carbocycle, and 3- to 10-membered heterocycle; and wherein the substituents on V are independently selected at each occurrence from:

halogen, —OR$^{30}$, —N(R$^{30}$)$_2$, —SR$^{30}$, —C(O)R$^{30}$, —C(O)N(R$^{30}$)$_2$, —N(R$^{30}$)C(O)R$^{30}$, —C(O)OR$^{30}$, —OC(O)R$^{30}$, —S(O)R$^{30}$, —S(O)$_2$R$^{30}$, —OP(O)(OR$^{30}$)$_2$, —OP(O)(OR$^{30}$)$_2$, —NO$_2$, =S, =N(R$^{30}$), and —CN;

$C_{1-10}$ alkyl, $C_{2-10}$ alkenyl, $C_{2-10}$ alkynyl, each of which is optionally substituted with one or more substituents independently selected from halogen, —OR$^{30}$, —SR$^{30}$, —N(R$^{30}$)$_2$, —C(O)R$^{30}$, —C(O)N(R$^{30}$)$_2$, —N(R$^{30}$)C(O)R$^{30}$, —C(O)OR$^{30}$, —OC(O)R$^{30}$, —S(O)R$^{30}$, —S(O)$_2$R$^{30}$, —P(O)(OR$^{30}$)$_2$, —OP(O)(OR$^{30}$)$_2$, —NO$_2$, =O, =S, =N(R$^{30}$), —CN, $C_{3-10}$ carbocycle and 3-to 10-membered heterocycle; and $C_{3-10}$ carbocycle and 3- to 10-membered heterocycle each of which is optionally substituted with one or more substituents independently selected from halogen, —OR$^{30}$, —SR$^{30}$, —N(R$^{30}$)$_2$, —C(O)R$^{30}$, —C(O)N(R$^{30}$)$_2$, —N(R$^{30}$)C(O)R$^{30}$, —C(O)OR$^{30}$, —OC(O)R$^{30}$, —S(O)R$^{30}$, —S(O)$_2$R$^{30}$, —P(O)(OR$^{30}$)$_2$, —OP(O)(OR$^{30}$)$_2$, —NO$_2$, =O, =S, =N(R$^{30}$), —CN, $C_{1-6}$ alkyl, $C_{1-6}$ haloalkyl, $C_{2-6}$ alkenyl, and $C_{2-6}$ alkynyl.

2. The compound or salt of claim 1, wherein R$^1$ is selected from —S(O)$_2$OH and —S(O)$_2$C$_{1-6}$ alkyl, wherein the C$_{1-6}$ alkyl is optionally substituted by one or more substituents selected from halogen, —OH, —NO$_2$, =O, —O—C$_{1-6}$ alkyl.

3. The compound or salt of claim 2, wherein R$^1$ is selected from —S(O)$_2$C$_{1-6}$ alkyl, wherein the C$_{1-6}$ alkyl is optionally substituted by one or more substituents selected from halogen, —OH, —NO$_2$, =O, —O—C$_{1-6}$ alkyl.

4. The compound or salt of claim 3, wherein R$^1$ is selected from —S(O)$_2$C$_{1-6}$ alkyl, wherein the C$_{1-6}$ alkyl is unsubstituted.

5. The compound or salt of claim 1, wherein —O-L-R$^1$ is selected from

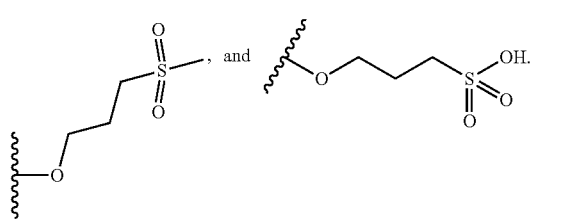

6. The compound or salt of claim 5, wherein —O-L-R$^1$ is selected from

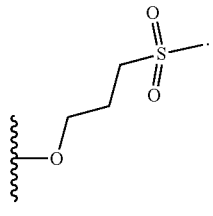 [SMILES: *OCCCS(C)(=O)=O]

7. The compound or salt of claim 1, wherein R$^{25}$ of R$^4$ is selected from, hydrogen, optionally substituted C$_1$-C$_6$ alkyl, -D-(CH$_2$—CH$_2$-G)$_y$-V, optionally substituted 3- to 10-membered heterocycle, and optionally substituted C$_{3-10}$ carbocycle.

8. The compound or salt of claim 7, wherein the optionally substituted C$_1$-C$_6$ alkyl of R$^{25}$ is substituted with one or more substituents selected from C$_{3-20}$ carbocycle, —OH and —O—C$_{1-10}$ alkyl.

9. The compound or salt of claim 8, wherein the optionally substituted C$_1$-C$_6$ alkyl of R$^{25}$ is substituted with one or more substituents selected from —OH and —O—C$_{1-10}$ alkyl.

10. The compound or salt of claim 7, wherein D is —O—, G is —O—, y is 1-3, and V is selected from —C$_1$-C$_6$ alkyl and hydrogen.

11. The compound or salt of claim 10, wherein R$^{25}$ is selected from hydrogen, and -D-(CH$_2$-CH$_2$-G)$_y$-V, wherein D is —O—, G is —O—, y is 1-3, and V is selected from —C$_1$-C$_6$ alkyl and hydrogen.

12. The compound or salt of claim 11, wherein R' and R" are independently selected at each occurrence from hydrogen.

13. The compound or salt of claim 1, wherein z is selected from 1, 2, and 3.

14. The compound or salt of claim 1, wherein R$^4$ is selected from

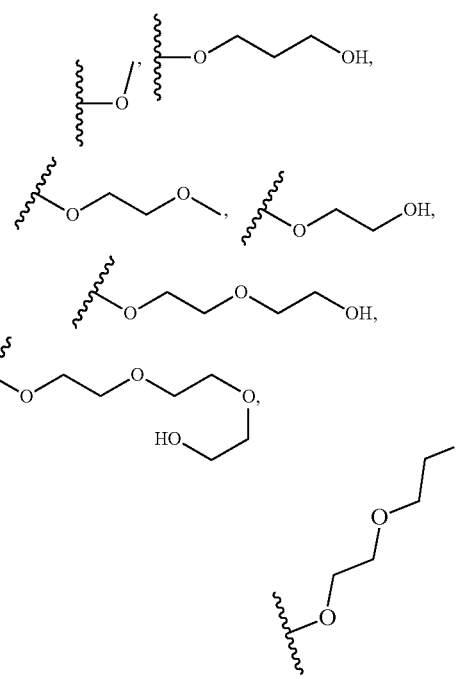

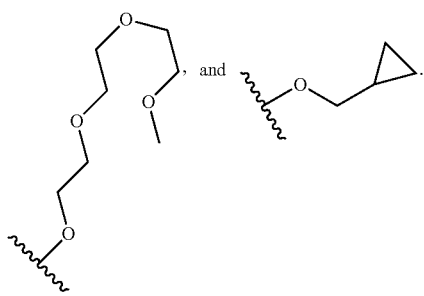
15. The compound or salt of claim 1, wherein R⁴ is selected from
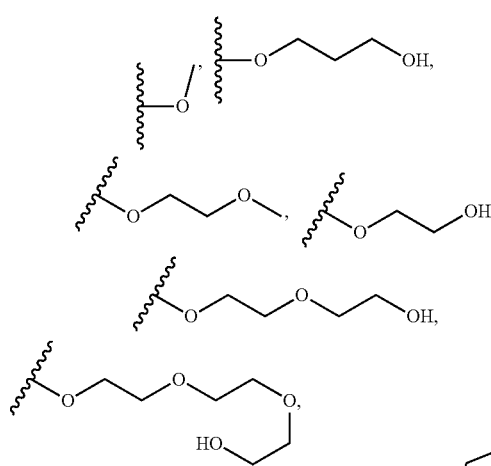
16. The compound or salt of claim 1, wherein R⁴ is selected from
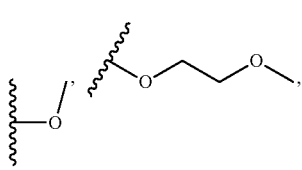
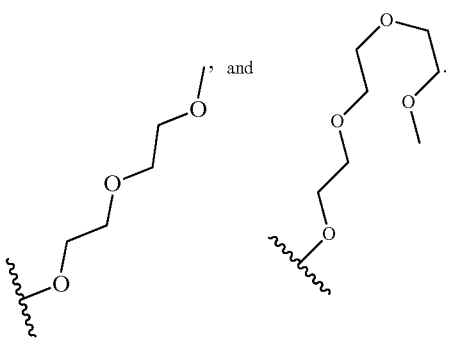
17. The compound or salt of claim 1, wherein R⁴ is selected from
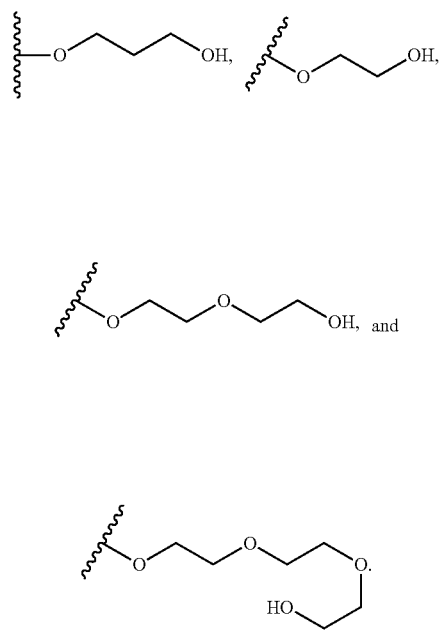
18. The compound or salt of claim 17, wherein R⁴ is selected from
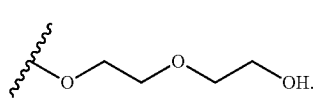

19. The compound or salt of claim 1, wherein the compound is selected from
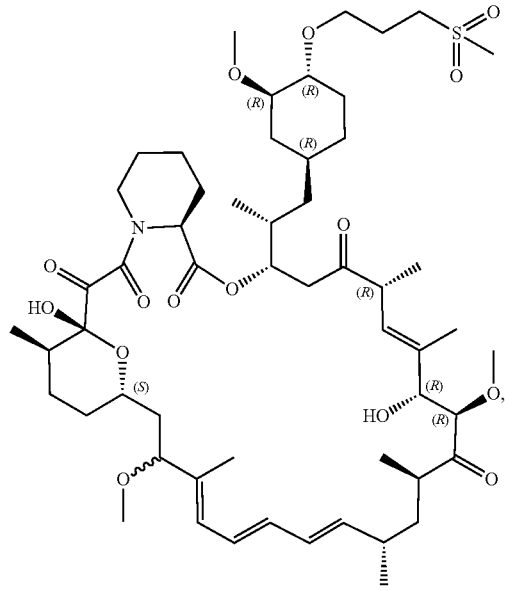
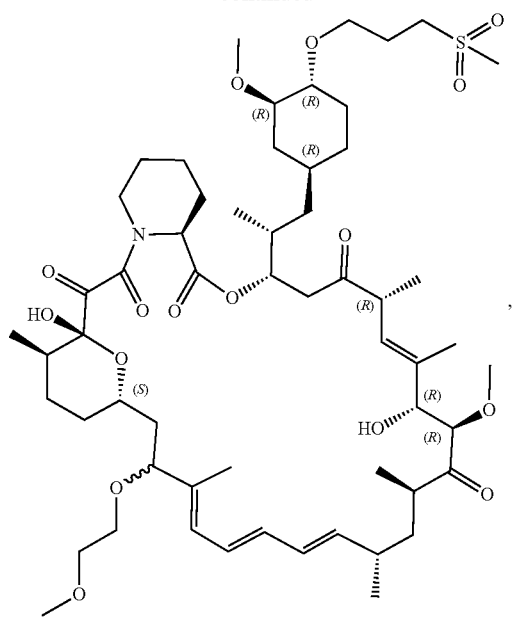
,
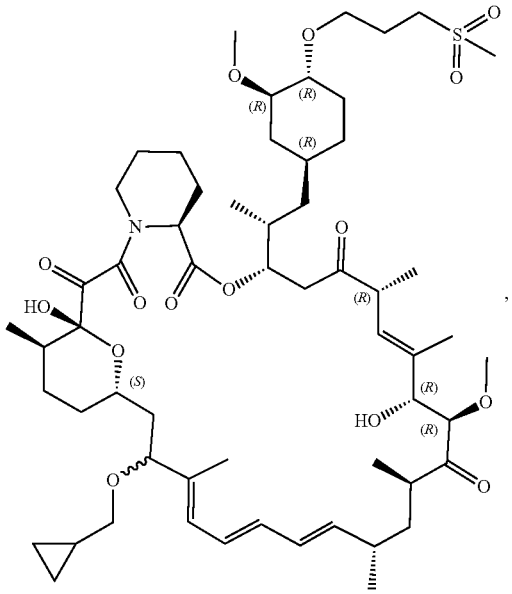
,
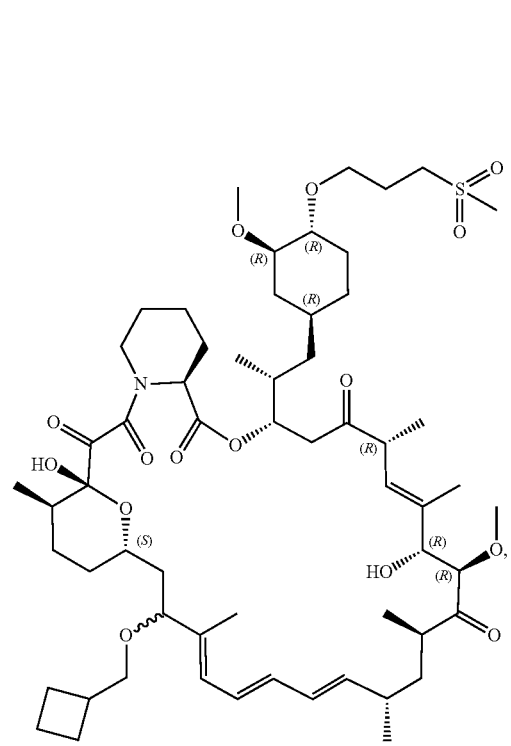
-continued 299
-continued
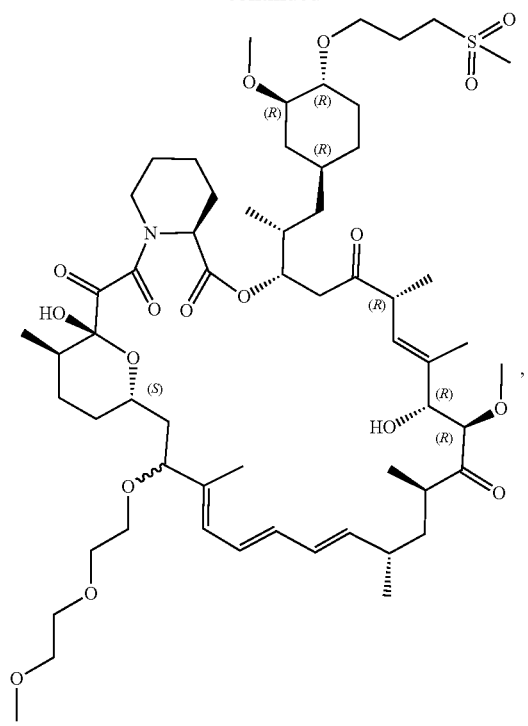
,
300
-continued
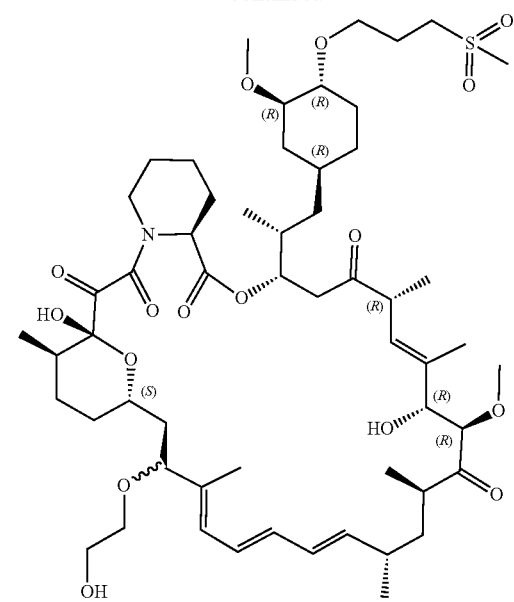
,
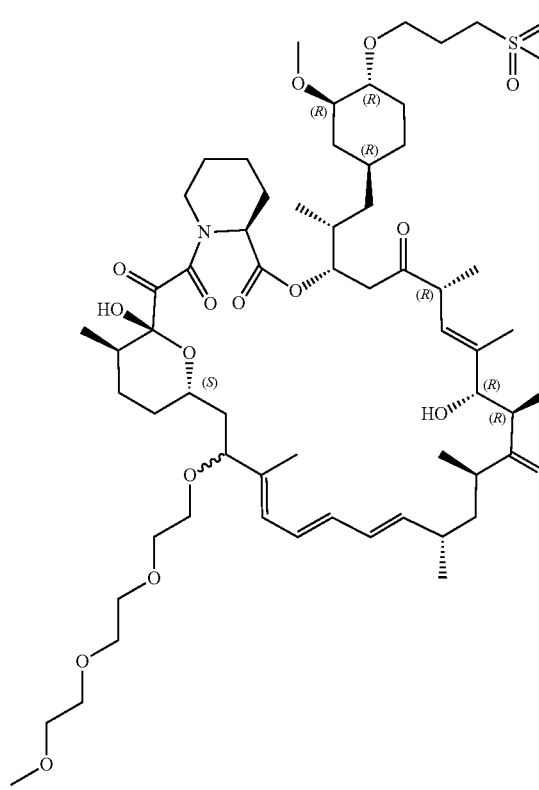
,
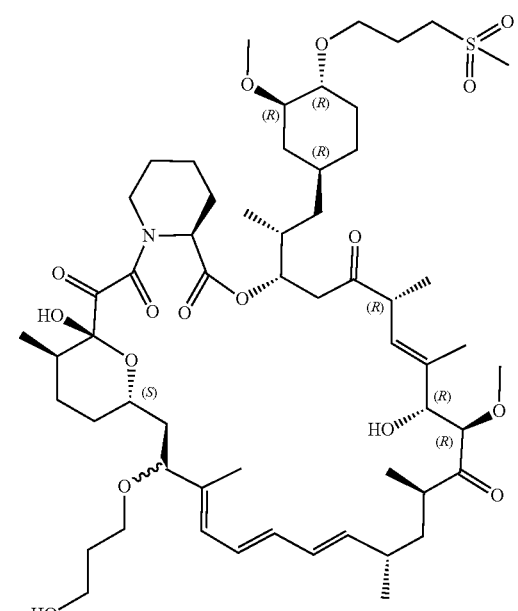
, 301
-continued
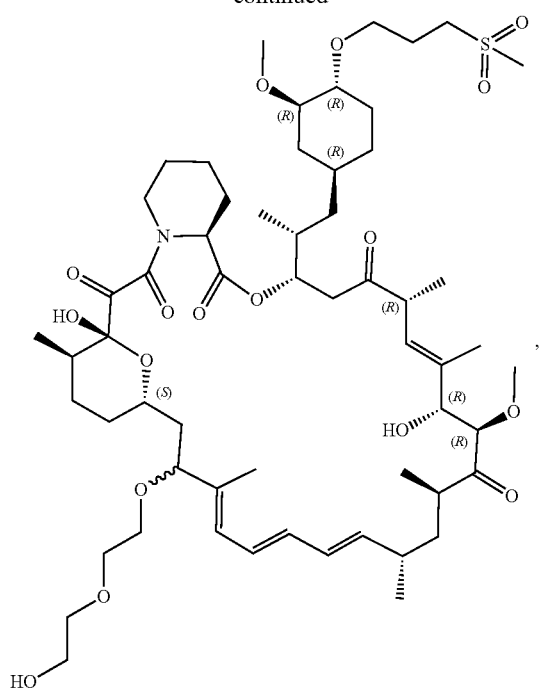
302
-continued
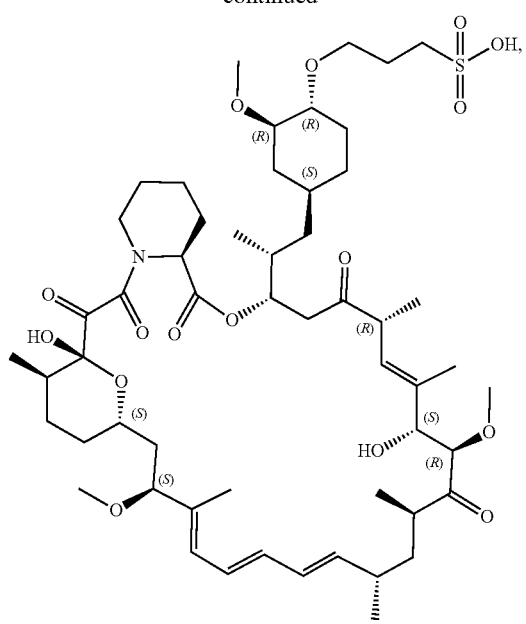
or a pharmaceutically acceptable salt of any one thereof.
20. The compound or salt of claim 1, wherein the compound is selected from
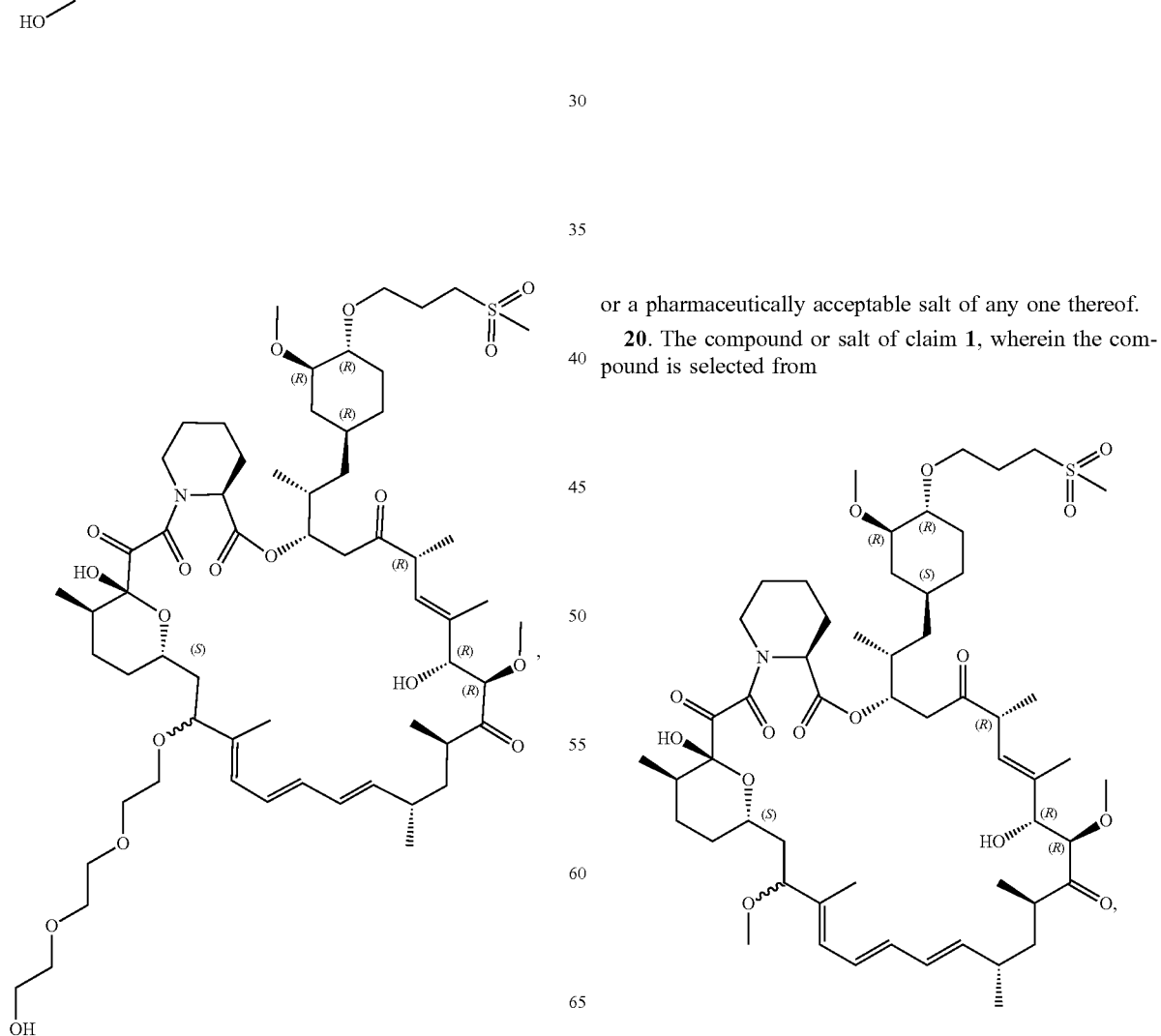

303
-continued
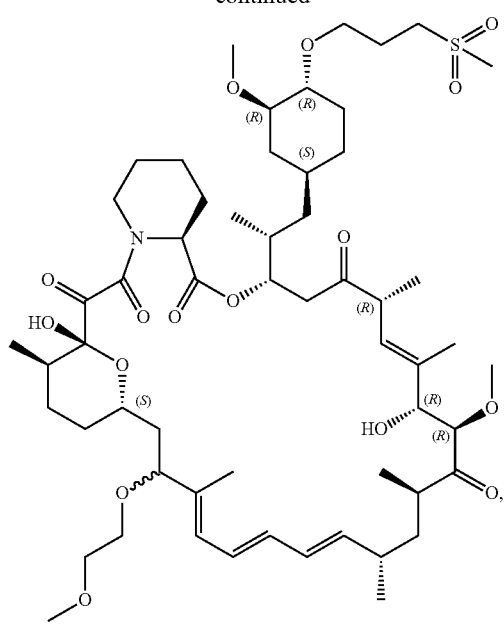
304
-continued
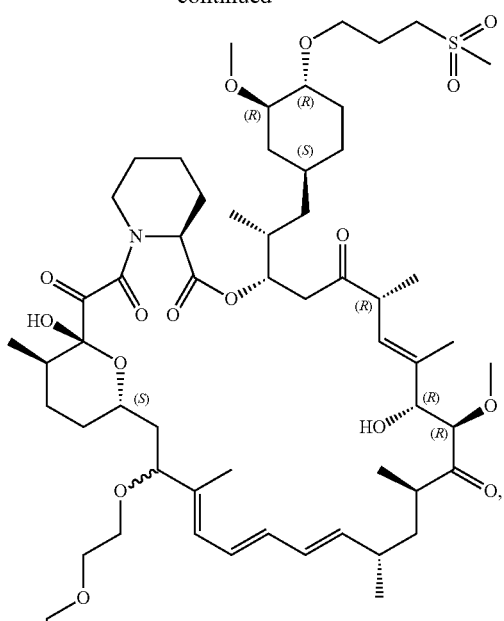
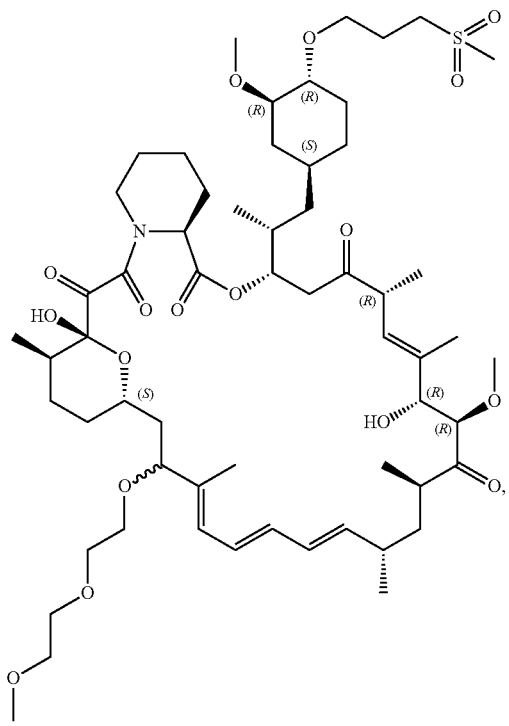
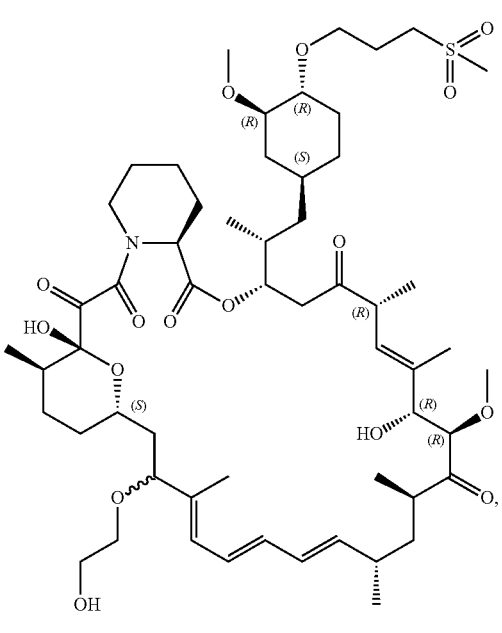

305

-continued

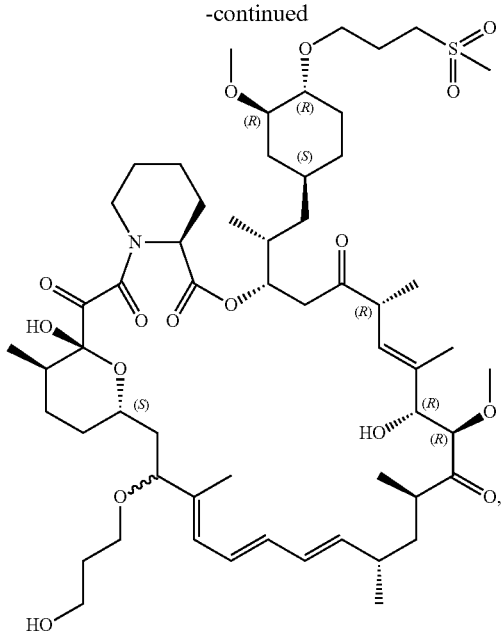

or a pharmaceutically acceptable salt of any one thereof.

21. The compound or salt of claim 1, wherein the compound is

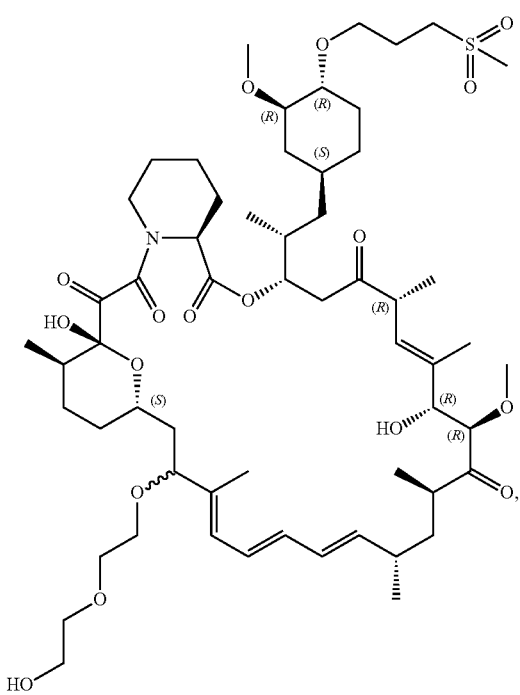

or a pharmaceutically acceptable salt thereof.

306

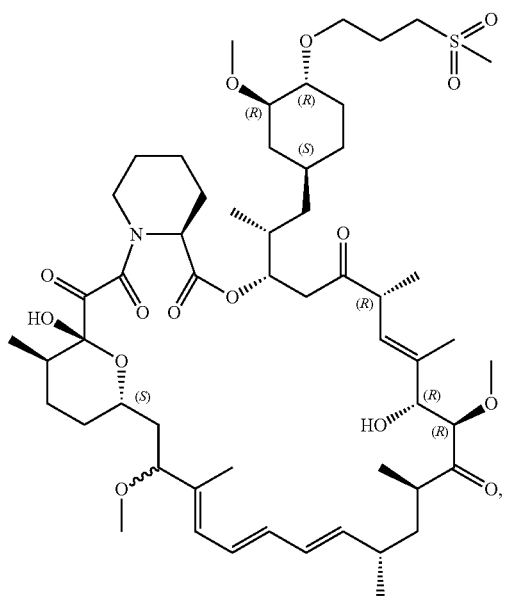

or a pharmaceutically acceptable salt thereof.

22. The compound or salt of claim 1, wherein the compound is

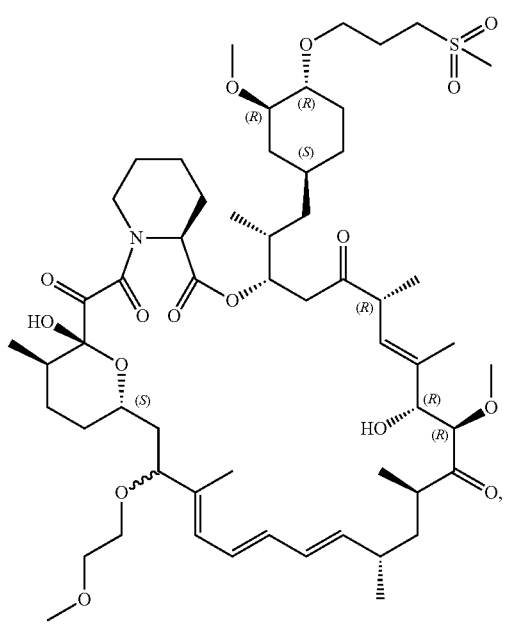

or a pharmaceutically acceptable salt thereof.

23. The compound or salt of claim 1, wherein the compound is

307

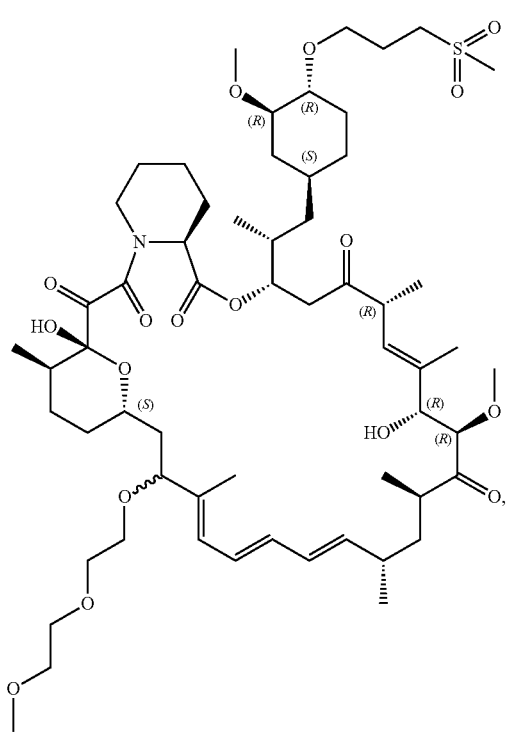

or a pharmaceutically acceptable salt thereof.

24. The compound or salt of claim 1, wherein the compound is

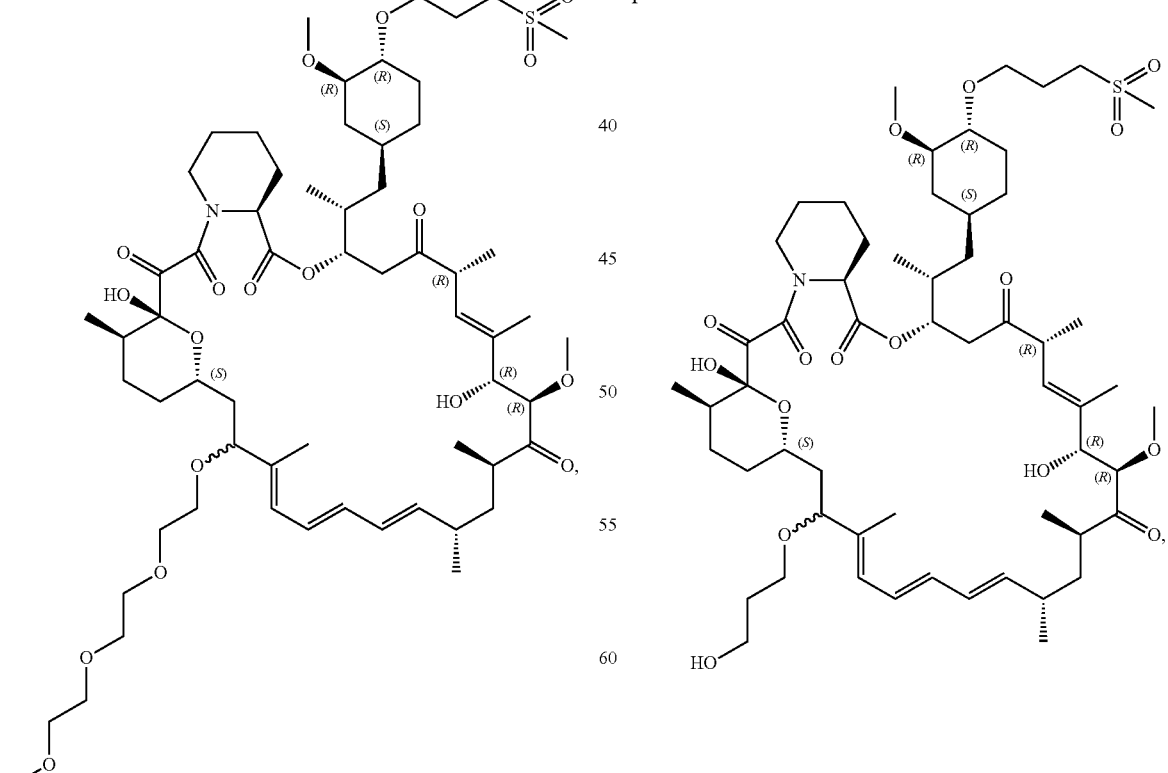

or a pharmaceutically acceptable salt thereof.

308

25. The compound or salt of claim 1, wherein the compound is

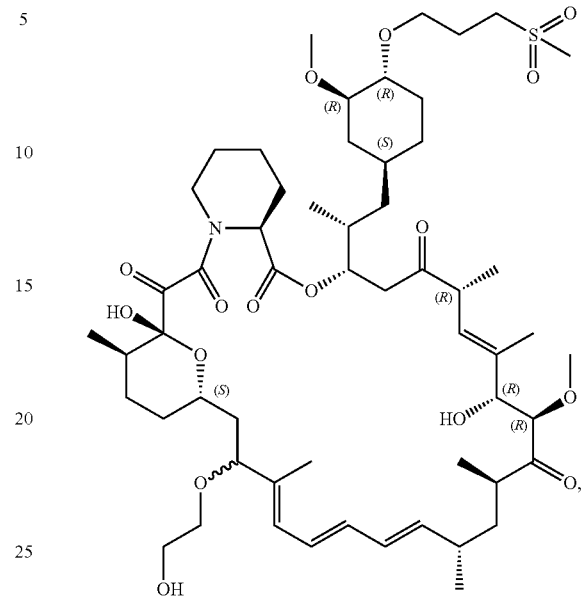

or a pharmaceutically acceptable salt thereof.

26. The compound or salt of claim 1, wherein the compound is

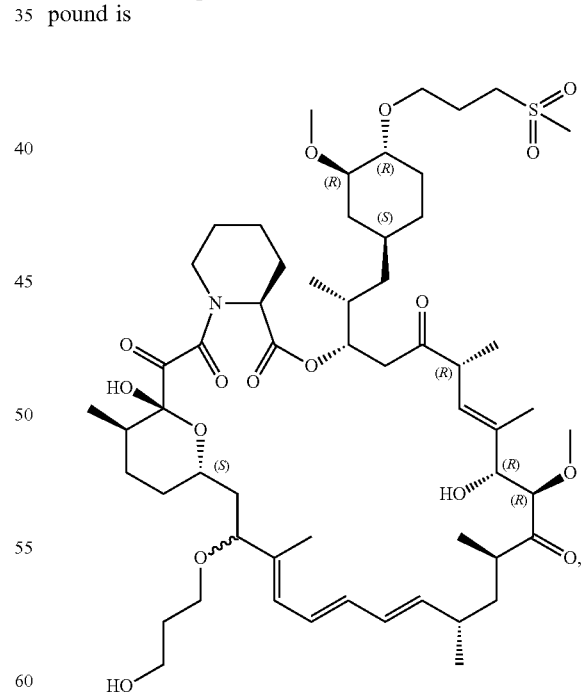

or a pharmaceutically acceptable salt thereof.

27. The compound or salt of claim 1, wherein the compound is

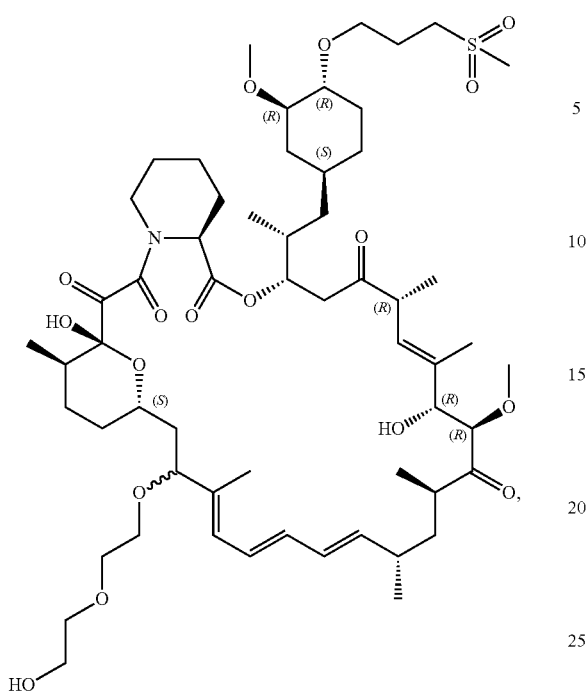

or a pharmaceutically acceptable salt thereof.

28. A pharmaceutical composition comprising a compound or salt of claim 1 and a pharmaceutically acceptable excipient.

29. A method of treating a subject with a chronic disease wherein the subject would benefit from inhibition of the activity of mTORC1, comprising administering to the subject a pharmaceutical composition of claim 28.

* * * * *